(12) United States Patent
Jalomäki et al.

(10) Patent No.: US 12,324,846 B2
(45) Date of Patent: *Jun. 10, 2025

(54) [$^{177}$LU] LUTETIUM-PSMA IandT COMPOSITION AND DOSIMETRY, KIT, METHOD OF MAKING, AND METHOD OF USING THEREOF

(71) Applicant: Curium US LLC, St. Louis, MO (US)

(72) Inventors: Jarno Jalomäki, Helsinki (FI); Salla Seppänen, Helsinki (FI); Amanda Donovan, St. Louis, MO (US); Jessica Salem, St. Louis, MO (US); Allan Casciola, St. Louis, MO (US); Anthony Vaughn, St. Louis, MO (US)

(73) Assignee: Curium US LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/791,270

(22) Filed: Jul. 31, 2024

(65) Prior Publication Data

US 2025/0041462 A1 Feb. 6, 2025

Related U.S. Application Data

(60) Provisional application No. 63/677,137, filed on Jul. 30, 2024, provisional application No. 63/677,276, filed on Jul. 30, 2024, provisional application No. 63/671,633, filed on Jul. 15, 2024, provisional application No. 63/671,625, filed on Jul. 15, 2024, provisional application No. 63/626,839, filed on Jan. 30, 2024, provisional application No. 63/620,262, filed on Jan. 12, 2024, provisional application No. 63/529,986, filed on Jul. 31, 2023.

(51) Int. Cl.
| | | |
|---|---|---|
| A61K 51/04 | (2006.01) | |
| A61K 47/18 | (2017.01) | |
| A61K 47/22 | (2006.01) | |
| A61P 35/00 | (2006.01) | |

(52) U.S. Cl.
CPC ........ *A61K 51/0497* (2013.01); *A61K 47/183* (2013.01); *A61K 47/22* (2013.01); *A61K 51/0402* (2013.01); *A61P 35/00* (2018.01); *A61K 2121/00* (2013.01); *A61K 2123/00* (2013.01)

(58) Field of Classification Search
CPC .. A61K 51/0497; A61K 47/183; A61K 47/22; A61K 51/0402; A61P 35/00
USPC ...................................... 424/1.65
See application file for complete search history.

(56) References Cited

U.S. PATENT DOCUMENTS

| | | |
|---|---|---|
| 5,081,232 A | 1/1992 | Latham et al. |
| 7,666,414 B2 | 2/2010 | Bander |
| 8,926,944 B2 | 1/2015 | Babich et al. |
| 9,694,091 B2 | 7/2017 | Pomper et al. |
| 10,232,058 B2 | 3/2019 | Pomper et al. |
| 10,406,240 B2 | 9/2019 | Low et al. |
| 10,485,878 B2 | 11/2019 | Low et al. |
| 10,517,956 B2 | 12/2019 | Low et al. |
| 10,517,957 B2 | 12/2019 | Low et al. |
| 10,624,969 B2 | 4/2020 | Low et al. |
| 10,624,970 B2 | 4/2020 | Low et al. |
| 10,624,971 B2 | 4/2020 | Low et al. |
| 10,646,581 B2 | 5/2020 | Low et al. |
| 10,683,272 B2 | 6/2020 | Ray et al. |
| 10,828,282 B2 | 11/2020 | Low et al. |
| 10,849,915 B2 | 12/2020 | Slusher et al. |
| 10,894,091 B2 | 1/2021 | Chang et al. |
| 10,912,840 B2 | 2/2021 | Mahov et al. |
| 11,083,710 B2 | 8/2021 | Low et al. |
| 11,129,912 B1 * | 9/2021 | McCann ............... C07B 59/002 |
| 11,484,607 B2 | 11/2022 | Kularatne |
| 11,491,246 B2 | 11/2022 | McCann |
| 11,491,247 B2 | 11/2022 | Bander |
| 11,497,819 B2 | 11/2022 | Wester et al. |
| 11,504,357 B2 | 11/2022 | Low et al. |
| 11,629,201 B2 | 4/2023 | Benesova et al. |
| 11,661,402 B2 | 5/2023 | Pomper et al. |
| 11,717,514 B2 | 8/2023 | Low et al. |
| 11,738,101 B2 | 8/2023 | Bander |
| 11,813,340 B2 | 11/2023 | Pomper et al. |
| 11,900,597 B2 | 2/2024 | Anand et al. |

(Continued)

FOREIGN PATENT DOCUMENTS

| | | |
|---|---|---|
| AU | 2021309907 A3 | 1/2022 |
| BR | 112023000763 A2 | 3/2023 |

(Continued)

OTHER PUBLICATIONS

Okamoto et al. J. Nucl. Med. 2017, 58, 445-450. (Year: 2017).*
Asti, et al., "Influence of cations on the complexation yield of Dotatate with yttrium and lutetium: a perspective study for enhancing the Y and LU labeling conditions," SciVerse ScienceDirect, Nuclear Medicine and Biology, 2012, vol. 39:509-517, 9 pages.
Basu, S., et al., "One decade of 'Bench-to-Bedside' peptide receptor radionuclide therapy with indigenous [Lu]Lu-Dotatate obtained through 'Direct' neutron activation route: lessons learnt including practice evolution in an Indian setting," Am. J. Nucl. Med. Mol. Imagaing, 2020, vol. 10(4), 34 pages.

(Continued)

*Primary Examiner* — Michael G. Hartley
*Assistant Examiner* — Sean R Donohue
(74) *Attorney, Agent, or Firm* — Polsinelli PC

(57) ABSTRACT

The present disclosure relates to a pharmaceutical composition comprising $^{177}$Lu-PSMA I&T and methods of administering the same. The administration of the composition results in a low absorbed radiation dose per gram of tissue in a human patient's body, including the kidneys, gastrointestinal tract, left colon, liver, rectum, red marrow, spleen, lacrimal glands, and salivary glands.

30 Claims, 29 Drawing Sheets

(2 of 29 Drawing Sheet(s) Filed in Color)

(56) References Cited

U.S. PATENT DOCUMENTS

| | | |
|---|---|---|
| 11,931,431 B2 | 3/2024 | Chi et al. |
| 2007/0269375 A1 | 11/2007 | Chen et al. |
| 2010/0297019 A1 | 11/2010 | Lanza et al. |
| 2015/0110814 A1 | 4/2015 | Olson et al. |
| 2016/0256579 A1 | 9/2016 | Shalom |
| 2020/0069706 A1 | 3/2020 | Slusher et al. |
| 2020/0138985 A1 | 5/2020 | Shalom |
| 2020/0290982 A1 | 9/2020 | Ray et al. |
| 2020/0297701 A1 | 9/2020 | Low et al. |
| 2020/0316233 A1 | 10/2020 | Garrison et al. |
| 2020/0360542 A1 | 11/2020 | Pomper et al. |
| 2021/0015949 A1 | 1/2021 | Ferro Flores et al. |
| 2021/0070696 A1 | 3/2021 | Babich et al. |
| 2021/0154311 A1 | 5/2021 | Vlahov et al. |
| 2021/0236666 A1 | 8/2021 | Kjaer et al. |
| 2021/0246103 A1 | 8/2021 | Babich et al. |
| 2021/0253690 A1 | 8/2021 | Johanns et al. |
| 2021/0276971 A1 | 9/2021 | Boros et al. |
| 2021/0338846 A1* | 11/2021 | Pomper .......... A61K 31/27 |
| 2021/0353783 A1 | 11/2021 | Kratz et al. |
| 2022/0016274 A1 | 1/2022 | McCann |
| 2022/0054659 A1 | 2/2022 | Pomper et al. |
| 2022/0080059 A1* | 3/2022 | Pipes .......... A61K 51/088 |
| 2022/0098564 A1 | 3/2022 | Low et al. |
| 2022/0135529 A1 | 5/2022 | Ray et al. |
| 2022/0152230 A1 | 5/2022 | Manning et al. |
| 2022/0251239 A1 | 8/2022 | Ludwig et al. |
| 2022/0304964 A1 | 9/2022 | Meckel et al. |
| 2023/0122957 A1 | 4/2023 | Wester et al. |
| 2023/0144805 A1 | 5/2023 | Huang et al. |
| 2023/0226201 A1 | 7/2023 | Kim et al. |
| 2023/0241256 A1 | 8/2023 | Sofou et al. |
| 2023/0293497 A1 | 9/2023 | Low et al. |
| 2023/0302163 A1 | 9/2023 | McCann |
| 2023/0346752 A1 | 11/2023 | Low et al. |
| 2023/0346986 A1 | 11/2023 | Basilion et al. |
| 2023/0364271 A1 | 11/2023 | Bander |
| 2023/0405129 A1 | 12/2023 | Hammers et al. |
| 2023/0417754 A1 | 12/2023 | Kularatne |
| 2024/0000979 A1 | 1/2024 | Bander |
| 2024/0101706 A1 | 3/2024 | Barinka et al. |
| 2024/0108765 A1 | 4/2024 | McCann |
| 2024/0156742 A1 | 5/2024 | Assaraf et al. |
| 2024/0197926 A1 | 6/2024 | Groaning et al. |

FOREIGN PATENT DOCUMENTS

| | | |
|---|---|---|
| CA | 3185565 A1 | 1/2022 |
| CN | 116547007 A | 8/2023 |
| EP | 4178628 A2 | 5/2023 |
| IL | 299760 A | 3/2023 |
| JP | 2023539990 A | 9/2023 |
| KR | 10-20240004205 A | 8/2024 |
| MX | 2023000623 A | 4/2023 |
| NZ | 796727 A1 | 2/2023 |
| SG | 11202300146 T | 9/2023 |
| WO | 2021/154939 A1 | 8/2021 |
| WO | 2021/205185 A1 | 10/2021 |
| WO | 2022/013610 A2 | 1/2022 |
| WO | 2023/015212 A1 | 2/2023 |
| WO | 2023/047319 A1 | 3/2023 |
| WO | 2023/070004 A1 | 4/2023 |
| WO | WO-2023097329 A1 * | 6/2023 .......... A61K 51/0402 |
| WO | 2023/148680 A1 | 8/2023 |
| WO | 2023/178313 A2 | 9/2023 |
| WO | 2023/215333 A1 | 11/2023 |
| WO | 2024/016071 A1 | 1/2024 |
| WO | 2024/050440 A1 | 3/2024 |
| WO | 2024/121722 A1 | 6/2024 |
| WO | 2024/133780 A1 | 6/2024 |

OTHER PUBLICATIONS

Begum, et al., "The effect of ligand amount, affinity and internalization on PSMA-targeted imaging and therapy: A simulation study using a PBPK model," Scientific Reports, NatureResearch, 2019, vol. 9(2004), 8 pages.

Weineisen, et al., "Supplemental Data-Annotated for Mole Ration," The Journal of Nuclear Medicine, Aug. 2015, vol. 56, No. 8, 8 pages.

Okamoto, et al., "Radiation Dosimetry for Lu-PSMA I&T in Metastatic Castration-Resistant Prostate Cancer: Absorbed Dose in Normal Organs and Tumor Lesions," J. Nucl. Med, 2017, vol. 58, 6 pages.

Piranfar, et al., "Radiopharmaceutical transport in solid turmors via a 3-dimensional image-based spatiotemporal model," NPJ Systems Biology and Applications, 2024, vol. 10 939 0, 17 pages.

International Search Report and Written Opinion for PCT Application No. PCT/US2023/071356, dated Sep. 24, 2024 (18 pages).

Ruigrok, et al., "In vitro dose effect relationships of actinium-225- and lutetium-177-labeled PSMA-I&T," European Journal of Nuclear Medicine and Molecular Imaging, May 12, 2022, vol. 49:3627-3638, 12 pages.

Soeda, et al., "Impact of F-PSMA-1007 Uptake in Prostate Cancer Using Different Peptide Concentrations: Preclinical PET/CT Study on Mice," The Journal of Nuclear Medicine, Nov. 2019, vol. 60:1594-1599, No. 11, 6 pages.

Thang, et al., Clinical outcomes of lutetium-prostate-specific membrane antigen therapy in advanced prostate cancer—a prospective pilot study in an Asian population, Nuclear Medicine Communications, 2020, vol. 41:618-628, 11 pages.

Wurzer, et al., "Molar Activity of Ga-68 Labeled PSMA Inhibitor Conjugates Determines PET Imaging Results," Molecular Pharmaceutics, Jul. 16, 2018, 21 pages.

Weineisen, et al., "Ga- and Lu-Labeled PSMA I&T: Optimization of a PSMA-Targeted Theranostic Concept and First Proof-of-concept Human Studies," Journal of Nuclear Medicine Technology 2015, vol. 56:1169-1176, 8 pages.

Vyas, et al., "Stability Matters: Radiochemical Stability of Therapeutic Radiopharmaceutical Lu-PSMA I&T," Journal of Nuclear Medicine Technology 2022, vol. 50:244-247, 4 pages.

Bodei, et al., "Long-term tolerability of PRRT in 807 patients with neuroendocrine tumours: the value and limitations of clinical factors," European Journal of Nuclear Medicine and Molecular Imaging, Oct. 2, 2014, 15 pages.

Kraeber-Bodere, et al., "Radioimmunoconjugates for the Treatment of Cancer," Seminars in Oncology, Oct. 2014, vol. 41, No. 5, pp. 613-622, 10 pages.

Mier, et al., "Radiopharmaceutical Therapy of Patients with Metastasized Melanoma with the Melanin-Binding Benzamide [131]I-BA52," The Journal of Nuclear Medicine, 2014, vol. 55:9-14, 6 pages.

Mohler, et al., "Prostate Cancer, Version 2.2019," Journal Natl Compr Canc Nat., May 2019, vol. 17(3):479-509, 27 pages.

Moreira, et al., "Predicting Time from Metastasis to Overall Survival in Castration-Resistant Prostate Cancer: Results from Search," Clin Genitourin Cancer, Feb. 2017, vol. 15(1):60-66.e2., 16 pages.

Silver, et al., "Prostate-specific Membrane Antigen Expression in Normal and Malignant Human Tissues," Clinical Cancer Research, Jan. 1997, vol. 3, 81-85, 5 pages.

Jean-Mathieu Beauregard, MD., "Dosimetry Results from the Splash Trial," Presented at SNMMI Mid-Winter Annual Meeting, Feb. 25-27, 2022, 11 pages.

Zechmann, et al., "Radiation dosimetry and first therapy results with a [124] I /[131] I-labeled small molecule (MIP-1095) targeting PSMA for prostate cancer therapy," European Journal of Nuclear Medicine and Molecular Imaging, Feb. 28, 2014, vol. 41:1280-1292, 13 pages.

Non-Final Office Action for U.S. Appl. No. 18/791,288, dated Sep. 18, 2024 (11 pages).

Nancy Lafreniere et al., "Compounding of [177Lu]Lu-PSMA-I&T using USP grade solvents in the radiopharmacy: experience in Quebec City", Journal of Nuclear Medicine, vol. 63, supplement 2, 4102, Aug. 22, 2022 (4 Pages).

Valentina Di Iorio et al., "Production and Quality Control of [177Lu]Lu-PSMA-I&T: Development of an Investigational Medici-

(56) References Cited

OTHER PUBLICATIONS nal Product Dossier for Clinical Trials", Molecules 2022, vol. 27, Issue 13, 4143, Jun. 28, 2022 (15 Pages).
International Search Report and Written Opinion for PCT Application No. PCT/US2024/040426, dated Nov. 27, 2024 (17 Pages).
International Search Report and Written Opinion for PCT Application No. PCT/US2024/040449 dated Dec. 4, 2024 (16 pages).
Final Office Action for U.S. Appl. No. 18/791,288, dated Jan. 17, 2025, 11 pages.

* cited by examiner

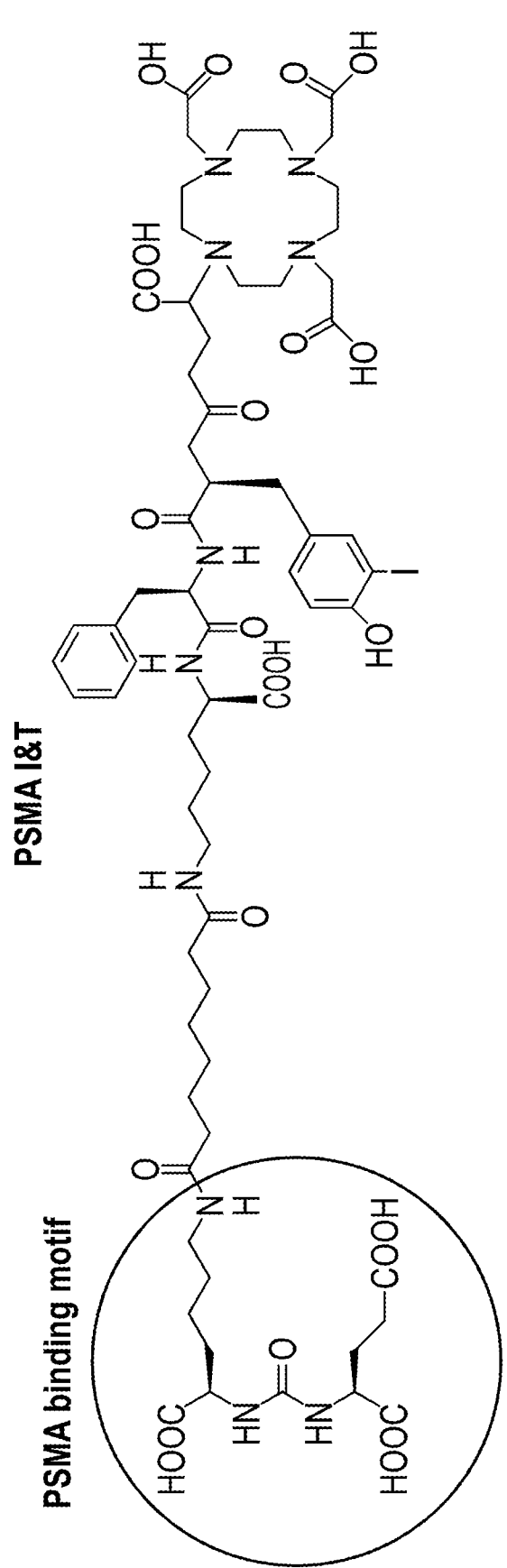
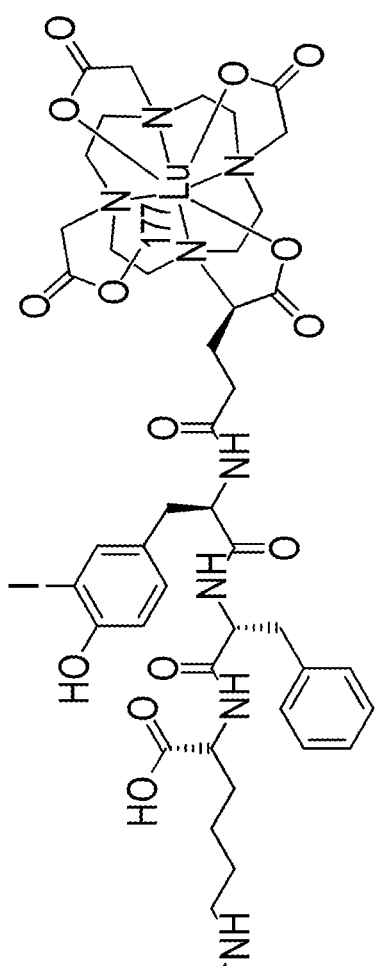
PSMA I&T
PSMA binding motif
FIG. 1A
FIG. 1B

[¹⁷⁷LU] LUTETIUM-PSMA IandT COMPOSITION AND DOSIMETRY, KIT, METHOD OF MAKING, AND METHOD OF USING THEREOF

CROSS-REFERENCE TO RELATED APPLICATIONS

The present invention claims priority to the following U.S. Provisional Applications: Nos. 63/529,986, 63/620,262, 63/626,839, 63/671,633, 63/671,625, 63/677,137 and 63/677,276 filed Jul. 31, 2023, Jan. 12, 2024, Jan. 30, 2024, Jul. 15, 2024, Jul. 15, 2024, Jul. 30, 2024, and Jul. 30, 2024, respectively, which are all hereby incorporated in their entirety, including all tables, figures, and claims.

FIELD

The present disclosure relates to a composition of a [$^{177}$Lu]Lutetium-PSMA I&T ([$^{177}$Lu]Lu-PSMA I&T or $^{177}$Lu-PSMA I&T) solution for injection, as well as a kit comprising $^{177}$Lu-PSMA I&T. The $^{177}$Lu-PSMA I&T solution and/or kit thereof may be used for prostate cancer radioligand therapy (PRLT). The present disclosure also relates to methods of administering a composition comprising $^{177}$Lu-PSMA I&T to a human patient in need thereof.

BACKGROUND

Prostate cancer (PC) is the most frequent non-cutaneous cancer and the second most frequent cause of cancer deaths for adult men. Overall increasing the survival rate for patients with metastatic castration-resistant prostate cancer (mCRPC) is challenging and there exists a clinical need for an effective treatment method for mCRPC patients.

Prostate-specific membrane antigen (PSMA) is highly expressed on prostate epithelial cells and strongly up-regulated in prostate cancer, which makes PSMA a promising molecular target for diagnosis and therapy of PC including, mCRPC. $^{177}$Lu-PSMA-617 and $^{177}$Lu-PSMA I&T are small molecule inhibitors of PSMA that are extremely desirable for targeted radionuclide therapy due to their low toxicity. However, the use of these small molecule inhibitors targeting PSMA with $^{177}$Lu to treat prostate cancer can also result in undesirable absorbed doses of radiation to healthy organs.

There continues to be a need for an improved formulation containing $^{177}$Lu-PSMA I&T that can be administered to patients which minimizes undesired cumulative absorbed doses of radiation to the patients' healthy organ tissue that is not being targeted for the treatment of cancer (e.g., prostate cancer). Provided herein are solutions to overcome these and other problems in the art by providing an improved $^{177}$Lu-PSMA I&T composition for PC and mCRPC treatment. Further, provided herein is an improved $^{177}$Lu-PSMA I&T composition and method of administration that provides lower cumulative absorbed dose of radiation, on a per administration basis. Also provided herein is an improved $^{177}$Lu-PSMA I&T composition and method of administration that provides lower cumulative absorbed dose of radiation, and/or on a per administration basis, to key individual organs (e.g., kidneys, lacrimal lands, salivary glands, and liver). Importantly, the improved compositions and methods described herein surprisingly allow for longer treatment cycles and/or lower cumulative absorbed dose radiation levels over the prior art.

BRIEF SUMMARY

Provided herein, inter alia, are compositions comprising $^{177}$Lu-PSMA I&T and methods of administering the same to a human patient in need thereof.

The compositions, methods, and kits described herein comprise 177Lu-PSMA I&T suitable for administration to a human patient at radiochemical purity of ≥95% and having a molar ratio of the PSMA I&T to 177Lu that is from 3.0:1.0 to 8.0:1.0. and/or from 4.4:1.0 to 7.6:1.0. This is highly surprising and unexpected because our own initial testing suggested that this embodiment would not be feasible, and that a molar ratio of the PSMA I&T to 177Lu of at least 11.0:1.0 or more would be required to maintain a radiochemical purity ≥95% for 72 hours or more. Indeed, according to our own initial expectations, anything below a ratio of 11.0:1.0 would likely have an unacceptable radiochemical purity (e.g., below 95%) at formation, and would continue to deteriorate such that it would be further unacceptable for a human patient at 24 hours after formation, 48 hours at formation, 72 hours after formation, or 96 hours after formation. See below PSMA: Lu-177 (mol/mol) graph showing unsuitable projected radiochemical formation at formulation below 11.0:1.0.

Yet, utilizing the unique parameters described herein, the compositions, methods, and kits described herein comprising 177Lu-PSMA I&T suitable for administration to a human patient at radiochemical purity of ≥95% and having a molar ratio of the PSMA I&T to 177Lu that is 3.0:1.0 to 8.0:1.0 and/or from 4.4:1.0 to 7.6:1.0, wherein the composition is stable for 72 hours or more, are provided herein.

In another embodiment, the compositions, methods, and kits described herein comprise 177Lu-PSMA I&T suitable for administration to a human patient at radiochemical purity of ≥95% and having a PSMA I&T to [177Lu]Lu3+ ratio (in µg:mCi) from about 0.20 to about 0.60. In another embodiment, the compositions, methods, and kits described herein comprise 177Lu-PSMA I&T suitable for administration to a human patient at radiochemical purity of ≥95% and having a PSMA I&T to [177Lu]Lu3+ ratio (in µg:mCi)≤0.60. This is also a highly surprising and unexpected because our own initial testing suggested that this embodiment would not be feasible, and having a PSMA I&T to [177Lu]Lu3+ ratio (in µg:mCi) of at least 0.70 or greater would be required to maintain a radiochemical purity ≥95% for 72 hours or more. See below PSMA: Lu-177 (mol/mol) graph showing unsuitable projected radiochemical formation at formulation at 0.60 and below.

Yet, utilizing the unique parameters described herein, the compositions, methods, and kits described herein comprising 177Lu-PSMA I&T suitable for administration to a human patient at radiochemical purity of ≥95% and having a PSMA I&T to [177Lu]Lu3+ ratio (in µg:mCi) of from about 0.20 to about 0.64, from about 0.20 to about 0.63, from about 0.20 to about 0.62, from about 0.20 to about 0.61, or from about 0.20 to about 0.60, wherein the composition is stable for 72 hours or more, are provided herein.

In some embodiments, the composition has a molar ratio of PSMA I&T to $^{177}$Lu from about 1.0:1 to about 8.0:1, from about 1.5:1 to about 8.0:1, from about 2.0:1 to about 8.0:1, from about 2.5:1 to about 8.0:1, from about 3.0:1 to about 8.0:1, from about 3.5:1 to about 8.0:1, from about 4.0:1.0 to about 8.0:1.0, from about 4.5:1.0 to about 5.5:1.0, or from about 5.0:1.0 to about 6.0:1.0. In some aspects, the composition has a molar ratio of PSMA I&T to $^{177}$Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0. In some aspects, the composition has a molar ratio of PSMA I&T to $^{177}$Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

In some embodiments, the composition comprises about 7.1 GBq to about 7.6 GBq of $^{177}$Lu-PSMA I&T. In some aspects, the composition comprises 7.4±15% GBq of $^{177}$Lu-PSMA I&T, 7.4±10% GBq of $^{177}$Lu-PSMA I&T, or 7.4±5% GBq of $^{177}$Lu-PSMA I&T. In an example, the composition comprises about 7.4 GBq of $^{177}$Lu-PSMA I&T.

Further provided herein is a method comprising administering to a human patient in need thereof a radiopharmaceutical composition comprising $^{177}$Lu-PSMA I&T, wherein the absorbed radiation dose per gram of tissue in the human patient's kidneys is from about 0.2 Gy/GBq to about 0.6 Gy/GBq, from about 0.25 Gy/GBq to about 0.55 Gy/GBq, from about 0.3 Gy/GBq to about 0.5 Gy/GBq, or from about 0.35 Gy/GBq to about 0.45 Gy/GBq. In some aspects, the absorbed radiation dose per gram of tissue in the human patient's kidneys is ≤0.60 Gy/GBq, ≤0.55 Gy/GBq, ≤0.50 Gy/GBq, ≤0.45 Gy/GBq, ≤0.40 Gy/GBq, ≤0.35 Gy/GBq, ≤0.30 Gy/GBq, ≤0.25 Gy/GBq, ≤0.20 Gy/GBq, or ≤0.15 Gy/GBq. In some aspects, the mean absorbed radiation dose per gram of tissue in the human patient's kidneys is about 0.39±0.15 Gy/GBq, about 0.40±0.15 Gy/GBq, about 0.41±0.15 Gy/GBq, about 0.42±0.15 Gy/GBq, about 0.43±0.15 Gy/GBq, about 0.44±0.15 Gy/GBq, or about 0.45+0.15 Gy/GBq. In some aspects, the mean absorbed radiation dose per gram of tissue in the human patient's kidneys is ≤0.39 Gy/GBq, ≤0.40 Gy/GBq, ≤0.41 Gy/GBq, or ≤0.42 Gy/GBq. In some aspects, the standard deviation of the mean absorbed radiation dose per gram of tissue in the human patient's kidneys is ≤0.19 Gy/GBq, ≤0.18 Gy/GBq, ≤0.17 Gy/GBq, ≤0.16 Gy/GBq, or ≤0.15 Gy/GBq. In some aspects, the absorbed radiation dose is determined via SPECT imaging, planar imaging, or a combination thereof.

Provided herein is a method comprising administering to a human patient in need thereof a radiopharmaceutical composition comprising $^{177}$Lu-PSMA I&T, wherein the absorbed radiation dose per gram of tissue in the human patient's lacrimal glands is from about 0.01 Gy/GBq to about 1.5 Gy/GBq. In some embodiments, the absorbed radiation dose per gram of tissue in the human patient's lacrimal glands is ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq. In some aspects, the absorbed radiation dose per gram of tissue in the human patient's lacrimal glands is from about 0.1 Gy/GBq to about 0.8 Gy/GBq. In some aspects, the absorbed radiation dose per gram of tissue in the human patient's lacrimal glands is about 0.01, 0.05, 0.1, 0.2, 0.3, 0.4, 0.5, 0.6, 0.7, 0.8, 0.9, 1.0, 1.1, 1.2, 1.3, 1.4, or 1.5 Gy/GBq. In some aspects, the mean absorbed radiation dose per gram of tissue in the human patient's lacrimal glands is 0.37±0.36 Gy/GBq, 0.38±0.36 Gy/GBq, 0.39±0.36 Gy/GBq, or 0.40±0.36 Gy/GBq. In some aspects, the mean absorbed radiation dose per gram of tissue in the human patient's lacrimal glands is ≤0.40 Gy/GBq, ≤0.50 Gy/GBq, ≤0.60 Gy/GBq, ≤0.70 Gy/GBq, ≤0.80 Gy/GBq, ≤0.90 Gy/GBq, or ≤1.0 Gy/GBq. In some aspects, the standard deviation of the mean absorbed radiation dose per gram of tissue in the human patient's lacrimal glands is ≤0.37 Gy/GBq. In some aspects, the absorbed radiation dose is determined via SPECT imaging, planar imaging, or a combination thereof.

Further provided herein is a method comprising administering to a human patient in need thereof a radiopharmaceutical composition comprising $^{177}$Lu-PSMA I&T, wherein the absorbed radiation dose per gram of tissue in the human patient's salivary glands is from about 0.01 Gy/GBq to about 1.0 Gy/GBq. In some embodiments, the absorbed radiation dose per gram of tissue in the human patient's salivary glands is ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq. In some aspects, the absorbed radiation dose per gram of tissue in the human patient's salivary glands is from about 0.1 Gy/GBq to about 0.5 Gy/GBq. In some aspects, the absorbed radiation dose per gram of tissue in the human patient's salivary glands is from about 0.01, 0.05, 0.1, 0.2, 0.3, 0.4, 0.5, 0.6, 0.7, 0.8, 0.9, or about 1.0 Gy/GBq. In some aspects, the mean absorbed radiation dose per gram of tissue in the human patient's salivary glands is about 0.17±0.16 Gy/GBq, 0.18±0.16 Gy/GBq, 0.19±0.16 Gy/GBq, or 0.20±0.16 Gy/GBq. In some aspects, the mean absorbed radiation dose per gram of tissue in the human patient's salivary glands is ≤0.18 Gy/GBq, ≤0.19 Gy/GBq, ≤0.20 Gy/GBq≤0.21 Gy/GBq, ≤0.22 Gy/GBq, ≤0.23 Gy/GBq, ≤0.24 Gy/GBq, ≤0.25 Gy/GBq, ≤0.26 Gy/GBq, ≤0.27 Gy/GBq, ≤0.28 Gy/GBq, ≤0.29 Gy/GBq, or ≤0.30 Gy/GBq. In some embodiments, the standard deviation of the mean absorbed radiation dose per gram of tissue in the human patient's salivary glands is ≤0.25 Gy/GBq, ≤0.24 Gy/GBq, ≤0.23 Gy/GBq, ≤0.22 Gy/GBq, ≤0.21 Gy/GBq, ≤0.20 Gy/GBq, ≤0.19 Gy/GBq, ≤0.18 Gy/GBq, ≤0.17 Gy/GBq, or ≤0.16 Gy/GBq. In some aspects, the absorbed radiation dose is determined via SPECT imaging, planar imaging, or a combination thereof.

Further provided herein is a method comprising administering to a human patient in need thereof a radiopharmaceutical composition comprising $^{177}$Lu-PSMA I&T, wherein the absorbed radiation dose per gram of tissue in the human patient's left colon is from about 0.01 Gy/GBq to about 1.6 Gy/GBq. In some embodiments, the absorbed radiation dose per gram of tissue in the human patient's left colon is ≤1.6 Gy/GBq, ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq. In some aspects, the absorbed radiation dose per gram of tissue in the human patient's left colon is from about 0.1 Gy/GBq to about 0.8 Gy/GBq. In some aspects, the absorbed radiation dose per gram of tissue in the human patient's left colon is about 0.01, 0.05, 0.1, 0.2, 0.3, 0.4, 0.5, 0.6, 0.7, 0.8, 0.9, 1.0, 1.1, 1.2, 1.3, 1.4, 1.5, or about 1.6 Gy/GBq. In some aspects, the mean absorbed radiation dose per gram of tissue in the human patient's left colon is 0.45±0.31 Gy/GBq, 0.46±0.31 Gy/GBq, or 0.47±0.31 Gy/GBq. In some aspects, the mean absorbed radiation dose per gram of tissue in the human patient's left colon is ≤0.47 Gy/GBq.

Further provided herein is a method comprising administering to a human patient in need thereof a radiopharmaceutical composition comprising $^{177}$Lu-PSMA I&T, wherein the absorbed radiation dose per gram of tissue in the human patient's rectum is from about 0.01 Gy/GBq to about 1.5 Gy/GBq. In some embodiments, the absorbed radiation dose per gram of tissue in the human patient's rectum is ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq. In some aspects, the absorbed radiation dose per gram of tissue in the human patient's rectum is from about 0.1 Gy/GBq to about 0.8 Gy/GBq. In some aspects, the absorbed radiation dose per gram of tissue in the human patient's rectum is about 0.01, 0.05, 0.1, 0.2, 0.3, 0.4, 0.5, 0.6, 0.7, 0.8, 0.9, 1.0, 1.1, 1.2, 1.3, 1.4, or about 1.5 Gy/GBq. In some aspects, the mean absorbed radiation dose per gram of tissue in the human patient's rectum is 0.44±0.30 Gy/GBq. In some aspects, the absorbed radiation dose is determined via SPECT imaging, planar imaging, or a combination thereof.

Further provided herein is a method comprising administering to a human patient in need thereof a radiopharmaceutical composition comprising $^{177}$Lu-PSMA I&T, wherein the fraction of activity of the $^{177}$Lu-PSMA I&T in the whole body of the human patient is about 0.5 or less within 24 hours, 48 hours, or 168 hours after administration of the composition. In some embodiments, the fraction of activity of the $^{177}$Lu-PSMA I&T in the whole body of the human patient is ≤0.5, ≤0.4, ≤0.3, ≤0.2, or ≤0.1 within 24 hours, 48 hours, or 168 hours after administration of the composition. In some aspects, the fraction of activity of the $^{177}$Lu-PSMA I&T in the whole body of the human patient is about 0.5, 0.4, 0.3, 0.2, 0.1, or less than 0.1 within 24 hours, 48 hours, or 168 hours after administration of the composition. In some aspects, the fraction of activity of the $^{177}$Lu-PSMA I&T in the whole body of the human patient is about 0.4 or less within 48 hours or 168 hours after administration of the composition. In some aspects, the fraction of activity of the $^{177}$Lu-PSMA I&T in the whole body of the human patient is about 0.4, about 0.3, about 0.2, about 0.1, or less than 0.1 within 48 hours or 168 hours after administration of the composition. In some aspects, the fraction of activity of the $^{177}$Lu-PSMA I&T in the whole body of the human patient is about 0.2 or less within 168 hours after administration of the composition. In some aspects, the administration is via injection. In some aspects, wherein the fraction of activity is determined via SPECT imaging, planar image-based dosimetry, or a combination thereof. Further provided herein is a method comprising administering to a human patient in need thereof a radiopharmaceutical composition comprising $^{177}$Lu-PSMA I&T, wherein the fraction of activity of the $^{177}$Lu-PSMA I&T in the kidneys of the human patient is about 0.05 or less within 24 hours, 48 hours, or 168 hours after administration of the composition.

Further provided herein is a method comprising administering to a human patient in need thereof a radiopharmaceutical composition comprising $^{177}$Lu-PSMA I&T, wherein the fraction of activity of the $^{177}$Lu-PSMA I&T in the kidneys of the human patient is about 0.05 or less within 24 hours, 48 hours, or 168 hours after administration of the composition. In some embodiments, the fraction of activity of the $^{177}$Lu-PSMA I&T in the kidneys of the human patient is ≤0.05, ≤0.04, ≤0.03, ≤0.02, or ≤0.01 within 24 hours, 48 hours, or 168 hours after administration of the composition. In some aspects, the fraction of activity of the $^{177}$Lu-PSMA I&T in the kidneys of the human patient is about 0.05, about 0.04, about 0.03, about 0.02, about 0.01, or less than 0.01 within 24 hours, 48 hours, or 168 hours after administration of the composition. In some aspects, the fraction of activity of the $^{177}$Lu-PSMA I&T in the kidneys of the human patient is ≤0.040 within 48 hours or 168 hours after administration of the composition. In some aspects, the fraction of activity of the $^{177}$Lu-PSMA I&T in the kidneys of the human patient is about 0.040 or less, about 0.035 or less, or about 0.030 or less within 48 hours or 168 hours after administration of the composition. In some aspects, the fraction of activity of the $^{177}$Lu-PSMA I&T in the kidneys of the human patient is about 0.04, 0.03, 0.02, 0.01, or less than 0.01 within 48 hours or 168 hours after administration of the composition. In some aspects, the fraction of activity of the $^{177}$Lu-PSMA I&T in the kidneys of the human patient is about 0.03 or less within 168 hours after administration of the composition. In some aspects, the fraction of activity of the $^{177}$Lu-PSMA I&T in the kidneys of the human patient is about 0.03, 0.02, 0.01, or less than 0.01 within 168 hours after administration of the composition. In some aspects, the administration is via injection. In some aspects, the fraction of activity is determined via SPECT imaging, planar imaging, or a combination thereof.

Further provided herein is a method comprising administering to a human patient in need thereof a radiopharmaceutical composition comprising $^{177}$Lu-PSMA I&T, wherein the fraction of activity of the $^{177}$Lu-PSMA I&T in the red marrow of the human patient is about 0.08 or less within 24 hours, 48 hours, or 168 hours after administration of the composition. In some embodiments, the fraction of activity of the $^{177}$Lu-PSMA I&T in the red marrow of the human patient is ≤0.08, ≤0.07, ≤0.06, ≤0.05, ≤0.04, ≤0.03, ≤0.02, ≤0.01, or less within 24 hours, 48 hours, or 168 hours after administration of the composition. In some aspects, the fraction of activity of the $^{177}$Lu-PSMA I&T in the red marrow of the human patient is about 0.08, 0.07, 0.06, 0.05, 0.04, 0.03, 0.02, 0.01, or less than 0.01 within 24 hours, 48 hours, or 168 hours after administration of the composition. In some aspects, the fraction of activity of the $^{177}$Lu-PSMA I&T in the red marrow of the human patient is about 0.06 or less within 48 hours or 168 hours after administration of the composition. In some aspects, the fraction of activity of the $^{177}$Lu-PSMA I&T in the red marrow of the human patient is about 0.06, 0.05, 0.04, 0.03, 0.02, 0.01, or less than 0.01 within 48 hours or 168 hours after administration of the composition. In some aspects, the fraction of activity of the $^{177}$Lu-PSMA I&T in the red marrow of the human patient is about 0.04 or less within 168 hours after administration of the composition. In some aspects, the fraction of activity of the $^{177}$Lu-PSMA I&T in the red marrow of the human patient is about 0.04, 0.03, 0.02, 0.01, or less than 0.01 within 168 hours after administration of the composition. In some aspects, the administration is via injection. In some aspects, the fraction of activity is determined via SPECT imaging, planar imaging, or a combination thereof.

Further provided herein is a method comprising administering to a human patient in need thereof a radiopharmaceutical composition comprising $^{177}$Lu-PSMA I&T, wherein the fraction of activity of the $^{177}$Lu-PSMA I&T in the salivary glands of the human patient is about 0.015 or less within 24 hours, 48 hours, or 168 hours after administration of the composition. In some embodiments, the fraction of activity of the $^{177}$Lu-PSMA I&T in the salivary glands of the human patient is ≤0.015, ≤0.014, ≤0.013, ≤0.012, ≤0.011, ≤0.010, ≤0.009, ≤0.008, ≤0.007, ≤0.006, ≤0.005, ≤0.004, ≤0.003, ≤0.002, ≤0.001, or less within 24 hours, 48 hours, or 168 hours after administration of the composition. In some aspects, the fraction of activity of the $^{177}$Lu-PSMA I&T in the salivary glands of the human patient is about 0.015, 0.014, 0.013, 0.012, 0.011, 0.010, 0.009, 0.008, 0.007, 0.006, 0.005, 0.004, 0.003, 0.002, 0.001 or less than 0.001 within 24 hours, 48 hours, or 168 hours after administration of the composition. In some aspects, the fraction of activity of the $^{177}$Lu-PSMA I&T in the salivary glands of the human patient is about 0.007 or less within 48 hours or 168 hours after administration of the composition. In some aspects, the fraction of activity of the $^{177}$Lu-PSMA I&T in the salivary glands of the human patient is about 0.007, 0.006, 0.005, 0.004, 0.003, 0.002, 0.001 or less than 0.001 within 48 hours or 168 hours after administration of the composition. In some aspects, the fraction of activity of the $^{177}$Lu-PSMA I&T in the salivary glands of the human patient is about 0.004 or less within 168 hours after administration of the composition. In some aspects, the fraction of activity of the $^{177}$Lu-PSMA I&T in the salivary glands of the human patient is about 0.004, 0.003, 0.002, 0.001 or less than 0.001 within 168 hours after administration of the composition. In some aspects, the administration is via injection. In some aspects, the fraction of activity is determined via SPECT imaging, planar imaging, or a combination thereof.

Further provided herein is a method comprising administering to a human patient in need thereof a radiopharmaceutical composition comprising $^{177}$Lu-PSMA I&T, wherein the fraction of activity of the $^{177}$Lu-PSMA I&T in the gastrointestinal tract of the human patient is about 0.10 or less within 24 hours, 48 hours, or 168 hours after administration of the composition. In some embodiments, the fraction of activity of the $^{177}$Lu-PSMA I&T in the gastrointestinal tract of the human patient is ≤0.10, ≤0.09, ≤0.08, ≤0.07, ≤0.06, ≤0.05, ≤0.04, ≤0.03, ≤0.02, ≤0.01, or less within 24 hours, 48 hours, or 168 hours after administration of the composition. In some aspects, the human patient is about 0.10, 0.09, 0.08, 0.07, 0.06, 0.05, 0.04, 0.03, 0.02, 0.01 or less than 0.01 within 24 hours, 48 hours, or 168 hours after administration of the composition. In some aspects, the fraction of activity of the $^{177}$Lu-PSMA I&T in the gastrointestinal tract of the human patient is about 0.10 or less within 48 hours or 168 hours after administration of the composition. In some aspects, the fraction of activity of the $^{177}$Lu-PSMA I&T in the gastrointestinal tract of the human patient is about 0.10, 0.09, 0.08, 0.07, 0.06, 0.05, 0.04, 0.03, 0.02, 0.01 or less than 0.01 within 48 hours or 168 hours after administration of the composition. In some aspects, the fraction of activity of the $^{177}$Lu-PSMA I&T in the gastrointestinal tract of the human patient is about 0.05 or less within 168 hours after administration of the composition. In some aspects, the fraction of activity of the $^{177}$Lu-PSMA I&T in the gastrointestinal tract of the human patient is about 0.05, 0.04, 0.03, 0.02, 0.01, or less than 0.01 within 168 hours after administration of the composition. In some aspects, the administration is via injection. In some aspects, the fraction of activity is determined via SPECT imaging, planar imaging, or a combination thereof.

Further provided herein is a method comprising administering to a human patient in need thereof a radiopharmaceutical composition comprising $^{177}$Lu-PSMA I&T, wherein the fraction of activity of the $^{177}$Lu-PSMA I&T in the liver of the human patient is about 0.04 or less within 24 hours, 48 hours, or 168 hours after administration of the composition. In some embodiments, the fraction of activity of the $^{177}$Lu-PSMA I&T in the liver of the human patient is ≤0.04, ≤0.03, ≤0.02, ≤0.01, or less within 24 hours, 48 hours, or 168 hours after administration of the composition. In some aspects, the fraction of activity of the $^{177}$Lu-PSMA I&T in the liver of the human patient is about 0.04, 0.03, 0.02, 0.01 or less than 0.01 within 24 hours, 48 hours, or 168 hours after administration of the composition. In some aspects, the fraction of activity of the $^{177}$Lu-PSMA I&T in the liver of the human patient is about 0.02 or less within 48 hours or 168 hours after administration of the composition. In some aspects, the fraction of activity of the $^{177}$Lu-PSMA I&T in the liver of the human patient is about 0.02, 0.01, or less than 0.01 within 48 hours or 168 hours after administration of the composition. In some aspects, the fraction of activity of the $^{177}$Lu-PSMA I&T in the liver of the human patient is about 0.01 or less within 168 hours after administration of the composition. In some aspects, the administration is via injection. In some aspects, the fraction of activity is determined via SPECT imaging, planar imaging, or a combination thereof.

Further provided herein is a method comprising administering to a human patient in need thereof a radiopharmaceutical composition comprising $^{177}$Lu-PSMA I&T, wherein the fraction of activity of the $^{177}$Lu-PSMA I&T in the spleen of the human patient is about 0.004 or less within 24 hours, 48 hours, or 168 hours after administration of the composition. In some embodiments, the fraction of activity of the $^{177}$Lu-PSMA I&T in the spleen of the human patient is ≤0.004, ≤0.003, ≤0.002, ≤0.001 or less within 24 hours, 48 hours, or 168 hours after administration of the composition. In some aspects, the fraction of activity of the $^{177}$Lu-PSMA I&T in the spleen of the human patient is about 0.004, 0.003, 0.002, 0.001 or less than 0.001 within 24 hours, 48 hours, or 168 hours after administration of the composition. In some aspects, the fraction of activity of the $^{177}$Lu-PSMA I&T in the spleen of the human patient is about 0.002 or less within 48 hours or 168 hours after administration of the composition. In some aspects, the fraction of activity of the $^{177}$Lu-PSMA I&T in the spleen of the human patient is about 0.002, 0.001, or less than 0.001 within 48 hours or 168 hours after administration of the composition. In some aspects, the fraction of activity of the $^{177}$Lu-PSMA I&T in the spleen of the human patient is about 0.001 or less within 168 hours after administration of the composition. In some aspects, the administration is via injection. In some aspects, the fraction of activity is determined via SPECT imaging, planar imaging, or a combination thereof.

Further provided herein is a method comprising administering to a human patient in need thereof a radiopharmaceutical composition comprising $^{177}$Lu-PSMA I&T, wherein the fraction of activity of the $^{177}$Lu-PSMA I&T in the lacrimal glands of the human patient is about 0.0004 or less within 24 hours, 48 hours, or 168 hours after injection of the composition. In some embodiments, the fraction of activity of the $^{177}$Lu-PSMA I&T in the lacrimal glands of the human patient is ≤0.0004, ≤0.0003, ≤0.0002, ≤0.0001, or less within 24 hours, 48 hours, or 168 hours after injection of the composition. In some aspects, the fraction of activity of the $^{177}$Lu-PSMA I&T in the spleen of the human patient is about 0.0004, 0.0003, 0.0002, 0.0001 or less than 0.0001 within 24 hours, 48 hours, or 168 hours after administration of the composition. In some aspects, the fraction of activity of the $^{177}$Lu-PSMA I&T in the spleen of the human patient is about 0.0002 or less within 48 hours or 168 hours after administration of the composition. In some aspects, the fraction of activity of the $^{177}$Lu-PSMA I&T in the spleen of the human patient is about 0.0002, 0.0001, or less than 0.0001 within 48 hours or 168 hours after administration of the composition. In some aspects, the fraction of activity of the $^{177}$Lu-PSMA I&T in the spleen of the human patient is less than 0.0001 within 168 hours after administration of the composition. In some aspects, the administration is via injection. In some aspects, the fraction of activity is determined via SPECT imaging, planar imaging, or a combination thereof.

BRIEF DESCRIPTION OF THE FIGURES

The patent or application file contains at least one drawing executed in color. Copies of this patent or patent application publication with color drawing(s) will be provided by the Office upon request and payment of the necessary fee.

Various features, aspects, and advantages of the present disclosure will become better understood when the following detailed description is read with reference to the accompanying figures in which like characters represent like parts throughout the figures, wherein:

FIG. 1A presents the structural formula of the precursor PSMA I&T.

FIG. 1B presents a structural formula for the R isomer of $^{177}$Lu-PSMA I&T.

DETAILED DESCRIPTION

Figure 2:
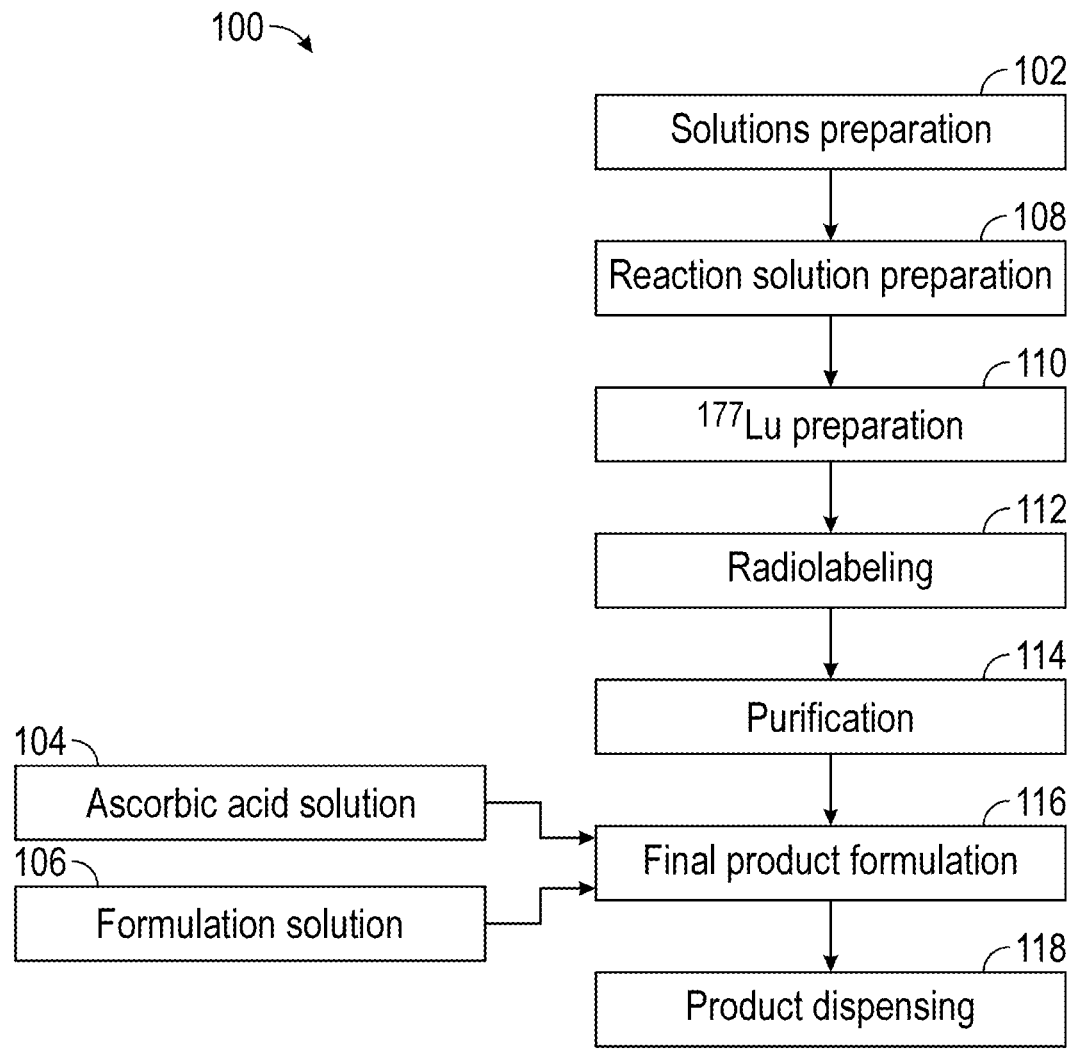
FIG. 2 is a flowchart representation of an example method of preparing the disclosed radiopharmaceutical composition.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Disclosed herein is a small molecular inhibitor of PSMA that has the desirable attributes of large monoclonal antibodies with reduced negative aspects, e.g., poor permeability and toxicity. The radiopharmaceutical composition disclosed herein comprises $^{177}$Lu-PSMA I&T. $^{177}$Lu-PSMA I&T is a short-lived radiolabeled substance from which the product is formulated immediately after finished synthesis.

Headings included herein are simply for ease of reference and are not intended to limit the disclosure in any way.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims or can be learned by the practice of the principles set forth herein. All publications, patents and patent applications cited herein, whether supra or infra, are hereby incorporated by reference in their entirety.

I. Definitions

Several definitions that apply throughout the above disclosure will now be presented. As used herein, the terms "comprising," "having," and "including" are used interchangeably in their open, non-limiting sense. The terms "a," "an," and "the" are understood to encompass the plural as well as the singular. Thus, the term "a mixture thereof" also relates to "mixtures thereof."

Generally, the ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

As used herein, "about" refers to numeric values, including whole numbers, fractions, per-centages, etc., whether or not explicitly indicated. The term "about" generally refers to a range of numerical values, for instance, ±0.5-1%, ±1-5% or ±5-10% of the recited value, that one would consider equivalent to the recited value, for example, having the same function or result.

As used herein, "PSMA" refers to prostate-specific membrane antigen, also known as folate hydrolase I or glutamate carboxypeptidase II, is a type II transmembrane protein, which is anchored in the cell membrane of prostate epithelial cells. PSMA is highly expressed on prostate epithelial cells and strongly up-regulated in prostate cancer. The PSMA expression levels are directly correlated to androgen independence, metastasis, and prostate cancer progression. Thus, PSMA is a promising molecular target for diagnosis and therapy of metastatic prostate cancer at present.

As used herein, "Lutetium-177" and "177Lu" are used interchangeably. 177Lu is a β- and γ-emitting radionuclide with a physical half-life of 6.7 days. It has a maximum and mean β-particle energy of 0.498 MeV and 0.133 MeV, respectively. The maximum and mean soft-tissue penetration depth of $^{177}$Lu is 1.7 mm and 0.23 mm, respectively. It has two main gamma emission lines: 113 keV (6% relative abundance) and 208 keV (11% relative abundance).

As used herein, "177Lu-PSMA-617," refers to a DOTA derivative of the Glu-urea-Lys motif that has been developed in the German Cancer Research Center (DKFZ) Heidelberg, Germany, for the treatment of patients with metastatic prostate cancer.

As used herein, "[177Lu]Lu-PSMA I&T" and "177Lu-PSMA I&T" refer to 177Lu-PSMA for imaging and therapy (I&T), a third-generation derivative of 177Lu-PSMA-compounds which has been used here. The chemical name of 177Lu-PSMA I&T is (3S,7S,26R,29R,32R,37R)-29-benzyl-32-(4-hydroxy-3-iodobenzyl)-5,13,20,28,31,34-hexaoxo-37-(4,7,10-tris(carboxymethyl)-1,4,7,10-tetraazacyclododecan-1-yl)-4,6,12,21,27,30,33-heptaazaheptatriacontane-1,3,7,26,37-pentacarboxylic acid; lutetium-177 (III). The chemical structure of 177Lu-PSMA I&T is provided in FIG. 1B.

The term "half-life" as used herein refers to the biological half-life, for example, the time required for a drug's blood or plasma concentration to decrease by one half. This decrease in drug concentration is a reflection of its excretion or elimination after absorption is complete and distribution has reached an equilibrium or quasi equilibrium state. The half-life of a drug in the blood may be determined graphically off of a pharmacokinetic plot of a drug's blood-concentration time plot, typically after intravenous administration to a sample population. The half-life can also be determined using mathematical calculations that are well known in the art. Further, as used herein the term "half-life" also includes the "apparent half-life" of a drug. The apparent half-life may be a composite number that accounts for contributions from other processes besides elimination, such as absorption, reuptake, or enterohepatic recycling.

As used herein, "PRLT" refers to prostate radioligand therapy and "RLT" refers to radioligand therapy. PRLT in this context involves the systemic intravenous administration of a specific radiopharmaceutical composed of a β-emitting radionuclide chelated to a small molecule for the purpose of delivering cytotoxic radiation to cancer cells. All compositions and methods described herein may be used for PRLT and/or treating cancer.

The term "CRPC," as used herein, refers to castrate resistant prostate cancer. In an example, a patient with CRPC may have castrate serum testosterone <50 μg/l or 1.7 nmol/l plus one of the following types of progression: biochemical progression or radiologic progression, as defined below. All compositions and methods described herein may be used for CRPC and/or treating cancer.

The term "biochemical progression," as used herein, refers to three consecutive rises in PSA one week apart, resulting in two 50% increases over the nadir, and PSA >2 μg/l. The term "RAC" as used herein, refers to radioactivity concentration.

The term "radiologic progression," as used herein, refers to the appearance of new lesions; either two or more new bone lesions on bone scan or a soft tissue lesion using the Response Evaluation Criteria in Solid Tumors (RECIST).

As used herein, the terms "end of synthesis", "after formulation", and "end of formulation" are used interchangeably to mean when the process of preparing the composition has completed. This may also include the time after quality control and release of the drug product by a Qualified Person.

The term "active agent" or "drug," as used herein, refers to any chemical that elicits a biochemical response when administered to a human or an animal. The drug may act as a substrate or product of a biochemical reaction, or the drug may interact with a cell receptor and elicit a physiological response, or the drug may bind with and block a receptor from eliciting a physiological response.

The term "adverse event" (AE) is any untoward medical occurrence in a subject administered an investigational drug, which does not necessarily have a causal relationship with the treatment. An AE can be any unfavorable or unintended sign (e.g., an abnormal laboratory finding), symptom, or disease temporally associated with the use of a drug, whether or not it is considered to be drug related. This includes any newly occurring event or previous condition that has increased in severity or frequency since the administration of the drug.

The terms "subject" or "patient" are used interchangeably herein and refer to a vertebrate, preferably a mammal. Mammals include, but are not limited to, humans.

As used herein, "composition" refers to radiopharmaceutical composition and vice-versa. Accordingly, "composition" and "radiopharmaceutical composition" can be used interchangeably.

The term "effective amount" or "effective dose" refers to the amount of a therapy (e.g., radiation provided herein, or another active agent described herein such as an anti-cancer treatment described herein) which is sufficient to accomplish a stated purpose or otherwise achieve the effect for which it is administered. An effective dose can be sufficient to reduce and/or ameliorate the progression, development, recurrence, severity and/or duration of a given disease, disorder or condition and/or a symptom related thereto. An effective dose can be a "therapeutically effective dose" which refers to an amount sufficient to provide a therapeutic benefit such as, for example, the reduction or amelioration of the advancement or progression of a given disease, disorder or condition, reduction or amelioration of the recurrence, development or onset of a given disease, disorder or condition, and/or to improve or enhance the prophylactic or therapeutic effect(s) of another therapy. A therapeutically effective amount of a composition described herein can also enhance the therapeutic efficacy of another therapeutic agent.

The terms "therapies," "therapy" and/or "treatment" refer to any protocol(s), method(s), and/or agent(s) that can be used in the prevention, treatment, management, and/or amelioration of a disease, disorder, or condition or one or more symptoms thereof. In certain instances the term refers to radioligand therapy (RLT) described herein. The terms "therapy" can refer to anti-viral therapy, anti-bacterial therapy, anti-fungal therapy, anti-cancer therapy, biological therapy, supportive therapy, and/or other therapies useful in treatment, management, prevention, or amelioration of a disease, disorder, or condition or one or more symptoms thereof known to one skilled in the art, for example, a medical professional such as a physician.

The term "cancer" refers to any physiological condition in mammals characterized by unregulated cell growth. Cancers described herein include solid tumors and hematological (blood) cancers, including but not limited to mCRPC. A "hematological cancer" refers to any blood home cancer and includes, for example, myelomas, lymphomas and leukemias. A "solid tumor" or "tumor" refers to a lesion and neoplastic cell growth and proliferation, whether malignant or benign, and all pre-cancerous and cancerous cells and tissues resulting in abnormal tissue growth. "Neoplastic," as used herein, refers to any form of dysregulated or unregulated cell growth, whether malignant or benign, resulting in abnormal tissue growth.

The terms "treating" or "treatment" refer to any indicia of success or amelioration of the progression, severity, and/or duration of a disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; or improving a patient's physical or mental well-being. In the context of treating a cancer or tumor, treating may comprise slowing growth of a tumor, ceasing growth of a tumor, shrinking or decreasing the size of a tumor, preventing a change in shape or morphology of a tumor, preventing the spread of a tumor (e.g., preventing metastases), increasing survivability, and/or decreasing mortality.

The term "enhance" refers to an increase or improvement in the function or activity of a protein or cell or improve the overall wellbeing of a patient after administration of the "treatment" or "therapy" described herein compared to the protein or cell prior to such administration or contact.

The term "administering" refers to the act of delivering a pharmaceutical composition or a radiopharmaceutical composition described herein into a subject by parenteral routes including intravenous, intramuscular, intra-arterial, intradermal, subcutaneous, intraperitoneal, intraventricular, and intracranial administration. Administration generally occurs after the onset of the disease, disorder, or condition, or its symptoms but, in certain instances, can occur before the onset of the disease, disorder, or condition, or its symptoms (e.g., administration for patients prone to such a disease, disorder, or condition). In some embodiments, "intravenous infusion" is interchangeably used with "injection."

II. Introduction

The present disclosure is directed to methods comprising administering a radiopharmaceutical composition comprising $^{177}$Lu-PSMA I&T to a human patient in need thereof, wherein the $^{177}$Lu has a low total absorbed radioactive dose in the human patient's organs. What is a low absorbed radioactive dose (total, fractional, or organ-specific) may be determined by one of skill in the art and relative to other compositions in the prior art, as well as what is objectively determined by SPECT imaging and/or planar imaging. For example, the methods for administering $^{177}$Lu-PSMA I&T as described herein may in some embodiments be described as a mathematical formula to ensure that the total cumulative dose to the patient's kidneys after all treatments remains below 23 Gy. By providing improvements to safety and reduction in total absorbed radioactive doses, the methods of the present invention may allow for more treatment cycles of the human patient (e.g., while staying below the 23 Gy limit). Further, this low absorbed dose prevents side effects associated with radiopharmaceutical use when the radiopharmaceutical composition is absorbed by the human patient's organs rather than the target of the composition, such as a malignant tumor. In some embodiments, the composition may be formulated as a radiopharmaceutical solution for injection. The present disclosure further relates to a high-energy, high purity, and/or low toxicity radiopharmaceutical composition comprising $^{177}$Lu-PSMA I&T that performs as an anti-tumor agent for targeted radionuclide therapy.

The present disclosure is also directed to methods of making the radiopharmaceutical composition.

The present disclosure further relates to the properties of the radiopharmaceutical composition and methods of use of the radiopharmaceutical composition.

$^{177}$Lu-PSMA I&T is also known by its synonyms as follows: [$^{177}$Lu]Lutetium-PSMA I&T, $^{177}$Lu-ITG-PSMA-1, PSMA-TUM3, $^{177}$Lu-DOTAGA-(I-y)fk(Sub-KuE) or $^{177}$Lu-(3S,7S)-29-benzyl-32 (3-iodo, 4-hydroxy)-benzyl-5, 12,20,28,31,34-hexaoxo-37-(4,7,10-tris(carboxymethyl)-1, 4,7,10-tetraazacyclododecan-1-yl)-4,6,12,21,27,30,33-heptaazaheptatriacontane-1,3,7,26,37-pentacarboxylic acid. The molecular formula of the unlabeled precursor is $C_{63}H_{92}IN_{11}O_{23}$·4TFA·3 $H_2O$ with a relative molecular mass of 1498 g/mol.

The labelled substance $^{177}$Lu-PSMA I&T may be labelled with non-carrier-added Lutetium-177 ($T_{1/2}$=6.6d) solution. $^{177}$Lu-PSMA I&T is a short-lived radiolabeled substance from which the product is formulated immediately after finished synthesis. Controls are performed on the labelled drug product. In other embodiments, the $^{177}$Lu-PSMA I&T may be labelled with carrier added or non-carrier-added Lutetium-177.

The synthetized $^{177}$Lu-PSMA I&T solution may be suitable for administration to a human patient in need thereof. The synthetized $^{177}$Lu-PSMA I&T solution may be formulated in an injections grade water solution containing stabilizing agents such as ascorbic acid. The solution may be sterilized by aseptic filtration through a 0.22 μm filter prior to dispensing in multidose vials. Administration of the formulated solution may be within 72 h of the end of the synthesis after quality control and release of the drug product by a Qualified Person. Administration of the formulated solution may be via injection to a human patient in need thereof within 72 h of the end of the synthesis after quality control and release of the drug product by a Qualified Person. Alternatively, administration of the formulated solution may be via injection to a human patient in need thereof within at least 1 week, at least 2 weeks, at least 3 weeks, at least 3.5 weeks, or at least 4 weeks after synthesis after quality control and release of the drug product by a Qualified Person. In such a manner, the compositions as described herein may be stable and suitable for administration to a human patient in need thereof for at least 1 day, 2 days, 3 days, 4 days, 5 days, 6 days, 7 days, 1 week, 1.5 weeks, 2 weeks, 2.5 weeks, 3 weeks, 3.5 weeks, and/or 4.0 weeks. Stable and suitable for administration to a human patient in need thereof may comprise a radiochemical purity of at least 95%, 95.5% or greater, 96.5% or greater, 97.0% or greater, 97.5% or greater, 98.0% or greater, 98.5% or greater, 99.0% or greater, or 99.5% or greater at administration.

Ascorbic acid may be employed to minimize radiolysis of radiolabeled preparations. In addition to ascorbic acid, dose formulation pH of 6.0, 5.5, 5.0 or below may stabilize the labelled product against radiolytic decomposition and enhancing it shelf life. Thus, in another aspect, the present disclosure further provides a dose formulation containing ascorbic acid at pH of 6, 5.5, 5 or below that improves stability of the radiopharmaceutical composition against radiolytic decomposition, thus improving the shelf life of the composition.

The stability enhancing conditions may be applied as early as possible in the manufacturing process. For example, ascorbic acid solutions at pH 6.0, 5.5, 5.0 or below (e.g., pH of 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.3, 3.2, 3.1, or 3.0) may be used instead of water in the purification steps of the labelled $^{177}$Lu-PSMA I&T to minimize radiolytic damage.

The composition, when administered to a subject, may result in low hematotoxicity, hepatotoxicity, and/or nephrotoxicity profiles, providing better effects and fewer adverse effects than monoclonal antibody treatments and other comparable third-line treatments.

The composition is an improved composition in that it has a shelf life of more than 72 hours after formulation. Additionally, the improved composition has a radiochemical purity of greater than 95% at administration. That is, the improved formulation maintains a high level of radiochemical purity more than 72 hours after formulation. Therefore, the improved formulation is suitable for administration up to 24 or up to 72 hours longer than other compositions comprising $^{177}$Lu-PSMA I&T.

III. Compositions

Disclosed herein inter alia is a composition that includes $^{177}$Lu, PSMA I&T and one or more optional agents including buffering agents and/or solvents. In one embodiment, the composition is suitable for administration to a human patient in need thereof.

In one embodiment, the composition has a radiochemical purity (RCP) of 95% or greater at administration. In another embodiment, the composition has a radiochemical purity (RCP) of 97% or greater at administration. In another embodiment, the composition has a radiochemical purity (RCP) of 97.5% or greater at administration. In another embodiment, the composition has a radiochemical purity (RCP) of 98.0% or greater, 98.5% or greater, 99.0% or greater, or 99.5% or greater at administration.

In one embodiment, the composition has a radiochemical purity (RCP) of 95% or greater at 72 hours after production. In another embodiment, the composition has a radiochemical purity (RCP) of 97% or greater at 72 hours after production. In another embodiment, the composition has a radiochemical purity (RCP) of 97.5% or greater at 72 hours after production. In another embodiment, the composition has a radiochemical purity (RCP) of 98.0% or greater, 98.5% or greater, 99.0% or greater, or 99.5% or greater at 72 hours after production. In another embodiment, the composition has a radiochemical purity (RCP) of 90% or greater, 91% or greater, 92% or greater, 93% or greater, 94% or greater, 95% or greater at 7 days after production.

In one embodiment, the composition has a radiochemical purity (RCP) of 96.0% or greater, 96.5% or greater, 97.0% or greater, 97.5% or greater, 98.0% or greater, 98.5% or greater, 99.0% or greater, or 99.5% or greater at 7 days after production.

In one embodiment, the composition is produced as part of a 4 Ci to 10 Ci batch scale. In another embodiment, the composition is produced as part of a 4 Ci to 15 Ci batch scale. In another embodiment, the composition is produced as part of a 20 Ci to 32 Ci batch scale. In still another embodiment, the composition is produced as part of a 32 Ci to 64 Ci batch scale.

Further disclosed herein is a radiopharmaceutical composition or formulation that includes a dose of $^{177}$Lu-PSMA I&T and at least one of a stabilizing agent, an antioxidant, a pH adjuster, a metal ion chelator, water, or a combination thereof.

In one specific embodiment, the stabilizing agent is ethanol. In another embodiment the antioxidant may be ethanol, ascorbic acid, gentisic acid, or a combination thereof. In another embodiment, the pH adjuster includes but is not limited to sodium hydroxide, sodium bicarbonate, hydrochloric acid, or combinations thereof. In yet another embodiment, the chelator may be EDTA or DTPA. In another specific embodiment, the stabilizing agent comprises no ethanol (i.e., 0% ethanol, less than 0.5% ethanol, or less than 1.0% ethanol (w/w) in the composition).

In one embodiment, the medicinal product or radiopharmaceutical composition (or formulation) may be a sterile filtered radiopharmaceutical solution containing a dose of $^{177}$Lu-PSMA I&T in an aqueous ascorbic acid solution containing ethanol. For example, the total amount of ascorbic acid in the solution may be about 25 to about 65 mg/ml and the total amount of ethanol in the solution may be about 3.8% (v/v) to about 7.5% (v/v). In some embodiments, the total amount of ascorbic acid in the solution is from about 21 mg/mL to about 42.5 mg/mL. The $^{177}$Lu-PSMA I&T is present in sufficient amounts of radioactivity for intended use. Experiments performed with various dose formulations suggests that $^{177}$Lu-PSMA I&T formulation composition containing about 31 mg/ml of ascorbic acid at pH of about 4.5 and radioactivity concentration of about 640 MBq/ml or below may provide adequate radiochemical stability of four days. The adequate radiochemical stability referred herein is a radiopharmaceutical composition where the radiochemical purity of the $^{177}$Lu-PSMA I&T is at least 95%, 95.5% or greater, 96.5% or greater, 97.0% or greater, 97.5% or greater, 98.0% or greater, 98.5% or greater, 99.0% or greater, or 99.5% or greater at administration.

In one embodiment, the radiopharmaceutical composition is a sterile filtered radiopharmaceutical solution containing a dose of [$^{177}$Lu]Lu-PSMA I&T in an aqueous ascorbic acid and ethanol solution. In another embodiment, the radiopharmaceutical composition is a sterile filtered radiopharmaceutical solution containing a dose of [$^{177}$Lu]Lu-PSMA I&T in an aqueous ascorbic acid without ethanol solution. For example, the radiopharmaceutical composition may be a sterile filtered radiopharmaceutical solution containing a micro dose of [$^{177}$Lu]Lu PSMA I&T in an aqueous ascorbic acid and acetate buffer comprising DTPA (e.g., comprising ethanol or in the complete absence of ethanol). The product is diluted to a standard radioactivity concentration and therefore the final volume of the bulk product varies depending on the starting radioactivity of $^{177}$Lu introduced.

One aspect of the disclosure provides for a radiopharmaceutical composition with a pH from about 3 to about 9, from about 4 to about 9, from about 5 to about 9, from about 3 to about 8, from about 4 to about 8, from about 3 to about 5, or from about 5 to about 8. The pH of the radiopharmaceutical composition may be about 3.0, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, or about 9.

Having a pH of 6.0 or below may stabilize the radiopharmaceutical composition against radiolytic decomposition and may enhance its shelf life.

In one embodiment, the pH of the radiopharmaceutical composition is from about 3 to about 5. This pH range may stabilize the radiopharmaceutical composition against radiolytic decomposition and may enhance its shelf life. In yet another embodiment, a radiopharmaceutical composition comprising ascorbic acid and having a pH from about 3 to about 5 has improved stability and extended shelf life compared to known radiopharmaceutical compositions of $^{177}$Lu-PSMA I&T which have higher pH values and may comprise gentisic acid. In other embodiments, the radiopharmaceutical composition may comprise an absence of gentisic acid (i.e., no gentisic acid).

The pH of the radiopharmaceutical composition may range from 3.0 to 6.0, 3.0 to 3.5, 3.0 to 3.05, 3.05 to 3.1, 3.0 to 3.1, 3.1 to 3.15, 3.1 to 3.2, 3.15 to 3.2, 3.2 to 3.25, 3.0 to 3.25, 3.2 to 3.3, 3.25 to 3.3, 3.3 to 3.35, 3.3 to 3.4, 3.35 to 3.4, 3.4 to 3.45, 3.4 to 3.5, 3.45 to 3.5, 3.25 to 3.5, 3.5 to 3.55, 3.5 to 3.6, 3.55 to 3.6, 3.6 to 3.65, 3.6 to 3.7, 3.65 to 3.7, 3.7 to 3.75, 3.5 to 3.75, 3.7 to 3.8, 3.75 to 3.8, 3.8 to 3.85, 3.8 to 3.9, 3.85 to 3.9, 3.9 to 3.95, 3.9 to 4.0, 3.95 to 4.0, 3.5 to 4.0, 3.75 to 4.0, 4.0 to 4.05, 4.0 to 4.1, 4.05 to 4.1, 4.1 to 4.15, 4.1 to 4.2, 4.15 to 4.2, 3.5 to 4.2, 4.2 to 4.25, 4.0 to 4.25, 4.2 to 4.3, 4.25 to 4.3, 4.3 to 4.35, 4.3 to 4.4, 4.35 to 4.4, 4.4 to 4.45, 4.4 to 4.5, 4.45 to 4.5, 4.25 to 4.5, 4.0 to 4.5, 4.5 to 4.55, 4.5 to 4.6, 4.55 to 4.6, 4.6 to 4.65, 4.6 to 4.7, 4.65 to 4.7, 4.7 to 4.75, 4.7 to 4.8, 4.75 to 4.8, 4.8 to 4.85, 4.8 to 4.9, 4.85 to 4.9, 4.9 to 4.95, 4.9 to 5.0, 4.95 to 5.0, 4.5 to 5.0, 4.75 to 5.0, 5.0 to 5.1, 5.05 to 5.1, 5.1 to 5.15, 5.1 to 5.2, 5.15 to 5.2, 5.2 to 5.25, 5.0 to 5.25, 5.2 to 5.3, 5.25 to 5.3, 5.3 to 5.35, 5.3 to 5.4, 5.35 to 5.4, 5.4 to 5.45, 5.4 to 5.5, 5.45 to 5.5, 5.25 to 5.5, 5.0 to 5.5, 5.5 to 5.55, 5.5 to 5.6, 5.55 to 5.6, 5.6 to 5.65, 5.6 to 5.7, 5.65 to 5.7, 5.7 to 5.75, 5.7 to 5.8, 5.75 to 5.8, 5.8 to 5.85, 5.8 to 5.9, 5.85 to 5.9, 5.9 to 5.95, 5.9 to 6.0, 5.95 to 6.0, 5.5 to 6.0, or 5.75 to 6.0. In some examples, the pH of the radiopharmaceutical composition may be adjusted to a final pH of 3.0, 3.5, 4.0, 4.5, 5.0, 5.5, or 6.0. In some embodiments, including the above listed pH numbers and ranges, the pH values are inclusive of ±0.05, ±0.10, ±0.15, ±0.20, or ±0.25.

In another embodiment, the radiopharmaceutical composition or formulation has a radiochemical purity of at least about 90%, at least about 95%, or at least about 99%. In another embodiment, the radiopharmaceutical composition or formulation has a purity of about 90%, about 91%, about 92%, about 93%, about 94%, about 95%, about 96%, about 97%, about 98%, about 99%, or about 99.5%.

Figure 5:
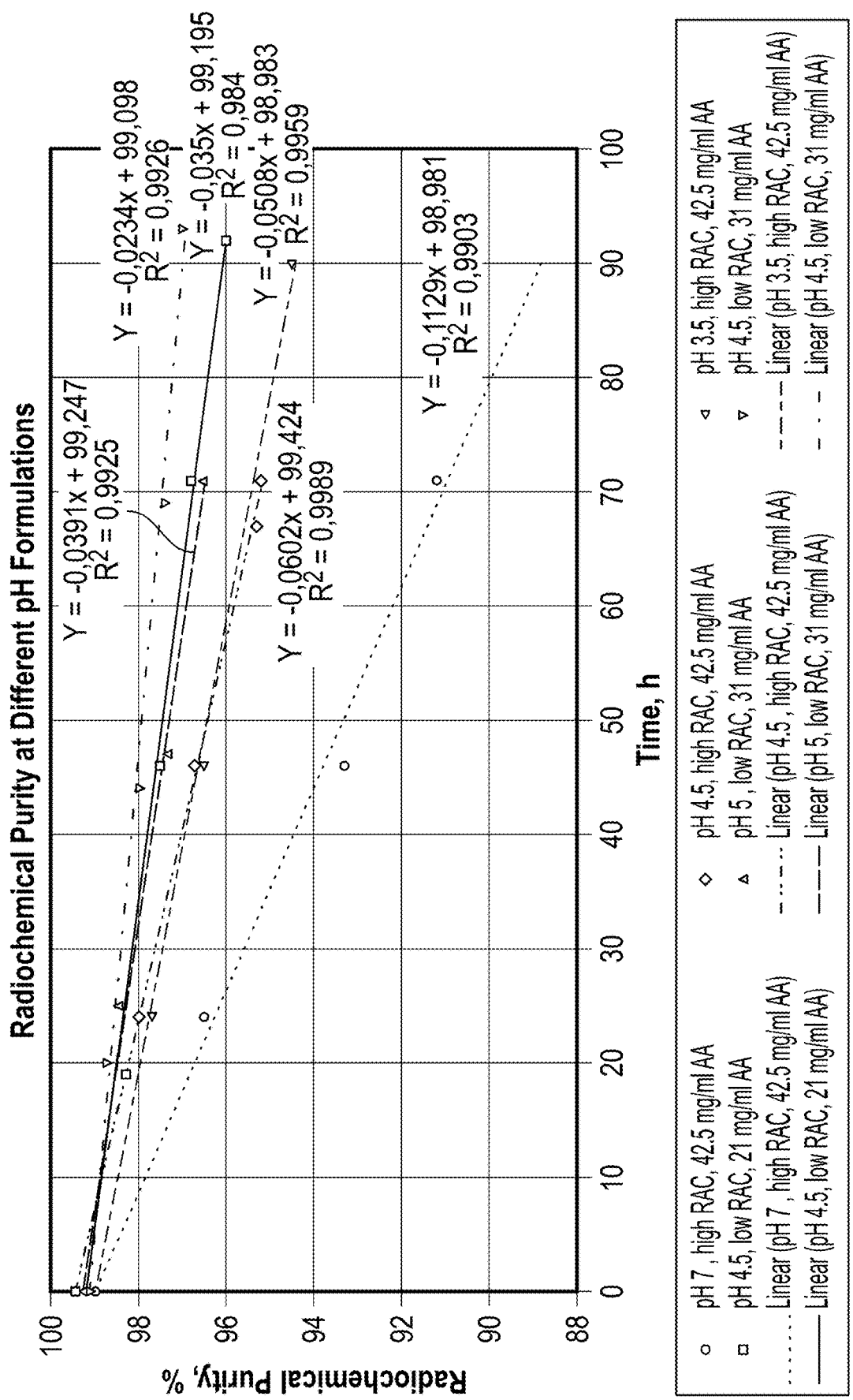
FIG. 5 shows $^{177}$Lu-PSMA I&T radiochemical purity measured by HPLC at different time points.

In another embodiment, radiopharmaceutical composition or formulation has a radiochemical purity of at least about 90%, at least about 95%, or at least about 99% as measured by HPLC, TLC, or liquid chromatography. In another embodiment, the radiopharmaceutical composition or formulation has a purity of at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, or at least about 99.5% as measured by HPLC, TLC, or liquid chromatography. In some examples, the radiopharmaceutical composition may have a radiochemical purity of 95.0% or greater, 95.5% or greater, 96.0% or greater, 96.5% or greater, 97.0% or greater, 97.5% or greater, 98.0% or greater, 98.5% or greater, 99.0% or greater, or 99.5% or greater at administration. FIG. 5 shows the radiochemical purity at different pH formulations.

In another embodiment, the radiochemical purity of the radiopharmaceutical composition or formulation is measured by HPLC, TLC, or liquid chromatography at any time post end of synthesis (EOS). In one embodiment, the purity of the radiopharmaceutical composition or formulation is measured by HPLC, TLC, or liquid chromatography at about 0 hour, about 10 hours, about 20 hours, about 30 hours, about 40 hours, about 50 hours, about 50 hours, about 60 hours, about 70 hours, about 80 hours, about 90 hours, about 100 hours post EOS.

In one specific embodiment, the radiopharmaceutical composition or formulation has a radiochemical purity of at least about 99% as measured by HPLC, TLC, or liquid chromatography 0 hours post EOS. In another specific embodiment, the radiopharmaceutical composition or formulation has a purity of at least about 96.5% as measured by HPLC, TLC, or liquid chromatography 24 hours post EOS, at least about 93% as measured by HPLC, TLC, or liquid chromatography 46 hours post EOS, at least about 95% as measured by HPLC, TLC, or liquid chromatography 67 hours post EOS, at least about 96% as measured by HPLC, TLC, or liquid chromatography 92 hours post EOS.

In another embodiment, the radioactivity is measured in a dose calibrator. The radioactive amount of [$^{177}$Lu]Lu-PSMA I&T is determined when the dose is dispensed.

In yet another embodiment, the radiochemical purity of $^{177}$Lu-PSMA I&T is determined by liquid chromatography with radioactivity detection and thin layer chromatography.

In one embodiment, bacterial endotoxin content is determined for each batch before release using a PTS-tester (Ph Eur method D) and sterility is determined according to Ph Eur.

In one embodiment, the radiopharmaceutical composition or formulation is stored at a temperature from about +5° C. to +40° C., about +10° C. to +35° C. or about +20° C. to +30° C. In one specific embodiment, the radiopharmaceutical composition or formulation is stored at a temperature at about +10° C., about +15° C., about +22° C., about +22.5° C., about +25° C., or at room temperature.

Another aspect of the disclosure provides for a radioactive content of about 70% to 130% of the target administered dose. The radioactive content of the radiopharmaceutical composition may be about 70% to 125%, 70% to 120%, 70% to 115%, 70% to 110%, 80% to 130%, 85% to 130%, 90% to 130%, 95% to 130%, 75% to 125%, 75% to 120%, 75% to 115%, 75% to 110%, 80% to 125%, 80% to 120%, 80% to 115%, 80% to 110%, 85% to 125%, 85% to 120%, 85% to 115%, 85% to 110%, 90% to 125%, 90% to 120%, 90% to 115%, or 90% to 110%.

In one specific embodiment, the radioactive content of the formulation is about 70%, about 75%, about 80%, about 85%, about 90%, about 95%, about 100%, about 105%, about 110%, about 115%, about 120%, about 125%, or about 130% of the target administered dose.

Another aspect of the disclosure provides for a radiopharmaceutical composition with a mean whole-body effective dose of about 23±20 Gy (3.3 Gy/GBq), with a mean absorbed organ doses of about 26±20 Gy (3.4 Gy/GBq), 24±16 Gy (3.2 Gy/GBq), 8.5±4.7 Gy (1.28 Gy/GBq), and 13±7.4 Gy (1.7 Gy/GBq) for the bone, lymph node, liver, and lung metastases, respectively.

In some embodiments, the radiopharmaceutical composition at the end of formulation may have a low radioactivity concentration ("low RAC") of about 563 MBq/ml to about 734 MBq/ml. For example, the radiopharmaceutical composition may have a low radioactivity that may be about 11,580 MBq (313 mCi), about 11,770 MBq (318 mCi), or about 12,520 MBq (338 mCi) in a 15 to 20 ml volume of the solution. In other embodiments the radiopharmaceutical composition may have a low radioactivity concentration of at least about 550 MBq/ml, at least about 560 MBq/ml, at least about 570 MBq/ml, at least about 580 MBq/ml, at least about 590 MBq/ml, at least about 600 MBq/ml, at least about 610 MBq/ml, at least about 620 MBq/ml, at least about 630 MBq/ml, at least about 640 MBq/ml, at least about 650 MBq/ml, at least about 660 MBq/mL, at least about 670 MBq/mL, at least about 680 MBq/mL, at least about 690 MBq/mL, at least about 700 MBq/mL, at least about 710 MBq/mL, at least about 720 MBq/mL, at least about 730 MBq/mL, at least about 740 MBq/mL, or at least about 750 MBq/mL. In still other embodiments the radiopharmaceutical composition may have a low radioactivity concentration from about 550 MBq/ml to about 575 MBq/ml, from about 575 MBq/ml to about 600 MBq/ml, from about 600 MBq/ml to about 625 MBq/ml, from about 625 MBq/ml to about 650 from about 650 MBq/ml to about 675 MBq/ml, from about 675 MBq/ml to about 700 MBq/ml, from about 700 MBq/ml to about 725 MBq/ml, from about 725 MBq/ml to about 750 MBq/ml . . .

In additional embodiments, the radiopharmaceutical composition at end of formulation may have a high radioactivity concentration ("High RAC") of about 1,270 MBq/ml to about 1,311 MBq/ml. For example, the radiopharmaceutical composition may have a high radioactivity that may be about 12,780 MBq (345 mCi), about 12,810 MBq (346 mCi), or about 13,110 MBq (354 mCi) in a 10 ml volume of the solution. In other embodiments the radiopharmaceutical composition may have a high radioactivity concentration of at least about 1,100 MBq/ml, at least about 1,110 MBq/ml, at least about 1,120 MBq/ml, at least about 1,130 MBq/ml, at least about 1,140 MBq/ml, at least about 1,150 MBq/ml, at least about 1,160 MBq/ml, at least about 1,170 MBq/ml, at least about 1,180 MBq/ml, at least about 1,190 MBq/ml, at least about 1,200 MBq/ml, 1,200 MBq/ml, at least about 1,210 MBq/ml, at least about 1,220 MBq/ml, at least about 1,230 MBq/ml, at least about 1,240 MBq/ml, at least about 1,250 MBq/ml, at least about 1,260 MBq/ml, at least about 1,270 MBq/ml, at least about 1,280 MBq/ml, at least about 1,290 MBq/ml, at least about 1,300 MBq/ml, at least about 1,310 MBq/ml, at least about 1,320 MBq/ml, at least about 1,330 MBq/ml, at least about 1,340 MBq/ml, or at least about 1,350 MBq/ml. In still other embodiments the radiopharmaceutical composition may have a high radioactivity concentration from about 1,000 MBq/ml to about 1,400 MBq/ml, from about 1,050 MBq/ml to about 1,350 MBq/ml, from about 1,100 MBq/ml to about 1,300 MBq/ml, from about 1,150 MBq/ml to about 1,250 MBq/ml, from about 1,200 MBq/ml to about 1,300 MBq/ml, from about 1,250 MBq/ml to about 1,350 MBq/ml, or from about 1,250 MBq/ml to about 1,300 MBq/ml.

(i) [$^{177}$Lu]Lu-PSMA I&T

The total amount of [$^{177}$Lu]Lu-PSMA I&T present in the radiopharmaceutical composition can and will vary. FIGS. 1A and 1B show the chemical structure of precursor PSMA I&T and $^{177}$Lu-PSMA I&T respectively.

In one embodiment, the mass of radioactive pharmaceutical ingredient ([$^{177}$Lu]Lu-PSMA I&T) in the drug product is less than about 40 µg, less than about 35 µg, less than about 30 µg, less than about 25 µg, less than about 20 µg, less than about 15 µg, or less than about 10 µg per vial. In yet another embodiment, the mass of radioactive pharmaceutical ingredient ([$^{177}$Lu]Lu-PSMA I&T) in the drug product is about 1 µg, about 2 µg, about 3 µg, about 4 µg, about 5 µg, about 6 µg, about 7 µg, about 8 µg, about 9 µg, or about 10 µg, about 11 µg, about 12 µg about, about 13 µg, about 14 µg, about 15 µg, about 16 µg, about 17 µg, about 18 µg, about 17.2 µg, about 18 µgm about 19 µg, about 20 µg, about 21 µg, about 22 µg, about 23 µg, about 24 µg, about 25 µg, about 26 µg, about 27 µg, about 28 µg, about 29 µg, about 30 µg, about 31 µg, about 32 µg, about 33 µg, about 34 µg, about 35 µg, about 36 µg, about 37 µg, about 38 µg, about 39 µg, or about 40 µg of [$^{177}$Lu]Lu-PSMA I&T per vial.

In one embodiment, the total amount of [$^{177}$Lu]Lu-PSMA I&T present in the pharmaceutical composition can and will vary. In the labeling process, the PSMA I&T ligand may be labeled with trace metals that are present to form a chelated trace metal-PSMA I&T complex (i.e., "M-PSMA I&T"). Excess PSMA I&T present in the labeling process may remain unlabeled with either $^{177}$Lu or trace metals. The amount of M-PSMA I&T and unlabeled PSMA I&T in the composition is hereinafter referred to as "related substances" or "RS". The composition may then contain both [$^{177}$Lu]Lu-PSMA I&T, M-PSMA I&T as well as unlabeled PSMA I&T. In an embodiment, the PSMA content comprising PSMA I&T and related substances (RS) is 250 µg/dose±15%, ±10%, or ±5%. In another embodiment, the PSMA I&T content is 120 µg/dose±15%, ±10%, or ±5% to about 250 µg/dose±15%, ±10%, or ±5%. In another embodiment, the PSMA I&T content is 120 µg/dose±15%, ±10%, or ±5% to about 200 µg/dose±15%, ±10%, or ±5%. In another embodiment, the PSMA I&T content is about 100 µg/dose±15%, ±10%, or ±5% to about 120 µg/dose±15%, ±10%, or ±5%. In yet another embodiment, the PSMA I&T content is about 40 µg/dose±15%, ±10%, or ±5% to about 100 µg/dose±15%, ±10%, or ±5%, 50 µg/dose±15%, ±10%, or ±5% to about 100 µg/dose±15%, ±10%, or ±5%, 60

μg/dose±15%, ±10%, or ±5% to about 100 μg/dose±15%, ±10%, or ±5%, or 70 μg/dose±15%, ±10%, or ±5% to about 100 μg/dose±15%, ±10%, or ±5%. In yet another embodiment, the PSMA I&T content is about 40 μg/dose±15%, ±10%, or ±5% to about 90 μg/dose±15%, ±10%, or ±5%, 50 μg/dose±15%, ±10%, or ±5% to about 90 μg/dose±15%, ±10%, or ±5%, 60 μg/dose±15%, ±10%, or ±5% to about 90 μg/dose±15%, ±10%, or ±5%, or 70 μg/dose±15%, ±10%, or ±5% to about 90 μg/dose±15%, ±10%, or ±5%. In yet another embodiment, the PSMA I&T content is about 40 μg/dose±15%, ±10%, or ±5% to about 80 μg/dose±15%, ±10%, or ±5%, 50 μg/dose±15%, ±10%, or ±5% to about 80 μg/dose±15%, ±10%, or ±5%, 60 μg/dose±15%, ±10%, or ±5% to about 80 μg/dose±15%, ±10%, or ±5%, or 70 μg/dose±15%, ±10%, or ±5% to about 80 μg/dose±15%, ±10%, or ±5%.

In another embodiment, the compositions comprising [$^{177}$Lu]Lu-PSMA I&T described herein may comprise a PSMA I&T content that is about 120 μg/dose to about 250 μg/dose, about 130 μg/dose to about 250 μg/dose, about 140 μg/dose to about 250 μg/dose, about 150 μg/dose to about 250 μg/dose, about 160 μg/dose to about 250 μg/dose, about 170 μg/dose to about 250 μg/dose, about 180 μg/dose to about 250 μg/dose, about 190 μg/dose to about 250 μg/dose, about 200 μg/dose to about 250 μg/dose, about 210 μg/dose to about 250 μg/dose, about 220 μg/dose to about 250 μg/dose, about 230 μg/dose to about 250 μg/dose, or about 240 μg/dose to about 250 μg/dose. In another embodiment, the compositions comprising [$^{177}$Lu]Lu-PSMA I&T described herein may comprise a PSMA I&T content that is about 100 μg/dose to about 120 μg/dose, about 105 μg/dose to about 120 μg/dose, about 110 μg/dose to about 120 μg/dose, or about 115 μg/dose to about 120 μg/dose. In another embodiment, the compositions comprising [$^{177}$Lu]Lu-PSMA I&T described herein may comprise a PSMA I&T content that is about 30 μg/dose to about 100 μg/dose, about 35 μg/dose to about 100 μg/dose, about 40 μg/dose to about 100 μg/dose, about 45 μg/dose to about 100 μg/dose, about 50 μg/dose to about 100 μg/dose, about 55 μg/dose to about 100 μg/dose, about 60 μg/dose to about 100 μg/dose, about 65 μg/dose to about 100 μg/dose, about 70 μg/dose to about 100 μg/dose, about 75 μg/dose to about 100 μg/dose, about 80 μg/dose to about 100 μg/dose, about 85 μg/dose to about 100 μg/dose, about 90 μg/dose to about 100 μg/dose, or about 95 μg/dose to about 100 μg/dose. In another embodiment, the compositions comprising [$^{177}$Lu]Lu-PSMA I&T described herein may comprise a PSMA I&T content that is about 45 μg/dose to about 95 μg/dose, 50 μg/dose to about 100 μg/dose, 55 μg/dose to about 95 μg/dose, 60 μg/dose to about 95 μg/dose, 65 μg/dose to about 95 μg/dose, 70 μg/dose to about 95 μg/dose, 75 μg/dose to about 95 μg/dose, 80 μg/dose to about 95 μg/dose, 85 μg/dose to about 95 μg/dose, or about 90 μg/dose to about 95 μg/dose. In another embodiment, the compositions comprising [$^{177}$Lu]Lu-PSMA I&T described herein may comprise a PSMA I&T content that is about 40 μg/dose to about 90 μg/dose, about 45 μg/dose to about 90 μg/dose, about 50 μg/dose to about 90 μg/dose, about 55 μg/dose to about 90 μg/dose, about 60 μg/dose to about 90 μg/dose, about 65 μg/dose to about 90 μg/dose, about 70 μg/dose to about 90 μg/dose, about 75 μg/dose to about 90 μg/dose, about 80 μg/dose to about 90 μg/dose, or about 85 μg/dose to about 90 μg/dose. In another embodiment, the compositions comprising [$^{177}$Lu]Lu-PSMA I&T described herein may comprise a PSMA I&T content that is about 40 μg/dose to about 85 μg/dose, about 45 μg/dose to about 85 μg/dose, about 50 μg/dose to about 85 μg/dose, about 55 μg/dose to about 85 μg/dose, about 60 μg/dose to about 85 μg/dose, about 65 μg/dose to about 85 μg/dose, about 70 μg/dose to about 85 μg/dose, about 75 μg/dose to about 85 μg/dose, or about 80 μg/dose to about 85 μg/dose. In another embodiment, the compositions comprising [$^{177}$Lu]Lu-PSMA I&T described herein may comprise a PSMA I&T content that is about 40 μg/dose to about 80 μg/dose, about 45 μg/dose to about 80 μg/dose, about 50 μg/dose to about 80 μg/dose, about 55 μg/dose to about 80 μg/dose, about 60 μg/dose to about 80 μg/dose, about 65 μg/dose to about 80 μg/dose, about 70 μg/dose to about 80 μg/dose, or about 75 μg/dose to about 80 μg/dose. In another embodiment, the compositions comprising [$^{177}$Lu]Lu-PSMA I&T described herein may comprise a PSMA I&T content that is about 40 μg/dose to about 75 μg/dose, about 45 μg/dose to about 75 μg/dose, about 50 μg/dose to about 75 μg/dose, about 55 μg/dose to about 75 μg/dose, about 60 μg/dose to about 75 μg/dose, about 65 μg/dose to about 75 μg/dose, about 70 μg/dose to about 75 μg/dose.

In one embodiment, the [$^{177}$Lu]Lu-PSMA I&T amount present in the pharmaceutical composition is about 30 μg to 120 μg per vial, 35 μg to 120 μg per vial, 40 μg to 120 μg per vial, 45 μg to 120 μg per vial, 50 μg to 120 μg per vial, 55 μg to 120 μg per vial, 60 μg to 120 μg per vial, 65 μg to 120 μg per vial, 70 μg to 120 μg per vial, 75 μg to 120 μg per vial, 85 μg to 120 μg per vial, 90 μg to 120 μg per vial, 95 μg to 120 μg per vial, 100 μg to 120 μg per vial, 105 μg to 120 μg per vial, 110 μg to 120 μg per vial, or 115 μg to 120 μg per vial. In one embodiment, the PSMA I&T amount present in the pharmaceutical composition is about 30 μg to 100 μg per vial, 35 μg to 100 μg per vial, 40 μg to 100 μg per vial, 45 μg to 100 μg per vial, 50 μg to 100 μg per vial, 55 μg to 100 μg per vial, 60 μg to 100 μg per vial, 65 μg to 100 μg per vial, 70 μg to 100 μg per vial, 75 μg to 100 μg per vial, 85 μg to 100 μg per vial, or 90 μg to 100 μg per vial. In another embodiment, the PSMA I&T amount present in the pharmaceutical composition is about 30 μg to 90 μg per vial, 35 μg to 90 μg per vial, 40 μg to 90 μg per vial, 45 μg to 90 μg per vial, 50 μg to 90 μg per vial, 55 μg to 90 μg per vial, 60 μg to 90 μg per vial, 65 μg to 90 μg per vial, 70 μg to 90 μg per vial, 75 μg to 90 μg per vial, or 85 μg to 90 μg per vial. In another embodiment, the PSMA I&T amount present in the pharmaceutical composition is about 30 μg to 80 μg per vial, 35 μg to 80 μg per vial, 40 μg to 80 μg per vial, 45 μg to 80 μg per vial, 50 μg to 80 μg per vial, 55 μg to 80 μg per vial, 60 μg to 80 μg per vial, 65 μg to 80 μg per vial, 70 μg to 80 μg per vial, or 75 μg to 80 μg per vial. In yet another embodiment, the PSMA I&T amount present in the pharmaceutical composition is about 30 μg to 70 μg per vial, 35 μg to 70 μg per vial, 40 μg to 70 μg per vial, 45 μg to 70 μg per vial, 50 μg to 70 μg per vial, 55 μg to 70 μg per vial, 60 μg to 70 μg per vial, or 65 μg to 70 μg per vial.

In one embodiment, the [$^{177}$Lu]Lu-PSMA I&T and related substances (RS) amount present in the pharmaceutical composition is about 30 μg to 120 μg per vial, 35 μg to 120 μg per vial, 40 μg to 120 μg per vial, 45 μg to 120 μg per vial, 50 μg to 120 μg per vial, 55 μg to 120 μg per vial, 60 μg to 120 μg per vial, 65 μg to 120 μg per vial, 70 μg to 120 μg per vial, 75 μg to 120 μg per vial, 85 μg to 120 μg per vial, 90 μg to 120 μg per vial, 95 μg to 120 μg per vial, 100 μg to 120 μg per vial, 105 μg to 120 μg per vial, 110 μg to 120 μg per vial, or 115 μg to 120 μg per vial. In one embodiment, the [$^{177}$Lu]Lu-PSMA I&T and related substances (RS) amount present in the pharmaceutical composition is about 30 μg to 100 μg per vial, 35 μg to 100 μg per vial, 40 μg to 100 μg per vial, 45 μg to 100 μg per vial, 50 μg to 100 μg per vial, 55 μg to 100 μg per vial, 60 μg to 100 μg per vial, 65 μg to 100 μg per vial, 70 μg to 100 μg per vial, 75 µg to 100 µg per vial, 85 µg to 100 µg per vial, or 90 µg to 100 µg per vial. In another embodiment the [$^{177}$Lu]Lu-PSMA I&T and related substances (RS) present in the pharmaceutical composition is about 30 µg to 90 µg per vial, 35 µg to 90 µg per vial, 40 µg to 90 µg per vial, 45 µg to 90 µg per vial, 50 µg to 90 µg per vial, 55 µg to 90 µg per vial, 60 µg to 90 µg per vial, 65 µg to 90 µg per vial, 70 µg to 90 µg per vial, 75 µg to 90 µg per vial, or 85 µg to 90 µg per vial. In another embodiment, the [$^{177}$Lu]Lu-PSMA I&T and related substances (RS) amount present in the pharmaceutical composition is about 30 µg to 80 µg per vial, 35 µg to 80 µg per vial, 40 µg to 80 µg per vial, 45 µg to 80 µg per vial, 50 µg to 80 µg per vial, 55 µg to 80 µg per vial, 60 µg to 80 µg per vial, 65 µg to 80 µg per vial, 70 µg to 80 µg per vial, or 75 µg to 80 µg per vial. In yet another embodiment, the [$^{177}$Lu]Lu-PSMA I&T and related substances (RS) amount present in the pharmaceutical composition is about 30 µg to 70 µg per vial, 35 µg to 70 µg per vial, 40 µg to 70 µg per vial, 45 µg to 70 µg per vial, 50 µg to 70 µg per vial, 55 µg to 70 µg per vial, 60 µg to 70 µg per vial, or 65 µg to 70 µg per vial.

In another embodiment, the [$^{177}$Lu]Lu-PSMA I&T and related substances (RS) amount present in the pharmaceutical composition is about 55 µg to 110 µg per vial. In another embodiment, the [$^{177}$Lu]Lu-PSMA I&T and related substances (RS) amount present in the pharmaceutical composition is about 75 µg to 100 µg per vial.

In one embodiment, the [$^{177}$Lu]Lu-PSMA I&T and related substances (RS) amount present in the pharmaceutical composition is about 80 µg to 110 µg per vial. In another embodiment, the [$^{177}$Lu]Lu-PSMA I&T and related substances (RS) amount present in the pharmaceutical composition is about 70 µg to 85 µg per vial. In another embodiment, the [$^{177}$Lu]Lu-PSMA I&T and related substances (RS) amount present in the pharmaceutical composition is about 73 µg to 85 µg per vial. In another embodiment, the [$^{177}$Lu]Lu-PSMA I&T and related substances (RS) amount present in the pharmaceutical composition is about 90 µg to 115 µg per vial. In another embodiment, the [$^{177}$Lu]Lu-PSMA I&T and related substances (RS) amount present in the pharmaceutical composition is about 100 µg to 80 µg per vial.

In one embodiment, the [$^{177}$Lu]Lu-PSMA I&T and related substances (RS) amount present in the pharmaceutical composition is about 110 µg to 80 µg per vial. In another embodiment, the [$^{177}$Lu]Lu-PSMA I&T and related substances (RS) amount present in the pharmaceutical composition is about 115 µg to 125 µg per vial. In another embodiment, the PSMA I&T and related substances (RS) amount present in the pharmaceutical composition is about 115 µg to 130 µg per vial.

In one embodiment, the [$^{177}$Lu]Lu-PSMA I&T and related substances (RS) amount present in the pharmaceutical composition is about 45 µg 50 µg, 57 µg, 60 µg, 70 µg, 75 µg, 80 µg, 85 µg, 99 µg, 100 µg, 115 µg, 80 µg, 125 µg, 130 µg, per vial. In another embodiment, the PSMA I&T and related substances (RS) amount present in the pharmaceutical composition is about 80 µg.

In one embodiment, the [$^{177}$Lu]Lu-PSMA I&T and related substances (RS) amount present in the pharmaceutical composition is about 57 µg. In one embodiment, the PSMA I&T and related substances (RS) amount present in the pharmaceutical composition is about 99 µg.

In one embodiment, the total volume of the vial comprising [$^{177}$Lu]Lu-PSMA I&T and related substances (RS) is about 5 to 30 mL. In another embodiment, the total volume of the vial comprising [$^{177}$Lu]Lu-PSMA I&T and related substances (RS) is about 10 to 20 mL. In another embodiment, the total volume of the vial comprising [$^{177}$Lu]Lu-PSMA I&T and related substances (RS) is about 15 to 20 mL. In another embodiment, the total volume of the vial comprising [$^{177}$Lu]Lu-PSMA I&T and related substances (RS) is about 15 to 17 mL. In another embodiment, the total volume of the vial comprising [$^{177}$Lu]Lu-PSMA I&T and related substances (RS) is about 15 mL.

In one embodiment, the [$^{177}$Lu]Lu-PSMA I&T and related substances (RS) concentration per vial is 3 to 8 µg/mL. In another embodiment, the [$^{177}$Lu]Lu-PSMA I&T and related substances (RS) concentration per vial is 4 to 7 µg/mL. In another embodiment, the [$^{177}$Lu]Lu-PSMA I&T and related substances (RS) concentration per vial is 4.5 to 6.5 µg/mL. In another embodiment, the [$^{177}$Lu]Lu-PSMA I&T and related substances (RS) concentration per vial is 4.8 to 6 µg/mL.

In one embodiment, the [$^{177}$Lu]Lu-PSMA I&T and related substances (RS) concentration per vial is 4 µg/mL. In another embodiment, the [$^{177}$Lu]Lu-PSMA I&T and related substances (RS) concentration per vial is 5 µg/mL. In another embodiment, the [$^{177}$Lu]Lu-PSMA I&T and related substances (RS) concentration per vial is 6 µg/mL. In another embodiment, the [$^{177}$Lu]Lu-PSMA I&T and related substances (RS) concentration per vial is 7 µg/mL. In another embodiment, the [$^{177}$Lu]Lu-PSMA I&T and related substances (RS) concentration per vial is 8 µg/mL.

In one embodiment, the molar ratio of the PSMA I&T to $^{177}$Lu in the composition is from 4.0:1.0 to 12.0:1.0. In another embodiment, the molar ratio of the PSMA I&T to $^{177}$Lu in the composition is from 4.0:1.0 to 12.0:1.0, 4.0:1.0 to 11.5:1.0, 4.0:1.0 to 11.0:1.0, 4.0:1.0 to 10.5:1.0, 4.0:1.0 to 10.0:1.0, 4.0:1.0 to 9.5:1.0, 4.0:1.0 to 9.0:1.0, 4.0:1.0 to 8.5:1.0, 4.0:1.0 to 8.0:1.0, 4.0:1.0 to 7.5:1.0, 4.0:1.0 to 7.0:1.0, 4.0:1.0 to 6.5:1.0, or 4.0:1.0 to 6.0:1.0.

In one embodiment, the molar ratio of the PSMA I&T to $^{177}$Lu in the composition is from 11.0:1.0 to 12.0:1.0, 11.1:1.0 to 11.9:1.0, 11.2:1.0 to 11.8:1.0, 11.3:1.0 to 11.7:1.0, or 11.4:1.0 to 11.6:1.0. In another embodiment, the molar ratio of the PSMA I&T to $^{177}$Lu in the composition is from 10.0:1.0 to 11.0:1.0, 10.1:1.0 to 10.9:1.0, 10.2:1.0 to 10.8:1.0, 10.3:1.0 to 10.7:1.0, or 10.4:1.0 to 10.6:1.0.

In one embodiment, the molar ratio of the PSMA I&T to $^{177}$Lu in the composition is from 9.0:1.0 to 10.0:1.0, 9.1:1.0 to 9.9:1.0, 9.2:1.0 to 9.8:1.0, 9.3:1.0 to 9.7:1.0, or 9.4:1.0 to 9.6:1.0. In another embodiment, the molar ratio of the PSMA I&T to $^{177}$Lu in the composition is from 8.0:1.0 to 9.0:1.0, 8.1:1.0 to 8.9:1.0, 8.2:1.0 to 8.8:1.0, 8.3:1.0 to 8.7:1.0, or 8.4:1.0 to 8.6:1.0. In another embodiment, the molar ratio of the PSMA I&T to $^{177}$Lu in the composition is from 7.0:1.0 to 8.0:1.0, 7.1:1.0 to 7.9:1.0, 7.2:1.0 to 7.8:1.0, 7.3:1.0 to 7.7:1.0, or 7.4:1.0 to 7.6:1.0. In another embodiment, the molar ratio of the PSMA I&T to $^{177}$Lu in the composition is from 6.0:1.0 to 7.0:1.0, 6.1:1.0 to 6.9:1.0, 6.2:1.0 to 7.8:1.0, 7.3:1.0 to 7.7:1.0, or 7.4:1.0 to 6.6:1.0. In another embodiment, the molar ratio of the PSMA I&T to $^{177}$Lu in the composition is from 5.0:1.0 to 6.0:1.0, 5.1:1.0 to 5.9:1.0, 5.2:1.0 to 5.8:1.0, 5.3:1.0 to 5.7:1.0, or 5.4:1.0 to 5.6:1.0.

In an embodiment, the molar ratio of the PSMA I&T to $^{177}$Lu in the composition is about 4.0:1.0 to about 4.5:1.0, about 4.5:1.0 to about 5.0:1.0, about 5.0:1.0 to about 5.5:1.0, about 5.5:1.0 to about 6.0:1.0, about 6.0:1.0 to about 6.5:1.0, about 6.5:1.0 to about 7.0:1.0, about 7.0:1.0 to about 7.5:1.0, about 7.5:1.0 to about 8.0:1.0, about 8.0:1.0 to about 8.5:1.0, about 8.5:1.0 to about 9.0:1.0, about 9.0:1.0 to about 9.5:1.0, about 9.5:1.0 to about 10.0:1.0, about 10.0:1.0 to about 10.5:1.0, about 10.5:1.0 to about 11.0:1.0, about 11.0:1.0 to about 11.5:1.0, or about 11.5:1.0 to about 12.0:1.0.

In an embodiment, the molar ratio of the PSMA I&T to $^{177}$Lu in the composition is about 4.0:1.0 to about 4.5:1.0, about 4.0:1.0 to about 5.0:1.0; about 4.0:1.0 to about 5.5:1.0, about 4.0:1.0 to about 6.0:1.0, about 4.0:1.0 to about 6.5:1.0, about 4.0:1.0 to about 7.0:1.0, about 4.0:1.0 to about 7.5:1.0, about 4.0:1.0 to about 8.0:1.0, about 4.5:1.0 to about 8.0:1.0, about 5.0:1.0 to about 8.0:1.0, about 5.0:1.0 to about 8.0:1.0, about 5.5:1.0 to about 8.0:1.0, about 6.0:1.0 to about 8.0:1.0, about 6.5:1.0 to about 8.0:1.0, about 7.0:1.0 to about 8.0:1.0, or about 7.5:1.0 to about 8.0:1.0.

In some embodiments, the total amount of [$^{177}$Lu]Lu-PSMA I&T present in the radiopharmaceutical composition may range from about 1.0 µg/ml to about 3 µg/ml, from about 1 µg/ml to about 2 µg/ml, from about 1.1 µg/ml to about 2 µg/ml, from about 1.1 µg/ml to about 1.5 µg/ml, from about 1.1 µg/ml to about 1.4 µg/ml, or from about 1.1 µg/ml to about 1.3 µg/ml. In another embodiment, the total amount of [$^{177}$Lu]Lu-PSMA I&T in the radiopharmaceutical composition may range from about 0.5 µg/ml to about 1.5 µg/ml. In various embodiments, the total amount of [$^{177}$Lu]Lu-PSMA I&T present in the radiopharmaceutical composition may be about 0.5 µg/ml, about 0.6 µg/ml, about 0.7 µg/ml, about 0.8 µg/ml, about 0.9 µg/ml, about 1.0 µg/ml, about 1.1 µg/ml, about 1.2 µg/ml, about 1.3 µg/ml, about 1.4 µg/ml, about 1.5 µg/ml, about 1.6 µg/ml, about 1.7 µg/ml, or about 1.8 µg/ml.

In some embodiments, the total amount of [$^{177}$Lu]Lu-PSMA I&T present in the radiopharmaceutical composition may range from about 3.0 µg/ml to about 9.0 µg/ml, from about 3.5 µg/ml to about 8.5 µg/ml, from about 4.0 µg/ml to about 8.0 µg/ml, from about 4.5 µg/ml to about 7.5 µg/ml, from about 5.0 µg/ml to about 7.0 µg/ml, or from about 5.5 µg/ml to about 6.5 µg/ml. In another embodiment, the total amount of [$^{177}$Lu]Lu-PSMA I&T in the radiopharmaceutical composition may range from about 0.5 µg/ml to about 1.5 µg/ml.

In some embodiments, the total amount of [$^{177}$Lu]Lu-PSMA I&T present in the radiopharmaceutical composition may be less than 3.0 µg/ml. In other embodiments, the total amount of [$^{177}$Lu]Lu-PSMA I&T present in the radiopharmaceutical composition may be less than 4.0 µg/ml. In other embodiments, the total amount of [$^{177}$Lu]Lu-PSMA I&T present in the radiopharmaceutical composition may be less than 5.0 µg/ml. In other embodiments, the total amount of [$^{177}$Lu]Lu-PSMA I&T present in the radiopharmaceutical composition may be less than 6.0 µg/ml.

In some embodiments, the total amount of [$^{177}$Lu]Lu-PSMA I&T present in the radiopharmaceutical composition may range from about 9 µg/ml to 20 µg/ml, 10 µg/ml to 20 µg/ml, 11 µg/ml to 20 µg/ml, 11 µg/ml to 15 µg/ml, 11 µg/ml to 14 µg/ml, or 11 µg/ml to 13 µg/ml. In another embodiment, the total amount of [$^{177}$Lu]Lu-PSMA I&T in the radiopharmaceutical composition may range from about 5 µg/ml to about 15 µg/ml. In various embodiments, the total amount of [$^{177}$Lu]Lu-PSMA I&T present in the radiopharmaceutical composition may be about 5 µg/ml, 6 µg/ml, 7 µg/ml, 8 µg/ml, 9 µg/ml, 10 µg/ml, 11 µg/ml, 12 µg/ml, 13 µg/ml, 14 µg/ml, 15 µg/ml, 16 µg/ml, 17 µg/ml, or 18 µg/ml. The composition may have less than 12 µg/ml or less than 6 µg/ml of Lu-PSMA I&T.

The radioactivity/volume of [$^{177}$Lu]Lu-PSMA I&T in the composition may be adjusted according to dose strength. In an embodiment, the composition may include 0.5 GBq (13.5 mCi) of [$^{177}$Lu]Lu-PSMA I&T in a 1 ml solution. In other words, the composition may include 10 GBq (270 mCi) of [$^{177}$Lu]Lu-PSMA I&T in a 20 ml solution. In another embodiment, the composition may include 1 GBq (27 mCi) of $^{177}$Lu-PSMA I&T in a 1 ml solution. In other words, the composition may include 10 GBq (270 mCi) of $^{177}$Lu-PSMA I&T in a 10 ml solution.

In one embodiment, the radioactivity concentration of the [$^{177}$Lu]Lu-PSMA I&T in the radiopharmaceutical composition is less than about 50 mCi/ml, less than about 45 mCi/ml, less than about 40 mCi/ml, less than about 35 mCi/ml, less than about 30 mCi/ml, less than about 25 mCi/ml, less than about 20 mCi/ml, or less than about 15 mCi/ml. In another embodiment, the radioactivity concentration of the $^{177}$Lu-PSMA I&T in the radiopharmaceutical composition is from about 5 mCi/ml to about 30 mCi/ml, from about 10 mCi/ml to about 20 mCi/ml, or from about 13 mCi/ml to about 30 mCi/ml. In one specific embodiment, the radioactivity concentration of the $^{177}$Lu-PSMA I&T in the radiopharmaceutical composition is about 5 mCi/ml, about 10 mCi/ml, about 13.5 mCi/ml, about 15 mCi/ml, about 20 mCi/ml, about 27 mCi/ml, about 30 mCi/ml, about 30 mCi/ml, about 35 mCi/ml or about 40 mCi/ml.

In one embodiment, the radioactivity of the [$^{177}$Lu]Lu-PSMA I&T in the radiopharmaceutical composition is less than about 500 mCi, less than about 450 mCi, less than about 400 mCi, less than about 350 mCi, less than about 300 mCi, less than about 250 mCi, or less than about 200 mCi per vial. In another embodiment, the radioactivity of the $^{177}$Lu-PSMA I&T in the radiopharmaceutical composition is from about 10 mCi to about 750 mCi, from about 200 mCi to about 600 mCi, from about 300 mCi to about 400 mCi per vial. In one specific embodiment, the radioactivity of the [$^{177}$Lu]Lu-PSMA I&T in the radiopharmaceutical composition is about 27 mCi, 150 mCi, about 160 mCi, about 170 mCi, about 180 mCi, about 190 mCi, about 200 mCi, about 250 mCi, about 270 mCi, about 300 mCi, about 313 mCi, about 318 mCi, about 338 mCi, about 345 mCi, about 346 mCi, about 354 mCi, about 360 mCi, about 370 mCi, about 380 mCi, about 390 mCi, about 400 mCi, about 450 mCi, about 500 mCi, about 550 mCi, about 600 mCi or about 700 mCi per vial.

In yet another embodiment, the [$^{177}$Lu]Lu-PSMA I&T drug product has a standard radioactivity concentration of about 12 mCi/ml or about 32 mCi/ml at the end of production. In one embodiment, the $^{177}$Lu-PSMA I&T drug product has standard radioactivity concentration of about 13.5 mCi/ml or about 27 mCi/ml at the end of production.

(ii) Antioxidant

The antioxidant may act as a buffer and/or stabilizing agent. The total amount of antioxidant in the radiopharmaceutical composition can and will vary. Examples of suitable antioxidants include but are not limited to ascorbic acid or gentisic acid. The amount of antioxidant in the composition may range from about 10 mg/ml to 90 mg/ml, about 15 mg/ml to 85 mg/ml, about 20 mg/ml to 80 mg/ml, about 25 mg/ml to 75 mg/ml, about 30 mg/ml to 70 mg/ml, about 35 mg/ml to 65 mg/ml, about 40 mg/ml to 60 mg/ml, or about 45 mg/ml to 55 mg/ml. Said in another way, the amount of antioxidant in the composition may range from about 10 mg to 90 mg, about 15 mg to 85 mg, about 20 mg to 80 mg, about 25 mg to 75 mg, about 30 mg to 70 mg, about 35 mg to 65 mg, about 40 mg to 60 mg, or about 45 mg to 55 mg per ml.

In an embodiment, there may be ≤10 mg/ml, ≤9.5 mg/ml, ≤9 mg/ml, ≤8.5 mg/ml, ≤8 mg/ml, ≤7.5 mg/ml, ≤7 mg/ml, ≤6.5 mg/ml, ≤6 mg/ml, ≤5.5 mg/ml, 5 mg/ml, ≤4.5 mg/ml, ≤4 mg/ml, ≤3.5 mg/ml, ≤3 mg/ml, ≤2.5 mg/ml, ≤2 mg/ml, ≤1.5 mg/ml, ≤1 mg/ml, or ≤0.5 mg/ml antioxidant.

In an embodiment, the antioxidant may be ascorbic acid and/or ascorbate. Ascorbic acid and/or ascorbate may minimize or reduce radiolysis of radiolabeled compositions.

In some embodiments, ascorbic acid present in the radiopharmaceutical composition may range from about 10 to about 50 mg, from about 20 to about 50 mg, from about 30 to about 50 mg or from about 35 to about 45 mg per ml. In another embodiment, ascorbic acid in the radiopharmaceutical composition may range from about 5 mg to about 50 mg per ml. In another embodiment, there may be ≤10 mg/ml, ≤9.5 mg/ml, ≤9 mg/ml, ≤8.5 mg/ml, ≤8 mg/ml, ≤7.5 mg/ml, ≤7 mg/ml, ≤6.5 mg/ml, ≤6 mg/ml, ≤5.5 mg/ml, 5 mg/ml, ≤4.5 mg/ml, ≤4 mg/ml, ≤3.5 mg/ml, ≤3 mg/ml, ≤2.5 mg/ml, ≤2 mg/ml, ≤1.5 mg/ml, ≤1 mg/ml, or ≤0.5 mg/ml ascorbic acid or ascorbate.

In various embodiments, ascorbic acid present in the radiopharmaceutical composition may be about 5 mg, about 10 mg, about 15 mg, about 20 mg, about 25 mg, about 30 mg, about 31 mg, about 35 mg, about 36 mg, about 37 mg, about 38 mg, about 39 mg, about 40 mg, about 40.5 mg, about 41 mg, about 41.5 mg, about 42 mg, about 42.5 mg, about 43 mg, about 43.5 mg, about 44 mg, about 44.5 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 85 mg, or about 90 mg per ml. For example, the amount of ascorbic acid in 1 ml of the composition may be about 25 mg to 30 mg, about 30 mg to 35 mg, about 35 mg to 40 mg, or about 40 mg to 45 mg per ml.

In yet another embodiment, the concentration of ascorbic acid in the radiopharmaceutical composition may be from about 10 mg/ml to about 80 mg/ml, from about 10 mg/ml to about 75 mg/ml, from about 10 mg/ml to about 70 mg/ml, from about 15 mg/ml to about 80 mg/ml, from about 15 mg/ml to about 75 mg/ml, from about 15 mg/ml to about 70 mg/ml, from about 20 mg/ml to about 80 mg/ml, from about 20 mg/ml to about 75 mg/ml, from about 20 mg/ml to about 70 mg/ml, or from about 20 mg/mL to about 40 mg/mL.

In one specific embodiment, the concentration of ascorbic acid in the radiopharmaceutical composition is about 10 mg/ml, about 15 mg/ml, about 20 mg/ml, about 25 mg/ml, about 21 mg/ml, about 25 mg/ml, about 30 mg/ml, about 31 mg/ml, about 35 mg/ml, about 40 mg/ml, about 42.5 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, or about 100 mg/ml.

In at least one embodiment, the total amount of ascorbic acid in the radiopharmaceutical composition may be about 31 mg/ml. In another embodiment, the total amount of ascorbic acid in the radiopharmaceutical composition may be about 33 mg/ml. In a further embodiment, the total amount of ascorbic acid in the radiopharmaceutical composition may be about 15 mg/ml, about 21 mg/ml, about 25 mg/ml, about 31 mg/ml, 33 mg/ml, 35 mg/ml, or about 42.5 mg/ml.

(iii) Stabilizing agent

The stabilizing agent may be separate from the antioxidant. The total amount of stabilizing agent present in the radiopharmaceutical composition can and will vary. The stabilizing agent may further be used to limit or reduce radiolysis. The stabilizing agent may also function as a vehicle for the composition.

The stabilizing agent may include but is not limited to ethanol, para-aminebenzoic acid (PABA), dihydroxybenzoic acid (gentisate compounds), gentisic acid, cysteine, selenomethionine, ascorbic acid/sodium ascorbate, methionine, and/or combinations thereof.

In some embodiments, the stabilizing agent is ethanol. Ethanol may be present in the pharmaceutical composition at about 0.01% (v/v) to about 10% (v/v), 0.01% (v/v) to 3% (v/v), about 0.5% (v/v) to 1% (v/v), about 1% (v/v) to 2% (v/v), about 2% (v/v) to about 3% (v/v), about 3% (v/v) to 4% (v/v), about 3.5% to 4.5% (v/v), about 4% to 5% (v/v), about 4.5% (v/v) to 5.5% (v/v), about 5% (v/v) to 6% (v/v), about 5.5% (v/v) to 6.5% (v/v), about 6% (v/v) to 7% (v/v), about 6.5% (v/v) to 7.5% (v/v), or about 7% (v/v) to 8% (v/v). In some embodiments, the pharmaceutical composition comprises zero (0.00% v/v) ethanol (i.e., ethanol may be absent from the pharmaceutical composition).

In one embodiment, the total amount of ethanol present in the radiopharmaceutical composition is from about 3% (v/v) to about 8% (v/v), or from 2% (v/v) to about 4% (v/v), or from about 7% (v/v) to about 8% (v/v). In various embodiments, the total amount of ethanol present in the radiopharmaceutical composition may be about 1% (v/v), about 2% (v/v), about 3% (v/v), about 3.5% (v/v), about 3.8% (v/v), about 4% (v/v), about 4.5% (v/v), about 5% (v/v), about 5.5% (v/v), about 6% (v/v), about 6.5% (v/v), about 7% (v/v), about 7.5% (v/v), about 8% (v/v), about 8.5% (v/v), about 9% (v/v), about 9.5% (v/v), or about 10% (v/v).

In another embodiment, there may be ≤10 mg/ml, ≤9.5 mg/ml, ≤9 mg/ml, ≤8.5 mg/ml, ≤8 mg/ml, ≤7.5 mg/ml, ≤7 mg/ml, ≤6.5 mg/ml, ≤6 mg/ml, ≤5.5 mg/ml, 5 mg/ml, ≤4.5 mg/ml, ≤4 mg/ml, ≤3.5 mg/ml, ≤3 mg/ml, ≤2.5 mg/ml, ≤2 mg/ml, ≤1.5 mg/ml, ≤1 mg/ml, or ≤0.5 mg/ml gentisic acid or gentisate.

In at least one example, the radiopharmaceutical composition includes 3.8% (v/v) ethanol. In another example, the radiopharmaceutical composition includes 7.5% (v/v).

Stated alternatively, the total amount of ethanol present in the radiopharmaceutical composition may be about 5 mg, about 10 mg, about 15 mg, about 20 mg, about 25 mg, about 30 mg, about 35 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 95 mg, about 100 mg, about 105 mg, about 110 mg, about 115 mg, or about 80 mg per ml.

In some embodiments, the total amount of ethanol present in the radiopharmaceutical composition may range from about 20 mg to about 35 mg per ml. In another embodiment, the total amount of ethanol in the radiopharmaceutical composition may range from about 43 mg to about 63 mg per ml.

In some embodiments, the total amount of ethanol present in the radiopharmaceutical composition may range from about 25 mg to 80 mg, about 30 to 40 mg, about 40 to 50 mg, about 50 to 60 mg, about 60 to 70 mg, or about 70 to 80 mg per. In another embodiment, the total amount of ethanol in the radiopharmaceutical composition may range from about 30 mg to about 60 mg per ml.

In a further embodiment, the ratio of ethanol in the radiopharmaceutical composition may be about 300 mg per 10 ml or about 30 mg/ml. In another embodiment, the ratio of ethanol in the radiopharmaceutical composition may be about 200 mg per 10 ml. In still another embodiment, the ratio of ethanol in the radiopharmaceutical composition may be about 350 mg per 10 ml.

Stated alternatively, the amount of ethanol in the composition may range from about 35 μl/ml to about 75 μl/ml. For example, the amount of ethanol in 1 ml of the composition may be about 35 μl to 40 μl, about 40 μl to 45 μl, about 45

μl to 50 μl, about 50 μl to 55 μl, about 55 μl to 60 μl, about 60 μl to 65 μl, about 65 μl to 70 μl, or about 70 μl to 75 μl. In at least one example, 1 ml of the composition includes 37.5 μl (29.5 mg) of ethanol. In another example, 1 ml of the composition includes 75 μl (58.9 mg) of ethanol.

(iv) Metal Ion Chelator (Chelating Agent)

In some embodiments, the disclosure provides for a radiopharmaceutical composition with a dose of $^{177}$Lu-PSMA I&T solution and at least one metal ion chelator. A suitable chelating agent may include ethylenediamine tetracetic acid (EDTA) and its salts, N-(hydroxy-ethyl)ethylenediaminetriacetic acid, nitrilotriacetic acid (NTA), ethylene-bis(oxyethylene-nitrilo) tetraacetic acid, 1,4,7,10-tetraazacyclodo-decane-N,N',N'',N''' "-tetraacetic acid, 1,4,7,10-tetraaza-cyclododecane-N,N',N''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetra-decane-N,N',N'',N'''-tetraacetic acid; diethylenetriamine-pentaacetic acid (DTPA), ethylenedicysteine, bis(aminoethanethiol) carboxylic acid, triethylenetetraamine-hexaacetic acid, 1,2-diaminocyclohexane-N,N,N',N'-tetraacetic acid, or a combination thereof. In one embodiment, the chelating agent may be the sodium salt of EDTA. In one embodiment, the chelating agent may comprise DTPA and an absence of EDTA.

In some embodiments, the metal ion chelator may be ethylenediamine tetracetic acid (EDTA) and its salts, N-(hydroxy-ethyl)ethylenediaminetriacetic acid, nitrilotriacetic acid (NTA), ethylene-bis(oxyethylene-nitrilo)tetraacetic acid, 1,4,7,10-tetraazacyclodo-decane-N,N',N'',N''-tetraacetic acid, 1,4,7,10-tetraaza-cyclododecane-N,N',N''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetra-decane-N,N',N'',N'''-tetraacetic acid; diethylenetriamine-pentaacetic acid (DTPA), ethylenedicysteine, bis(aminoethanethiol) carboxylic acid, triethylenetetraamine-hexaacetic acid, and 1,2-diaminocyclohexane-N,N,N',N'-tetraacetic acid. In one embodiment, the metal ion chelator may be disodium EDTA. In one embodiment, the metal ion chelator may be DPTA.

In one embodiment, the amount of chelating agent present in the radiopharmaceutical composition may range from about 5 μg to 500 μg. In some embodiments, the amount of metal ion chelator present in the radiopharmaceutical composition may range from about 5 μg to 50 μg.

In some embodiments, the amount of chelating agent present may be about 5 μg, about 6 μg, about 7 μg, about 8 μg, about 9 μg, about 10.5 μg, about 11 μg, about 12 μg, about 13 μg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29 μg, about 30 μg, about 31 μg, about 32 μg, about 33 μg, about 34 μg, about 35 μg, about 36 μg, about 37 μg, about 38 μg, about 39 μg, about 40 μg, about 45 μg, about 50 μg, about 60 μg, about 70 μg, about 80 μg, about 90 μg, about 100 μg, about 110 μg, about 80 μg, about 130 μg, about 140 μg, about 150 μg, about 160 μg, about 170 μg, about 180 μg, about 190 μg, about 200 μg, about 210 μg, about 220 μg, about 230 μg, about 240 μg, about 250 μg, about 260 μg, about 270 μg, about 280 μg, about 290 μg, about 300 μg, about 310 μg, about 320 μg, about 330 μg, about 340 μg, about 350 μg, about 360 μg, about 370 μg, about 380 μg, about 390 μg, about 400 μg, about 410 μg, about 420 μg, about 430 μg, about 440 μg, about 450 μg, about 460 μg, about 470 μg, about 480 μg, about 490 μg, or about 500 μg.

The concentration of metal ion chelator in the composition may range from about 5 μg/ml to about 500 μg/ml. In another embodiment, the concentration of chelating agent present in the radiopharmaceutical composition may range from about 5 μg/ml to 200 μg/ml about 5 μg/ml to 75 μg/ml, 10 μg/ml to about 25 μg/ml, about 25 μg/ml to about 50 μg/ml, about 50 μg/ml to about 75 μg/ml, or about 75 μg/ml to about 100 μg/ml, about 100 μg/ml to about 125 μg/ml, about 125 μg/ml to about 150 μg/ml, or about 150 μg/ml to about 200 μg/ml. In some embodiments, the concentration of chelating agent present may be about 5 μg/ml, about 6 μg/ml, about 7 μg/ml, about 8 μg/ml, about 9 μg/ml, about 10.5 μg/ml, about 11 μg/ml, about 12 μg/ml, about 13 μg/ml, about 14 μg/ml, about 15 μg/ml, about 16 μg/ml, about 17 μg/ml, about 18 μg/ml, about 19 μg/ml, about 20 μg/ml, about 21 μg/ml, about 22 μg/ml, about 23 μg/ml, about 24 μg/ml, about 25 μg/ml, about 26 μg/ml, about 27 μg/ml, about 28 μg/ml, about 29 μg/ml, about 30 μg/ml, about 31 μg/ml, about 32 μg/ml, about 33 μg/ml, about 34 μg/ml, about 35 μg/ml, about 36 μg/ml, about 37 μg/ml, about 38 μg/ml, about 39 μg/ml, about 40 μg/ml, about 45 μg/ml, or about 50 μg/ml.

In other embodiments, the concentration of chelating agent present may be about 80 μg/ml, about 90 μg/ml, about 91 μg/ml, about 92 μg/ml, about 93 μg/ml, about 94 μg/ml, about 95 μg/ml, about 96 μg/ml, about 97 μg/ml, about 98 μg/ml, about 99 μg/ml, about 100 μg/ml, about 101 μg/ml, about 102 μg/ml, about 103 μg/ml, about 104 μg/ml, about 105 μg/ml, about 106 μg/ml, about 107 μg/ml, about 108 μg/ml, about 109 μg/ml, about 110 μg/ml, about 115 μg/ml, about 120 μg/ml, about 125 μg/ml, about 130 μg/ml, about 135 μg/ml, about 140 μg/ml, about 145 μg/ml, about 150 μg/ml, about 155 μg/ml, about 160 μg/ml, about 170 μg/ml, about 180 μg/ml, about 190 μg/ml, or about 200 μg/ml.

In another embodiment, the amount of metal ion chelator in the radiopharmaceutical composition may be from about 0.001% to about 0.20% (w/w), about 0.20% to about 0.40% (w/w), about 0.40% to about 0.60% (w/w), about 0.60% to about 0.80% (w/w), or about 0.80% to about 1.00% (w/w) of such radiopharmaceutical composition. In some embodiments, the amount of metal ion chelator present in a radiopharmaceutical composition may be about 0.001%, 0.002%, 0.003%, 0.004%, 0.005%, 0.01%, 0.02%, 0.03%, 0.04%, 0.05%, 0.06%, 0.07%, 0.08%, 0.09%, 0.10%, 0.11%, 0.12%, 0.13%, 0.14%, or 0.15% (w/w) of the total weight of the radiopharmaceutical composition.

For example, the amount of disodium EDTA, diethylenetriamine-pentaacetic acid (DTPA), or a combination thereof in 1 ml of the composition may be about 10 μg to 15 μg, about 13 μg to 18 μg, about 15 μg to 20 μg, about 20 μg to 25 μg, about 25 μg to 50 μg, about 50 μg to 75 μg, or about 75 μg to 150 μg. In some embodiments, the amount of disodium EDTA present may be about 5 μg, about 6 μg, about 7 μg, about 8 μg, about 9 μg, about 10.5 μg, about 11 μg, about 12 μg, about 13 μg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29 μg, about 30 μg, about 31 μg, about 32 μg, about 33 μg, about 34 μg, about 35 μg, about 36 μg, about 37 μg, about 38 μg, about 39 μg, about 40 μg, about 45 μg, or about 50 μg.

In at least one example, 1 ml of the composition includes 15.5 μg of disodium EDTA. In another example, 1 ml of the composition includes 21 μg of disodium EDTA.

In one embodiment, other trace metal content in the composition is undetectable. In another embodiment, the Fe metal content in the composition is ≤0.05 µg/GBq, ≤0.03 µg/GBq, ≤0.01 µg/GBq, or below the detectable limit. In another embodiment, the Cu metal content in the composition is ≤0.05 µg/GBq, ≤0.03 µg/GBq, ≤0.01 µg/GBq, or below the detectable limit. In another embodiment, the Zn metal content in the composition is ≤0.05 µg/GBq, ≤0.03 µg/GBq, ≤0.01 µg/GBq, or below the detectable limit. In another embodiment, the Pb metal content in the composition is ≤0.05 µg/GBq, ≤0.03 µg/GBq, ≤0.01 µg/GBq, or below the detectable limit.

(v) pH adjuster

Suitable pH adjusters include but are not limited to any one of hydrochloric acid, sodium hydroxide, sodium bicarbonate, or combinations thereof.

In some embodiments, hydrochloric acid may be used to adjust the pH of the radiopharmaceutical composition. In an embodiment, the amount of hydrochloric acid in the composition may range from 0 mg/ml to about 2 mg/ml. In some embodiments, the amount of HCl may range from 1.6 ml of 0.05 M HCl to 2 ml of 0.04 M HCl. The amount of HCl in the composition may vary, to adjust the final formulation pH in a production batch. In one embodiment, the batch has an activity of about 10 to 20 Ci. In another embodiment the batch has an activity of about 16 Ci. In various embodiments, the final formulation pH ranges from pH 3.0 to 5.0. In at least one example, HCl is added to the composition until a final pH of 3.5±0.1 to 4.5±0.1 is reached.

In an embodiment, the amount of sodium bicarbonate in the composition may be a sufficient quantity control the pH of the composition to 5.5 to 7.0 prior to the addition of HCl.

In an embodiment, the amount of NaOH in the composition may be a sufficient quantity control the pH of the composition to 5.5 to 7.0 prior to the addition of HCl.

(vi) Water

The composition may further include a sufficient amount of water to make the desired final volume for the solution for injection. For example, water may be added to make a final volume of 1 ml, 10 ml, or 20 ml. The 10 ml or 20 ml solutions may be stored in a vial and divided into smaller volumes for administration.

IV. Process of Making the Radiopharmaceutical Composition

The whole manufacturing process is a one-step radiolabelling process using a PSMA I&T precursor. The success of the labelling is dependent on temperature, time and pH. The reaction takes place in a reactor vial at elevated temperatures. For example, the reactor may be heated at setpoint of 110° C. and the maximum temperature reached in the reaction solution is about 95° C. The radiolabeled product is isolated on a C18 cartridge and formulated to the final composition after elution to the bulk vial. The final product is dispensed in a grade A controlled environment.

The $^{177}$Lu-PSMA I&T composition solution may be prepared using the following method 100, for example as shown in FIG. 2. The order of the steps may vary, such as the order of preparing the various solutions.

In an embodiment, step 102 may include preparing four solutions for the synthesis. The four solutions may include 0.04 M hydrochloric acid, 0.4 M sodium acetate, 20% (w/w) L-ascorbic acid, and PSMA I&T in water at about 460 to about 500 µg/ml. The PSMA I&T precursor may be dissolved in sterile water for injection. For example, 80 µg to 600 µg of precursor may be used in the reaction depending on the number of doses produced. In at least one example, 463 µl/ml of PSMA I&T precursor may be used to produce the composition.

In an embodiment, step 104 may include preparing an ascorbic acid solution (dilution buffer). In some examples, the ascorbic acid solution may be a 50 mg/ml ascorbic acid solution. The solution pH may be adjusted to 4.5±0.25, 4.5±0.30, 4.5±0.35, 4.5±0.40, 4.5±0.45, or 4.5±0.50. For example, 50 mg/ml ascorbic acid solution is prepared, and the pH of the solution is adjusted to 4.5 using 30% hydrochloric acid. In another example, the ascorbic acid solution may include 33 mg/ml ascorbic acid/sodium ascorbate at pH 4.25±0.25 and 0.1 mg/ml DTPA.

In an embodiment, optional step 106 may include preparing a formulation solution/buffer. The formulation solution is prepared from an injections grade solution containing ascorbic acid, absolute ethanol and injections grade water. In an example, the formulation solution is prepared by adding sufficient amounts of following solutions into the bulk vial: about 50 mg/ml ascorbic acid pH 4.5 solution (prepared in step 104), 30% ethanol solution, and water. The formulation solution may include 31 mg/ml to 42.5 mg/ml ascorbic acid and 3.8% to 7.5% ethanol (v/v %). In some embodiments, the formulation buffer may be adjusted to enable the final composition to have an extended shelf life. In at least one example, the formulation solution comprises 31 mg/ml ascorbic acid, 3.8% (v/v) ethanol, and pH 4.5. The formulation buffer is prepared ex tempore as part of the synthesis preparation and predetermined amount is added to the bulk vial as part of the synthesis preparations.

In an embodiment, step 108 may include preparing a reaction solution. A reaction solution may include sodium acetate, HCl, and L-ascorbic acid. Alternatively, a reaction solution may include sodium ascorbate. The reaction solution may be prepared in the reactor using solutions prepared in step 102. In an example, the reaction solution may include 4 ml 0.4 M sodium acetate, a volume of about 463 µg/ml PSMA I&T solution, and 150 µl 20% (w/w) L-ascorbic acid. In another example, the reaction solution may include 0.33M sodium ascorbate (reaction buffer) and PSMA I&T in the reaction buffer. In some examples, the reaction solution may include 1.6 ml 0.05 M HCl or 2 ml 0.04 M HCl (0.08 mmol HCl). Ascorbic acid concentration in the reaction solution may range from 3.75 mg/ml to 5.00 mg/ml.

In an embodiment, step 110 may include preparing $^{177}$Lu. In some embodiments, $^{177}$Lu may be provided in HCl. [$^{177}$Lu]LuCl$_3$ may be provided in 0.04 M or 0.05 M HCl. For example, 40-44 GBq/ml of $^{177}$Lu may be provided in 0.04 M HCl. In another example, less than 61 GBq of $^{177}$Lu may be provided in 0.05 M HCl. The [$^{177}$Lu]LuCl$_3$ in 0.04 M or 0.05 M hydrochloric acid may be transferred into the reactor and the [$^{177}$Lu]LuCl$_3$ vial may be rinsed with an additional required volume of 0.04 M hydrochloric acid (prepared in step 102) that is also then transferred into the reactor.

The reaction volume may range from 6 ml to 8 ml. The volume may be dependent on the amount of precursor used.

In an embodiment, step 112 may include radiolabeling the PSMA-I&T with $^{177}$Lu. The reaction mixture may be heated up to about 75° C., up to about 80° C., up to about 85° C., up to about 90° C., or up to about 95° C. In an example, the setpoint for heating is 110° C. and the actual maximum temperature reached is about 95° C. The reaction volume may be heated for up to 5 minutes, up to 10 minutes, up to 15 minutes, or up to 20 minutes. In at least one example, the reaction mixture is heated at setpoint of 110° C. for 15 minutes. In at least one additional example, the reaction mixture is heated at a setpoint of 75° C. for 10 minutes.

In an embodiment, optional step 114 may include purifying the reaction mixture. For example, the solution may be run through a cassette/cartridge containing a hydrophobic, reverse-phase, silica-based bonded phase. A Sep-Pak C18 may be used to purify the composition. In at least one example, the reaction mixture may be passed through a C18 Sep Pak cartridge and the cartridge is rinsed with water. $^{177}$Lu-PSMA I&T product is retained in the cartridge. In some embodiments, the reaction mixture may not be purified.

In an embodiment, step 116 may include eluting or diluting the final product. In an example, the $^{177}$Lu-PSMA I&T is diluted with dilution buffer prepared in step 104 to the desired radioactivity concentration. The composition may be eluted using 1.5 ml of ethanol-water in a 1:1 ratio. The cassette may then be flushed using 8.5 ml ascorbic acid 50 mg/ml. A formulation solution may then be added to form the final composition. In at least one example, $^{177}$Lu-PSMA I&T is eluted from the C18 cartridge with 1.5 ml of 50% (v/v) ethanol followed by 8.5 ml of 50 mg/ml pH 4.5 ascorbic acid solution (prepared in step 104) into the bulk vial where it is diluted with formulation solution/buffer (prepared in step 106, already in the bulk vial). The resulting solution may have a pH of 3.5 to 4.5. In some embodiments, the pH may be adjusted. In an example, the 50 mg/ml ascorbic acid solution pH is adjusted to 3.5 to 4.5. In other examples the pH is adjusted to 5.0 or less.

The stability enhancing conditions, such as ascorbic acid solution at pH of about 5 or below, should preferably be applied as early as possible in the process. For example, ascorbic acid solutions at pH 5 or below may be used instead of water at step 114 to minimize radiolytic damage.

In some embodiments, at step 118 the final composition may be sterile filtered. The sterile filter may be a 0.22 μm sterile filter. The final product may be dispensed through a 0.22 μm sterile filter into single dose vials containing suitable volume and radioactivity referenced to the prescribed calibration time. For example, the final composition may be dispensed through a 0.22 μm sterile filter under a Class A environment into doses containing suitable volume and radioactivity at a calibration time.

In other embodiments, the reactor may be heated at setpoint of 110° C. and the maximum temperature reached in the reaction solution is about 90° C., is about 85° C., is about 80° C., is about 75° C., or is about 70° C. The final composition may be formulated as a solution suitable for injection. The product is diluted to a standard radioactivity concentration, and therefore, the final volume of the bulk composition varies depending on the starting radioactivity of $^{177}$Lu introduced. The solution meets the requirements for sterility and bacterial endotoxins according to the European pharmacopoeia confirming an acceptable manufacturing process from a microbial point of view.

Figure 3A:
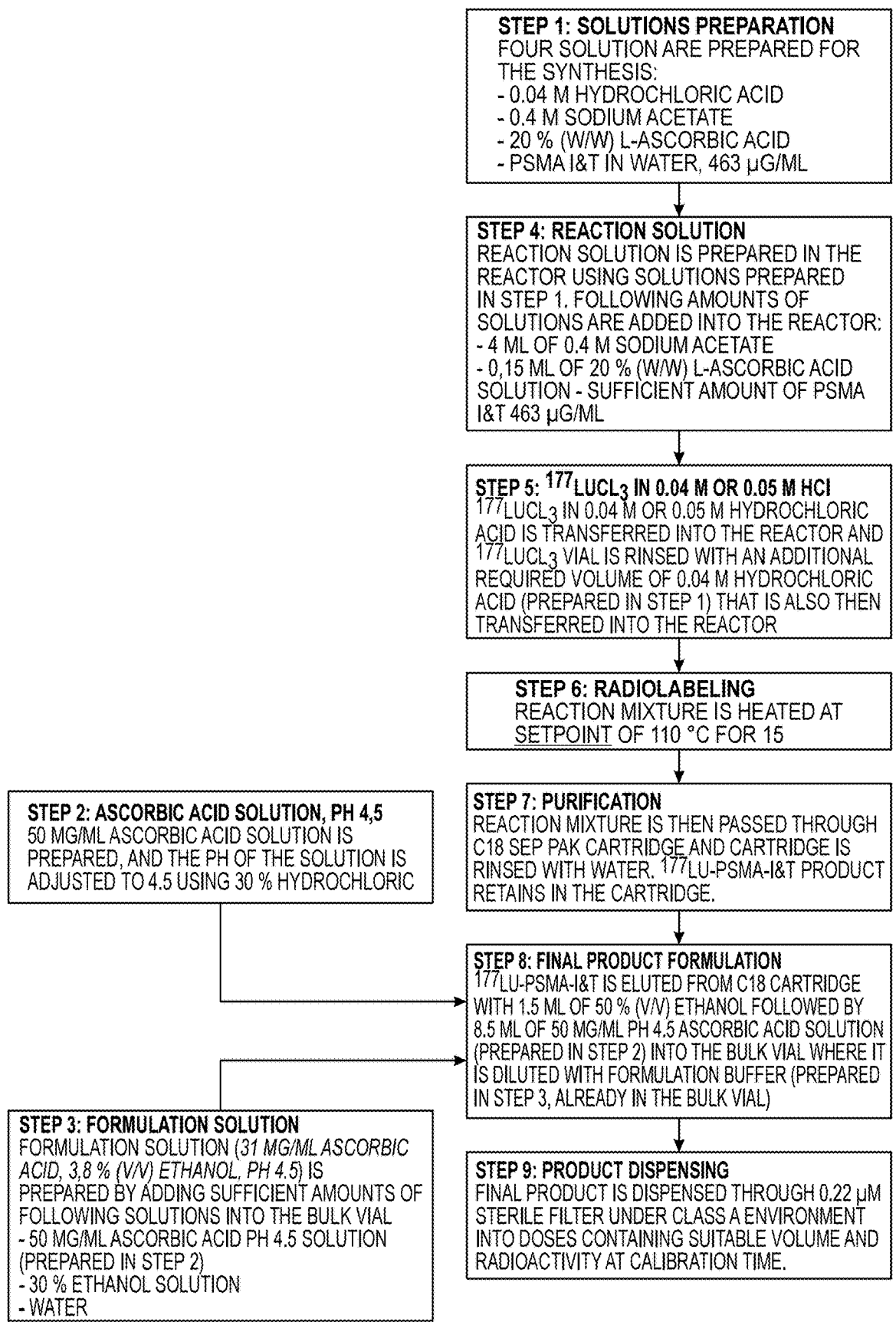
FIG. 3A is a flowchart of the synthetic procedure of the $^{177}$Lu-PSMA I&T in one embodiment.
Figure 3B:
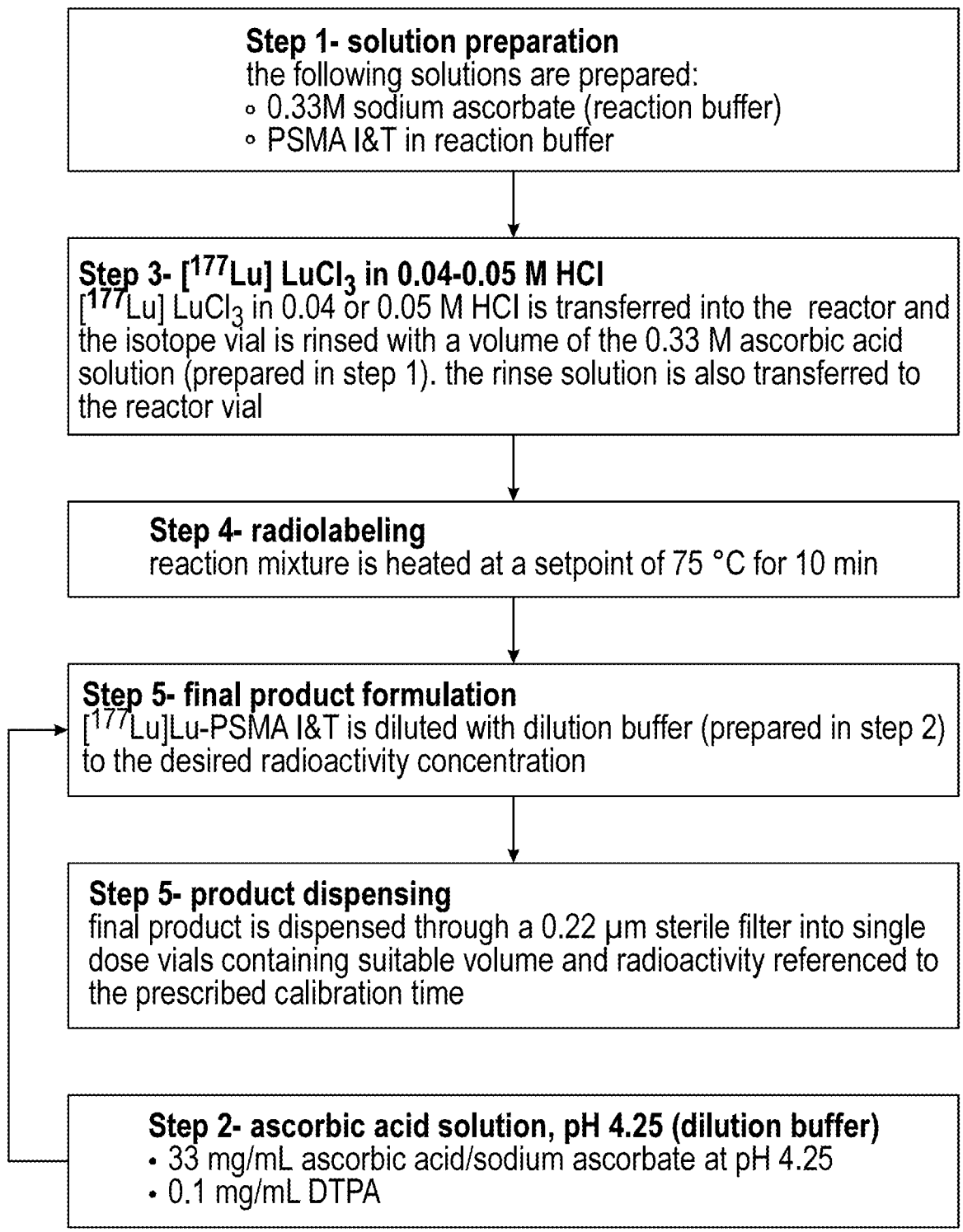
FIG. 3B is a flowchart of the synthetic procedure of the $^{177}$Lu-PSMA I&T in one embodiment.

FIG. 3A provides one example of the process of making a radiopharmaceutical composition with purification of the reaction mixture and the formulation solution with ethanol. FIG. 3B provides one example of the process of making a radiopharmaceutical composition without purification and without ethanol.

Provided herein are methods of increasing the shelf life of a radiopharmaceutical product comprising $^{177}$Lu-PSMA I&T. The method may include adjusting the pH of the composition to 3.5, 3.75, 4.0, 4.25, or 4.5, adjusting the amount of ascorbic acid in the composition, and/or adjusting the radioactivity to increase the shelf life of the composition by 0.25, 0.5, 0.75, 1, 1.25, 1.5, 2, 2.25, 2.5, 2.75, or 3 days. For example, the radiopharmaceutical composition may have a shelf life of 1, 1.5, 2, 2.25, 2.5, 2.75, 3, 3.25, 3.5, 3.75, 4, 4.25, 4.5, 4.75, or 5 days. In an embodiment, adjusting the pH, radioactivity, and/or ascorbic acid may increase the radiochemical purity of the composition to at least 99%, at least 98.5%, at least 98%, at least 97.5%, at least 97%, at least 96.5%, at least 96%, at least 95.5%, or at least 95% for up to 1, 1.5, 2, 2.25, 2.5, 2.75, 3, 3.25, 3.5, 3.75, 4, 4.25, 4.5, 4.75, or 5 days.

Target pharmaceutical formulations in accordance with the present disclosure are as provided in Table 1A.

TABLE 1A

Target pharmaceutical formulations

| | Target Pharmaceutical Formulation | | |
|---|---|---|---|
| Component | Compositions 1 and 2[a] | Composition 3[b] | Composition 4[c] |
| Radioactivity concentration | ~1.0 GBq/mL or 27 mCi/mL | 0.5-0.6 GBq/mL or 13.5-16.2 mCi/mL | 0.5 GBq/mL or 13.3 mCi/mL |
| PSMA I&T | 5-12 μg/mL | 2.5-6 μg/mL | 3-8 μg/mL |
| Ascorbic acid | 42.5 mg/mL | 31 mg/mL | 33 mg/mL |
| Disodium EDTA | 21 μg/mL | 15.5 μg/mL | N/A |
| DTPA | N/A | N/A | 100 μg/mL |
| Ethanol | 7.5% (v/v %) | 3.8% (v/v %) | N/A |
| pH | 5.5 | 4.5 | 4.25 |
| Shelf-life (tested up to 40° C.) | 48 h | 72 h | 72 h |

[a]Max volume per vial is 10 ml
[b]Max volume per vial is 20 ml
[c]Max volume per vial is 15 ml In another embodiment in making the Composition 4 disclosed in Table 1A above may be performed using a one-step radiolabelling process performed in the following steps.

The success of the labelling is dependent on temperature, time and pH. The reaction takes place in a reactor vial at elevated temperatures. For example, the reactor may be pre-heated at setpoint of 100° C. for 5 minutes and then reduced to 85° C. to achieve a reaction temperature of about 75° C. for 10 minutes. The radiolabeled product is formulated to the final composition, sterile filtered, and dispensed in a grade A controlled environment.

The $^{177}$Lu-PSMA I&T composition solutions may be prepared as shown in FIG. 2b (201, 202, 203). The order of the steps may vary, such as the order of preparing the various solutions.

In an embodiment, step 201 may include preparing reaction buffer for the synthesis. The solution may include 82 mg/mL sodium ascorbate in water with pH>5. The PSMA I&T precursor may be dissolved in reaction buffer as shown in step 202. For example, 1000 μg to 5000 μg of precursor may be used in the reaction depending on the batch size.

In an embodiment, the amount of [$^{177}$Lu]LuCl$_3$ used in radiolabeling, step 204, can range from 50 mCi up to 15,200 mCi. The corresponding amount of PSMA I&T used during radiolabeling can range from 0.1 to 0.9 μg/mCi. For example, 15,000 mCi of [$^{177}$Lu]LuCl$_3$ and 4200 μg of PSMA I&T are added to the reactor during radiolabeling.

In an embodiment, step 203 may include preparing an ascorbic acid solution (dilution buffer). In some examples, the ascorbic acid solution may be a 33 mg/ml ascorbic acid solution. The solution pH may be adjusted to 4.25±0.05, 4.25±0.10, 4.25±0.15, 4.25±0.20, or 4.25±0.25. For example, the ascorbic acid solution may include 33 mg/ml ascorbic acid/sodium ascorbate at pH 4.25±0.25 and 0.1 mg/ml DTPA.

In an embodiment, step 204 may include preparing $^{177}$Lu. In some embodiments, $^{177}$Lu may be provided in HCl. [$^{177}$Lu]LuCl$_3$ may be provided in 0.05 M HCl. For example, 2 Ci/ml of $^{177}$Lu may be provided in 0.05 M HCl. [$^{177}$Lu] LuCl$_3$ in 0.05 M hydrochloric acid may be transferred into the reactor and the [$^{177}$Lu]LuCl$_3$ vial may be rinsed with an additional required volume of 82 mg/mL sodium ascorbate (prepared in step 201) that is also then transferred into the reactor.

The reaction volume may range from 8 ml to 15 ml. The volume may be dependent on the amount of [$^{177}$Lu]LuCl$_3$ used in the radiolabeling reaction.

In an embodiment, step 204 may include radiolabeling the PSMA-I&T with $^{177}$Lu. The reaction mixture may be heated up to about 70° C., up to about 75° C., up to about 80° C., up to about 85° C., up to about 90° C., or up to about 95° C. In an example, the setpoint for heating is 85° C. and the actual maximum temperature reached is about 75° C. The reaction volume may be heated for up to 5 minutes, up to 10 minutes, up to 15 minutes, up to 20 minutes, up to 25 minutes, up to 30 minutes, up to 35 minutes, up to 40 minutes, or up to 45 minutes. In at least one example, the reaction mixture is heated at setpoint of 80° C. for 10 minutes. In at least one additional example, the reaction mixture is heated at a setpoint of 70° C. for 10 minutes.

The stability enhancing conditions, such as ascorbic acid solution at pH of about 5 or below, should preferably be applied as early as possible in the process. For example, ascorbic acid solutions at pH 5 or below may be used instead of water at step 205 to minimize radiolytic damage.

The final composition may be formulated as a solution suitable for injection. The product is diluted to a standard radioactivity concentration, and therefore, the final volume of the bulk composition varies depending on the starting radioactivity of $^{177}$Lu introduced.

In some embodiments, at step 206 the final composition may be sterile filtered. The sterile filter may be a 0.22 μm sterile filter. The final product may be dispensed through a 0.22 μm sterile filter into single dose vials containing suitable volume and radioactivity referenced to the prescribed calibration time. For example, the final composition may be dispensed through a 0.22 μm sterile filter under a Class A environment into doses containing suitable volume and radioactivity at a calibration time.

FIG. 3B provides one example of the process of making a radiopharmaceutical composition without purification and without ethanol.

Provided herein are methods for increasing the shelf life of a radiopharmaceutical product comprising $^{177}$Lu-PSMA I&T. The methods may include adjusting the pH of the composition to 4.0, 4.25, 4.5, or 4.75 by adjusting the amount of ascorbic acid in the composition, and/or adjusting the radioactivity to increase the shelf life of the composition by 0.25, 0.5, 0.75, 1, 1.25, 1.5, 2, 2.25, 2.5, 2.75, or 3 days. For example, the radiopharmaceutical composition may have a shelf life of 1, 1.5, 2, 2.25, 2.5, 2.75, 3, 3.25, 3.5, 3.75, or 4 days. In an embodiment, adjusting the pH, radioactivity, and/or ascorbic acid may increase the radiochemical purity of the composition to at least 99%, at least 98.5%, at least 98%, at least 97.5%, at least 97%, at least 96.5%, at least 96%, at least 95.5%, or at least 95% for up to 1, 1.5, 2, 2.25, 2.5, 2.75, 3, 3.25, 3.5, 3.75, 4 days.

V. Stability

A stable non-radioactive labelled standard may be used for identifying the product peak in the HPLC analysis. The formulation may be prepared from an injection grade solution containing ascorbic acid, chelating agent (EDTA, DTPA, or combination thereof), optionally dehydrated ethanol, and injections grade water. The formulation matrix may be prepared ex tempore as part of the synthesis preparation and a predetermined amount is added to the bulk vial as part of the synthesis preparations.

Without being limited to any one theory, the radioactivity, the amount of ascorbic acid, and/or the pH of the solution may have an impact on the shelf life of the composition. Surprisingly, a lower concentration of ascorbic acid (e.g. 31 mg/ml vs. 42.5 mg/ml) in the composition, a pH 4.5 or lower, a low RAC, and/or the combinations thereof may result in a higher stability profile and a longer shelf life for the composition as compared to compositions with a pH 5 or higher, a high RAC, and/or combinations thereof. For example, this may be seen in FIG. 5. The shelf life may generally be determined based on the radiochemical purity of the composition after formulation or at the time of expiration of the composition. The radiochemical purity may be confirmed by HPLC.

In one or more embodiments, 177Lu-PSMA I&T formulation compositions with 31 mg/ml of ascorbic acid and pH of about 4.5 in a dose formulation at radioactivity concentration of 640 MBq/ml or below, can provide adequate stability of four days.

A composition having a low radioactivity concentration (e.g., 588.5 MBq/ml), a pH of 4.5, and 31 mg/ml ascorbic acid has 99.1% radiochemical purity 0 hours post EOS, 98.7% radiochemical purity 20 hours post EOS, 98.0% radiochemical purity 44 hours post EOS, 97.4% radiochemical purity 69 hours post EOS, and 97.0% radiochemical purity 93 hours post EOS. A composition having a low radioactivity concentration (e.g., 626 MBq/ml), a pH of 5.0, and 31 mg/ml ascorbic acid has 99.2% radiochemical purity 0 hours post EOS, 98.4% radiochemical purity 25 hours post EOS, 97.3% radiochemical purity 47 hours post EOS, and 96.5% radiochemical purity 71 hours post EOS. A composition having a low radioactivity concentration (e.g., 579 MBq/ml), a pH of 4.5, and 21 mg/ml ascorbic acid has 99.4% radiochemical purity 0 ours post EOS, 98.3% radiochemical purity 19 hours post EOS, 97.5% radiochemical purity 46 hours post EOS, 96.8% radiochemical purity 71 hours post EOS, and 96.0% radiochemical purity 92 hours post EOS. A composition having a high radioactivity concentration (e.g., 1,278 MBq/ml), a pH of 4.5, and 42.5 mg/ml ascorbic acid has 99.4% radiochemical purity 0 hours post EOS, 98.0% radiochemical purity 24 hours post EOS, 96.7% radiochemical purity 46 hours post EOS, 95.3% radiochemical purity 67 hours post EOS, and 95.2% radiochemical purity 71 hours post EOS.

The radiopharmaceutical composition may be stored at temperatures ranging from 2° C. to 40° C., about 2° C. to 5° C., about 5° C. to 10° C., about 10° C. to 15° C., about 15° C. to 20° C., about 20° C. to 25° C., about 25° C. to 30° C., about 30° C. to 35° C., or about 35° C. to 40° C.

In an embodiment, the radiopharmaceutical composition is stored at a temperature from about 5° C. to 40° C., about 10° C. to 35° C. or about 20° C. to 30° C. In one specific embodiment, the radiopharmaceutical composition is stored at a temperature at about 10° C., about 15° C., about 22° C., about 22.5° C., about 25° C., or at room temperature.

In one embodiment, the radiopharmaceutical composition is stored at about 22.5° C. In another embodiment, the radiopharmaceutical composition is stored at room temperature.

VI. Specific Radiopharmaceutical Composition

In some embodiments, the medicinal product is a sterile filtered radiopharmaceutical solution containing a dose of $^{177}$Lu-PSMA I&T solution in a 42.5 mg/ml aqueous ascorbic acid solution containing 7.5% (v/v) or 59 mg/ml ethanol. The product is diluted to a standard radioactivity concentration and therefore the final volume of the bulk product varies depending on the starting radioactivity introduced. The composition of the final product described in Table 1B ($^{177}$Lu-PSMA I&T composition 1):

TABLE 1B

Composition of Final Product[a] ($^{177}$Lu-PSMA I&T composition 1)

| Component | Quantity | Function |
|---|---|---|
| $^{177}$Lu-PSMA I&T | q.s.[b] | API |
| PSMA I&T | 5-12 µg/ml | Precursor |
| Ethanol | 7.5% (v/v) | Vehicle/ Stabilizing agent (radiolysis) |
| Ascorbic acid | 42.5 mg/ml | Stabilizing agent (radiolysis) |
| Disodium EDTA | 21 µg/ml | Metal ion chelator |
| Sodium bicarbonate* | q.s. | pH adjuster |
| Sodium hydroxide* | q.s. | pH adjuster |
| WFI (injections grade water) | ad 1 ml | Vehicle |

[a]Max volume per vial is 10 ml
[b]sufficient amount of radioactivity for intended use In yet another embodiment, the medicinal product is a sterile filtered radiopharmaceutical solution containing a dose of $^{177}$Lu-PSMA I&T solution in 31 mg/ml aqueous ascorbic acid solution containing 3.8% (v/v) or 30 mg/ml ethanol, at a pH of about 4.5. The product is diluted to a standard radioactivity concentration, and therefore, the final volume of the bulk product varies depending on the starting radioactivity introduced. The composition is described below in Table 1C ($^{177}$Lu-PSMA I&T composition 3):

TABLE 1C

Composition of Final Product* ($^{177}$Lu-PSMA I&T composition 3)

| Component | Quantity | Function |
|---|---|---|
| $^{177}$Lu-PSMA I&T | q.s.** | API |
| Ethanol | 3.8% (v/v) | Vehicle/ Stabilizing agent (radiolysis) |
| Ascorbic acid | 31 mg/ml | Stabilizing agent (radiolysis) |
| Disodium EDTA | 15.5 µg | Metal ion chelator |
| Sodium bicarbonate | q.s | pH adjuster |
| Sodium hydroxide | q.s | pH adjuster |
| Hydrochloric acid | q.s | pH adjuster |
| WFI (injections grade water) | ad 1 ml | Vehicle |

*Max volume per vial is 20 ml
**sufficient amount of radioactivity for intended use In yet another embodiment, the medicinal product is a sterile filtered radiopharmaceutical solution containing a dose of $^{177}$Lu-PSMA I&T solution in 33 mg/ml aqueous ascorbic acid solution at a pH of about 4.25. The product is diluted to a standard radioactivity concentration, and therefore, the final volume of the bulk product varies depending on the starting radioactivity introduced. The composition is described below in Table 1D ($^{177}$Lu-PSMA I&T composition 4):

TABLE 1D

Composition of Final Product* ($^{177}$Lu-PSMA I&T composition 4)

| Component | Quantity | Function |
|---|---|---|
| $^{177}$Lu-PSMA I&T | q.s.** | API |
| PSMA I&T | 3-8 µg/ml | Precursor |
| Ascorbic acid | 33 mg/ml | Stabilizing agent (radiolysis) |
| DTPA | 0.075-0.15 mg/mL | Metal ion chelator |
| Hydrochloric acid | q.s | pH adjuster |
| WFI (injections grade water) | ad 1 ml | Vehicle |

*Max volume per vial is 20 ml
**sufficient amount of radioactivity for intended use

VII. Formulating the Drug Product

Figure 4:
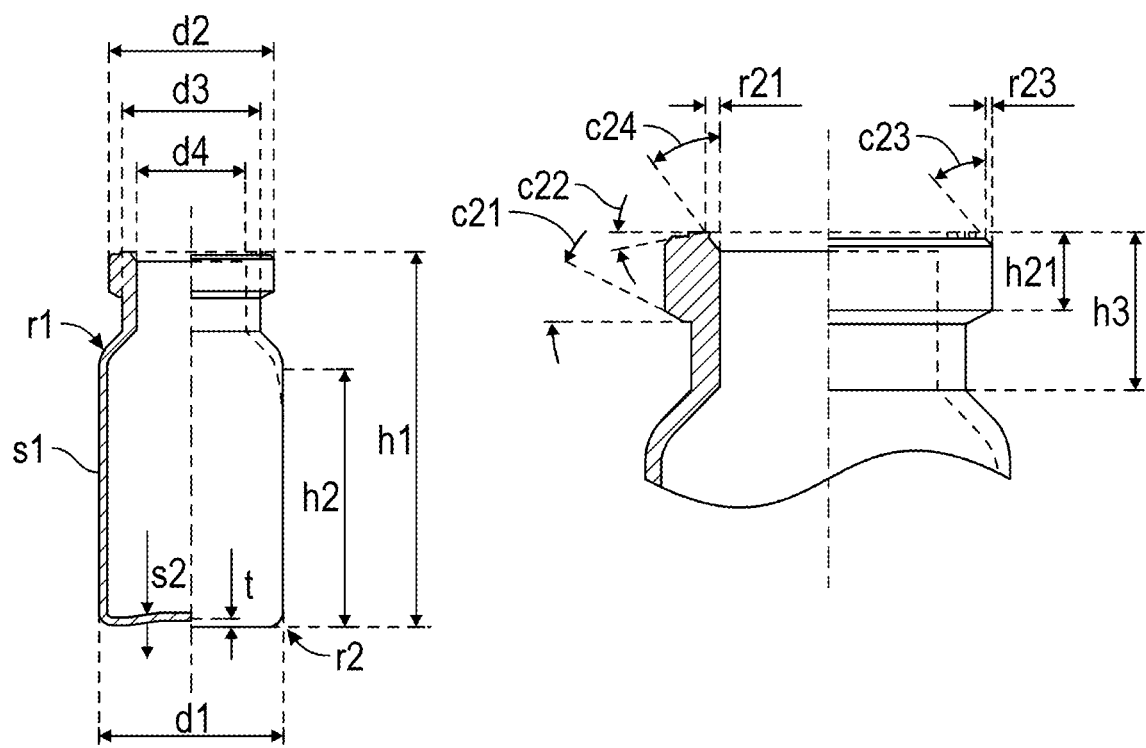
FIG. 4 depicts a drawing of an example product vial. The drug product is delivered in a sterile pyrogen free glass vial of Type 1 glass with a fluorocoated bromobutyl rubber septum. The septum is sealed with a crimped aluminum capsule. During transportation, the glass vial containing the radiopharmaceutical is kept in a lead shielded container. The transport container including lead shield and outer packaging complies to type A requirements (IAEA standards).

The drug product may be delivered in a sterile pyrogen free glass vial of Type 1 glass with a fluorocoated bromobutyl rubber septum. The septum is sealed with a crimped aluminum capsule. During transportation, the glass vial containing the radiopharmaceutical is kept in a lead shielded container. The transport container including lead shield and outer packaging complies to type A requirements (IAEA standards). FIG. 4 depicts a drawing of a product vial that can be used in this embodiment.

In one embodiment, the volume of the solution comprising the formulation or radiopharmaceutical composition is from about 10 ml to about 20 ml, from about 20 ml to about 30 ml, from about 30 ml to about 40 ml, from about 40 ml to about 50 ml, from about 50 ml to about 60 ml, from about 60 ml to about 70 ml, from about 70 ml to about 80 ml, from about 80 ml to about 90 ml, or from about 90 ml to about 100 ml. In one specific embodiment, the volume of the solution comprising the formulation or radiopharmaceutical composition is about 1 ml, about 5 ml, about 7 ml, about 8 ml, about 9 ml, about 10 ml, about 11 ml, about 12 ml, about 13 ml, about 14 ml, about 15 ml, about 16 ml, about 17 ml, about 18 ml, about 19 ml, about 20 ml, about 25 ml, or about 30 ml.

In one embodiment, the volume of the solution comprising the formulation or radiopharmaceutical composition is from about 100 ml to about 200 ml, from about 200 ml to about 300 ml, from about 300 ml to about 400 ml, from about 400 ml to about 500 ml, from about 500 ml to about 600 ml, from about 600 ml to about 700 ml, from about 700 ml to about 800 ml, from about 800 ml to about 900 ml, or from about 900 ml to about 1000 ml. In one specific embodiment, the volume of the solution comprising the formulation or radiopharmaceutical composition is about 200 ml, about 225 ml, about 250 ml, about 275 ml, about 300 ml, about 325 ml, about 350 ml, about 375 ml, about 400 ml, about 425 ml, about 450 ml, about 475 ml, about 500 ml, about 525 ml, about 550 ml, about 575 ml, about 600 ml, about 625 ml, about 650 ml, about 675 ml, about 700 ml, about 725 ml or about 750 ml.

In one specific embodiment, the final volume in the dose vial is adjusted to between 7 ml and 10 ml, between 10 ml and 15 ml, or between 15 ml and 20 ml in order to provide the required amount of radioactivity at the date and time of infusion.

In another embodiment, $^{177}$Lu-PSMA I&T injection is supplied as a single-dose vial. For example, provided herein is a radiopharmaceutical kit including a vial comprising a single dose of the $^{177}$Lu-PSMA I&T injection product composition. In one embodiment, the strength of the $^{177}$Lu-PSMA I&T injection product composition is about 0.1 GBq/ml, about 0.2 GBq/ml, about 0.3 GBq/ml, about 0.4 GBq/ml, about 0.5 GBq/ml, about 0.6 GBq/ml, about 0.7 GBq/ml, about 0.8 GBq/ml, about 0.9 GBq/ml, about 1.0 GBq/ml, about 1.1 GBq/ml, about 1.2 GBq/ml, about 1.3 GBq/ml, about 1.4 GBq/ml, about 1.5 GBq/ml, about 1.6 GBq/ml, about 1.7 GBq/ml, about 1.8 GBq/ml, about 1.9 GBq/ml, or about 2.0 GBq/ml. In another embodiment, the strength of the $^{177}$Lu-PSMA I&T injection product composition is less than about 2.0 GBq/ml, less than about 1.5 GBq/ml, less than about 1.0 GBq/ml, or less than about 0.5 GBq/ml.

In yet another embodiment, the shelf life of the $^{177}$Lu-PSMA I&T injection product composition is from about 30 hours to about 90 hours, from about 40 hours to about 80 hours, or from about 48 hours to about 72 hours. In one specific embodiment, the shelf life of the $^{177}$Lu-PSMA I&T injection product composition is about 30 hours, about 35 hours, about 40 hours, about 45 hours, about 48 hours, about 50 hours, about 55 hours, about 60 hours, about 65 hours, about 70 hours, about 72 hours, about 75 hours, about 80 hours, about 85 hours, or about 90 hours.

In some embodiments, the radiopharmaceutical composition should have a radiochemical purity of ≥95% for $^{177}$Lu-PSMA I&T to be sufficient for administration to a patient. The combined radiochemical impurities in the composition may be ≤5%. In various embodiments, the radiopharmaceutical composition may have a chemical purity such that Lu-PSMA I&T is present in the composition in a concentration of less than about 12 μg/ml, less than about 11 μg/ml, less than about 10 μg/ml, less than about 9 μg/ml, less than about 8 μg/ml, less than about 7 μg/ml, less than about 6 μg/ml, less than about 5 μg/ml, less than about 4 μg/ml, less than about 3 μg/ml, less than about 2 μg/ml, or less than about 1 μg/ml.

In some embodiments, the radiopharmaceutical composition may have an amount of colloidal $^{177}$Lu of less than about 5% of radioactivity, less than about 4.5% of radioactivity, less than about 4% of radioactivity, less than about 3.5% of radioactivity, less than about 3% of radioactivity, less than about 2.5% of radioactivity, less than about 2% of radioactivity, less than about 1.5% of radioactivity, less than about 1% of radioactivity, less than about 0.5% of radioactivity, less than about 0.3% of radioactivity, less than about 0.2% of radioactivity, or less than about 0.1% of radioactivity In one embodiment, the radiopharmaceutical composition administered to the human patient in need thereof comprises less than 0.5%, less than 0.4%, less than 0.3%, less than 0.2%, or less than 0.1% colloidal $^{177}$Lu.

In some embodiments, the radiopharmaceutical composition may have less than about 17.5 EU/ml, less than about 17 EU/ml, less than about 16.5 EU/ml, less than about 16 EU/ml, less than about 15.5 EU/ml, less than about 15 EU/ml, less than about 14.5 EU/ml, less than about 14 EU/ml less than about 13.5 EU/ml, less than about 13 EU/ml, less than about 12.5 EU/ml, less than about 12 EU/ml, less than about 11.5 EU/ml, less than about 11 EU/ml, less than about 10.5 EU/ml, less than about 10 EU/ml, less than about 9.5 EU/ml, less than about 9 EU/ml, less than about 8.5 EU/ml, less than about 8 EU/ml, less than about 7.5 EU/ml, less than about 7 EU/ml, less than about 6.5 EU/ml, less than about 6 EU/ml, less than about 5.5 EU/ml, less than about 5 EU/ml, less than about 4.5 EU/ml, less than about 4 EU/ml, less than about 3.5 EU/ml, less than about 3 EU/ml, less than about 2.5 EU/ml, less than about 2 EU/ml, less than about 1.5 EU/ml, less than about 1 EU/ml, less than about 0.5 EU/ml, or no bacterial endotoxins.

In an embodiment, the radiochemical purity of the composition is ≥95% at 1 day, up to 2 days, up to 3 days, up to 4 days, or up to 5 days after formulation. In additional embodiments, the radiochemical purity of the composition is ≥95% at 24 hours, up to 36 hours, up to 48 hours, up to 72 hours, or up to 96 hours after formulation. In further embodiments, the radiochemical purity of the composition is suitable for injection and suitable for administration to a patient in need thereof more than 72 hours after formulation, more than 96 hours after formulation, or more than 100 hours after formulation. The radiopharmaceutical composition may have a radiochemical purity of at least 95%, at least 95.5%, at least 96%, at least 96.5%, at least 97%, at least 97.5%, at least 98%, at least 98.5%, or at least 99% at 24 hours, 48 hours, 72 hours, and/or 96 hours after formulation. In some examples, the radiopharmaceutical composition may have a radiochemical purity of 95.0% or greater, 95.5% or greater, 96.0% or greater, 96.5% or greater, 97.0% or greater, 97.5% or greater, 98.0% or greater, 98.5% or greater, 99.0% or greater, or 99.5% or greater at administration. For example, the radiopharmaceutical composition may have a radiochemical purity of more than 95% at 46 to 48 hours after formulation, a radiochemical purity of more than 96% at 46 to 48 hours after formulation, a radiochemical purity of more than 97% at 46 to 48 hours after formulation, a radiochemical purity of more than 95% at 69 to 72 hours after formulation, a radiochemical purity of more than 96% at 69 to 72 hours after formulation, a radiochemical purity of more than 97% at 69 to 72 hours after formulation, a radiochemical purity of more than 95% at 90 to 93 hours after formulation, a radiochemical purity of more than 96% at 90 to 93 hours after formulation, and/or a radiochemical purity of more than 97% at 90 to 93 hours after formulation.

In some examples, the radiochemical purity of the composition may range from about 99.0% to about 99.4% 0 hours post EOS. In various embodiments, the radiochemical purity of the composition may range from about 96.5% to about 98.7% 19-25 hours post EOS. In other examples, the radiochemical purity of the composition may range from about 93.3% to about 98.0% 44-47 hours post EOS. In additional examples, the radiochemical purity of the composition may range from about 91.2% to about 97.4% 69-71 hours post EOS. In some examples, the radiochemical purity of the composition may range from about 94.5% to about 97.0% 90-93 hours post EOS.

In another embodiment, $^{177}$Lu-PSMA I&T injection is supplied as a single-dose vial vial.

In yet another embodiment, a patient in need of radioligand therapy during a treatment receives a single intravenous radioactive dose at the beginning of a treatment cycle. The treatment cycle is from 1 to 10 weeks. In one embodiment, the treatment includes 1 to 6 treatment cycles. In another embodiment, a dose reduction or a dose increase is introduced during treatment.

In one embodiment, the volume of the patient dose is calculated depending on the radioactive dose to be administered.

In another embodiment, $^{177}$Lu-PSMA I&T is injected by intravenous (IV) route slowly, over about 10 minutes, and followed by infusion of 500-1000 mL of Ringer's or normal saline solution. An extra 7 mL injection when the total blood volume is over 5,000 mL is of no consequence. The dose is administered every 6 weeks for 4 cycles.

In yet another embodiment, a patient in need of radioligand therapy during a treatment receives a single intravenous radioactive dose at the beginning of a treatment cycle. The treatment cycle is from 1 to 10 weeks. In one embodiment, the treatment includes 1-6 treatment cycles. In another embodiment, a dose reduction or a dose increase is introduced during treatment.

In one embodiment, the volume of the patient dose is calculated depending on the radioactive dose to be administered.

IX. Administration

Further provided herein are methods of administering the radiopharmaceutical composition. The radiopharmaceutical composition may be administered by injection to a human patient in need thereof.

There can be about six main aspects of administration.

First, cooling the salivary glands, the patients receive ice packs over the parotid and submandibular glands from 30 min prior to and up to 4 hours after administration of $^{177}$Lu-PSMA I&T to reduce the risk of salivary gland radiation injuries. There is no scientific evidence of whether cooling the salivary glands is an effective therapy for saving these glands from radiation; however, it is tolerable and not harmful for the patients.

Second, using a urinary catheter in incontinent patients in the first 48 hours to avoid any contamination.

Third, activity of 6.5-7.5 GBq (range: 6.0-8.0 GBq) $^{177}$Lu-PSMA I&T. The amount of activity can be reduced to 4.0-5.0 GBq in the case of impaired renal function (e.g., Creatinine within 1.0-1.5 UNL). According to the preliminary results, an activity of 7.4 GBq can be administered safely; however, more data are required to increase the amount of activity.

Fourth, infusion of the activity intravenously as a slow bolus (over about 1-15 minutes) followed by 500-1000 ml Ringer or NaCl solution. The patients should be encouraged to void as frequently as possible and drink about 2 liters of water daily. In patients with dilated non-obstructive renal disease an administration of diuretics may be meaningful.

Fifth, in average 3-5 cycles of the RLT every 5-8 weeks, experience up to 11 cycles has been reported. In the case of continuously increasing PSA, after the first two cycles accompanied by worsening of the general condition, the indication of further RLTs should be re-evaluated. In case of a decreasing PSA to <1.0 μg/l during the therapy cycles, a PSMA imaging could evaluate existence of small PSMA-positive metastases after completion of RLT when post injection SPECT study is not informative enough. In case of a significant decline of platelets or leukocytes, the time interval between the 2 cycles can be prolonged.

Sixth, at least one whole body scan 24-48 hours post injection (preferably with SPECT(/CT). In patients with diffuse bone and bone marrow metastases as well as in patients with brain metastases a concomitant corticosteroid therapy (e.g., prednisolone 20 mg/daily) in the first two weeks after administration is advisable.

In some embodiments, the method may include injecting the radiopharmaceutical composition into a patient in need thereof more than 48 hours after formulation. In some examples, the radiopharmaceutical composition may include $^{177}$Lu-PSMA I&T and ascorbic acid in a solution having a pH of 3.5 to 4.5, and the solution may have a radiochemical purity of more than 96% when administered. In an embodiment, the pH of the solution is about 3.5 to 4.2. The composition may include <6 μg/ml of $^{177}$Lu-PSMA I&T, about 7 μg/ml to about 18 μg/ml disodium EDTA, about 25 μl/ml to about 45 μl/ml ethanol, and/or about 15 to about 35 mg/ml ascorbic acid. Alternatively, the composition may include 5 μg/ml of $^{177}$Lu-PSMA I&T, about 0.1 mg/ml DTPA, and about 30 to about 35 mg/ml ascorbic acid. The composition may have a radioactivity of about 0.5 GBq/ml or about 13.3 mCi/mL, and have a radiochemical purity of at least 98% at 44 hours after formulation, at least 97% at 69 hours after formulation, and/or at least 97% at 93 hours after formulation.

The pharmaceutical composition may be administered as 2-11 cycles/treatments every 5-8 weeks. In some embodiments, the patient may be administered up to 1, 2, 3, 4, 5, 6, 7, 8, 9, 10, or 11 treatments and the treatments may be administered every 4, 5, 6, 7, or 8 weeks. In an example, the patient may be administered up to 4 treatments, with each treatment administered every 6 weeks.

In various embodiments, the patient may be administered $^{177}$Lu-PSMA I&T at a dose of 0.5 GBq to 10 GBq per dose per cycle. For example, the radiopharmaceutical composition may contain a standard radioactivity of about 200 mCi at the time of expiry with a standard radioactivity concentration of about 27 mCi/mL at end of production; therefore, the final volume of the dose vial may be adjusted to between 7 and 10 mL in order to provide the required amount of radioactivity at the date and time of infusion. In some embodiments, the dose vial contains between 10 to 20 mL. In some embodiments, the dose vial contains between 7 to 15 mL. In at least one example, the patient may be administered a dose of about 200 mCi (7.4 GBq±0.1 GBq) for each treatment. In one aspect, the patient may be administered a dose of about 200 mCi (7.4 GBq±0.1 GBq) for each treatment for four, five, six, seven, or more treatments. In another aspect, the patient may be administered a dose of about 200 mCi (7.4 GBq±0.1 GBq) for each treatment for four or more treatments, five or more, six or more, seven or more, or eight or more treatments. In yet another aspect, the patient may be administered a dose of about 200 mCi (≥7.1 GBq) for each treatment for four, five, six, seven, eight, or more treatments. In another example, the patient may be administered a dose of about 6.8 GBq±0.3 GBq for each treatment. In one aspect, the patient may be administered a dose of about 6.8 GBq±0.3 GBq for each treatment for four, five, six, seven, eight or more treatments.

In various embodiments, the patient may be administered $^{177}$Lu-PSMA I&T at a dose of about 0.5 GBq to about 10 GBq, about 1.0 GBq to about 9.0 GBq, about 1.5 GBq to about 8.5 GBq, about 2.0 GBq to about 8.0 GBq, about 2.5 GBq to about 7.5 GBq, or about 3.0 GBq to about 7.0 GBq, wherein the total cumulative dose to the patient's kidneys per each administration is ≤3.9 Gy, ≤3.8 Gy, ≤3.7 Gy, ≤3.6 Gy, ≤3.5 Gy, ≤3.4 Gy, ≤3.3 Gy, ≤3.2 Gy, ≤3.1 Gy, ≤3.0 Gy, ≤2.9 Gy, ≤2.8 Gy, ≤2.7 Gy, ≤2.6 Gy, ≤2.5 Gy, or ≤2.4 Gy, and wherein the patient may be administered a dose for each treatment for one, two, three, four, five, six, seven, eight, or more treatments (i.e., cycles of treatment). In various embodiments, the patient may be administered $^{177}$Lu-PSMA I&T at a dose of about 0.5 GBq to about 10.0 GBq, about 0.5 GBq to about 9.5 GBq, about 0.5 GBq to about 9.0 GBq, about 0.5 GBq to about 8.5 GBq, about 0.5 GBq to about 8.0 GBq, about 0.5 GBq to about 7.5 GBq, about 1.0 GBq to about 10.0 GBq, about 1.0 GBq to about 9.5 GBq, about 1.0 GBq to about 9.0 GBq, about 1.0 GBq to about 8.5 GBq, about 1.0 GBq to about 1.0 GBq, about 1.0 GBq to about 7.5 GBq, about 1.5 GBq to about 10.0 GBq, about 1.5 GBq to about 9.5 GBq, about 1.5 GBq to about 9.0 GBq, about 1.5 GBq to about 8.5 GBq, about 1.5 GBq to about 8.0 GBq, about 1.5 GBq to about 7.5 GBq, about 2.0 GBq to about 10.0 GBq, about 2.0 GBq to about 9.5 GBq, about 2.0 GBq to about 9.0 GBq, about 2.0 GBq to about 8.5 GBq, about 2.0 GBq to about 8.0 GBq, about 2.5 GBq to about 10.0 GBq, about 2.5 GBq to about 2.5 GBq, about 2.5 GBq to about 9.0 GBq, about 2.5 GBq to about 8.5 GBq, about 2.5 GBq to about 8.0 GBq, about 2.5 GBq to about 7.5 GBq, about 3.0 GBq to about 10.0 GBq, about 3.0 GBq to about 9.5 GBq, about 3.0 GBq to about 9.0 GBq, about 3.0 GBq to about 8.5 GBq, about 3.0 GBq to about 8.0 GBq, about 3.0 GBq to about 7.5 GBq, about 3.5 GBq to about 10.0 GBq, about 3.5 GBq to about 9.5 GBq, about 3.5 GBq to about 9.0 GBq, about 3.5 GBq to about 8.5 GBq, about 3.5 GBq to about 8.0 GBq, about 3.5 GBq to about 7.5 GBq, about 0.5 GBq to about 7.5 GBq, about 0.5 GBq to about 7.4 GBq, about 1.0 GBq to about 7.4 GBq, about 1.5 GBq to about 7.4 GBq, about 2.0 GBq to about 7.4 GBq, about 2.5 GBq to about 7.4 GBq, about 3.0 GBq to about 7.4 GBq, about 3.5 GBq to about 7.4 GBq, about 4.0 GBq to about 7.4 GBq, about 4.5 GBq to about 7.4 GBq, about 5.0 GBq to about 7.4 GBq, about 5.5 GBq to about 7.4 GBq, about 6.0 GBq to about 7.4 GBq, about 6.5 GBq to about 7.4 GBq, about 6.6 GBq to about 7.4 GBq, about 6.7 GBq to about 7.4 GBq, about 6.8 GBq to about 7.4 GBq, about 6.9 GBq to about 7.4 GBq, about 7.0 GBq to about 7.4 GBq, about 7.1 GBq to about 7.4 GBq, about 7.2 GBq to about 7.4 GBq, or about 7.3 GBq to about 7.4 GBq, wherein the total cumulative dose to the patient's kidneys per each administration is ≤3.9 Gy, ≤3.8 Gy, ≤3.7 Gy, ≤3.6 Gy, ≤3.5 Gy, ≤3.4 Gy, ≤3.3 Gy, ≤3.2 Gy, ≤3.1 Gy, ≤3.0 Gy, ≤2.9 Gy, ≤2.8 Gy, ≤2.7 Gy, ≤2.6 Gy, ≤2.5 Gy, or ≤2.4 Gy, and wherein the patient may be administered a dose for each treatment for one, two, three, four, five, six, seven, eight, or more treatments (i.e., cycles of treatment). In other various embodiments, the patient may be administered $^{177}$Lu-PSMA I&T at a dose of about 0.5 GBq to about 6.8 GBq, about 1.0 GBq to about 6.8 GBq, about 1.5 GBq to about 6.8 GBq, about 2.0 GBq to about 6.8 GBq, about 2.5 GBq to about 6.8 GBq, about 3.0 GBq to about 6.8 GBq, about 3.5 GBq to about 6.8 GBq, about 4.0 GBq to about 6.8 GBq, about 4.5 GBq to about 6.8 GBq, about 5.0 GBq to about 6.8 GBq, about 5.5 GBq to about 6.8 GBq, about 6.0 GBq to about 6.8 GBq, about 6.1 GBq to about 6.8 GBq, about 6.2 GBq to about 6.8 GBq, about 6.3 GBq to about 6.8 GBq, about 6.4 GBq to about 6.8 GBq, about 6.5 GBq to about 6.8 GBq, about 6.6 GBq to about 6.8 GBq, or about 6.7 GBq to about 7.4 GBq, wherein the total cumulative dose to the patient's kidneys per each administration is ≤3.9 Gy, ≤3.8 Gy, ≤3.7 Gy, ≤3.6 Gy, ≤3.5 Gy, ≤3.4 Gy, ≤3.3 Gy, ≤3.2 Gy, ≤3.1 Gy, ≤3.0 Gy, ≤2.9 Gy, ≤2.8 Gy, ≤2.7 Gy, ≤2.6 Gy, ≤2.5 Gy, or ≤2.4 Gy, and wherein the patient may be administered a dose for each treatment for one, two, three, four, five, six, seven, eight, or more treatments (i.e., cycles of treatment).

In various embodiments, the patient may be administered greater than 10 treatments, and the treatments may be administered every 4, 5, 6, 7, or 8 weeks, so long as the total cumulative dose to the patient's kidneys after all treatments remains below 23 grays (Gy). For example, the patient may be administered greater than 10, greater than 15, greater than 20, greater than 25, greater than 30, greater than 35, greater than 40, greater than 45, greater than 50, greater than 55, greater than 60, greater than 65, greater than 70, or greater than 75 treatments, and the treatments may be administered every 4, 5, 6, 7, or 8 weeks, so long as the total cumulative dose to the patient's kidneys after all treatments remains below 23 grays (Gy).

In various embodiments, the administration of the $^{177}$Lu-PSMA I&T results in an absorbed dose per gram of tissue to the patient's kidneys of 0.2 Gy/MBq to about 0.6 Gy/GBq (i.e., about 0.2 to about 0.6 Gy per GBq of the administered $^{177}$Lu-PSMA I&T per gram of tissue). In some additional embodiments, the administration of the $^{177}$Lu-PSMA I&T results in an absorbed dose to the patient's kidneys of less than or equal to 0.43 Gy/GBq.

In some embodiments, the administration of the 177Lu-PSMA I&T results in an absorbed dose to the patient's kidneys of 0.46 Gy/GBq±0.23 Gy/GBq (i.e., 0.46 Gy per GBq of the administered 177Lu-PSMA I&T). In some additional embodiments, the administration of the 177Lu-PSMA I&T results in an absorbed dose to the patient's kidneys of less than or equal to 0.46 Gy/GBq.

In various embodiments, the administration of the 177Lu-PSMA I&T results in an absorbed dose to the patient's kidneys of 0.43 Gy/GBq±0.18 Gy/GBq (i.e., 0.43 Gy per GBq of the administered 177Lu-PSMA I&T). In some additional embodiments, the administration of the 177Lu-PSMA I&T results in an absorbed dose to the patient's kidneys of less than or equal to 0.43 Gy/GBq.

In other embodiments, the administration of the 177Lu-PSMA I&T results in an absorbed dose to the patient's kidneys of 0.41 Gy/GBq±0.15 Gy/GBq (i.e., 0.41 Gy per GBq of the administered 177Lu-PSMA I&T). In some additional embodiments, the administration of the 177Lu-PSMA I&T results in an absorbed dose to the patient's kidneys of less than or equal to 0.41 Gy/GBq.

In various embodiments, the administration of the 177Lu-PSMA I&T results in an absorbed dose to the patient's lacrimal glands of 0.67 Gy/GBq±0.33 Gy/GBq (i.e., 0.67 Gy per GBq of the administered 177Lu-PSMA I&T). In some additional embodiments, the administration of the 177Lu-PSMA I&T results in an absorbed dose to the patient's lacrimal glands of less than or equal to 0.67 Gy/GBq.

In other embodiments, the administration of the 177Lu-PSMA I&T results in an absorbed dose to the patient's lacrimal glands of 0.40 Gy/GBq±0.37 Gy/GBq (i.e., 0.40 Gy per GBq of the administered 177Lu-PSMA I&T). In some additional embodiments, the administration of the 177Lu-PSMA I&T results in an absorbed dose to the patient's lacrimal glands of less than or equal to 0.40 Gy/GBq.

In other embodiments, the administration of the 177Lu-PSMA I&T results in an absorbed dose to the patient's salivary glands of 0.10 Gy/GBq±0.06 Gy/GBq (i.e., 0.10 Gy per GBq of the administered 177Lu-PSMA I&T). In some additional embodiments, the administration of the 177Lu-PSMA I&T results in an absorbed dose to the patient's salivary glands of less than or equal to 0.10 Gy/GBq.

In various embodiments, the administration of the 177Lu-PSMA I&T results in an absorbed dose to the patient's salivary glands of 0.13 Gy/GBq±0.08 Gy/GBq (i.e., 0.13 Gy per GBq of the administered 177Lu-PSMA I&T). In some additional embodiments, the administration of the 177Lu-PSMA I&T results in an absorbed dose to the patient's salivary glands of less than or equal to 0.13 Gy/GBq.

In other embodiments, the administration of the 177Lu-PSMA I&T results in an absorbed dose to the patient's salivary glands of 0.18 Gy/GBq±0.16 Gy/GBq (i.e., 0.18 Gy per GBq of the administered 177Lu-PSMA I&T). In some additional embodiments, the administration of the 177Lu-PSMA I&T results in an absorbed dose to the patient's salivary glands of less than or equal to 0.18 Gy/GBq.

In various embodiments, the administration of the 177Lu-PSMA I&T results in an absorbed dose to the patient's liver of 0.03 Gy/GBq±0.02 Gy/GBq (i.e., 0.03 Gy per GBq of the administered 177Lu-PSMA I&T). In some additional embodiments, the administration of the 177Lu-PSMA I&T results in an absorbed dose to the patient's liver of less than or equal to 0.03 Gy/GBq.

In other embodiments, the administration of the 177Lu-PSMA I&T results in an absorbed dose to the patient's liver of 0.04 Gy/GBq±0.02 Gy/GBq (i.e., 0.04 Gy per GBq of the administered 177Lu-PSMA I&T). In some additional embodiments, the administration of the 177Lu-PSMA I&T results in an absorbed dose to the patient's liver of less than or equal to 0.04 Gy/GBq.

The administration of $^{177}$Lu-PSMA I&T may be described as a mathematical formula to ensure that the total cumulative dose to the patient's kidneys after all treatments remains below 23 Gy. An example formula is shown below to determine the number of cycles allowable.

$$X = \frac{23}{Y*Z}$$

where X is the total number of cycles allowable at a given activity of $^{177}$Lu-PSMA I&T, Y is the activity of each dose of the $^{177}$Lu-PSMA I&T, Y is the absorbed dose of radiation in Gy per GBq of the administered $^{177}$Lu-PSMA I&T, and Z is the activity of the of the administered $^{177}$Lu-PSMA I&T in GBq.

In various embodiments, the patient may be administered 1 GBq of $^{177}$Lu-PSMA I&T for 53 treatments, 2 GBq of $^{177}$Lu-PSMA I&T for 26 treatments, 3 GBq of $^{177}$Lu-PSMA I&T for 17 treatments, 4 GBq of $^{177}$Lu-PSMA I&T for 13 treatments, 5 GBq of $^{177}$Lu-PSMA I&T for 10 treatments, 6 GBq of $^{177}$Lu-PSMA I&T for 8 treatments, 7 GBq of $^{177}$Lu-PSMA I&T for 7 treatments, 8 GBq of $^{177}$Lu-PSMA I&T for 6 treatments, 9 GBq of $^{177}$Lu-PSMA I&T for 5 treatments, 10 GBq of $^{177}$Lu-PSMA I&T for 5 treatments, etc.

In various embodiments, the present disclosure is further related to a radiopharmaceutical kit, comprising a vial containing at least a single dose of a $^{177}$Lu-PSMA I&T solution for injection to a human patient in need thereof, wherein the injection comprises a 6.5 GBq±0.10 GBq dose, 6.5 GBq±0.15 GBq dose, 6.5 GBq±0.20 GBq dose, 6.5 GBq±0.25 GBq dose, or 6.5 GBq±0.30 GBq dose, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

In various embodiments, the present disclosure is further related to a radiopharmaceutical kit, comprising a vial containing at least a single dose of a $^{177}$Lu-PSMA I&T solution for injection to a human patient in need thereof, wherein the injection comprises a 6.6 GBq±0.10 GBq dose, 6.6 GBq±0.15 GBq dose, 6.6 GBq±0.20 GBq dose, 6.6 GBq±0.25 GBq dose, or 6.6 GBq±0.30 GBq dose, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

In various embodiments, the present disclosure is further related to a radiopharmaceutical kit, comprising a vial containing at least a single dose of a $^{177}$Lu-PSMA I&T solution for injection to a human patient in need thereof, wherein the injection comprises a 6.7 GBq±0.10 GBq dose, 6.7 GBq±0.15 GBq dose, 6.7 GBq±0.20 GBq dose, 6.7 GBq±0.25 GBq dose, or 6.7 GBq±0.30 GBq dose, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

In various embodiments, the present disclosure is further related to a radiopharmaceutical kit, comprising a vial containing at least a single dose of a $^{177}$Lu-PSMA I&T solution for injection to a human patient in need thereof, wherein the injection comprises a 6.8 GBq±0.10 GBq dose, 6.8 GBq±0.15 GBq dose, 6.8 GBq±0.20 GBq dose, 6.8 GBq±0.25 GBq dose, or 6.8 GBq±0.30 GBq dose, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

In various embodiments, the present disclosure is further related to a radiopharmaceutical kit, comprising a vial containing at least a single dose of a $^{177}$Lu-PSMA I&T solution for injection to a human patient in need thereof, wherein the injection comprises a 6.9 GBq±0.10 GBq dose, 6.9 GBq±0.15 GBq dose, 6.9 GBq±0.20 GBq dose, 6.9 GBq±0.25 GBq dose, or 6.9 GBq±0.30 GBq dose, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

In various embodiments, the present disclosure is further related to a radiopharmaceutical kit, comprising a vial containing at least a single dose of a $^{177}$Lu-PSMA I&T solution for injection to a human patient in need thereof, wherein the injection comprises a 7.0 GBq±0.10 GBq dose, 7.0 GBq±0.15 GBq dose, 7.0 GBq±0.20 GBq dose, 7.0 GBq±0.25 GBq dose, or 7.0 GBq±0.30 GBq dose, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

In various embodiments, the present disclosure is further related to a radiopharmaceutical kit, comprising a vial containing at least a single dose of a $^{177}$Lu-PSMA I&T solution for injection to a human patient in need thereof, wherein the injection comprises a 7.1 GBq±0.10 GBq dose, 7.1 GBq±0.15 GBq dose, 7.1 GBq±0.20 GBq dose, 7.1 GBq±0.25 GBq dose, or 7.1 GBq±0.30 GBq dose, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

In various embodiments, the present disclosure is further related to a radiopharmaceutical kit, comprising a vial containing at least a single dose of a $^{177}$Lu-PSMA I&T solution for injection to a human patient in need thereof, wherein the injection comprises a 7.2 GBq±0.10 GBq dose, 7.2 GBq±0.15 GBq dose, 7.2 GBq±0.20 GBq dose, 7.2 GBq±0.25 GBq dose, or 7.2 GBq±0.30 GBq dose, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

In various embodiments, the present disclosure is further related to a radiopharmaceutical kit, comprising a vial containing at least a single dose of a $^{177}$Lu-PSMA I&T solution for injection to a human patient in need thereof, wherein the injection comprises a 7.3 GBq±0.10 GBq dose, 7.3 GBq±0.15 GBq dose, 7.3 GBq±0.20 GBq dose, 7.3 GBq±0.25 GBq dose, or 7.3 GBq±0.30 GBq dose, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

In various embodiments, the present disclosure is further related to a radiopharmaceutical kit, comprising a vial containing at least a single dose of a $^{177}$Lu-PSMA I&T solution for injection to a human patient in need thereof, wherein the injection comprises a 7.4 GBq±0.10 GBq dose, 7.4 GBq±0.15 GBq dose, 7.4 GBq±0.20 GBq dose, 7.4 GBq±0.25 GBq dose, or 7.4 GBq±0.30 GBq dose, and wherein $^{177}$Lu-PSMA I&T treatment with 6 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

In various embodiments, the present disclosure is further related to a radiopharmaceutical kit, comprising a vial containing at least a single dose of a $^{177}$Lu-PSMA I&T solution for injection to a human patient in need thereof, wherein the injection comprises a 7.5 GBq±0.10 GBq dose, 7.5 GBq±0.15 GBq dose, 7.5 GBq±0.20 GBq dose, 7.5 GBq±0.25 GBq dose, or 7.5 GBq±0.30 GBq dose, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 6 cycles is less than 23 Gy and no renal toxicities are observed.

In various embodiments, the present disclosure is further related to a radiopharmaceutical kit, comprising a vial containing at least a single dose of a $^{177}$Lu-PSMA I&T solution for injection to a human patient in need thereof, wherein the injection comprises a 7.4 GBq (mean 7.52±0.16 GBq) dose of $^{177}$Lu-PSMA-I&T, and wherein $^{177}$Lu-PSMA I&T treatment with 6 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed. The present disclosure is also further related to a radiopharmaceutical kit, comprising a vial containing at least a single dose of a $^{177}$Lu-PSMA I&T solution for injection to a human patient in need thereof, wherein the injection comprises a 7.4 GBq (mean 7.52±0.16 GBq) dose of $^{177}$Lu-PSMA-I&T, wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

The present disclosure is also further related to a radiopharmaceutical kit, comprising a vial containing at least a single dose of a $^{177}$Lu-PSMA I&T solution for injection to a human patient in need thereof, wherein the injection comprises a 6.5 GBq+/−10% GBq dose, 6.5 GBq+/−5% GBq dose, or 6.5 GBq+/−3% GBq dose of $^{177}$Lu-PSMA-I&T, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

The present disclosure is also further related to a radiopharmaceutical kit, comprising a vial containing at least a single dose of a $^{177}$Lu-PSMA I&T solution for injection to a human patient in need thereof, wherein the injection comprises a 6.8 GBq+/−10% GBq dose, 6.8 GBq+/−5% GBq dose, or 6.8 GBq+/−3% GBq dose of $^{177}$Lu-PSMA-I&T, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

The present disclosure is also further related to a radiopharmaceutical kit, comprising a vial containing at least a single dose of a $^{177}$Lu-PSMA I&T solution for injection to a human patient in need thereof, wherein the injection comprises a 7.4 GBq+/−10% GBq dose, 7.4 GBq+/−5% GBq dose, or 7.4 GBq+/−3% GBq dose of $^{177}$Lu-PSMA-I&T, and wherein $^{177}$Lu-PSMA I&T treatment with 1, 2, 3, 4, 5, 6, or 7 cycles at the dose is possible without the risk of kidney toxicities and/or wherein $^{177}$Lu-PSMA I&T treatment with 1, 2, 3, 4, 5, 6, or 7 cycles provides a mean projected dose that is below a cumulative absorbed dose to the kidney of 23 Gy and/or the projected or actual cumulative absorbed dose to the kidneys at 1, 2, 3, 4, 5, 6, or 7 cycles is less than 23 Gy and no renal toxicities are observed.

The present disclosure is also further related to a radiopharmaceutical kit, comprising a vial containing at least a single dose of a $^{177}$Lu-PSMA I&T solution for injection to a human patient in need thereof, wherein the injection comprises a 7.4 (+/−10%) GBq dose of $^{177}$Lu-PSMA-I&T, and wherein $^{177}$Lu-PSMA I&T treatment with 6 cycles at the dose is possible without the risk of kidney toxicities and/or wherein $^{177}$Lu-PSMA I&T treatment with 6 cycles provides a mean projected dose that is below a cumulative absorbed dose to the kidney of 23 Gy and/or the projected or actual cumulative absorbed dose to the kidneys at 6 cycles is less than 23 Gy and no renal toxicities are observed.

The present disclosure is further related to a radiopharmaceutical kit, comprising a vial containing at least a single dose of a $^{177}$Lu-PSMA I&T solution for injection to a human patient in need thereof, wherein the injection comprises a 7.4 GBq±0.10 GBq dose, 7.4 GBq±0.15 GBq dose, 7.4 GBq±0.20 GBq dose, 7.4 GBq±0.25 GBq dose, or 7.4 GBq±0.30 GBq dose, and wherein the projected cumulative absorbed dose to the kidneys at 6 cycles will be 20.4+10.2 Gy. The present disclosure is further related to a radiopharmaceutical kit, comprising a vial containing at least a single dose of a $^{177}$Lu-PSMA I&T solution for injection to a human patient in need thereof, wherein the injection comprises a 7.5 GBq±0.10 GBq dose, 7.5 GBq±0.15 GBq dose, 7.5 GBq±0.20 GBq dose, 7.5 GBq±0.25 GBq dose, or 7.5 GBq±0.30 GBq dose, and wherein the projected cumulative absorbed dose to the kidneys at 6 cycles will be 20.4+10.2 Gy.

In some embodiments, the present disclosure includes a kit that includes a predetermined amount of a composition that includes $^{177}$Lu-PSMA I&T. In another embodiment the molar ratio of the PSMA I&T to $^{177}$Lu is from 5.0:1.0 to 12.0:1.0. In another embodiment, the composition is suitable for administration to a human patient in need thereof.

Upon administration of the radiopharmaceutical composition to a patient, the patient may maintain low levels of hematotoxic and nephrotoxic toxicity. In some embodiments, the prostate-specific antigen (PSA) decline is more than about 40%, more than about 45%, more than about 50%, more than about 55%, more than about 60%, more than about 65%, more than about 70%, more than about 75%, or more than about 80%.

Further provided herein are methods of treating a patient with mCRPC by administering the radiopharmaceutical composition comprising $^{177}$Lu-PSMA I&T. The method may further comprise imaging the patient using PSMA-PET to document and confirm the patient is mCRPC positive prior to administering the radiopharmaceutical composition. For example, the patient may have a PSMA-PET scan (e.g. [$^{68}$Ga]Ga-PSMA-11 or [$^{18}$F]DCFPyL) positive as determined by central reader.

In an embodiment provided herein is a method of imaging cancer in a human patient in thereof. In another embodiment, the method further includes administering to the human patient a composition that includes $^{177}$Lu-PSMA I&T. In another embodiment the molar ratio of the PSMA I&T to $^{177}$Lu is from 5.0:1.0 to 12.0:1.0.

The absorbed radiation dose from administration of the composition may be measured via SPECT/CT imaging, planar imaging, or a combination thereof, or through other techniques known to those having ordinary skill in the art.

The anatomical coverage of the imaging may extend from the salivary glands to the pelvis of the human patient.

After administration of one of the compositions provided herein, the absorbed radiation dose per gram of tissue in the human patient's kidneys may be from about 0.2 Gy/GBq to about 0.6 Gy/GBq, from about 0.25 Gy/GBq to about 0.55 Gy/GBq, from about 0.3 Gy/GBq to about 0.5 Gy/GBq, or from about 0.35 Gy/GBq to about 0.45 Gy/GBq. In some embodiments, the absorbed radiation dose per gram of tissue in the human patient's kidneys may be ≤0.60 Gy/GBq, ≤0.55 Gy/GBq, ≤0.50 Gy/GBq, ≤0.45 Gy/GBq, ≤0.40 Gy/GBq, ≤0.35 Gy/GBq, ≤0.30 Gy/GBq, ≤0.25 Gy/GBq, ≤0.20 Gy/GBq, or ≤0.15 Gy/GBq.

The molar ratio of PSMA I&T to $^{177}$Lu in the composition may be from about 4.0:1 to about 8.0:1, such as from about 4.5:1 to about 5.5:1, or from about 5.0:1 to about 6.0:1. In some aspects, the composition has a molar ratio of PSMA I&T to $^{177}$Lu of about 4.0:1, about 4.1:1, about 4.2:1, about 4.3:1, about 4.4:1, about 4.5:1, about 4.6:1, about 4.7:1, about 4.8:1, about 4.9:1, about 5.0:1, about 5.1:1, about 5.2:1, about 5.3:1, about 5.4:1, about 5.5:1, about 5.6:1, about 5.7:1, about 5.8:1, about 5.9:1, about 6.0:1, about 6.1:1, about 6.2:1, about 6.3:1, about 6.4:1, about 6.5:1, about 6.6:1, about 6.7:1, about 6.8:1, about 6.9:1, about 7.0:1, about 7.1:1, about 7.2:1, about 7.3:1, about 7.4:1, about 7.5:1, about 7.6:1, about 7.7:1, about 7.8:1, about 7.9:1, or about 8.0:1. In some aspects, the composition has a molar ratio of PSMA I&T to $^{177}$Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

The composition may comprise about 7.1 GBq to about 7.6 GBq of $^{177}$Lu-PSMA I&T. For example, the composition may comprise about 7.1 GBq, about 7.2 GBq, about 7.3 GBq, about 7.4 GBq, about 7.5 GBq, or about 7.6 GBq of $^{177}$Lu-PSMA I&T. In some particular embodiments, the composition may comprise 7.4±15% GBq of $^{177}$Lu-PSMA I&T, 7.4±10% GBq of $^{177}$Lu-PSMA I&T, or 7.4±5% GBq of $^{177}$Lu-PSMA I&T.

In some aspects, the mean absorbed radiation dose per gram of tissue in the human patient's kidneys may be about 0.39±0.15 Gy/GBq, about 0.40±0.15 Gy/GBq, about 0.41±0.15 Gy/GBq, about 0.42±0.15 Gy/GBq, about 0.43±0.15 Gy/GBq, or about 0.45±0.15 Gy/GBq. In some additional aspects, the mean absorbed radiation dose per gram of tissue in the human patient's kidneys may be ≤0.39 Gy/GBq, ≤0.40 Gy/GBq, ≤0.41 Gy/GBq, or ≤0.42 Gy/GBq.

In some aspects, the standard deviation of the mean absorbed radiation dose per gram of tissue in the human patient's kidneys may be ≤0.19 Gy/GBq, ≤0.18 Gy/GBq, ≤0.17 Gy/GBq, ≤0.16 Gy/GBq, or ≤0.15 Gy/GBq.

The absorbed radiation dose per gram of tissue in the human patient's lacrimal glands may be from about 0.01 Gy/GBq to about 1.5 Gy/GBq, such as from about 0.1 Gy/GBq to about 0.8 Gy/GBq. In some embodiments, the absorbed radiation dose per gram of tissue in the human patient's lacrimal glands may be ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq. The absorbed radiation dose may be measured via SPECT/CT imaging, planar imaging, or a combination thereof, or through other techniques known to those having ordinary skill in the art.

In some embodiments, the absorbed radiation dose per gram of tissue in the human patient's lacrimal glands may be about 0.01, about 0.05, about 0.1, about 0.2, about 0.3, about 0.4, about 0.5, about 0.6, about 0.7, about 0.8, about 0.9, about 1.0, about 1.1, about 1.2, about 1.3, about 1.4, or about 1.5 Gy/GBq.

In some embodiments, the mean absorbed radiation dose per gram of tissue in the human patient's lacrimal glands may be 0.37±0.36 Gy/GBq, 0.38±0.36 Gy/GBq, 0.39±0.36 Gy/GBq, or 0.40±0.36 Gy/GBq. In some embodiments, the mean absorbed radiation dose per gram of tissue in the human patient's lacrimal glands may be ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq. In some additional embodiments, the standard deviation of the mean absorbed radiation dose per gram of tissue in the human patient's lacrimal glands may be ≤0.40 Gy/GBq, ≤0.39 Gy/GBq, ≤0.38 Gy/GBq, ≤0.37 Gy/GBq, ≤0.36 Gy/GBq, ≤0.35 Gy/GB, ≤0.34 Gy/GBq, ≤0.33 Gy/GBq, ≤0.32 Gy/GBq, ≤0.31 Gy/GBq, or ≤0.30 Gy/GBq.

After administration of the composition, the absorbed radiation dose per gram of tissue in the human patient's salivary glands may be from about 0.01 Gy/GBq to about 1.0 Gy/GBq, such as from about 0.1 Gy/GBq to about 0.5 Gy/GBq. In some embodiments, the absorbed radiation dose per gram of tissue in the human patient's salivary glands may be ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq.

In some embodiments, the absorbed radiation dose per gram of tissue in the human patient's salivary glands may be from about 0.01, about 0.05, about 0.1, about 0.2, about 0.3, about 0.4, about 0.5, about 0.6, about 0.7, about 0.8, about 0.9, or about 1.0 Gy/GBq.

In some embodiments, the mean absorbed radiation dose per gram of tissue in the human patient's salivary glands may be about 0.17±0.16 Gy/GBq, about 0.18±0.16 Gy/GBq, about 0.19±0.16 Gy/GBq, or about 0.20±0.16 Gy/GBq. In some additional embodiments, the mean absorbed radiation dose per gram of tissue in the human patient's salivary glands may be ≤0.18 Gy/GBq, ≤0.19 Gy/GBq, ≤0.20 Gy/GBq, ≤0.21 Gy/GBq, ≤0.22 Gy/GBq, ≤0.23 Gy/GBq, ≤0.24 Gy/GBq, ≤0.25 Gy/GBq, ≤0.26 Gy/GBq, ≤0.27 Gy/GBq, ≤0.28 Gy/GBq, ≤0.29 Gy/GBq, or ≤0.30 Gy/GBq.

In some embodiments, the standard deviation of the mean absorbed radiation dose per gram of tissue in the human patient's salivary glands may be ≤0.25 Gy/GBq, ≤0.24 Gy/GBq, ≤0.23 Gy/GBq, ≤0.22 Gy/GBq, ≤0.21 Gy/GBq, ≤0.20 Gy/GBq, ≤0.19 Gy/GBq, ≤0.18 Gy/GBq, ≤0.17 Gy/GBq, or ≤0.16 Gy/GBq.

After administration of the composition, the absorbed radiation dose per gram of tissue in the human patient's left colon may be from about 0.01 Gy/GBq to about 1.6 Gy/GBq, such as from about 0.1 Gy/GBq to about 0.8 Gy/GBq. In some aspects, the absorbed radiation dose per gram of tissue in the human patient's left colon may be ≤1.6 Gy/GBq, ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq.

In some embodiments, the absorbed radiation dose per gram of tissue in the human patient's left colon may be about 0.01, about 0.05, about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, or about 1.6 Gy/GBq.

In some embodiments, the mean absorbed radiation dose per gram of tissue in the human patient's left colon may be 0.45±0.31 Gy/GBq, 0.46±0.31 Gy/GBq, or 0.47±0.31 Gy/GBq. In some aspects, the mean absorbed radiation dose per gram of tissue in the human patient's left colon may be ≤0.50 Gy/GBq, ≤0.49 Gy/GBq, ≤0.48 Gy/GBq, ≤0.47 Gy/GBq, ≤0.46 Gy/GBq, ≤0.45 Gy/GBq, ≤0.44 Gy/GBq, ≤0.43 Gy/GBq, ≤0.42 Gy/GBq, ≤0.41 Gy/GBq, or ≤0.40 Gy/GBq.

After administration of the composition, the absorbed radiation dose per gram of tissue in the human patient's rectum may be from about 0.01 Gy/GBq to about 1.5 Gy/GBq, such as from about 0.1 Gy/GBq to about 0.8 Gy/GBq. In some aspects, the absorbed radiation dose per gram of tissue in the human patient's rectum may be ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq.

In some embodiments, the absorbed radiation dose per gram of tissue in the human patient's rectum may be about 0.01, about 0.05, about 0.1, about 0.2, about 0.3, about 0.4, about 0.5, about 0.6, about 0.7, about 0.8, about 0.9, about 1.0, about 1.1, about 1.2, about 1.3, about 1.4, or about 1.5 Gy/GBq.

In some embodiments, the mean absorbed radiation dose per gram of tissue in the human patient's rectum may be 0.50±0.30 Gy/GBq, 0.49±0.30 Gy/GBq, 0.48±0.30 Gy/GBq, 0.47±0.30 Gy/GBq, 0.46±0.30 Gy/GBq, 0.45±0.30 Gy/GBq, 0.44±0.30 Gy/GBq, 0.43±0.30 Gy/GBq, 0.42±0.30 Gy/GBq, 0.41±0.30 Gy/GBq, or 0.40±0.30 Gy/GBq.

After administration of the composition, the fraction of activity of the $^{177}$Lu-PSMA I&T in the whole body of the human patient may be about 0.5 or less within 24 hours, 48 hours, or 168 hours after administration of the composition. In some aspects, the fraction of activity of the $^{177}$Lu-PSMA I&T in the whole body of the human patient may be ≤0.5, ≤0.4, ≤0.3, ≤0.2, or ≤0.1 within 24 hours, 48 hours, or 168 hours after administration of the composition. The activity from administration of the composition may be measured via SPECT/CT imaging, planar imaging, or a combination thereof, or through other techniques known to those having ordinary skill in the art. The anatomical coverage of the imaging may extend from the salivary glands to the pelvis of the human patient.

In some embodiments, the fraction of activity of the $^{177}$Lu-PSMA I&T in the whole body of the human patient may be about 0.5, about 0.4, about 0.3, about 0.2, about 0.1, or less than about 0.1 within 24 hours, 48 hours, or 168 hours after administration of the composition.

In some aspects, the fraction of activity of the $^{177}$Lu-PSMA I&T in the whole body of the human patient may be about 0.4 or less within 48 hours or 168 hours after administration of the composition. For example, the fraction of activity of the $^{177}$Lu-PSMA I&T in the whole body of the human patient may be about 0.4, about 0.3, about 0.2, about 0.1, or less than 0.1 within 48 hours or 168 hours after administration of the composition. In some aspects, the fraction of activity of the $^{177}$Lu-PSMA I&T in the whole body of the human patient may be ≤0.4, ≤0.3, <0.2, or ≤0.1 within 48 hours or 168 hours after administration of the composition.

In some aspects, the fraction of activity of the $^{177}$Lu-PSMA I&T in the whole body of the human patient is about 0.2 or less within 168 hours after administration of the composition.

After administration of the composition, the fraction of activity of the $^{177}$Lu-PSMA I&T in the kidneys of the human patient may be about 0.05 or less within 24 hours, 48 hours, or 168 hours after administration of the composition, such as about 0.04, about 0.03, about 0.02, about 0.01, or less than about 0.01. In some embodiments, the fraction of activity of the $^{177}$Lu-PSMA I&T in the kidneys of the human patient may be ≤0.05, ≤0.04, ≤0.03, ≤0.02, ≤0.01, or less within 24 hours, 48 hours, or 168 hours after administration of the composition.

In some embodiments, the fraction of activity of the $^{177}$Lu-PSMA I&T in the kidneys of the human patient may be ≤0.040, ≤0.03, ≤0.02, ≤0.01, within 48 hours or 168 hours after administration of the composition. In some aspects, the fraction of activity of the $^{177}$Lu-PSMA I&T in the kidneys of the human patient may be about 0.040, about 0.03, about 0.02, about 0.01, or less than about 0.01 within 48 hours or 168 hours after administration of the composition.

In some embodiments, the fraction of activity of the $^{177}$Lu-PSMA I&T in the kidneys of the human patient is about 0.03 or less within 168 hours after administration of the composition, such as about 0.03, about 0.02, about 0.01, or less than about 0.01.

After administration of the composition, the fraction of activity of the $^{177}$Lu-PSMA I&T in the red marrow of the human patient may be about 0.08 or less within 24 hours, 48 hours, or 168 hours after administration of the composition. In some embodiments, the fraction of activity of the $^{177}$Lu-PSMA I&T in the red marrow of the human patient may be ≤0.08, ≤0.07, ≤0.06, ≤0.05, ≤0.04, ≤0.03, ≤0.02, ≤0.01, or less within 24 hours, 48 hours, or 168 hours after administration of the composition.

In some aspects, the fraction of activity of the $^{177}$Lu-PSMA I&T in the red marrow of the human patient may be about 0.08, about 0.07, about 0.06, about 0.05, about 0.04, about 0.03, about 0.02, about 0.01, or less than about 0.01 within 24 hours, 48 hours, or 168 hours after administration of the composition.

In some embodiments, the fraction of activity of the $^{177}$Lu-PSMA I&T in the red marrow of the human patient may be about 0.06 or less within 48 hours or 168 hours after administration of the composition. In some aspects, the fraction of activity of the $^{177}$Lu-PSMA I&T in the red marrow of the human patient may be about 0.06, about 0.05, about 0.04, about 0.03, about 0.02, about 0.01, or less than about 0.01 within 48 hours or 168 hours after administration of the composition. In some aspects, the fraction of activity of the $^{177}$Lu-PSMA I&T in the red marrow of the human patient may be ≤0.06, ≤0.05, ≤0.04, ≤0.03, ≤0.02, ≤0.01, or less within 48 hours or 168 hours after administration of the composition.

In some embodiments, the fraction of activity of the $^{177}$Lu-PSMA I&T in the red marrow of the human patient may be about 0.04 or less within 168 hours after administration of the composition. In some aspects, the fraction of activity of the $^{177}$Lu-PSMA I&T in the red marrow of the human patient may be about 0.04, about 0.03, about 0.02, about 0.01, or less than 0.01 within 168 hours after administration of the composition. In some aspects, the fraction of activity of the $^{177}$Lu-PSMA I&T in the red marrow of the human patient may be ≤0.04, ≤0.03, ≤0.02, ≤0.01, or less within 168 hours after administration of the composition.

After administration of the composition, the fraction of activity of the $^{177}$Lu-PSMA I&T in the salivary glands of the human patient may be about 0.015 or less within 24 hours, 48 hours, or 168 hours after administration of the composition. In some aspects, the fraction of activity of the $^{177}$Lu-PSMA I&T in the salivary glands of the human patient may be ≤0.015, ≤0.014, ≤0.013, ≤0.012, ≤0.011, ≤0.010, ≤0.009, ≤0.008, ≤0.007, ≤0.006, ≤0.005, ≤0.004, ≤0.003, ≤0.002, ≤0.001, or less within 24 hours, 48 hours, or 168 hours after administration of the composition. In some aspects, the fraction of activity of the $^{177}$Lu-PSMA I&T in the salivary glands of the human patient may be about 0.015, about 0.014, about 0.013, about 0.012, about 0.011, about 0.010, about 0.009, about 0.008, about 0.007, about 0.006, about 0.005, about 0.004, about 0.003, about 0.002, about 0.001 or less than about 0.001 within 24 hours, 48 hours, or 168 hours after administration of the composition.

In some embodiments, the fraction of activity of the $^{177}$Lu-PSMA I&T in the salivary glands of the human patient may be about 0.007 or less within 48 hours or 168 hours after administration of the composition. In some aspects, the fraction of activity of the $^{177}$Lu-PSMA I&T in the salivary glands of the human patient may be about 0.007, about 0.006, about 0.005, about 0.004, about 0.003, about 0.002, about 0.001 or less than about 0.001 within 48 hours or 168 hours after administration of the composition. In some aspects, the fraction of activity of the $^{177}$Lu-PSMA I&T in the salivary glands of the human patient may be ≤0.007, ≤0.006, ≤0.005, ≤0.004, ≤0.003, ≤0.002, ≤0.001, or less within 48 hours or 168 hours after administration of the composition.

In some embodiments, the fraction of activity of the $^{177}$Lu-PSMA I&T in the salivary glands of the human patient may be about 0.004 or less within 168 hours after administration of the composition. In some aspects, the fraction of activity of the $^{177}$Lu-PSMA I&T in the salivary glands of the human patient may be about 0.004, about 0.003, about 0.002, about 0.001 or less than about 0.001 within 168 hours after administration of the composition. In some aspects, the fraction of activity of the $^{177}$Lu-PSMA I&T in the salivary glands of the human patient may be ≤0.004, ≤0.003, ≤0.002, ≤0.001, or less within 168 hours after administration of the composition.

After administration of the composition, the fraction of activity of the $^{177}$Lu-PSMA I&T in the gastrointestinal tract of the human patient may be about 0.10 or less within 24 hours, 48 hours, or 168 hours after administration of the composition. In some aspects, the fraction of activity of the $^{177}$Lu-PSMA I&T in the gastrointestinal tract of the human patient may be about 0.10, about 0.09, about 0.08, about 0.07, about 0.06, about 0.05, about 0.04, about 0.03, about 0.02, about 0.01 or less than about 0.01 within 24 hours, 48 hours, or 168 hours after administration of the composition. In some aspects, the fraction of activity of the $^{177}$Lu-PSMA I&T in the gastrointestinal tract of the human patient may be ≤0.10, ≤0.09, ≤0.08, ≤0.07, ≤0.06, ≤0.05, ≤0.04, ≤0.03, ≤0.02, ≤0.01, or less within 24 hours, 48 hours, or 168 hours after administration of the composition.

In some embodiments, the fraction of activity of the $^{177}$Lu-PSMA I&T in the gastrointestinal tract of the human patient may be about 0.10 or less within 48 hours or 168 hours after administration of the composition. In some aspects, the fraction of activity of the $^{177}$Lu-PSMA I&T in the gastrointestinal tract of the human patient may be about 0.10, about 0.09, about 0.08, about 0.07, about 0.06, about 0.05, about 0.04, about 0.03, about 0.02, about 0.01 or less than about 0.01 within 48 hours or 168 hours after administration of the composition. In some aspects, the fraction of activity of the $^{177}$Lu-PSMA I&T in the gastrointestinal tract of the human patient may be ≤0.10, ≤0.09, ≤0.08, ≤0.07, ≤0.06, ≤0.05, ≤0.04, ≤0.03, ≤0.02, ≤0.01, or less within 48 hours or 168 hours after administration of the composition.

In some embodiments, the fraction of activity of the $^{177}$Lu-PSMA I&T in the gastrointestinal tract of the human patient may be about 0.05 or less within 168 hours after administration of the composition. In some aspects, the fraction of activity of the $^{177}$Lu-PSMA I&T in the gastrointestinal tract of the human patient may be about 0.05, about 0.04, about 0.03, about 0.02, about 0.01, or less than about 0.01 within 168 hours after administration of the composition. In some aspects, the fraction of activity of the $^{177}$Lu-PSMA I&T in the gastrointestinal tract of the human patient may be ≤0.05, ≤0.04, ≤0.03, ≤0.02, ≤0.01, or less within 168 hours after administration of the composition.

After administration of the composition, the fraction of activity of the $^{177}$Lu-PSMA I&T in the liver of the human patient may be about 0.04 or less within 24 hours, 48 hours, or 168 hours after administration of the composition. In some aspects, the fraction of activity of the $^{177}$Lu-PSMA I&T in the liver of the human patient may be about 0.04, about 0.03, about 0.02, about 0.01 or less than about 0.01 within 24 hours, 48 hours, or 168 hours after administration of the composition. In some aspects, the fraction of activity of the $^{177}$Lu-PSMA I&T in the liver of the human patient may be ≤0.04, ≤0.03, ≤0.02, ≤0.01, or less within 24 hours, 48 hours, or 168 hours after administration of the composition.

In some embodiments, the fraction of activity of the $^{177}$Lu-PSMA I&T in the liver of the human patient may be about 0.02, about 0.01, or less than 0.01 within 48 hours or 168 hours after administration of the composition. In some aspects, the fraction of activity of the $^{177}$Lu-PSMA I&T in the liver of the human patient may be ≤0.02, ≤0.01, or less within 48 hours or 168 hours after administration of the composition.

In some embodiments, the fraction of activity of the $^{177}$Lu-PSMA I&T in the liver of the human patient may be about 0.01 or less within 168 hours after administration of the composition.

After administration of the composition, the fraction of activity of the $^{177}$Lu-PSMA I&T in the spleen of the human patient may be about 0.004 or less within 24 hours, 48 hours, or 168 hours after administration of the composition. In some aspects, the fraction of activity of the $^{177}$Lu-PSMA I&T in the spleen of the human patient may be about 0.004, about 0.003, about 0.002, about 0.001 or less than about 0.001 within 24 hours, 48 hours, or 168 hours after administration of the composition. In some aspects, the fraction of activity of the $^{177}$Lu-PSMA I&T in the spleen of the human patient may be ≤0.004, ≤0.003, ≤0.002, ≤0.001 or less within 24 hours, 48 hours, or 168 hours after administration of the composition.

In some embodiments, the fraction of activity of the $^{177}$Lu-PSMA I&T in the spleen of the human patient may be about 0.002 or less within 48 hours or 168 hours after administration of the composition. In some aspects, the fraction of activity of the $^{177}$Lu-PSMA I&T in the spleen of the human patient may be about 0.002, about 0.001 or less than about 0.001 within 48 hours or 168 hours after administration of the composition. In some aspects, the fraction of activity of the $^{177}$Lu-PSMA I&T in the spleen of the human patient may be ≤0.002, ≤0.001 or less within 48 hours or 168 hours after administration of the composition.

In some embodiments, the fraction of activity of the $^{177}$Lu-PSMA I&T in the spleen of the human patient is about 0.001 or less within 168 hours after administration of the composition.

After administration of the composition, the fraction of activity of the $^{177}$Lu-PSMA I&T in the lacrimal glands of the human patient may be about 0.0004 or less within 24 hours, 48 hours, or 168 hours after injection of the composition. In some aspects, the fraction of activity of the $^{177}$Lu-PSMA I&T in the spleen of the human patient may be about 0.0004, about 0.0003, about 0.0002, about 0.0001 or less than about 0.0001 within 24 hours, 48 hours, or 168 hours after administration of the composition. In some aspects, the fraction of activity of the $^{177}$Lu-PSMA I&T in the lacrimal glands of the human patient may be ≤0.0004, ≤0.0003, ≤0.0002, ≤0.0001, or less within 24 hours, 48 hours, or 168 hours after injection of the composition.

In some embodiments, the fraction of activity of the $^{177}$Lu-PSMA I&T in the spleen of the human patient may be about 0.0002 or less within 48 hours or 168 hours after administration of the composition. In some aspects, the fraction of activity of the $^{177}$Lu-PSMA I&T in the spleen of the human patient may be about 0.0002, about 0.0001, or less than about 0.0001 within 48 hours or 168 hours after administration of the composition. In some aspects, the fraction of activity of the $^{177}$Lu-PSMA I&T in the spleen of the human patient may be ≤0.0002, ≤0.0001, or less within 48 hours or 168 hours after administration of the composition.

In some embodiments, the fraction of activity of the $^{177}$Lu-PSMA I&T in the spleen of the human patient may be less than 0.0001 within 168 hours after administration of the composition.

Indications and Contraindications

RLT with 177Lu-PSMA I&T may be indicated for the treatment of patients with mCRPC, who do not have any other approved therapy option planned by a multidisciplinary team.

In another embodiment, the method includes administering to the human patient a composition that includes $^{177}$Lu-PSMA I&T. In another embodiment the molar ratio of the PSMA I&T to $^{177}$Lu is from 1.0:1.0 to 12.0:1.0, 3.0:1.0 to 12.0:1.0, 5.0:1.0 to 12.0:1.0. In another embodiment the molar ratio of the PSMA I&T to $^{177}$Lu is from 1.0:1.0 to 8.0:1.0, 1.5:1.0 to 8.0:1.0, 2.0:1.0 to 8.0:1.0, 2.5:1.0 to 8.0:1.0, 3.0:1.0 to 8.0:1.0, 3.5:1.0 to 8.0:1.0, or 4.0:1.0 to 8.0:1.0. In another embodiment the molar ratio of the PSMA I&T to $^{177}$Lu is from 4.1:1.0 to 7.9:1.0, 4.2:1.0 to 7.8:1.0, 4.3:1.0 to 7.7:1.0, 4.4:1.0 to 7.6:1.0, 4.5:1.0 to 7.5:1.0, 4.6:1.0 to 7.4:1.0, 4.7:1.0 to 7.3:1.0, 4.8:1.0 to 7.2:1.0, 4.9:1.0 to 7.1:1.0, or 5.0:1.0 to 7.0:1.0. In another embodiment the molar ratio of the PSMA I&T to $^{177}$Lu is from 5.0:1.0 to 7.6:1.0, 5.1:1.0 to 7.5:1.0, 5.2:1.0 to 7.4:1.0, 5.3:1.0 to 7.3:1.0, or 5.4:1.0 to 7.2:1.0. In another embodiment the molar ratio of the PSMA I&T to $^{177}$Lu is from 8.0:1.0 to 10.0:1.0, 8.1:1.0 to 10.0:1.0, 8.2:1.0 to 10.0:1.0, 8.3:1.0 to 10.0:1.0, 8.4:1.0 to 10.0:1.0, 8.5:1.0 to 10.0:1.0, 8.6:1.0 to 10.0:1.0, 8.7:1.0 to 10.0:1.0, 8.8:1.0 to 10.0:1.0, 8.9:1.0 to 10.0:1.0, 9.0:1.0 to 10.0:1.0, 9.1:1.0 to 10.0:1.0, 9.2:1.0 to 10.0:1.0, 9.3:1.0 to 10.0:1.0, 9.4:1.0 to 10.0:1.0, 9.5:1.0 to 10.0:1.0, 9.6:1.0 to 10.0:1.0, 9.7:1.0 to 10.0:1.0, 9.8:1.0 to 10.0:1.0, or 9.9:1.0 to 10.0:1.0. In another embodiment the molar ratio of the PSMA I&T to $^{177}$Lu is from 8.0:1.0 to 11.0:1.0, 8.1:1.0 to 11.0:1.0, 8.2:1.0 to 11.0:1.0, 8.3:1.0 to 11.0:1.0, 8.4:1.0 to 11.0:1.0, 8.5:1.0 to 11.0:1.0, 8.6:1.0 to 11.0:1.0, 8.7:1.0 to 11.0:1.0, 8.8:1.0 to 11.0:1.0, 8.9:1.0 to 11.0:1.0, 9.0:1.0 to 11.0:1.0, 9.1:1.0 to 11.0:1.0, 9.2:1.0 to 11.0:1.0, 9.3:1.0 to 11.0:1.0, 9.4:1.0 to 11.0:1.0, 9.5:1.0 to 11.0:1.0, 9.6:1.0 to 11.0:1.0, 9.7:1.0 to 11.0:1.0, 9.8:1.0 to 11.0:1.0, 9.9:1.0 to 11.0:1.0, 10.0:1.0 to 11.0:1.0, 10.1:1.0 to 11.0:1.0, 10.2:1.0 to 11.0:1.0, 10.3:1.0 to 11.0:1.0, 10.4:1.0 to 11.0:1.0, 10.5:1.0 to 11.0:1.0, 10.6:1.0 to 11.0:1.0, 10.7:1.0 to 11.0:1.0, 10.8:1.0 to 11.0:1.0, or 10.9:1.0 to 11.0:1.0. The molar ratio of the PSMA I&T to $^{177}$Lu may be from 3.0:1.0 to 12.0:1.0, 3.5:1.0 to 12.0:1.0, 4.0:1.0 to 12.0:1.0, 4.4:1.0 to 12.0:1.0, 4.4:1.0 to 11.5:1.0, 4.4:1.0 to 11.0:1.0, 4.4:1.0 to 10.5:1.0, 4.4:1.0 to 10.0:1.0, 4.4:1.0 to 9.5:1.0, 4.4:1.0 to 9.0:1.0, 4.4:1.0 to 8.5:1.0, 4.4:1.0 to 8.0:1.0, 4.4:1.0 to 7.5:1.0, 4.4:1.0 to 7.0:1.0, 4.4:1.0 to 6.5:1.0, 4.4:1.0 to 6.0:1.0, 4.5:1.0 to 5.9:1.0, 4.6:1.0 to 4.7:1.0, 4.8:1.0 to 5.7:1.0, or 4.9:1.0 to 5.6:1.0. The molar ratio of the PSMA I&T to $^{177}$Lu may be from 5.0:1.0 to 12.0:1.0, 5.0:1.0 to 11.5:1.0, 5.0:1.0 to 11.0:1.0, 5.0:1.0 to 10.5:1.0, 5.0:1.0 to 10.0:1.0, 5.0:1.0 to 9.5:1.0, 5.0:1.0 to 9.0:1.0, 5.0:1.0 to 8.5:1.0, 5.0:1.0 to 8.0:1.0, 5.0:1.0 to 7.5:1.0, 5.0:1.0 to 7.0:1.0, 5.0:1.0 to 6.5:1.0, 5.0:1.0 to 6.0:1.0, 5.1:1.0 to 5.9:1.0, 5.2:1.0 to 5.8:1.0, 5.3:1.0 to 5.7:1.0, 5.4:1.0 to 5.6:1.0, or 5.45:1.0 to 5.55:1.0. The molar ratio of the PSMA I&T to $^{177}$Lu may be from 8.0:1.0 to 12.0:1.0, 8.0:1.0 to 11.5:1.0, 8.0:1.0 to 11.0:1.0, 8.0:1.0 to 10.5:1.0, 8.0:1.0 to 10.4:1.0, 8.0:1.0 to 10.3:1.0, 8.0:1.0 to 10.2:1.0, 8.0:1.0 to 10.1:1.0, 8.0:1.0 to 10.0:1.0, 8.0:1.0 to 9.9:1.0, 8.0:1.0 to 9.8:1.0, 8.0:1.0 to 9.7:1.0, 8.0:1.0 to 9.6:1.0, 8.0:1.0 to 9.5:1.0, 8.0:1.0 to 9.4:1.0, 8.0:1.0 to 9.3:1.0, 8.0:1.0 to 9.2:1.0, 8.0:1.0 to 9.1:1.0, or 8.0:1.0 to 9.0:1.0. The molar ratio of the PSMA I&T to $^{177}$Lu may be from 9.0:1.0 to 12.0:1.0, 9.0:1.0 to 11.5:1.0, 9.0:1.0 to 11.0:1.0, 9.0:1.0 to 10.5:1.0, 9.0:1.0 to 10.4:1.0, 9.0:1.0 to 10.3:1.0, 9.0:1.0 to 10.2:1.0, 9.0:1.0 to 10.1:1.0, 9.0:1.0 to 10.0:1.0, 9.0:1.0 to 9.9:1.0, 9.0:1.0 to 9.8:1.0, 9.0:1.0 to 9.7:1.0, 9.0:1.0 to 9.6:1.0, or 9.0:1.0 to 9.5:1.0.

The molar ratio of the PSMA I&T to $^{177}$Lu may be from 11.0:1.0 to 12.0:1.0, 11.1:1.0 to 11.9:1.0, 11.2:1.0 to 11.8:1.0, 11.3:1.0 to 11.7:1.0, or 11.4:1.0 to 11.6:1.0. The molar ratio of the PSMA I&T to $^{177}$Lu may be from 10.0:1.0 to 11.0:1.0, 10.1:1.0 to 10.9:1.0, 10.2:1.0 to 10.8:1.0, 10.3:1.0 to 10.7:1.0, or 10.4:1.0 to 10.6:1.0. The molar ratio of the PSMA I&T to $^{177}$Lu may be from 9.0:1.0 to 10.0:1.0, 9.1:1.0 to 9.9:1.0, 9.2:1.0 to 9.8:1.0, 9.3:1.0 to 9.7:1.0, or 9.4:1.0 to 9.6:1.0. The molar ratio of the PSMA I&T to $^{177}$Lu may be from 8.0:1.0 to 9.0:1.0, 8.1:1.0 to 8.9:1.0, 8.2:1.0 to 8.8:1.0, 8.3:1.0 to 8.7:1.0, or 8.4:1.0 to 8.6:1.0. The molar ratio of the PSMA I&T to $^{177}$Lu may be from 7.0:1.0 to 8.0:1.0, 7.1:1.0 to 7.9:1.0, 7.2:1.0 to 7.8:1.0, 7.3:1.0 to 7.7:1.0, or 7.4:1.0 to 7.6:1.0. The molar ratio of the PSMA I&T to $^{177}$Lu may be from 6.0:1.0 to 7.0:1.0, 6.1:1.0 to 6.9:1.0, 6.2:1.0 to 7.8:1.0, 7.3:1.0 to 7.7:1.0, or 7.4:1.0 to 6.6:1.0. The molar ratio of the PSMA I&T to $^{177}$Lu may be from 5.0:1.0 to 6.0:1.0, 5.1:1.0 to 5.9:1.0, 5.2:1.0 to 5.8:1.0, 5.3:1.0 to 5.7:1.0, or 5.4:1.0 to 5.6:1.0. The molar ratio of the PSMA I&T to $^{177}$Lu may be from 4.4:1.0 to 5.0:1.0, 4.5:1.0 to 5.0:1.0, 4.6:1.0 to 5.0:1.0, 4.7:1.0 to 5.0:1.0, 4.8:1. to 5.0:1.0, or 4.9:1. to 5.0:1.0.

The molar ratio of the PSMA I&T to $^{177}$Lu may be about 5.0:1.0 to about 5.5:1.0, about 5.5:1.0 to about 6.0:1.0, about 6.0:1.0 to about 6.5:1.0, about 6.5:1.0 to about 7.0:1.0, about 7.0:1.0 to about 7.5:1.0, about 7.5:1.0 to about 8.0:1.0, about 8.0:1.0 to about 8.5:1.0, about 8.5:1.0 to about 9.0:1.0, about 9.0:1.0 to about 9.5:1.0, about 9.5:1.0 to about 10.0:1.0, about 10.0:1.0 to about 10.5:1.0, about 10.5:1.0 to about 11.0:1.0, about 11.0:1.0 to about 11.5:1.0, or about 11.5:1.0 to about 12.0:1.0.

In another embodiment, in the compositions, kits, and methods described herein, the PSMA I&T to [177Lu]Lu3+ ratio in μg:mCi may be ≤0.65, ≤0.64, ≤0.63, ≤0.62, ≤0.61, or ≤0.60. In another embodiment, in the compositions, kits, and methods described herein, the PSMA I&T to [177Lu]Lu3+ ratio in μg:mCi may be from about 0.20 to about 0.64, about 0.20 to about 0.63, about 0.20 to about 0.62, about 0.20 to about 0.61, or about 0.20 to about 0.60. In another embodiment, in the compositions, kits, and methods described herein, the PSMA I&T to [177Lu]Lu3+ ratio in μg:mCi may be from about 0.21 to about 0.59, about 0.22 to about 0.58, about 0.23 to about 0.57, about 0.24 to about 0.56, about 0.25 to about 0.55, about 0.26 to about 0.54, about 0.27 to about 0.53, about 0.28 to about 0.52, about 0.29 to about 0.51, about 0.30 to about 0.50, about 0.31 to about 0.49, about 0.32 to about 0.48, about 0.33 to about 0.47, about 0.34 to about 0.46, about 0.35 to about 0.45, about 0.36 to about 0.44, about 0.37 to about 0.43, about 0.38 to about 0.42, about 0.39 to about 0.41. In another embodiment, in the compositions, kits, and methods described herein, the PSMA I&T to [177Lu]Lu3+ ratio in μg:mCi may be from about 0.50 to about 0.64, about 0.50 to about 0.63, about 0.50 to about 0.62, about 0.50 to about 0.61, about 0.50 to about 0.60, about 0.50 to about 0.59, about 0.50 to about 0.58, about 0.50 to about 0.57, about 0.50 to about 0.56, about 0.50 to about 0.55, about 0.50 to about 0.54, about 0.50 to about 0.53, about 0.50 to about 0.52, or about 0.50 to about 0.51. In another embodiment, in the compositions, kits, and methods described herein, the PSMA I&T to [177Lu]Lu3+ ratio in μg:mCi may be from about 0.40 to about 0.64, about 0.40 to about 0.63, about 0.40 to about 0.62, about 0.40 to about 0.61, about 0.40 to about 0.60, about 0.40 to about 0.59, about 0.40 to about 0.58, about 0.40 to about 0.57, about 0.40 to about 0.56, about 0.40 to about 0.55, about 0.40 to about 0.54, about 0.40 to about 0.53, about 0.40 to about 0.52, about 0.40 to about 0.51, about 0.40 to about 0.50, about 0.40 to about 0.49, about 0.40 to about 0.48, about 0.40 to about 0.47, about 0.40 to about 0.46, about 0.40 to about 0.45, about 0.40 to about 0.44, about 0.40 to about 0.43, about 0.40 to about 0.42, about 0.40 to about 0.41. In another embodiment, in the compositions, kits, and methods described herein, the PSMA I&T to [177Lu]Lu3+ ratio in μg:mCi may be from about 0.35 to about 0.64, about 0.35 to about 0.63, about 0.35 to about 0.62, about 0.35 to about 0.61, about 0.35 to about 0.60, about 0.35 to about 0.59, about 0.35 to about 0.58, about 0.35 to about 0.57, about 0.35 to about 0.56, about 0.35 to about 0.55, about 0.35 to about 0.54, about 0.35 to about 0.53, about 0.35 to about 0.52, about 0.35 to about 0.51, about 0.35 to about 0.50, about 0.35 to about 0.49, about 0.35 to about 0.48, about 0.35 to about 0.47, about 0.35 to about 0.46, about 0.35 to about 0.45, about 0.35 to about 0.44, about 0.35 to about 0.43, about 0.35 to about 0.42, about 0.35 to about 0.41, about 0.35 to about 0.40, about 0.35 to about 0.39, about 0.35 to about 0.38, about 0.35 to about 0.37, or about 0.35 to about 0.36. In another embodiment, in the compositions, kits, and methods described herein, the PSMA I&T to [177Lu]Lu3+ ratio in μg:mCi may be from about 0.30 to about 0.64, about 0.30 to about 0.63, about 0.30 to about 0.62, about 0.30 to about 0.61, about 0.30 to about 0.60, about 0.30 to about 0.59, about 0.30 to about 0.58, about 0.30 to about 0.57, about 0.30 to about 0.56, about 0.30 to about 0.55, about 0.30 to about 0.54, about 0.30 to about 0.53, about 0.30 to about 0.52, about 0.30 to about 0.51, about 0.30 to about 0.50, about 0.30 to about 0.49, about 0.30 to about 0.48, about 0.30 to about 0.47, about 0.30 to about 0.46, about 0.30 to about 0.45, about 0.30 to about 0.44, about 0.30 to about 0.43, about 0.30 to about 0.42, about 0.30 to about 0.41, about 0.30 to about 0.40, about 0.30 to about 0.39, about 0.30 to about 0.38, about 0.30 to about 0.37, about 0.30 to about 0.36, about 0.30 to about 0.35, about 0.30 to about 0.34, about 0.30 to about 0.33, about 0.30 to about 0.32, or about 0.30 to about 0.31. In another embodiment, in the compositions, kits, and methods described herein, the PSMA I&T to [177Lu]Lu3+ ratio in μg:mCi may be from about 0.25 to about 0.64, about 025 to about 0.63, about 0.25 to about 0.62, about 0.25 to about 0.61, about 0.25 to about 0.60, about 0.25 to about 0.59, about 0.25 to about 0.58, about 0.25 to about 0.57, about 0.25 to about 0.56, about 0.25 to about 0.55, about 0.25 to about 0.54, about 0.25 to about 0.53, about 0.25 to about 0.52, about 0.25 to about 0.51, about 0.25 to about 0.50, about 0.25 to about 0.49, about 0.25 to about 0.48, about 0.25 to about 0.47, about 0.25 to about 0.46, about 0.25 to about 0.45, about 0.25 to about 0.44, about 0.25 to about 0.43, about 0.25 to about 0.42, about 0.25 to about 0.41, about 0.25 to about 0.40, about 0.25 to about 0.39, about 0.25 to about 0.38, about 0.25 to about 0.37, about 0.25 to about 0.36, about 0.25 to about 0.35, about 0.25 to about 0.34, about 0.25 to about 0.33, about 0.25 to about 0.32, about 0.25 to about 0.31, about 0.25 to about 0.30, about 0.25 to about 0.29, about 0.25 to about 0.28, about 0.25 to about 0.27, or about 0.25 to about 0.26. In another embodiment, in the compositions, kits, and methods described herein, the PSMA I&T to [177Lu]Lu3+ ratio in μg:mCi may be from about 0.20 to about 0.30.

In an embodiment, a method of treating cancer in a patient in need thereof is provided herein. In another embodiment, the method includes administering to the human patient a composition that includes $^{177}$Lu-PSMA I&T. In another embodiment the molar ratio of the PSMA I&T to $^{177}$Lu is from 5.0:1.0 to 12.0:1.0, such as from about 4.0:1 to about 8.0:1, about 4.5:1 to about 5.5:1, or from about 5.0:1 to about 6.0:1. In another embodiment, the patient is treatment naïve. In another embodiment, the patient is not treatment naïve.

In an embodiment, the pharmaceutical composition is administered to the cancer patient as a first line therapy. In another embodiment, the pharmaceutical composition is administered to the patient as a regimen. In another embodiment, the pharmaceutical composition being administered has a radiochemical purity of greater than 95% at administration.

In an embodiment, the method of treating cancer prolongs a disease progression time of said cancer in a patient in thereof. In another embodiment, the method of treating cancer prolongs a survival of the patient. In another embodiment, the method of treating cancer increases progression-free survival of said patient. In another embodiment, the cancer is metastatic castration-resistant prostate cancer (mCRPC).

In some embodiments, the patient also has histologically or pathologically confirmed prostate adenocarcinoma without predominant small cell component, has progressive disease by one or more of the following criteria: a) Serum/plasma PSA progression defined as 2 consecutive increases in PSA over a previous reference value measured at least 1 week apart with a minimum start value of >2 ng/ml; or b) Progression of measurable disease (RECIST 1.1) or presence of at least two new bone lesions (PCWG3 criteria), and/or has had previous treatment with a next-generation androgen receptor (AR)-directed therapy (e.g. abiraterone, enzalutamide, apalutamide, darolutamide). In additional embodiments, the patient may have effective castration with a serum testosterone level of <50 ng/dL and plan to continue with chronic medical or surgical castration. mCRPC patients should undergo hormone therapy and chemotherapy as well as bone targeted therapy, if indicated.

In at least one example, a patient in need of RLT using $^{177}$Lu-PSMA I&T may fulfill the following criteria:
1) mCRPC with PSMA positive metastatic disease based upon PSMA-PET or SPECT imaging. There are no limitations regarding the number or site of metastases, i.e. bone or soft tissue metastases. Caution should be given to patients e.g. with diffuse bone marrow, perineural and brain metastases.
2) After initial hormone therapy (LH-RH agonists/antagonists). Progressive disease, i.e. biochemical and/or radiologic progression, despite newly developed hormone therapies (Abiraterone/Enzalutamide) or these medications may be avoided by the patient. Progressive disease despite chemotherapy (Docetaxel and Cabazitaxel) or the patient being unfit for chemotherapy or avoiding chemotherapy.
3) Not suitable for $^{153}$Sm-EDTMP or [$^{223}$Ra]RaCl$_2$ or other local available radiopharmaceuticals for bone-targeted therapies due to extra-osseous metastases or diffuse bone marrow metastases or avoided by the patient. In patients without adequate response to bone-targeted therapies for pain palliation or exacerbation of pain even by such therapy, an RLT with $^{177}$Lu-PSMA I&T can be evaluated.
4) Life expectancy longer than 4-6 months.
5) Decision for salvage therapy at the institutional interdisciplinary tumor board.

In summary, mCRPC patients should undergo hormone therapy and chemotherapy as well as bone targeted therapy, if indicated. In the case of any contraindication for one of these therapies, it should be discussed and documented in an interdisciplinary tumor board.

Contraindications are as follows:

$$WBC \leq 1 \times 10^9/l. \tag{1}$$

(2) Hb≤80 g/l. (In the case of symptomatic anemia, a red blood cell transfusion should precede the therapy. RLT with $^{177}$Lu-PSMA I&T may have a positive effect on bone marrow depression, causing the need for less blood to be transfused due to tumor regression in bone marrow. It should be noted that pure anemia without thrombocytopenia and leucopenia is not a contraindication for RLT.)

$$Platelets \leq 70 \times 10^9/l. \tag{3}$$

(4) Creatinine >1.5 UNL; Kidney failure with creatinine clearance <30 mL/min
(5) Absolute obstruction in renal excretion.
(6) Previous chemotherapy or bone-targeted radionuclide therapy and extended external beam irradiation fields to the bone marrow (pelvis, spine), if performed during 4 weeks preceding the RLT
(7) ECOG performance status >2.
(8) Hypersensitivity to the active substance or to any of the excipients.

After a patient in need thereof has been identified, the activity of the radiopharmaceutical composition may be confirmed prior to administration. The radioactivity of the $^{177}$Lu-PSMA I&T composition may be 6.5-7.5 GBq or within a range of 6.0-8.0 GBq. The radioactivity may be reduced to 4.0-5.0 GBq in the case of impaired renal function (e.g. Creatinine within 1.0-1.5 UNL).

The radiopharmaceutical composition solution may be infused intravenously as a slow bolus (over about 10-15 minutes) followed by 500-1000 ml Ringer or NaCl solution. The patient may be encouraged to void as frequently as possible and drink about 2 liters of water daily. Patients with dilated non-obstructive renal disease may be administered diuretics.

The pharmaceutical composition may be administered as 2-11 cycles of the RLT every 5-8 weeks. In the case of continuously increasing PSA, after the first two cycles accompanied by worsening of the general condition, the indication of further RLTs may be re-evaluated. In the case of a decreasing PSA to <1.0 µg/l during the therapy cycles, a PSMA imaging may evaluate existence of small PSMA-positive metastases after completion of RLT when a post injection SPECT study is not enough to be informative. In the case of a significant decline of platelets or leukocytes, the time interval between 2 cycles may be prolonged.

At least one whole body scan 24-48 hours post injection (preferably with SPECT/CT) may be performed. In patients with diffuse bone and bone marrow metastases as well as in patients with brain metastases, a concomitant corticosteroid therapy (e.g. prednisolone 20 mg/daily) may be administered in the first two weeks after administration of the radiopharmaceutical composition.

In some embodiments, after administration of the radiopharmaceutical composition, the patient may have improved radiographic progression free survival (rPFS). A patient administered the radiopharmaceutical composition may have an rPFS of about 6 to about 12 months after initiating administration of the radiopharmaceutical composition. In various embodiments, the patient administered the radiopharmaceutical composition may have an rPFS of at least 6 months, 7 months, 8 months, 9 months, 10 months, 11 months, or 12 months after initiating administration of the radiopharmaceutical composition. For example, treatment of patients with $^{177}$Lu-PSMA I&T may increase the rPFS from 6 months using standard of care to up to 10 months using the radiopharmaceutical composition. Radiographic progression free survival may be defined as the time from randomization to radiographic progression (using PCWG3 and RECIST 1.1 criteria as assessed by blinded independent central review [BICR]) or death due to any cause.

In an embodiment, the patient may have improved overall survival (OS) after initiating administration of the radiopharmaceutical composition. A patient administered the radiopharmaceutical composition may have an overall survival of about 18 to about 26 months after initiating administration of the radiopharmaceutical composition. In various embodiments, the patient administered the radiopharmaceutical composition may have an OS of at least 18 months, 19 months, 20 months, 21 months, 22 months, 23 months, 24 months, 25 months, or 26 months after initiating administration of the radiopharmaceutical composition. For example, treatment of patients with $^{177}$Lu-PSMA I&T may increase the OS from 18 months using standard of care to up to 25 months using the radiopharmaceutical composition.

In another embodiment, the patient may have improved second radiographic progression free survival (rPFS 2) after initiating administration of the radiopharmaceutical composition.

In some embodiments, the patient may have improved progression free survival after initiating administration of the radiopharmaceutical composition. In additional embodiments, the patient may have improved second progression-free survival after initiating administration of the radiopharmaceutical composition. The second progression-free survival may be the second occurrence of PCWG3 progression, clinical/symptomatic progression and/or pain progression, or death due to any cause.

In an embodiment, the patient may have an improved $PSA_{50}$ response rate after initiating administration of the radiopharmaceutical composition. The $PSA_{50}$ response rate may be the response rate of patients who achieve a reduction of ≥50% in PSA from the baseline PSA assessment.

In an embodiment, the patient may have an improved time to first symptomatic skeletal event (SSE) after initiating administration of the radiopharmaceutical composition. An SSE may be the occurrence of either bone-directed radiotherapy to relieve bone pain, new symptomatic pathologic fractures, spinal cord compression, or tumor-related orthopedic surgery.

In an embodiment, the patient may have an improved time to soft tissue progression (STP) after initiating administration of the radiopharmaceutical composition. STP may include the occurrence of radiographic progression in soft tissue. In another embodiment, the patient may have an improved time to chemotherapy (TTC) after initiating administration of the radiopharmaceutical composition.

In an embodiment, the patient may have improved results on a Quality of Life Questionnaire after initiating administration of the radiopharmaceutical composition. For example, the Quality of Life (QoL) may be assessed via European Organisation for Research and Treatment of Cancer Quality of Life Questionnaire C30 (EORTC QLQ-C30). The EORTC QLQ-C30 is a questionnaire of thirty quality of life (QoL) questions developed to assess the QoL of cancer patients. The EORTC QLQ-C30 comprises 30 items, 24 of which are aggregated into nine multi-item scales, which are scored from 0 to 100.

EXAMPLES

The following non-limiting examples are provided for illustrative purposes only, and therefore should not be viewed in a limiting sense.

Example 1: Method of Manufacturing $^{177}$Lu-PSMA I&T Radiopharmaceutical Formulation Multiple radiopharmaceutical compositions were produced using the process as outlined in Table 2A and 2B below. Radiolabeling was performed using non-carrier added [$^{177}$Lu]LuCl$_3$. Compositions 1 and 2 are essentially the same. In Composition 3, the pH of the ascorbic acid solution was adjusted to 4.5, the amount of ascorbic acid was lowered, the amount of ethanol was lowered, and the pH of the final radiopharmaceutical composition was adjusted to 4.5. This resulted in Composition 3 having an extended shelf life as compared to Compositions 1 and 2.

The synthesis of $^{177}$Lu-PSMA I&T utilizes an automated synthesis module in a controlled environment. The labelling solution containing [$^{177}$Lu]Lutetium chloride ([$^{177}$Lu]LuCl$_3$) is connected to the synthesis cassette containing the other chemicals components required for the labeling process. $^{177}$LuCl$_3$ solution is transferred into reactor for radiolabeling and may be rinsed with additional required amount of 0.04 M HCl solution. The labelling solutions varies in volume depending on the $^{177}$Lu radioactivity.

The [$^{177}$Lu]Lu Cl$_3$ solution is mixed in the reaction chamber with a solution of 0.4 M Sodium acetate buffer containing the diluted PSMA I&T precursor. The solution is heated in the reactor. After heating, the produced $^{177}$Lu-PSMA I&T is trapped on a C18 cartridge pre-conditioned with water. The cartridge is rinsed with sterile water and the final product is eluted from the C18 cartridge with 1.5 ml of 50% sterile ethanol-water mixture into a bulk vial. The drug substance is formed in situ and is directly formulated into the drug product.

For final volume adjustment a formulation matrix containing 50 mg/ml ascorbic acid and ethanol in water for injection is added to the bulk vial. The composition of final product is fixed, and the amount of formulation matrix added depends on the radioactivity of $^{177}$Lu used in the batch.

The formulation matrix is prepared from a solution of ascorbic acid that is diluted to 50 mg/ml concentration using water for injection. The ethanol concentration is adjusted to 3.8%±1.0% (v/v) to match the concentration of the synthesis bulk product regardless of the extent of dilution required.

The synthesis is a one-step labelling process with C18 purification using injections grade ethanol and water as the only solvents, therefore no residual solvents are present.

Radiochemical impurities are quantified by chromatographical methods (HPLC and TLC). Radiochemical purity determined by HPLC must not be less than 95.0%

Depending on the total produced radioactivity the bulk product is diluted to a fixed radioactivity concentration of about 500 MBq/ml.

The solution is filtered through a 0.22 μm membrane filter into sterile product vials. In addition to patient doses, sample vials are also dispensed from each production batch (chemical QC sample, microbiological QC sample, and a reference sample for retention). The final product is dispensed in a Grade A controlled environment. The integrity of the filters is tested after filtration by performing a bubble point test prior to product release. The fill weight/volume and radioactivity is checked for dispensed patient vials. The solution is ready for use after pre-release quality control and QP release.

Radioactivity is monitored with a dose calibrator after the labelling process in order to ensure successful labelling and during dispensing to verify dispensed doses.

TABLE 2A

Radiolabeling Process

| | Process 1 | Process 2 | Process 3 | Process 4 |
|---|---|---|---|---|
| Lu-177 | 40 GBq/ml in 0.04M HCl | 40 GBq/ml in 0.04M HCl | ~40 GBq/ml in 0.05M HCl | 5500-15200 mCi |
| PSMA-I&T precursor | 1 000 μg/ml | 463 μg/ml | 463 μg/ml | 1000 μg/mL |
| Reaction Buffer | 4 ml 0.4M Sodium Acetate 2 ml 0.04M HCl (0.08 mmol HCl) 150 μl 20% L-ascorbic acid | 4 ml 0.4M Sodium Acetate 2 ml 0.04M HCl (0.08 mmol HCl) 150 μl 20% L-ascorbic acid | 4 ml 0.4M Sodium Acetate 1.6 ml 0.05M HCl (0.08 mmol HCl) 150 μl 20 % L-ascorbic acid | 82 mg/mL Sodium Ascorbate |
| Reaction Volume | 6-8 ml | 6-8 ml | 6-8 ml | Dependent on reaction scale; 16 mL maximum |
| Heating | Setpoint 110° C., 15 min | Setpoint 110° C., 15 min | Setpoint 110° C., 15 min | 85° C., 10 min |
| Purification | Sep Pak C18 | Sep Pak C18 | Sep Pak C18 | N/A |
| Elution | 1.5 ml Ethanol-Water 1:1 | 1.5 ml Ethanol-Water 1:1 | 1.5 ml Ethanol-Water 1:1 | N/A |
| Cassette flush | 8.5 ml Ascorbic acid 50 mg/ml (pH 5.5-7.0) | 8.5 ml Ascorbic acid 50 mg/ml (pH 5.5-7.0) | 50 mg/ml, pH 4.5 8.5 ml Ascorbic acid 50 mg/ml, pH 4.5 | N/A |
| Formulation buffer | 42.5 mg/ml ascorbic acid, 7.5% Ethanol (v/v %), pH 5.5-7.0 | 42.5 mg/ml ascorbic acid, 7.5% Ethanol (v/v %), pH 5.5-7.0 | 31 mg/ml ascorbic acid, 3.8% Ethanol (v/v %), pH 4.5 | 33.0 mg/mL sodium ascorbate; 0.1 mg/mL DTPA; pH 4.25 |

The resulting Compositions 1-3 from Processes 1-3 are provided below in Table 2B, which provides the compositions for both a 1 ml volume and a vial of 10 ml or 20 ml for each composition.

TABLE 2B

[$^{177}$Lu]Lu-PSMA I&T compositions 1-3.

| | Compositions 1 and 2 | | Composition 3 | | |
|---|---|---|---|---|---|
| Component | Quantity per mL | Quantity/ 10 mL vial | Quantity per mL | Quantity/ 20 mL vial | Function |
| $^{177}$Lu-PSMA I&T | 1 GBq (27 mCi) | 10 GBq (270 mCi) | 0.5 GBq (13.5 mCi) | 10 GBq (270 mCi) | Radioactive pharmaceutical ingredient (exact activity/volume adjusted according to dose strength) |

TABLE 2B-continued

[¹⁷⁷Lu]Lu-PSMA I&T compositions 1-3.

| Component | Compositions 1 and 2 | | Composition 3 | | Function |
|---|---|---|---|---|---|
| | Quantity per mL | Quantity/ 10 mL vial | Quantity per mL | Quantity/ 20 mL vial | |
| Lu-PSMA I&T and related substances | <12 μg | <80 μg | <6 μg | <80 μg | Mass of pharmaceutical ingredient |
| Ascorbic acid | 42.5 mg | 425 mg | 31 mg | 620 mg | Radioprotectant |
| Disodium EDTA | 21 μg | 210 μg | 15.5 μg | 310 μg | Metal scavenger |
| Sodium Bicarbonate | A sufficient quantity | A sufficient quantity | A sufficient quantity | A sufficient quantity | Present in formulated Ascorbic acid Injection (USP) in sufficient amounts to control pH to 5.5-7.0 |
| NaOH | A sufficient quantity | A sufficient quantity | A sufficient quantity | A sufficient quantity | |
| Hydrochloric acid | None | None | 1.7 mg/ml * | 34 mg/ml * | *Theoretical amount. Added to adjust final formulation pH to 4.5 |
| Ethanol | 75 μL (58.9 mg) | 750 μL (589 mg) | 37.5 μL (29.5 mg) | 750 μL (589 mg) | Stabilizing agent |
| Water for Injection | Sufficient to make 1 mL | Sufficient to make 10 mL | Sufficient to make 1 mL | Sufficient to make 20 mL | Vehicle |

Example 2: Stability of the Radiochemical Compositions

Stability of ¹⁷⁷Lu-PSMA I&T composition 1 was tested and the radiochemical purity and chemical properties were shown to provide adequate stability of 48 hours from the end-of-synthesis time for samples stored at +5° C., +20° C. and +40° C., Table 3.

Stability studies show that [¹⁷⁷Lu]Lu-PSMA I&T composition 3 (Tables 4A-H) comprising ascorbic acid 31 mg/ml and ethanol 3.8% (v/v) at a pH of 4.5 had improved stability and extended shelf life compared to [¹⁷⁷Lu]Lu-PSMA I&T composition 1.

The radiochemical purity and chemical properties (pH, impurities, visual properties) of [¹⁷⁷Lu]Lu-PSMA I&T in the formulation composition 3 were tested on the seven batches over a time span of 70 to 72 hours from the end-of-synthesis time. Stability samples of typical therapeutic dose radioactivity and volume were stored in different conditions covering typical storage, shipment and usage of the product, including temperatures ranging from +5 C to +40° C.

Final radioactivity concentration in the sample solutions varied from 497 MBq/ml to 642 MBq/ml at the end of dispensing.

All stability samples met the set acceptance criteria. Radiochemical purity was ≥95,7% after 70 hours or 72 hours after end of synthesis time in all samples analyzed.

Based on the results ¹⁷⁷Lu-PSMA I&T solution in formulation composition 3 was stable under the different storage conditions tested.

TABLE 3

Stability Data of ¹⁷⁷Lu-PSMA I&T Composition 1.

| Stability criteria | | Stability data at 48 h after end of synthesis | | | | |
|---|---|---|---|---|---|---|
| Test | Specification | Batch #1 | Batch #2 | Batch #3, +5° C. | Batch #3, +20° C. | Batch #3, +40° C. |
| Visual inspection | Clear, colorless or slightly yellow liquid, no visible particles | Pass | Pass | Pass | Pass | Pass |
| pH | 5.0-8.0 | 6.0 | 5.5 | 6.0 | 6.0 | 5.5 |
| Radiochemical Purity (HPLC), % | ≥95, 0% as ¹⁷⁷Lu-PSMA I&T | 97.4% | 96.2% | 95.6% | 96.1 | 95.1% |
| Radiochemical Purity by TLC, % | ¹⁷⁷Lu-colloid ≤5.0% of radioactivity | 0% | 0% | 0% | 0% | 0% |
| Chemical purity Lu-PSMA I&T | Lu-PSMA I&T-concentration ≤12.0 μg/ml | 1.6 μg/ml | 2.2 μg/ml | 1.9 μg/ml | 1.8 μg/ml | 1.8 μg/ml |

TABLE 4A

Chemical Quality in the Validation Batches of $^{177}$Lu-PSMA I&T Composition 3.

| Quality Attribute | | VALIDATION BATCH # | | |
|---|---|---|---|---|
| Test | Specification | 1 | 2 | 3 |
| Visual inspection | Clear, colorless to yellow solution, no visible particles | Pass | Pass | Pass |
| Radiochemical Identity | Co-elutes with reference standard † | Pass | Pass | Pass |
| pH | 4.0-5.0 | 4.5 | 4.5 | 4.5 |
| Radionuclidic Identification keV | Gamma ray energy 113 ± 2 keV 208 ± 4 keV (HPGe-detector) No other significant peaks with gamma energy >100 keV are detected | 113 keV and 209 keV no other significant peaks detected | 113 keV and 209 keV no other significant peaks detected | 113 keV and 209 keV no other significant peaks detected |
| Radiochemical Purity (HPLC), % | ≥95.0% as $^{177}$Lu-PSMA I&T | 98.2% | 98.2% | 97.9% |
| Radiochemical Purity by TLC, % | $^{177}$Lu-colloid ≤5.0% of radioactivity | 0% | 0% | 0% |
| Ethanol content, % (v/v) (GC) | 2.5-4.5% | 3.5% | 3.5% | 3.2% |
| Chemical purity Lu-PSMA I&T | Lu-PSMA I&T-concentration ≤6.0 μg/ml | 1.2 μg/ml | 1.2 μg/ml | 1.2 μg/ml |
| $^{177}$Lu-PSMA-I&T Specific activity | Reported | 271 GBq/μmol | 275 GBq/μmol | 191 GBq/μmol |
| Ascorbic acid concentration mg/ml | 15-35 mg/ml | 25 mg/ml | 25 mg/ml | 25 mg/ml |
| Radionuclidic purity | ≥99.9 % of the total activity of $^{177}$Lu | 100.0% | 100.0% | 100.0% |
| Bacterial endotoxins EU/ml | <175 EU/20 ml (measured <8.75 (EU/ml)) | <5.00 EU/ml | <5.00 EU/ml | <5.00 EU/ml |
| Filter integrity test | ≥3.32 bar tested with water | Pass | Pass | Pass |
| Sterility | Sterile | Pass | Pass | Pass |

† The radiometric RT of the test sample = UV RT of Reference Standard ± 5%.

TABLE 4B

Stability Data of $^{177}$Lu-PSMA I&T Composition 3.

| | | STABILITY BATCH #1 70 h post End of Synthesis | | | |
|---|---|---|---|---|---|
| VIAL # | | 1 | 2 | 3 | 4 |
| Radioactivity | | 9430 MBq | 9440 MBq | 9440 MBq | 9430 MBq |
| Fill Volume | | 18.04 ml | 18.10 ml | 18.07 ml | 18.03 ml |
| Storage Condition | | +22.5° C. | +32.5° C. | +22.5° C./ Inverted | +22.5° C. |

QC TESTING

| Validation criteria Test | Specification | | | | |
|---|---|---|---|---|---|
| Visual inspection | Clear, colorless to yellow solution, no visible particles | Pass | Pass | Pass | Pass |
| Radio-chemical Identity | Co-elutes with reference standard † | Pass | Pass | Pass | Pass |
| pH | 4.0-5.0 | 4.5 | 4.5 | 4.5 | 4.5 |
| Radio-nuclidic Identification keV | Gamma ray energy 113 ± 2 keV 208 ± 4 keV (HPGe-detector) No other significant peaks with gamma energy >100 keV are detected | 113 keV and 209 keV no other significant peaks detected | 113 keV and 209 keV no other significant peaks detected | 113 keV and 209 keV no other significant peaks detected | 113 keV and 209 keV no other significant peaks detected |
| Radio-chemical Purity (HPLC), % | ≥95.0% as $^{177}$Lu-PSMA I&T | 96.7% | 96.2% | 95.9% | 96.0% |
| Radio-chemical Purity by TLC, % | $^{177}$Lu-colloid ≤5.0% of radioactivity | 0% | 0% | 0% | 0% |
| Ethanol content, % (v/v) (GC) | 2.5-4.5% | N/A | N/A | N/A | N/A |
| Chemical purity Lu-PSMA I&T | Lu-PSMA I&T-concentration ≤6.0 µg/ml | 1.3 µg/ml | 1.3 µg/ml | 1.2 µg/ml | 1.3 µg/ml |
| Ascorbic acid concentration mg/ml | 15-35 mg/ml | 25 mg/ml | 25 mg/ml | 25 mg/ml | 25 mg/ml |

† The radiometric RT of the test sample = UV RT of Reference Standard ±5%.

TABLE 4C

Stability Data of $^{177}$Lu-PSMA I&T Composition 3.

| | | STABILITY BATCH #2 72 h post End of Synthesis | | | |
|---|---|---|---|---|---|
| VIAL # | | 1 | 2 | 3 | 4 |
| Radioactivity | | 9650 MBq | 9550 MBq | 9540 MBq | 9540 MBq |
| Fill Volume | | 15.02 ml | 14.86 ml | 14.86 ml | 14.87 ml |
| Storage Condition | | +22.5° C. | +32.5° C. | +22.5° C./ Inverted | +22.5° C. |

QC TESTING

| Validation criteria Test | Specification | | | | |
|---|---|---|---|---|---|
| Visual inspection | Clear, colorless to yellow solution, no visible particles | Pass | Pass | Pass | Pass |
| Radio-chemical Identity | Co-elutes with reference standard † | Pass | Pass | Pass | Pass |
| pH | 4.0-5.0 | 4.5 | 4.5 | 4.5 | 4.5 |
| Radio-nuclidic Identification keV | Gamma ray energy 113 ± 2 keV 208 ± 4 keV (HPGe-detector) No other significant peaks with gamma energy >100 keV are detected | 113 keV and 209 keV no other significant peaks detected | 113 keV and 209 keV no other significant peaks detected | 113 keV and 209 keV no other significant peaks detected | 113 keV and 209 keV no other significant peaks detected |
| Radio-chemical Purity (HPLC), % | ≥95.0% as $^{177}$Lu-PSMA I&T | 96.0% | 95.7% | 96.1% | 96.1% |
| Radio-chemical Purity by TLC, % | $^{177}$Lu-colloid ≤5.0% of radioactivity | 0% | 0% | 0% | 0% |
| Ethanol content, % (v/v) (GC) | 2.5-4.5% | N/A | N/A | N/A | N/A |
| Chemical purity Lu-PSMA I&T | Lu-PSMA I&T-concentration ≤6.0 µg/ml | 1.2 µg/ml | 1.2 µg/ml | 1.2 µg/ml | 1.1 µg/ml |
| Ascorbic acid concentration mg/ml | 15-35 mg/ml | 25 mg/ml | 25 mg/ml | 25 mg/ml | 25 mg/ml |

† The radiometric RT of the test sample = UV RT of Reference Standard ±5%.

TABLE 4D

Stability Data of $^{177}$Lu-PSMA I&T composition 3.

STABILITY BATCH #3 — 72 h post End of Synthesis

| | | VIAL # 1 | 2 | 3 | 4 |
|---|---|---|---|---|---|
| Radioactivity | | 9840 MBq | 9540 MBq | 9530 MBq | 9530 MBq |
| Fill Volume | | 17.51 ml | 17.01 ml | 16.99 ml | 16.98 ml |
| Storage Condition | | +22.5° C. | +32.5° C. | ≥75% RH (Ambient) | +5° C. |

QC TESTING

| Test | Validation criteria Specification | 1 | 2 | 3 | 4 |
|---|---|---|---|---|---|
| Visual inspection | Clear, colorless to yellow solution, no visible particles | Pass | Pass | Pass | Pass |
| Radio-chemical Identity | Co-elutes with reference standard † | Pass | Pass | Pass | Pass |
| pH | 4.0-5.0 | 4.5 | 4.5 | 4.5 | 4.5 |
| Radio-nuclidic Identification keV | Gamma ray energy 113 ± 2 keV 208 ± 4 keV (HPGe-detector) No other significant peaks with gamma energy >100 keV are detected | 113 keV and 209 keV no other significant peaks detected | 113 keV and 209 keV no other significant peaks detected | 113 keV and 209 keV no other significant peaks detected | 113 keV and 209 keV no other significant peaks detected |
| Radio-chemical Purity (HPLC), % | ≥95.0% as $^{177}$Lu-PSMA I&T | 95.8% | 96.0% | 96.1% | 96.0% |
| Radio-chemical Purity by TLC, % | $^{177}$Lu-colloid ≤5.0% of radioactivity | 0% | 0% | 0% | 0% |
| Ethanol content, % (v/v) (GC) | 2.5-4.5% | N/A | N/A | N/A | N/A |
| Chemical purity Lu-PSMA I&T | Lu-PSMA I&T-concentration ≤6.0 μg/ml | 1.0 μg/ml | 0.9 μg/ml | 1.0 μg/ml | 1.0 μg/ml |
| Ascorbic acid concentration mg/ml | 15-35 mg/ml | 15 mg/ml | 15 mg/ml | 15 mg/ml | 15 mg/ml |

† The radiometric RT of the test sample = UV RT of Reference Standard ±5%.

TABLE 4E

Stability Data of $^{177}$Lu-PSMA I&T composition 3.

STABILITY BATCH #4 — 72 h post End of Synthesis

| Test | Validation criteria Specification | VIAL # 1 | 2 | 3 | 4 | 5 |
|---|---|---|---|---|---|---|
| Radioactivity | | 9490 MBq | 9600 MBq | 9600 MBq | 9600 MBq | 9590 MBq |
| Fill Volume | | 17.19 ml | 17.42 ml | 17.45 ml | 17.44 ml | 17.42 ml |
| Storage Condition | | +22.5° C. | +32.5° C. | +40° C. | +5° C. | +5° C. |
| QC TESTING | | | | | | |
| Visual inspection | Clear, colorless to yellow solution, no visible particles | Pass | Pass | Pass | Pass | Pass |
| Radiochemical Identity | Co-elutes with reference standard † | Pass | Pass | Pass | Pass | Pass |
| pH | 4.0-5.0 | 4.5 | 4.5 | 4.5 | 4.5 | 4.5 |
| Radionuclidic Identification keV | Gamma ray energy 113 ± 2 keV 208 ± 4 keV (HPGe-detector) No other significant peaks with gamma energy >100 keV are detected | 113 keV and 209 keV no other significant peaks detected | 113 keV and 209 keV no other significant peaks detected | 113 keV and 209 keV no other significant peaks detected | 113 keV and 209 keV no other significant peaks detected | 113 keV and 209 keV no other significant peaks detected |

TABLE 4E-continued

Stability Data of $^{177}$Lu-PSMA I&T composition 3.

| STABILITY BATCH #4 | | 72 h post End of Synthesis | | | | |
|---|---|---|---|---|---|---|
| VIAL # | | 1 | 2 | 3 | 4 | 5 |
| Radiochemical Purity (HPLC), % | ≥95.0% as $^{177}$Lu-PSMA I&T | 96.5% | 95.9% | 95.8% | 96.3% | 96.6% |
| Radiochemical Purity by TLC, % | $^{177}$Lu-colloid ≤5.0% of radioactivity | 0% | 0% | 0% | 0% | 0% |
| Ethanol content, % (v/v) (GC) | 2.5-4.5% | N/A | N/A | N/A | N/A | N/A |
| Chemical purity Lu-PSMA I&T | Lu-PSMA I&T-concentration ≤6.0 µg/ml | 1.0 µg/ml | 1.0 µg/ml | 1.0 µg/ml | 1.0 µg/ml | 1.0 µg/ml |
| Ascorbic acid concentration mg/ml | 15-35 mg/ml | 25 mg/ml | 25 mg/ml | 25 mg/ml | 25 mg/ml | 25 mg/ml |

† The radiometric RT of the test sample = UV RT of Reference Standard ±5%.

TABLE 4F

Stability Data of $^{177}$Lu-PSMA I&T Composition 3.

| | | STABILITY BATCH #5 72 h post End of Synthesis | | | |
|---|---|---|---|---|---|
| VIAL # | | 1 | 2 | 3 | 4 |
| Radioactivity | | 9930 MBq | 9800 MBq | 9800 MBq | 9810 MBq |
| Fill Volume | | 19.91 ml | 19.69 ml | 19.68 ml | 19.73 ml |
| Storage Condition | | +22.5° C. | +32.5° C. | +5° C. | +5° C. |
| QC TESTING | | | | | |
| Validation criteria Test | Specification | | | | |
| Visual inspection | Clear, colorless to yellow solution, no visible particles | Pass | Pass | Pass | Pass |
| Radiochemical Identity | Co-elutes with reference standard † | Pass | Pass | Pass | Pass |
| pH | 4.0-5.0 | 4.5 | 4.5 | 4.5 | 4.5 |
| Radionuclidic Identification keV | Gamma ray energy 113 ± 2 keV 208 ± 4 keV (HPGe-detector) No other significant peaks with gamma energy >100 keV are detected | 113 keV and 209 keV no other significant peaks detected | 113 keV and 209 keV no other significant peaks detected | 113 keV and 209 keV no other significant peaks detected | 113 keV and 209 keV no other significant peaks detected |
| Radiochemical Purity (HPLC), % | ≥95.0% as $^{177}$Lu-PSMA I&T | 97.0% | 97.0% | 96.8% | 97.3% |
| Radiochemical Purity by TLC, % | $^{177}$Lu-colloid ≤5.0% of radioactivity | 0% | 0% | 0% | 0% |
| Ethanol content, % (v/v) (GC) | 2.5-4.5% | N/A | N/A | N/A | N/A |
| Chemical purity Lu-PSMA I&T | Lu-PSMA I&T-concentration ≤6.0 µg/ml | 0.9 µg/ml | 0.9 µg/ml | 0.9 µg/ml | 0.9 µg/ml |
| Ascorbic acid concentration mg/ml | 15-35 mg/ml | 25 mg/ml | 25 mg/ml | 25 mg/ml | 25 mg/ml |

† The radiometric RT of the test sample = UV RT of Reference Standard ±5%.

TABLE 4G

Stability Data of $^{177}$Lu-PSMA I&T Composition 3.

| | | STABILITY BATCH #6 72 h post End of Synthesis | |
|---|---|---|---|
| VIAL # | | 1 | 4 * |
| Radioactivity | | 9960 MBq | 9800 MBq |
| Fill Volume | | 19.69 ml | 19.40 ml |
| Storage Condition | | +22.5° C. | +40° C. |
| QC TESTING | | | |
| Validation criteria Test | Specification | | |
| Visual inspection | Clear, colorless to yellow solution, no visible particles | Pass | Pass |
| Radiochemical Identity | Co-elutes with reference standard † | Pass | Pass |
| PH | 4.0-5.0 | 4.5 | 4.5 |
| Radionuclidic Identification keV | Gamma ray energy 113 ± 2 keV 208 ± 4 keV (HPGe-detector) No other significant | 113 keV and 209 keV no other significant peaks | 113 keV and 209 keV no other significant peaks |

TABLE 4G-continued

Stability Data of $^{177}$Lu-PSMA I&T Composition 3.

| | | | |
|---|---|---|---|
| | peaks with gamma energy >100 keV are detected | detected | detected |
| Radiochemical Purity (HPLC), % | ≥95.0% as $^{177}$Lu-PSMA I&T | 96.7% | 95.8% |
| Radiochemical Purity by TLC, % | $^{177}$Lu-colloid ≤5.0% of radioactivity | 0% | 0% |
| Ethanol content, % (v/v) (GC) | 2.5-4.5% | N/A | N/A |
| Chemical purity Lu-PSMA I&T | Lu-PSMA I&T-concentration ≤6.0 µg/ml | 1.0 µg/ml | 1.0 µg/ml |
| Ascorbic acid concentration mg/ml | 15-35 mg/ml | 25 mg/ml | 25 mg/ml |

† The radiometric RT of the test sample = UV RT of Reference Standard ±5%.

TABLE 4H

Stability Data of $^{177}$Lu-PSMA I&T composition 3.

| | STABILITY BATCH #7 72 h post End of Synthesis | | |
|---|---|---|---|
| VIAL # | 1 | 2 | 3 |
| Radioactivity | 9870 MBq | 9880 MBq | 9910 MBq |
| Fill Volume | 19.31 ml | 19.34 ml | 19.43 ml |
| Storage Condition | +22.5° C/ Inverted | +32.5° C/ Inverted | +5° C./ Inverted |

QC TESTING

| Validation criteria Test | Specification | | | |
|---|---|---|---|---|
| Visual inspection | Clear, colorless to yellow solution, no visible particles | Pass | Pass | Pass |
| Radio-chemical Identity | Co-elutes with reference standard † | Pass | Pass | Pass |
| pH | 4.0-5.0 | 4.5 | 4.5 | 4.5 |
| Radio-nuclidic Identification keV | Gamma ray energy 113 ± 2 keV 208 ± 4 keV (HPGe-detector) No other significant peaks with gamma energy >100 keV are detected | 113 keV and 209 keV no other significant peaks detected | 113 keV and 209 keV no other significant peaks detected | 113 keV and 209 keV no other significant peaks detected |
| Radiochemical Purity (HPLC), % | ≥95.0% as $^{177}$Lu-PSMA I&T | 96.5% | 96.4% | 96.3% |
| Radiochemical Purity by TLC, % | $^{177}$Lu-colloid ≤5.0% of radioactivity | 0% | 0% | 0% |
| Ethanol content, % (v/v) (GC) | 2.5-4.5% | N/A | N/A | N/A |

TABLE 4H-continued

Stability Data of $^{177}$Lu-PSMA I&T composition 3.

| | | | | |
|---|---|---|---|---|
| Chemical purity Lu-PSMA I&T | Lu-PSMA I&T-concentration ≤6.0 µg/ml | 1.0 µg/ml | 0.9 µg/ml | 1.0 µg/ml |
| Ascorbic acid concentration mg/ml | 15-35 mg/ml | 25 mg/ml | 25 mg/ml | 25 mg/ml |

† The radiometric RT of the test sample = UV RT of Reference Standard ±5%.

TABLE 4I

Release Data from Composition 4 Commercial Scale Development Batches

| Characteristics | Specification (Composition 4) | 8017-PD15 | 8017-PD16 | 8017-PD17 |
|---|---|---|---|---|
| Appearance | Clear, colorless to yellow solution without visible particles | Pass | Pass | Pass |
| pH | 4.0-4.5 | 4.2 | 4.2 | 4.2 |
| Ascorbic Acid | 28-38 mg/mL | 32 | 33 | 35 |
| Ethanol | N/A | N/A | N/A | N/A |
| Radionuclidic identification | Gamma ray energy 113 ± 1 keV and 208 ± 1 keV | 113 keV and 209 keV no other significant peaks detected | 113 keV and 209 keV no other significant peaks detected | 113 keV and 209 keV no other significant peaks detected |
| Radiochemical Identity | Relative retention time of 0.70 to 0.75 compared to PSMA I&T in HPLC standard | Pass | Pass | Pass |
| Radiochemical purity by HPLC method | Not less than (NLT, ≤) 95% | 96 | 97 | 97 |
| Radiochemical purity by TLC method | N/A | N/A | N/A | N/A |
| Unbound [$^{177}$Lu]lutetium | Not more than (NMT, ≥) 1% | 0% | 0% | 0% |
| PSMA I&T Content | 3.0-8.0 µg/mL | 4.5 | 5.0 | 5.0 |
| Radionuclidic purity | Not less than (NLT, ≥) 99.9% [$^{177}$Lu]Lu$^{3+}$ | 100% | 100% | 100% |
| $^{177}$Lu-PSMA-I&T Specific activity | N/A | N/A | N/A | N/A |
| Apparent Molar Activity | 2.0-7.0 mCi/nmol | 4.9 | 4.4 | 4.5 |
| Endotoxins | 11.7 EU/mL | N/A | N/A | N/A |
| Radioactivity Concentration | 12.0-14.6 mCi/mL | 13.2 | 13.3 | 13.4 |
| Sterility | Sterile | N/A | N/A | N/A |

TABLE 4J

Stability data from composition 4

| Characteristics | Specification (Composition 4) | 8017-PD15 | 8017-PD16 | 8017-PD17 |
|---|---|---|---|---|
| pH | 4.0-4.5 | 4.3 | 4.2 | 4.2 |
| Ascorbic Acid | 28-38 mg/mL | 32 | 33 | 34 |
| Radiochemical purity by HPLC method | Not less than (NLT, ≤) 95% | 95 | 95 | 95 |
| Unbound [$^{177}$Lu]lutetium | Not more than (NMT, ≥) 1% | 0% | 0% | 0% |
| PSMA I&T Content | 3.0-8.0 µg/mL | 4.5 | 4.8 | 5.0 |
| Apparent Molar Activity | 2.0-7.0 mCi/nmol | 4.9 | 4.6 | 4.5 |
| Stability Testing Time | >72 hours | 72 | 72 | 96 |

Specifications for the [$^{177}$Lu]Lu-PSMA I&T solution are presented in the Table 5 below. The specifications listed were used as release parameters except for sterility testing. Sterility was tested on all batches post-release.

TABLE 5

Specifications for [$^{177}$Lu]Lu-PSMA I&T

| Characteristics | Specification (Composition 1) | Specification (Composition 3) | Specification (Composition 4) |
|---|---|---|---|
| Appearance | Clear, colorless or slightly yellow liquid, no visible particles | Clear, colorless or slightly yellow liquid, no visible particles | Clear, colorless to yellow solution without visible particles |
| pH | 5.0-8.0 | 4.0-5.0 | 4.0-4.5 |
| Ascorbic Acid | 20-70 mg/ml | 15-35 mg/ml | 28-38 mg/mL |
| Ethanol | 5.0% to 8.0% | 2.5% to 4.5% | N/A |
| Radionuclidic identification | Gamma ray energy 113 ± 10 keV and 208 ± 12 keV | Gamma ray energy 113 ± 10 keV and 208 ± 12 keV | Gamma ray energy 113 ± 1 keV and 208 ± 1 keV |
| Radiochemical Identity | The radiometric RT of the test sample = UV RT of Reference Standard ±5%. | The radiometric RT of the test sample = UV RT of Reference Standard ±5%. | Relative retention time of 0.70 to 0.75 compared to PSMA I&T in HPLC standard |
| Radiochemical purity by HPLC method | ≥95.0% | ≥95.0% | Not less than (NLT, ≤) 95% |
| Radiochemical purity by TLC method | $^{177}$Lu-colloid ≤5.0% | $^{177}$Lu-colloid ≤5.0% | N/A |
| Unbound [$^{177}$Lu]lutetium | N/A | N/A | Not more than (NMT, ≥) 1% |
| PSMA I&T Content | Lu-PSMA I&T-concentration ≤12.0 µg/mL | Lu-PSMA I&T-concentration ≤12.0 µg/mL | 3.0-8.0 µg/mL |
| Radionuclidic purity | ≥99.9% of the total activity of $^{177}$Lu at the end of the shelf life | ≥99.9% of the total activity of $^{177}$Lu at the end of the shelf life | Not less than (NLT, ≥) 99.9% [$^{177}$Lu]Lu$^{3+}$ |
| $^{177}$Lu-PSMA-I&T Specific activity | Reported | Reported | N/A |
| Apparent Molar Activity | N/A | N/A | 2.0-7.0 mCi/nmol |
| Endotoxins | <17.5 IU/ml | <17.5 IU/ml | 11.7 EU/mL |
| Radioactive content | 90%-110% at the date and time stated on the label | 90%-110% at the date and time stated on the label | |
| Sterility | Sterile | Sterile | Sterile |

Example 3: Radiochemical Purity of $^{177}$Lu-PSMA I&T in Different Formulations Compositions The example demonstrates radiochemical stability of $^{177}$Lu-PSMA I&T in formulation compositions at different pH values. The shelf life of $^{177}$Lu-PSMA I&T is restricted by high rate of radiolysis during preparation and storage resulting in decomposition of $^{177}$Lu-PSMA I&T and formation of radiochemical impurities. This eventually results in radiochemical purity of $^{177}$Lu-PSMA I&T solution to fall below acceptance limit of 95.0%.

Formation of a particular radiochemical impurity of $^{177}$Lu-PSMA I&T have been observed having retention time of about 5.2 minutes by HPLC with Phenomenex Luna C18 column (3 µm, 150 mm×4.6 mm) using 0.1% trifluoroacetic acid in water (Mobile phase A) and 0.1% trifluoroacetic acid in water:acetonitrile (10:90% v/v) (Mobile phase B) and isocratic method of 23% Mobile phase B at temperature of 40° C. The impurity referred herein having retention time of about 5.2 minutes is exemplified in the chromatograms in FIGS. 6A-11B.

In experiments conducted previously, lowering formulation radioactivity concentration was sufficient to reduce the formation of the impurity eluting at about 5.2 minutes and maintaining radiochemical stability of [$^{177}$Lu]Lu-PSMA I&T solutions above 95.0% for 72 hours.

In this example, six experiments were conducted where [$^{177}$Lu]Lu-PSMA I&T was prepared in different formulation compositions with varying ascorbic acid concentration, pH and radioactivity concentration. Product formulation details are described in Table 6.

TABLE 6

[$^{177}$Lu]Lu-PSMA I&T formulation compositions evaluated

| Experiment no. | Formulation composition | pH | Sample Radioactivity | Sample Volume | Radioactivity Concentration | Storage Temperature |
|---|---|---|---|---|---|---|
| 1 | high RAC, 42.5 mg/ml Ascorbic acid | 7 | 12 810 MBq | 10 ml | 1281 MBq/ml | 22.5° C. |
| 2 | high RAC, 42.5 mg/ml Ascorbic acid | 4.5 | 12 780 MBq | 10 ml | 1278 MBq/ml | 22.5° C. |

TABLE 6-continued

[$^{177}$Lu]Lu-PSMA I&T formulation compositions evaluated

| Experiment no. | Formulation composition | pH | Sample Radioactivity | Sample Volume | Radioactivity Concentration | Storage Temperature |
|---|---|---|---|---|---|---|
| 3 | high RAC, 42.5 mg/ml Ascorbic acid | 3.5 | 13 110 MBq | 10 ml | 1311 MBq/ml | 22.5° C. |
| 4 | low RAC, 31 mg/ml Ascorbic acid | 4.5 | 11 580 MBq | 20 ml | 579 MBq/ml | 22.5° C. |
| 5 | low RAC, 31 mg/ml Ascorbic acid | 5 | 12 520 MBq | 20 ml | 626 MBq/ml | 22.5° C. |
| 6 | low RAC, 31 mg/ml Ascorbic acid | 4.5 | 11 770 MBq | 20 ml | 589 MBq/ml | 22.5° C. |

High radioactivity concentration (high RAC) in sample solutions were 1278 MBq/ml, 1281 MBq/ml and 1311 MBq/ml measured at the end of production. Low radioactivity concentration (low RAC) in sample solutions were 579 MBq/ml, 589 MBq/ml and 626 MBq/ml measured at the end of production. Radiochemical purity of each solution was followed by HPLC up to 71-93 hours post-radiolabeling. All solutions were stored at 22.5° C.

FIG. 5 shows results of radiochemical purity analyses at different time points determined by HPLC.

Figure 6A:
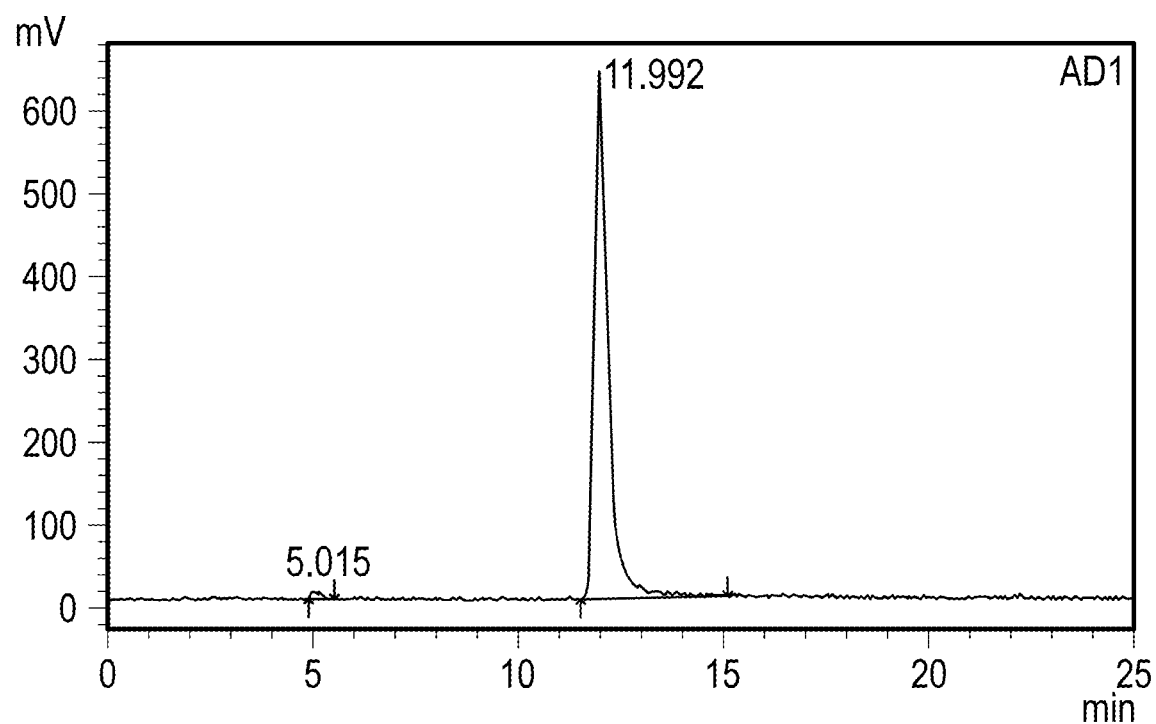
FIGS. 6A and 6B show HPLC radio-chromatograms of high radioactivity concentration formulation containing 42.5 mg/ml ascorbic acid at pH of 7±0.1, 0 hours and 71 hours post EOS as detailed in the example.
Figure 6B:
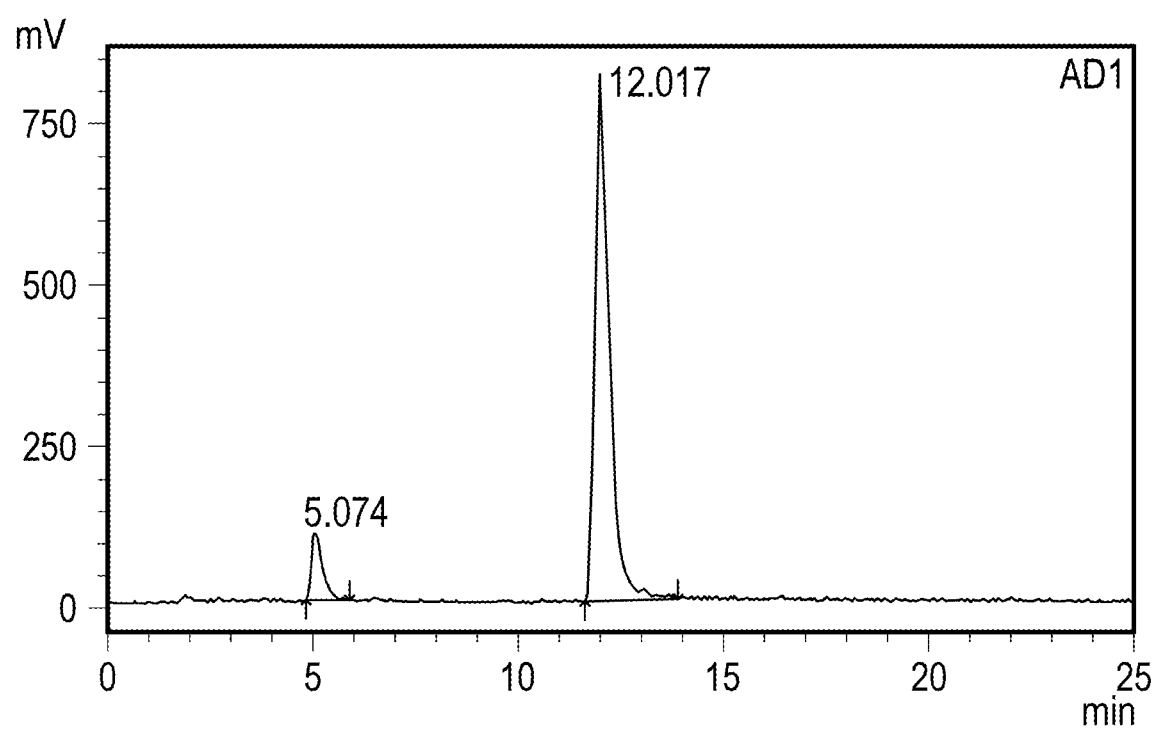

FIG. 6A and FIG. 6B show HPLC radio-chromatograms of experiment 1 at 0 and 71 hours post EOS, respectively.

Figure 7A:
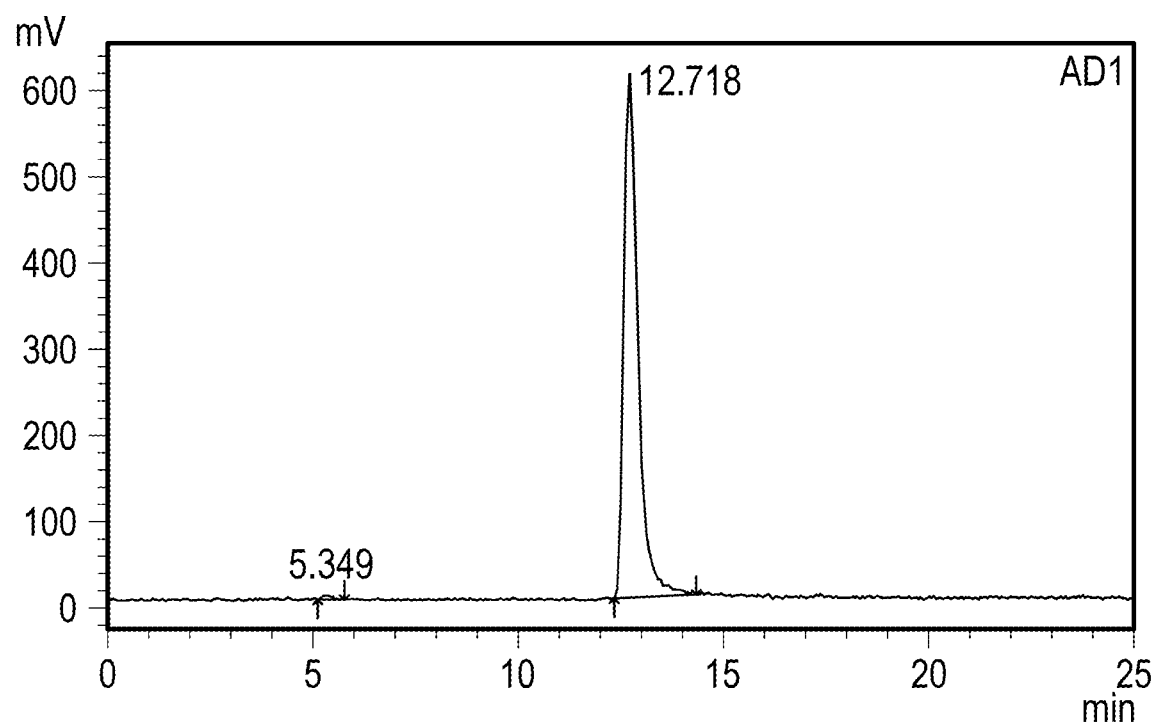
FIGS. 7A and 7B show HPLC radio-chromatograms of high radioactivity concentration formulation containing 42.4 mg/ml ascorbic acid at pH of 4.5±0.1, 0 hours and 71 hours post EOS as detailed in the example.
Figure 7B:
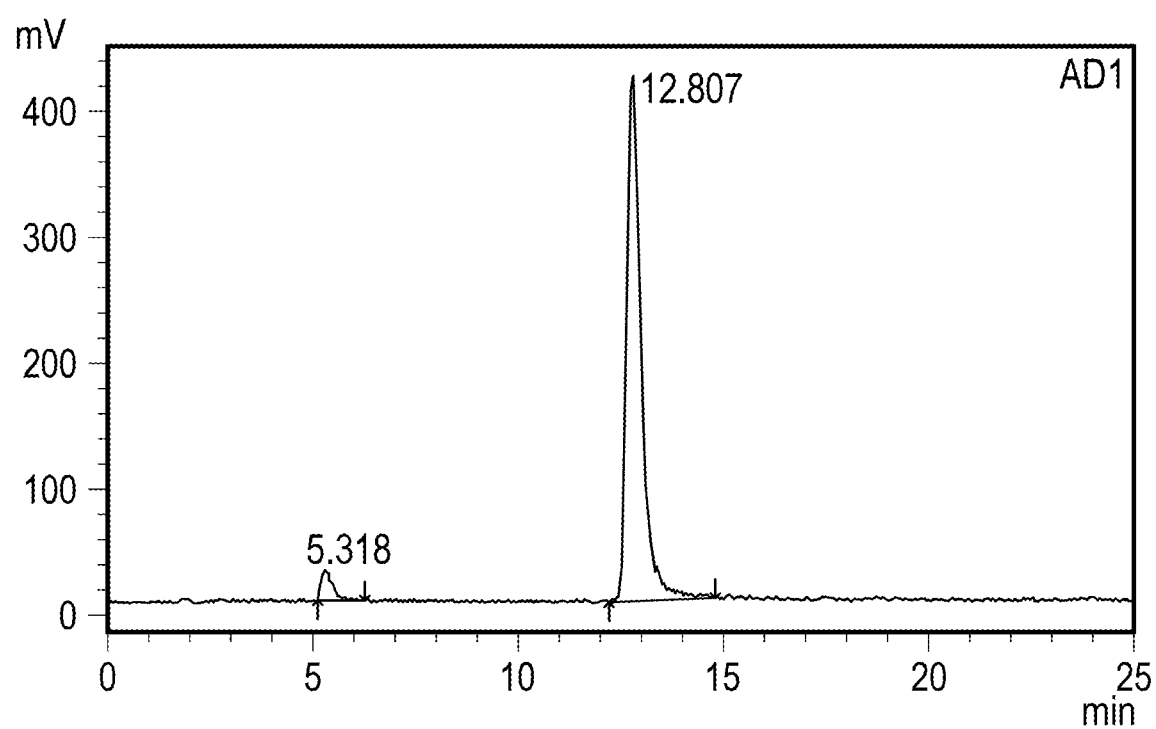

FIG. 7A and FIG. 7B show HPLC radio-chromatograms of experiment 2 at 0 and 71 hours post EOS, respectively.

Figure 8A:
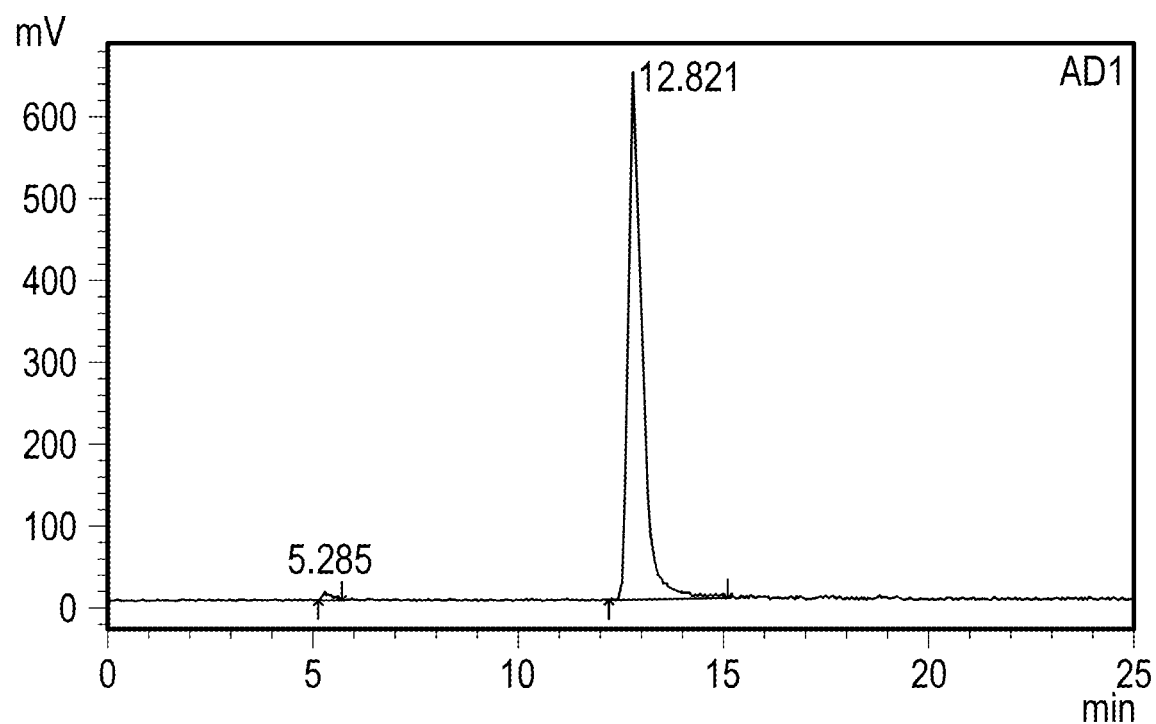
FIGS. 8A and 8B show HPLC radio-chromatograms of high radioactivity concentration formulation containing 42.5 mg/ml ascorbic acid at pH of 3.5±0.1, 0 hours and 90 hours post EOS as detailed in the example.
Figure 8B:
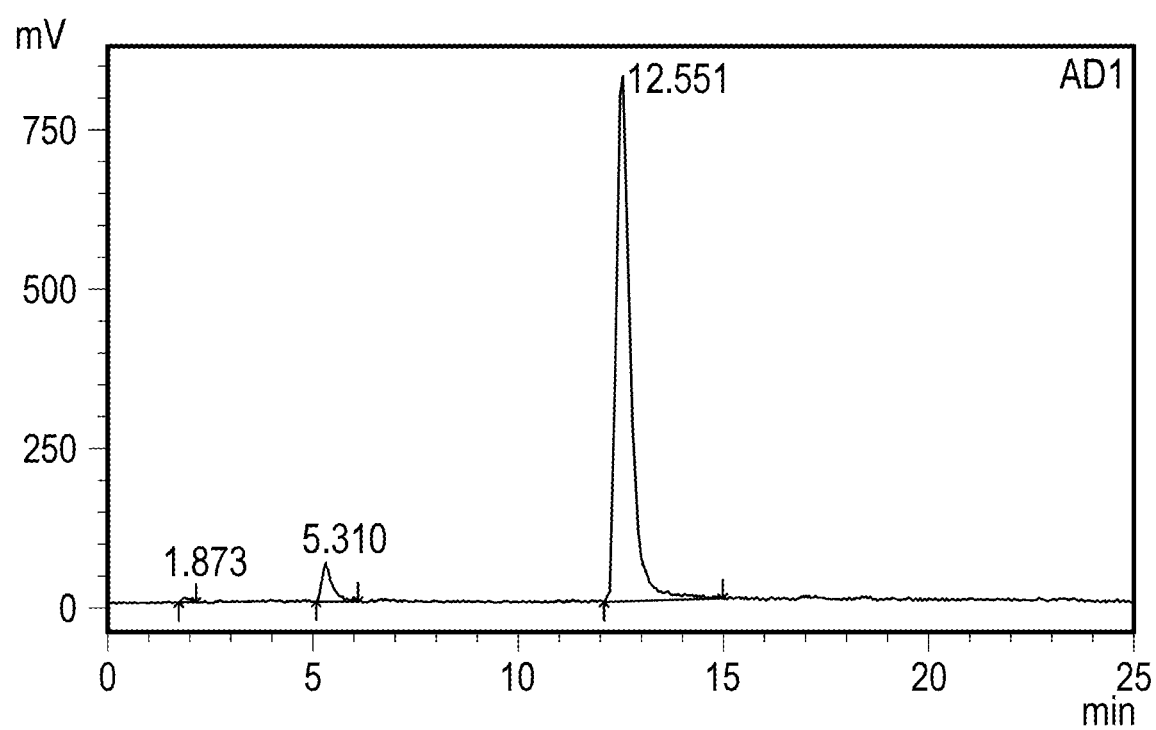

FIG. 8A and FIG. 8B show HPLC radio-chromatograms of experiment 3 at 0 and 90 hours post EOS, respectively.

Figure 9A:
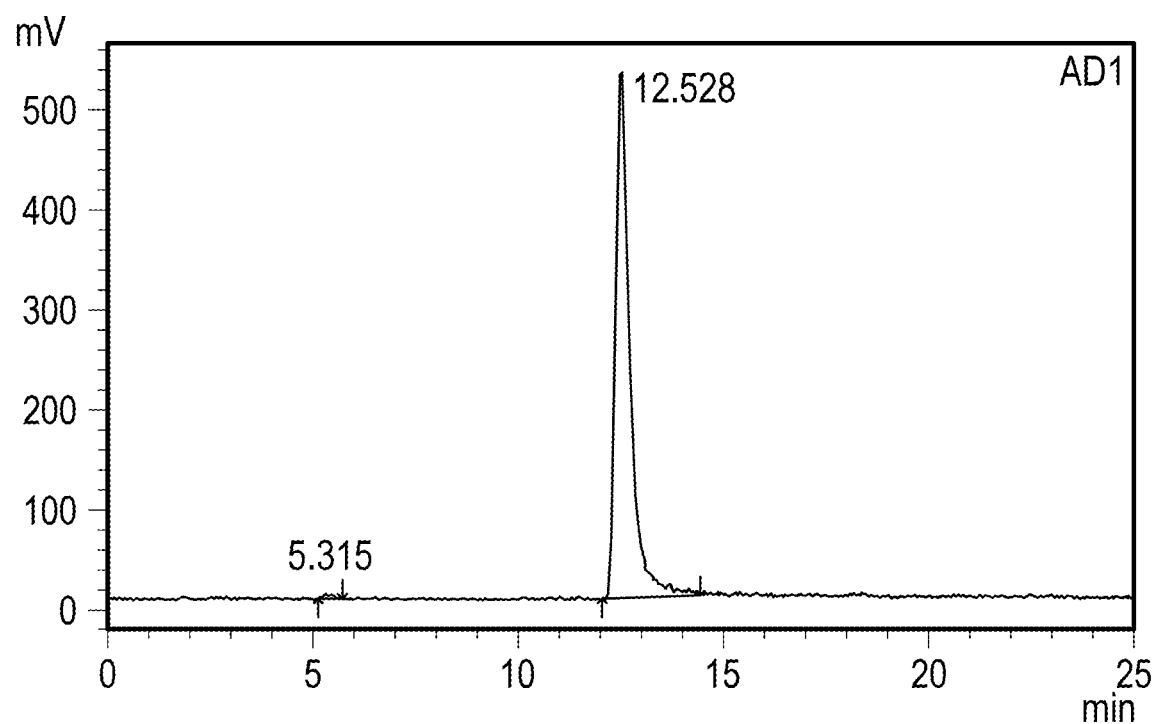
FIGS. 9A and 9B show HPLC radio-chromatograms of low radioactivity concentration formulation containing 21 mg/ml ascorbic acid at pH of 4.5±0.1, 0 hours and 92 hours post EOS as detailed in the example.
Figure 9B:
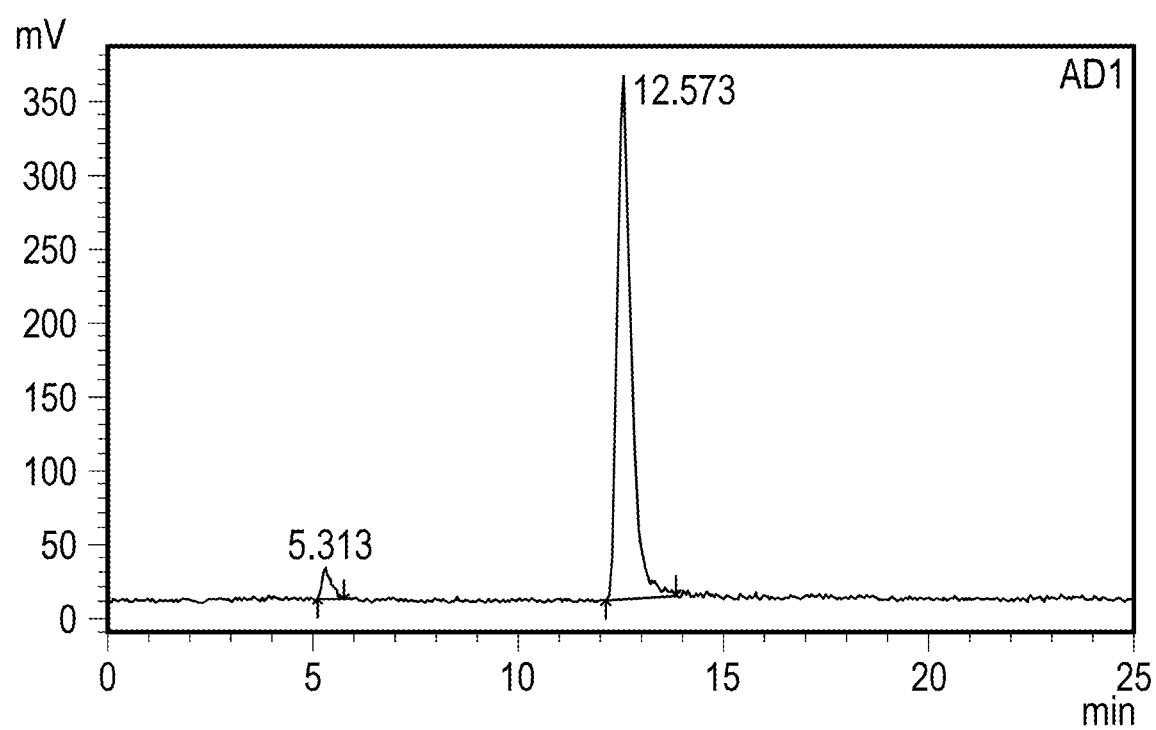

FIG. 9A and FIG. 9B show HPLC radio-chromatograms of experiment 4 at 0 and 92 hours post EOS, respectively.

Figure 10A:
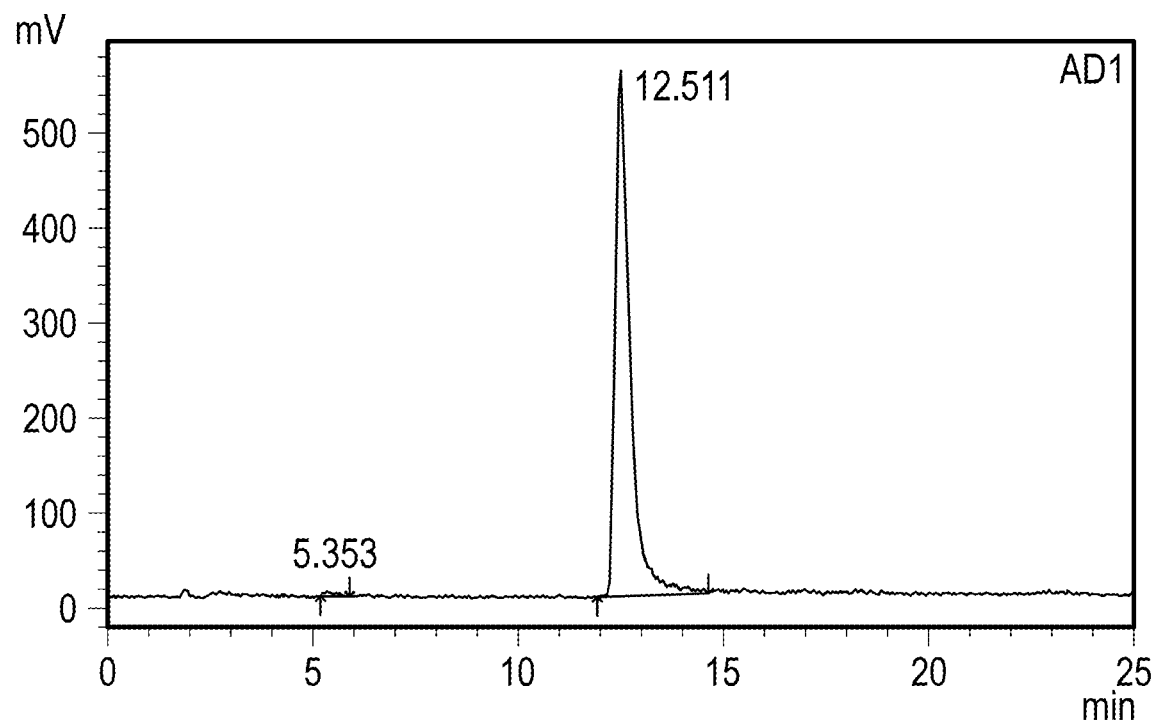
FIGS. 10A and 10B show HPLC radio-chromatograms of low radioactivity concentration formulation containing 31 mg/ml ascorbic acid at pH of 5±0.1, 0 hours and 71 hours post EOS as detailed in the example.
Figure 10B:
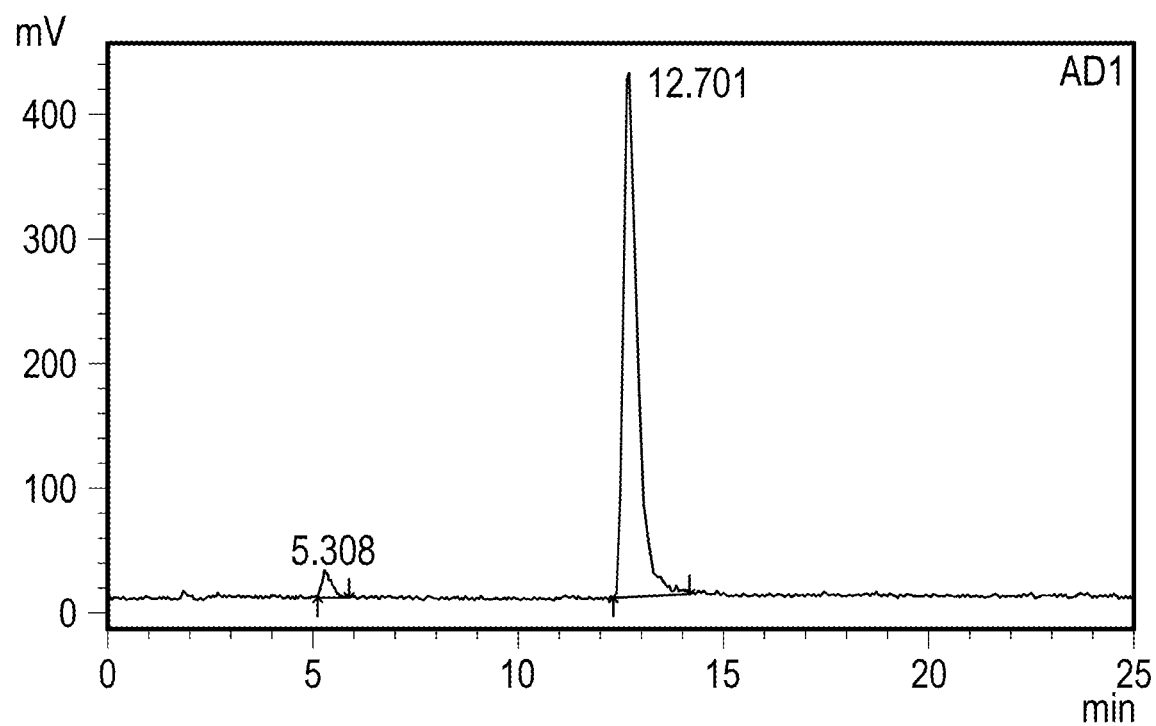

FIG. 10A and FIG. 10B show HPLC radio-chromatograms of experiment 5 at 0 and 71 hours post EOS, respectively.

Figure 11A:
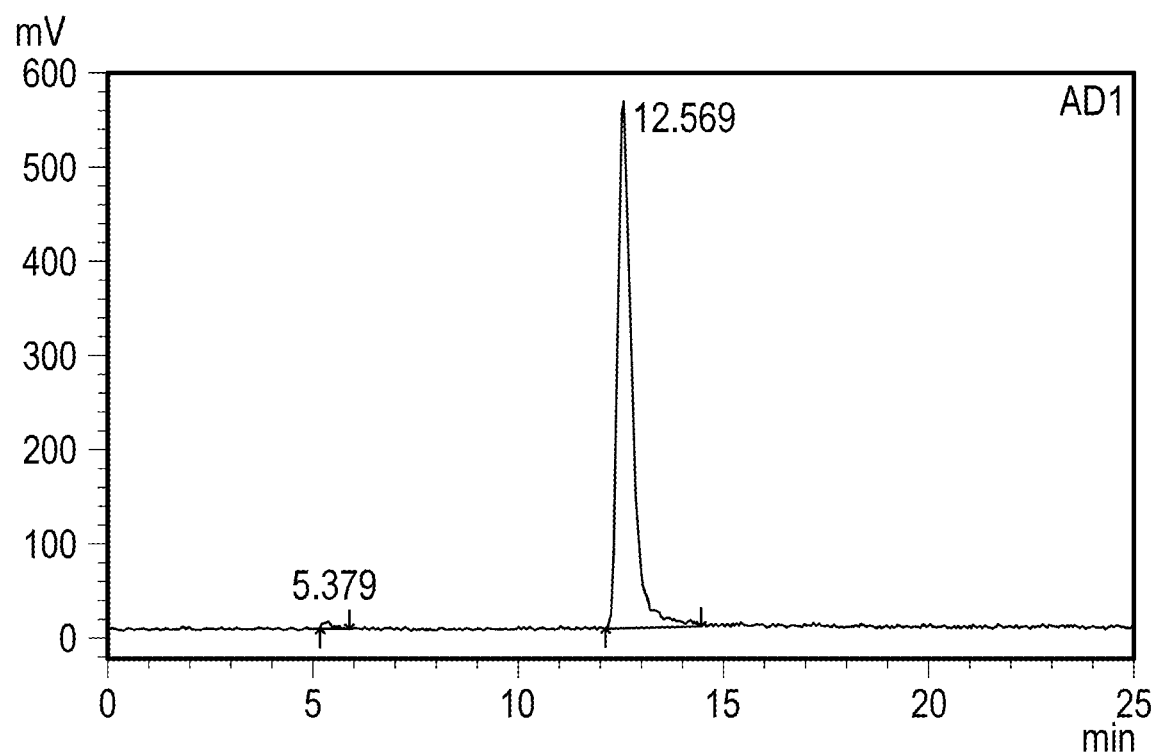
FIGS. 11A and 11B show HPLC radio-chromatograms of low radioactivity concentration formulation containing 31 mg/ml ascorbic acid at pH of 4.5±0.1, 0 hours and 93 hours post EOS as detailed in the example.
Figure 11B:
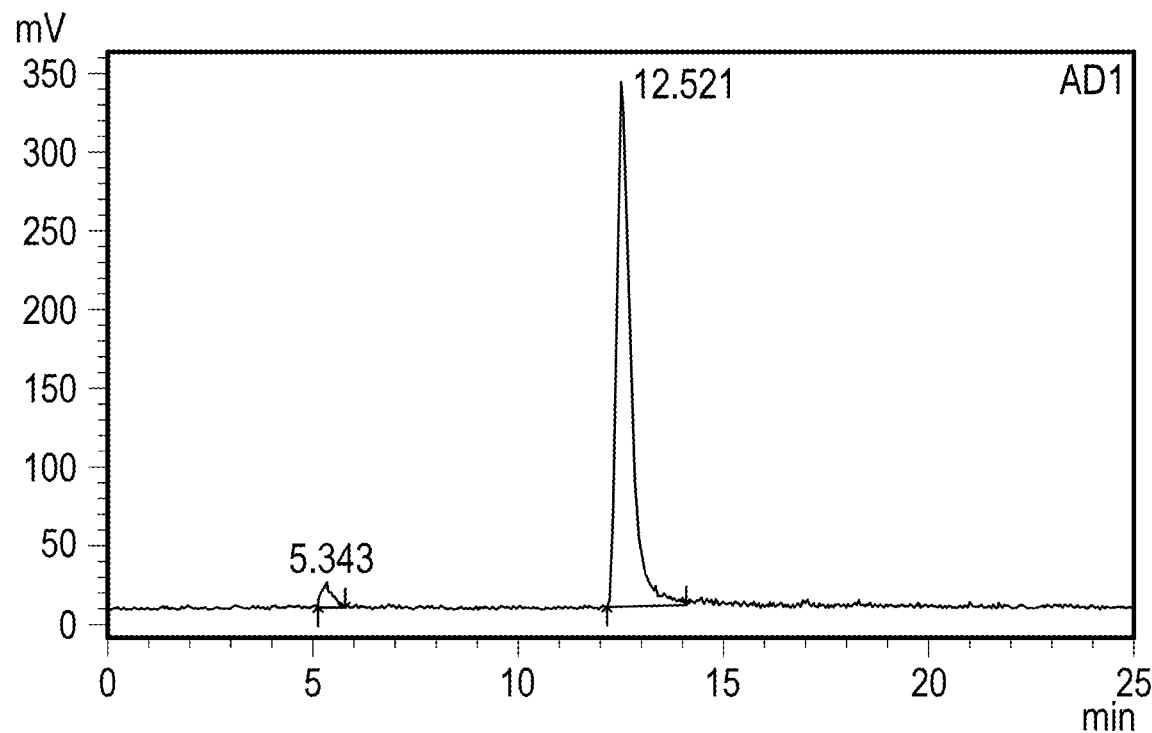
Figure 12:
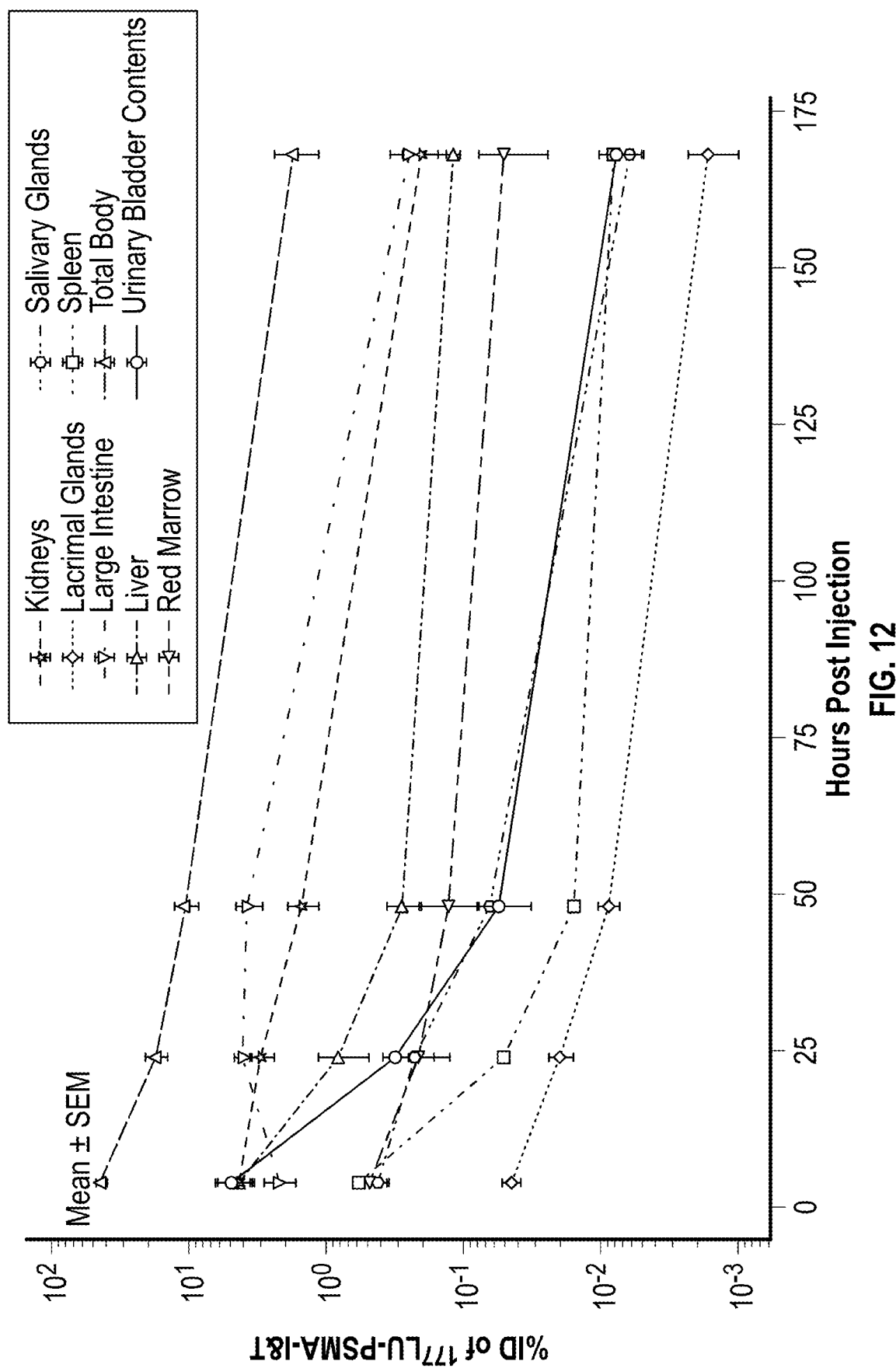
FIG. 12 presents a chart of the % ID of 177Lu-PSMA-I&T against hours post-injection for various regions of the body.
Figure 13:
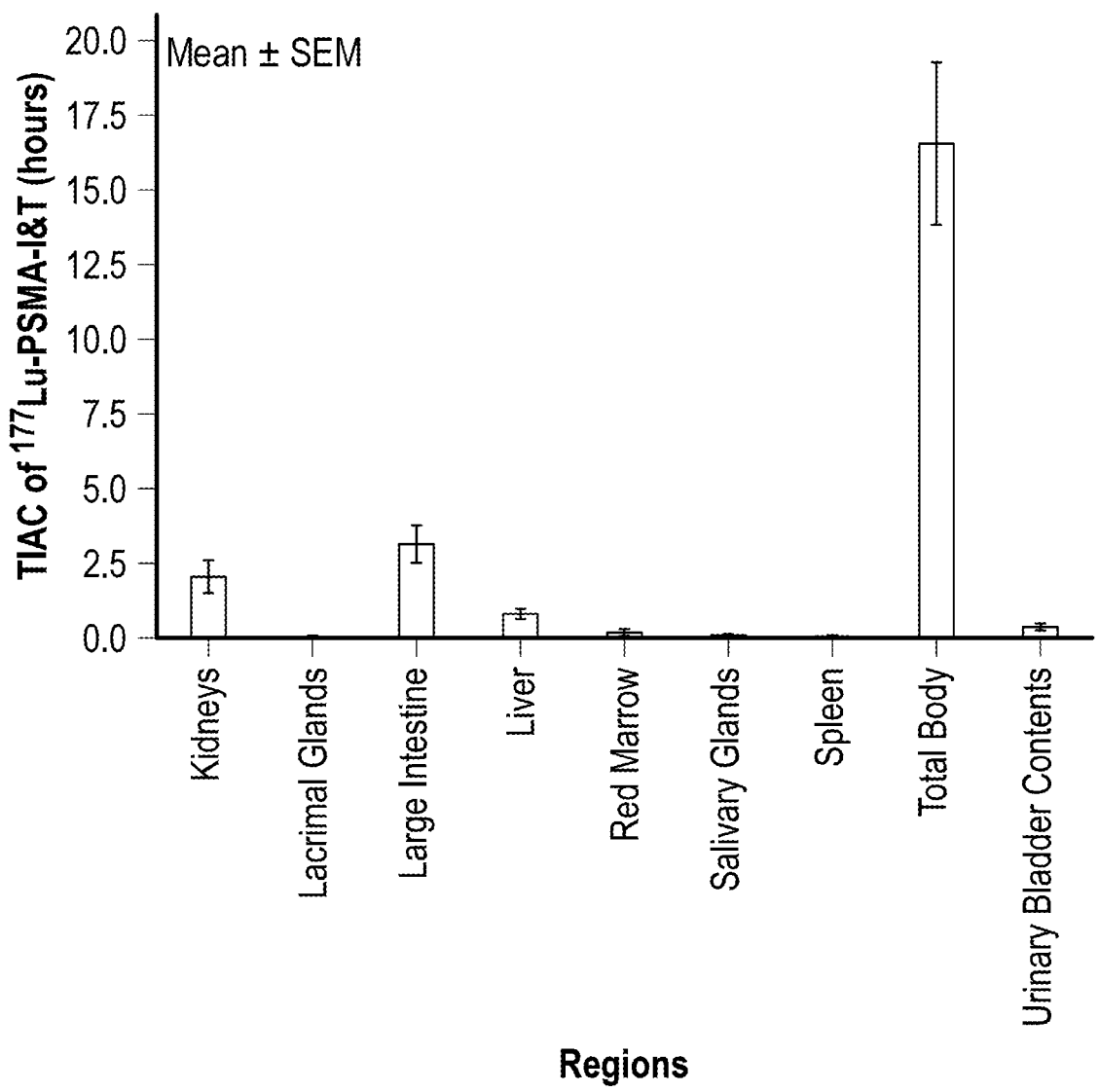
FIG. 13 presents a chart of the TIAC of 177Lu-PSMA-I&T (hours) against regions of the body.

FIG. 11A and FIG. 11B show HPLC radio-chromatograms of experiment 6 at 0 and 93 hours post EOS, respectively.

The radiochemical stability results for each experiment at different time points are provided in Tables 5-10.

TABLE 5

Experiment 1
Radiochemical purity by HPLC (hours post EOS)

| T = 0 h | T = 24 h | T = 46 h | T = 64 h | T = 71 h |
|---|---|---|---|---|
| 99.0% | 96.5% | 93.3% | N/A | 91.2% |

TABLE 6

Experiment 2
Radiochemical purity by HPLC (hours post EOS)

| T = 0 h | T = 24 h | T = 46 h | T = 67 h | T = 71 h |
|---|---|---|---|---|
| 99.4% | 98.0% | 96.7% | 95.3% | 95.2% |

TABLE 7

Experiment 3
Radiochemical purity by HPLC (hours post EOS)

| T = 0 h | T = 24 h | T = 46 h | T = 64 h | T = 72 h | T = 90 h |
|---|---|---|---|---|---|
| 99.1% | 97.7% | 96.5% | N/A | N/A | 94.5% |

TABLE 8

Experiment 4
Radiochemical purity by HPLC (hours post EOS)

| T = 0 h | T = 19 h | T = 46 h | T = 71 h | T = 92 h |
|---|---|---|---|---|
| 99.4% | 98.3% | 97.5% | 96.8% | 96.0% |

TABLE 9

Experiment 5
Radiochemical purity by HPLC (hours post EOS)

| T = 0 h | T = 25 h | T = 47 h | T = 71 h |
|---|---|---|---|
| 99.2% | 98.4% | 97.3% | 96.5% |

TABLE 10

Experiment 6
Radiochemical purity by HPLC (hours post EOS)

| T = 0 h | T = 20 h | T = 44 h | T = 69 h | T = 93 h |
|---|---|---|---|---|
| 99.1% | 98.7% | 98.0% | 97.4% | 97.0% |

In the example, formulation composition pH had a considerable effect on the radiochemical stability of $^{177}$Lu-PSMA I&T and more specifically in the formation of radiochemical impurity eluting at about 5.2 minutes as exemplified in FIGS. 6A-11B. In high RAC solutions, the decrease in radiochemical purity over time at pH 4.5 was two times slower than at pH 7.

Further decrease of formulation pH to 3.5 did not show measurable improvement in radiochemical stability compared to pH 4.5 solution. It is possible that ascorbic acid solution at pH 4.5, being near pKa value of ascorbic acid, already possesses sufficient quantity of protons to serve as inhibitors against radiolysis of $^{177}$Lu-PSMA I&T and reduce formation of the radiochemical impurity eluting at about 5.2 minutes.

Incorporation of solution pH of 4.5 in the lower RAC formulation further improved radiochemical stability of $^{177}$Lu-PSMA I&T. In the lower RAC formulation, change in formulation pH from 5 to 4.5 had similar effect on radiochemical stability as increasing ascorbic acid concentration from 21 mg/ml to 31 mg/ml.

The radiochemical purity of a 10 ml high RAC $^{177}$Lu-PSMA I&T formulation composition comprising 42.5 mg/ml ascorbic acid is at least about 99% at 0 hours post EOS and at least about 93.3% at 46 hours post EOS, as measured by HPLC. The radiochemical purity decreases as the pH of the formulation is increased from pH 4.5.

The radiochemical purity of a 20 ml low RAC $^{177}$Lu-PSMA I&T formulation comprising 31 mg/ml ascorbic acid is at least about 99.1% at 0 hours post EOS as measured by HPLC. The rate in which the radiochemical purity decreases over time is slower for low RAC $^{177}$Lu-PSMA-I&T formulations having a pH of 4.5 compared to a pH of 5.

The results demonstrate that, formulation composition pH of 5 or below can substantially reduce formation of radiochemical impurity eluting at about 5.2 minutes and therefore enhance radiochemical stability of $^{177}$Lu-PSMA I&T compared to formulation compositions at pH above 5. In addition, radiochemical stability of $^{177}$Lu-PSMA I&T can further be improved by incorporation of lower solution RAC. In the example, $^{177}$Lu-PSMA I&T solution showed highest radiochemical stability in low RAC solution of pH 4.5 and ascorbic acid concentration of 31 mg/ml. This formulation is considered a preferred composition to minimize formation of radiochemical impurities and to maintain radiochemical stability of $^{177}$Lu-PSMA I&T above 95.0% for 72 hours or longer.

Example 4—Dosimetry Study Results

This Example presents the biodistribution, dosimetry, and pharmacokinetics (PK) results of a PK/Dosimetry sub-study performed as part of a Phase III trial. Twenty-seven (27) patients were administered a target activity of 7.4±10% GBq of $^{177}$Lu-PSMA-I&T and underwent single photon emission computed tomography (SPECT)/computed tomography (CT) imaging at four timepoints (4 h, 24 h, 48 h, and 168 h). Image data was analysed to compute time-activity curves (TACs) and subsequently time-integrated activity coefficients (TIACs) in each organ of interest and in organs showing appreciable and meaningful $^{177}$Lu-PSMA-I&T activity. Organ Level Internal Dose Assessment (OLINDA 2.2.3) was used to compute organ and whole body absorbed radiation doses for each patient.

Additionally, for PK assessment, whole blood samples were collected at six timepoints (Pre-Infusion, 1 h, 4 h, 24 h, 48 h, and 168 h) and processed to extract plasma. All plasma samples were gamma counted locally for analysis of pharmacokinetics.

The organs with moderate or higher absorbed dose for $^{177}$Lu-PSMA-I&T were the organs involved in the elimination of the radioligand and/or those expressing PSMA, that is, kidneys (0.41±0.15 Gy/GBq), urinary bladder (0.41±0.05 Gy/GBq), salivary and lacrimal glands (0.19±0.16 and 0.40+0.36 Gy/GBq, respectively) and some parts of the gastrointestinal (GI) tract (left colon, 0.47±0.31 Gy/GBq and rectum, 0.44±0.30 Gy/GBq).

The mean red marrow absorbed radiation dose was 0.08±0.12 Gy/GBq. The relatively high variability in marrow absorbed dose is attributed to some patients having diffuse metastatic disease within the bone, resulting in an increased bone uptake and hence a higher estimated marrow absorbed dose. Moreover, in a few patients, the presence of metastases in the lumbar vertebrae L2-L4, the region used for bone marrow dosimetry imaging, potentially led to an overestimation of the marrow dose.

The whole-body time-activity curves were fitted with bi-exponential equation and the distribution half-life was 2.16±1.30 hours and the elimination half-life was 46.29±23.83 hours.

PK assessment performed based on plasma radioactivity concentration data showed a mean distribution half-life of 1.89±0.34 h and a mean elimination half-life of 14.7±10.1 hours.

A subset of patients (16/27) underwent imaging after both the first and third treatment cycles to evaluate organ dose following multiple treatment cycles. By comparing the organ absorbed doses between Cycle 1 and Cycle 3 for these 16 patients, it was observed that the normal organ absorbed doses remained similar between the two cycles. This finding supports the validity of estimating cumulative organ absorbed radiation doses through extrapolation from Cycle 1 data.

Introduction

This was a Phase 3, open-label, multicenter, randomized trial evaluating the safety and efficacy of $^{177}$Lu-PSMA-I&T radioligand therapy compared to hormone therapy in men with metastatic castration-resistant prostate cancer (mCRPC). $^{177}$Lu-PSMA-I&T is a radioactive therapeutic agent that specifically targets the prostate specific membrane antigen (PSMA) that is expressed on both primary and metastatic prostate cancer cells.

A sub-study was conducted to evaluate the PK and radiation dosimetry of $^{177}$Lu-PSMA-I&T, in which patients underwent PK sampling and SPECT/CT imaging after the first and third $^{177}$Lu-PSMA I&T infusion.

Methods

Data Acquisition

All participating sites underwent a rigorous site setup process during which all dose calibrators, scanners, and gamma counters used in the sub-study were calibrated. Sites were allowed to enroll patients in the sub-study only after the completion and approval of all site setup processes by Invicro. Patients underwent SPECT/CT imaging, with anatomical coverage typically extending from the salivary glands to the pelvis, following the administration of a targeted 7.4±10% GBq of $^{177}$Lu-PSMA-I&T at cycle 1. SPECT/CT imaging was performed at four timepoints: 4 h, 24 h, 48 h, and 168 h post-injection. Additionally, a subset of patients imaged at Cycle 1 (16 out of 27), were also imaged at Cycle 3 (Table 2).

TABLE 2

SPECT imaging timepoints acquired at cycle 3

| Patient ID | SPECT imaging timepoints at cycle 3 |
|---|---|
| 80-004 | 24 h and 48 h |
| 80-007 | 24 h and 48 h |
| 25-007 | 24 h |
| 25-005 | 24 h and 48 h |
| 25-008 | 24 h and 48 h |
| 37-015 | 4 h, 24 h, 48 h, 168 h |
| 37-016 | 4 h, 24 h, 48 h, 168 h |

TABLE 2-continued

SPECT imaging timepoints acquired at cycle 3

| Patient ID | SPECT imaging timepoints at cycle 3 |
|---|---|
| 25-009 | 24 h and 48 h |
| 12-004 | 24 h |
| 37-017 | 4 h, 24 h, 48 h, 168 h |
| 37-019 | 24 h and 48 h |
| 37-020 | 24 h and 48 h |
| 80-018 | 24 h and 48 h |
| 80-019 | 24 h and 48 h |
| 80-020 | 24 h and 48 h |
| 80-022 | 24 h and 48 h |

Image acquisition and reconstruction protocols were standardized across all imaging timepoints and patients at each site. Furthermore, each site consistently utilized the same SPECT/CT scanner throughout the duration of the study to ensure uniformity.

In general, raw projection data was acquired into a 128×128 matrix with medium energy general purpose (MEGP) collimation using a step and shoot acquisition mode, acquiring 60 projections per detector (180 degrees rotation per detector), 20 seconds per projection, with an acquisition zoom of 1.0, and a 20% (±10%) energy window centered over 208 keV.

A low-dose CT scan was performed prior to beginning the SPECT scan for attenuation correction. Sites were instructed to use the Institutional standard parameters for acquisition of the low-dose CT. Institutional standard reconstruction parameters were used. Scatter correction was required to be applied using a 20% (±10%) scatter window centered over 170 keV.

PK plasma samples were collected at pre-Infusion, 1 h, 4 h, 24 h, 48 h, and 168 h, and counted for radioactivity. Blood samples were first centrifuged to extract plasma, and then the radioactivity in plasma was counted in a gamma counter.

For a detailed summary of site qualification and set up and data acquisition procedures, refer to the Technical Operations Manual (TOM).

Image Analysis Method

The imaging data was analyzed using Invicro's Vivo-Quant software, a validated software used in a 21 CFR § 11-compliant workflow. The general quantification approach was based on the principles detailed in the Medical Internal Radiation Dose (MIRD) Pamphlet No. 16, No 23, and No 26 as appropriate.

SPECT images were calibrated in units of Becquerel (Bq) using a calibration factor derived from a source of known activity, measured during site set up with the same acquisition and reconstruction parameters employed for patient imaging. A patient-specific calibration factor was also derived at each clinical time point after acquisition of the patient SPECT/CT. As a quality control measure, if the patient-specific calibration factor differed by more than 10% from the site set up calibration factor, an investigation was conducted.

Volume of interest (VOI) (kidneys, bladder, liver, lumbar vertebrae L2-L4, lacrimal glands, salivary glands [parotid and submandibular glands], and whole body) were delineated on each dataset by a trained image analyst. The GI tract and spleen were delineated only in a subset of patients where these organs displayed visible uptake. Organs were segmented either by drawing the entire contour of the organ, or by placing a sphere in a representative region of the organ and then multiplying by the organ's effective mass (based on patient's height and weight). Segmentation methods for each organ are specified in Table 3 and were consistently applied to each patient.

TABLE 14

Organ VOIs and delineation method

| Organ | Method |
|---|---|
| Bladder | CT and SPECT Uptake |
| Liver | Sphere based off CT |
| Spleen | Sphere based off CT |
| Kidney | SPECT Uptake |
| L2-L4 | CT |
| Salivary Glands | SPECT Uptake |
| GI Tract | SPECT Uptake |
| Lacrimal Glands | SPECT Uptake |

Plasma Quantitative Analysis

Whole blood samples were collected as detailed in the protocol Schedule of Events i.e. pre-injection, and then at 1 h, 4 h, 24 h, 48 h, and 168 h post-injection. The samples were first centrifuged to separate plasma, and the radioactivity in the plasma was then measured using a gamma counter. Plasma concentrations were subsequently fitted with a bi-exponential function to derive outcome parameters such as the half-life and clearance rate of the radiopharmaceutical in the plasma.

Normal Organ Dosimetry Analysis

Clearance of the radiopharmaceutical was derived from a data-appropriate fit of each organ's TAC. Depending on the TAC's shape, the data was fitted with the sum of one, two, or three exponentials, or using a rise and fall model. Fitting was performed with in-house Python software. TIACs were calculated through analytical integration of the curve fit extrapolated to infinity. If no appropriate fit was found, the area under the curve (AUC) was estimated using the sum of the trapezoidal integration of imaging measurements and physical decay from the last timepoint onward (the fraction of injected activity at t=0 was set to zero for organs and to 1 for the whole body). A whole-body TAC was derived from delineating the imaged body. The remainder activity was determined by subtracting the cumulative organ TIACs from the whole body TIAC.

Organ TIACs were input into OLINDA 2.2.3 for the computation of organ and whole-body absorbed doses, using International Commission on Radiological Protection (ICRP)-103 weighing factors. The ICRP-89 derived male phantom was used for dose estimation. Organs and body mass as defined by ICRP-89 were scaled based on height and mass using patient effective mass.[4] The voiding bladder model as implemented in OLINDA was used to determine bladder TIAC, assuming a voiding interval of 4 hours. The human alimentary tract model (HAT model) described in ICRP 100 and implemented in OLINDA was used to compute doses to the small intestine, right colon, left colon and rectum for patients showing clearance through the GI tract. The fraction of injected activity (fIA) cleared via the GI tract was determined by taking the peak fIA in the GI tract over all the imaging timepoints. Red marrow dose estimation was derived from segmenting the Lumbar Vertebrae L2-L4 as seen on CT. The Red Marrow mass in L2-L4 was assumed to be 6.7% of the total red marrow mass.

To evaluate potential changes in the tracer's kinetics and uptake after multiple treatment cycles, 16 of the 27 patients included in the dosimetry sub study, were imaged at both cycle 1 and cycle 3. Among these, at cycle 3, three patients were imaged at all 4 timepoints and the other 13 were imaged at one or two timepoints only (24 h, 48 h or both 24 h and 48 h) (Table 2). For these 13 patients, the TACs obtained at cycle 1 were used for each source organ and scaled to the normalized activity value(s) measured at Cycle 3. For patients imaged at two timepoints, the TACs were preferably scaled using the average scaling factor between the two timepoints. If the two timepoints yielded significantly different scaling factors, the more conservative timepoint was preferred, provided the dose estimation derived was reasonable.

Data Acquisition Quality Control

Quantitative accuracy of each SPECT image was controlled using a $^{177}$Lu reference standard of known activity. Before a patient was scanned, a reference standard was prepared by injecting 100 μCi (taken from the patient dose vial) into a 100 mL saline bag. The saline bag's radioactivity was subsequently imaged immediately after each imaging timepoint using the same acquisition and reconstruction parameters. The number of counts in the images attributed to the reference standard activity was measured, and the calibration factor was obtained by dividing the number of counts by the known activity in the reference standard at the time of imaging. This calibration factor is expected to be the same (<10% difference compared to the value determined at site setup) for all images acquired with the same SPECT/CT system. For patients where the calibration factor differed by more than 10% compared to the site set-up, an investigation was launched to determine the cause of this variation, and if it reflected a difference in patient data acquisition and/or reconstruction.

Gamma-counted plasma samples were quality controlled using the same $^{177}$Lu reference standard by measuring 0.5 ml of the 100 mL in the saline bag. For each patient, triplicates were made and measured right before all plasma samples were counted. A long-lived isotope was also counted to ensure that the protocol was properly followed by each site. Similarly to the imaging standard, when the gamma counter efficiency factor differed by more than 10% compared to that at site set-up, an investigation was launched to determine the cause of this variation, and if it reflected a difference in data acquisition.

Results

All twenty-seven (27) patients enrolled in the sub-study had SPECT/CT images acquired for dosimetry purposes at the first cycle. Sixteen out of the 27 patients were additionally imaged at cycle 3. The activity injected into each patient at cycles 1 and 3 is shown in Table 15.

TABLE 15

| Patient ID | Cycle 1 (GBq) | Cycle 3 (GBq) |
| --- | --- | --- |
| 12-004 | 7.93 | 7.97 |
| 25-005 | 7.58 | 7.51 |
| 25-007 | 7.56 | 7.44 |
| 25-008 | 7.21 | 7.35 |
| 25-009 | 7.71 | 7.72 |
| 37-013 | 7.42 | NA |
| 37-015 | 7.49 | 7.53 |
| 37-016 | 7.46 | 7.50 |
| 37-017 | 7.59 | 7.53 |
| 37-019 | 7.35 | 7.40 |
| 37-020 | 7.19 | 7.37 |
| 37-022 | 7.48 | NA |
| 37-023 | 7.53 | NA |
| 42-027 | 7.56 | NA |
| 42-028 | 7.62 | NA |
| 42-030 | 7.56 | NA |
| 62-032 | 7.48 | NA |
| 66-024 | 7.26 | NA |

TABLE 15-continued

| Patient ID | Cycle 1 (GBq) | Cycle 3 (GBq) |
| --- | --- | --- |
| 80-001 | 7.67 | NA |
| 80-004 | 7.52 | 7.22 |
| 80-007 | 7.54 | 7.14 |
| 80-018 | 7.31 | 7.16 |
| 80-019 | 7.43 | 7.58 |
| 80-020 | 7.39 | 7.42 |
| 80-022 | 7.32 | 7.48 |
| 80-023 | 7.44 | NA |
| 80-024 | 7.49 | NA |
| Mean | 7.48 | 7.46 |
| SD | 0.16 | 0.20 |

Dosimetry analysis included all acquired and/or evaluable imaging. Patient 37-016 did not have SPECT/CT imaging conducted at the 168 h timepoint, and thus the results were based on only 3 timepoints for this patient. For patient 12-004, the 48 h scan presented unrealistically high values (the whole-body fraction of injected activity at 48 h was above that at 4 h and 24 h, despite no additional activity being administered to the patient after the initial $^{177}$Lu-PSMA-I&T injection). In addition, the image quality at 48 h was unusually poor for unknown reasons. Therefore, this timepoint was excluded from further analysis, and dosimetry was performed using the 4 h, 24 h and 168 h SPECT images.

Cycle 1 Biodistribution

Figure 14:
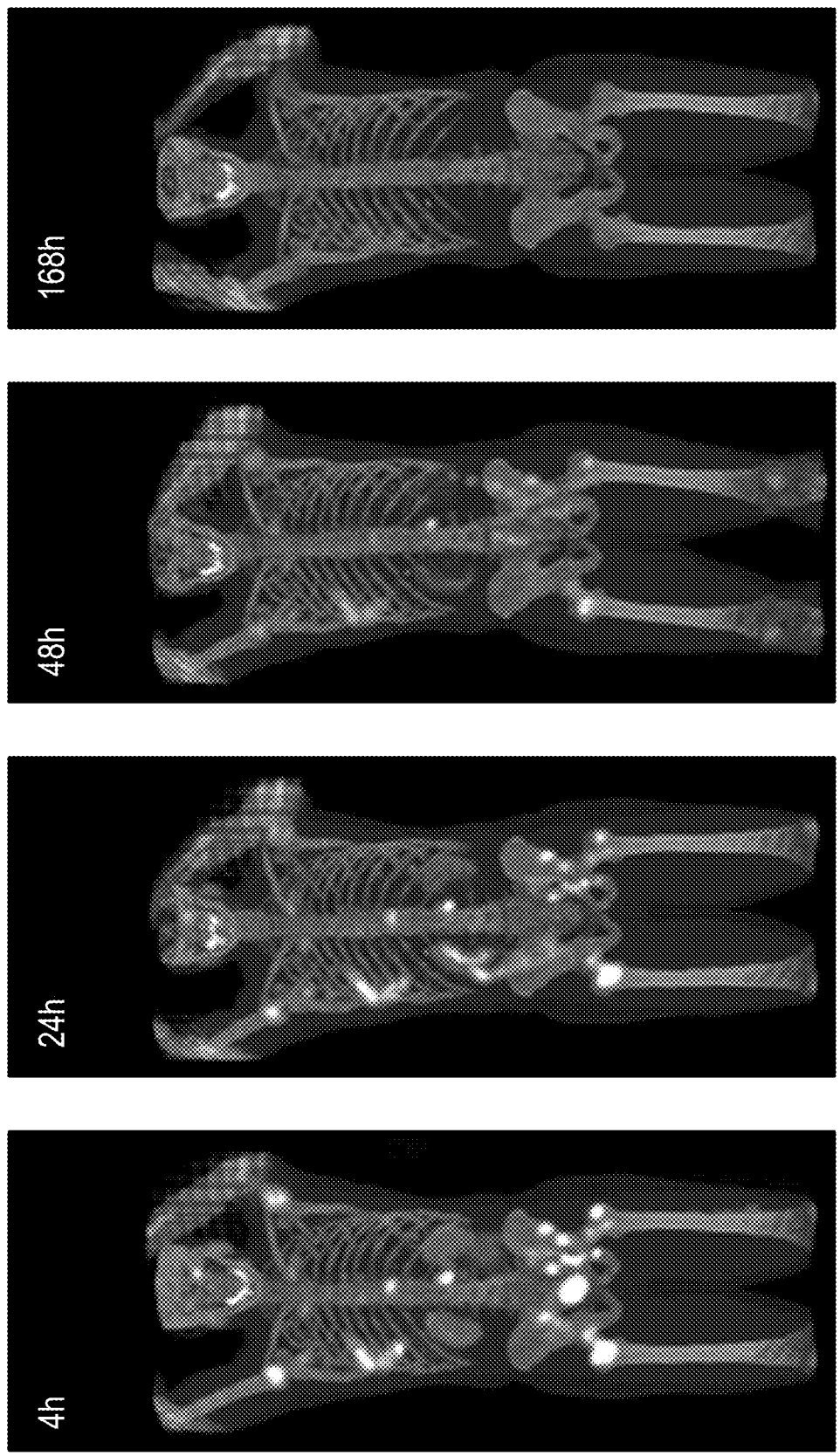
FIG. 14 shows the maximum intensity projection of Cycle 1 SPECT/CT images acquired for one patient (80-001) at 4 h, 24 h, 48 h, and 168 h post-injection.

Based on the images and dosimetry data, physiologic uptake of $^{177}$Lu-PSMA-I&T was predominantly observed in the kidneys, urinary bladder, lacrimal glands, GI tract, and salivary glands. $^{177}$Lu-PSMA-I&T was primarily excreted through the urine, as indicated by visible accumulation in the urinary bladder. In 25 patients, uptake in the intestines was observed, while no appreciable uptake was found in 2 of the patients analysed (80-004 and 25-005). Salivary glands were not in the SPECT/CT field of view for 1 patient (12-004), and lacrimal glands were outside the field of view for 5 patients (12-004, 25-009, 42-027, 80-018, 66-024). $^{177}$Lu-PSMA-I&T distribution in a patient imaged over time is represented in FIG. 14.

The individual time-activity curves for each source organ, expressed as fIA at the different timepoints are shown in FIGS. 17-25. Note: the time-activity curves in these figures are not decay-corrected to time of injection.

All patients showed similar whole-body clearance except for patient 42-030 who had a visibly slower clearance. This slower clearance was likely due to the patient's diffuse bone metastatic disease, confirmed by exposure measurements performed by the site 24 hours after investigational product (IP) injection. An ionization chamber (Ludlum 9DP*) was used for the measurement, performed 1 meter from the patient. After each cycle, this patient had dose rates approximately three times higher than those of the other two patients from the same site:

patient 42-027:7 uSv/h; 6 uSv/h; 5 uSv/h.
patient 42-028:6 uSv/h; 8 uSv/h; 5 uSv/h.
patient 42-030:16 uSv/h; 18 uSv/h; 17 uSv/h.

Figure 18:
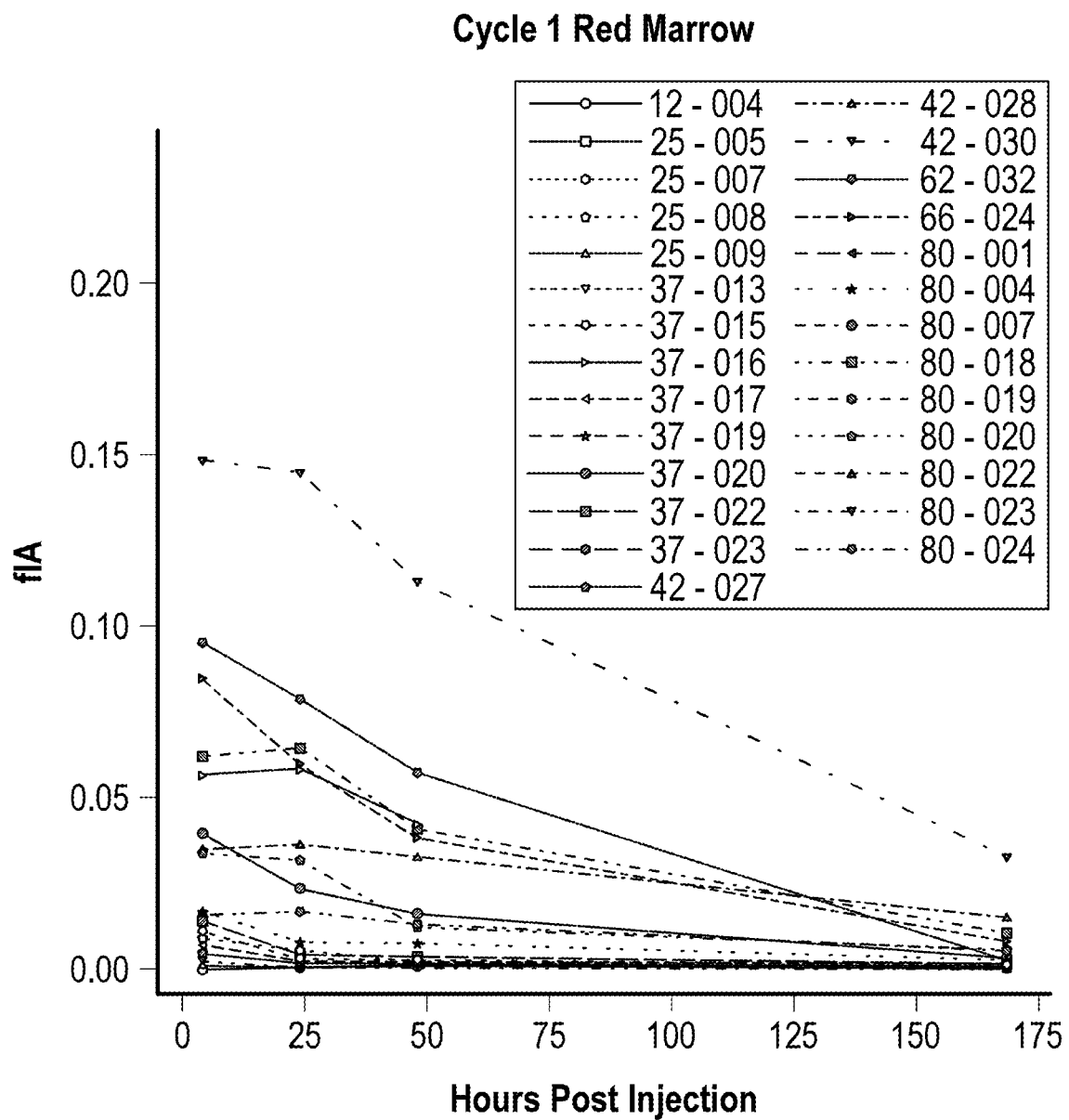
FIG. 18 shows the red marrow time-activity curve expressed as fraction of injected activity for each patient imaged at cycle 1. The highest curve is that of the patient with superscan (42-030) and reflects a higher dose to the bone marrow due to the widespread metastatic disease of the bones.
Figure 19:
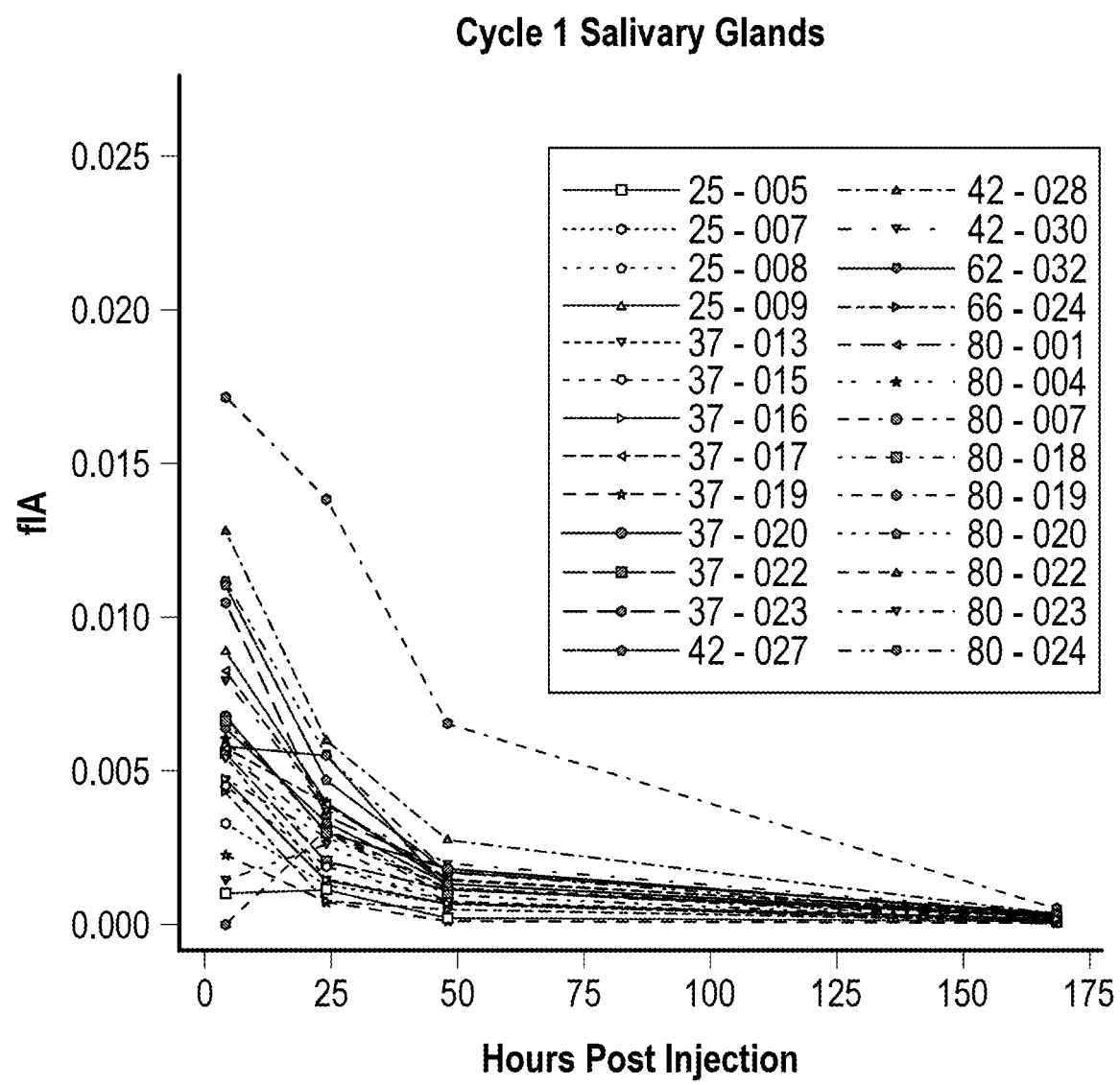
FIG. 19 shows the salivary glands time-activity curve expressed as fraction of injected activity for each patient imaged at cycle 1. Salivary glands were not in the SPECT field of view for patient 12-004.
Figure 20:
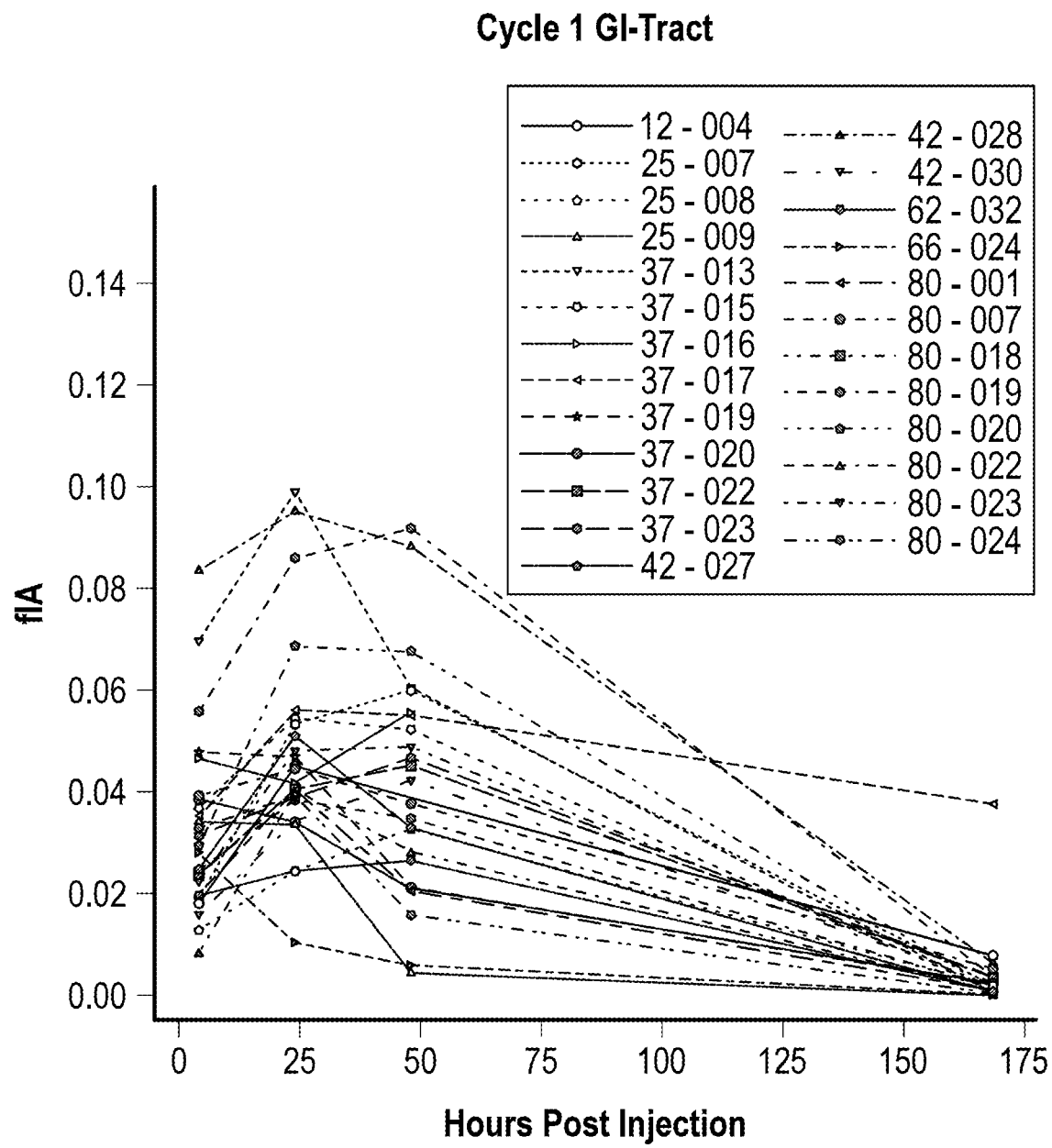
FIG. 20 shows the GI tract time-activity curve expressed as fraction of injected activity for each patient imaged at cycle 1. Two patients (80-004 and 25-005) did not have appreciable uptake in the GI tract and are not included here.
Figure 21:
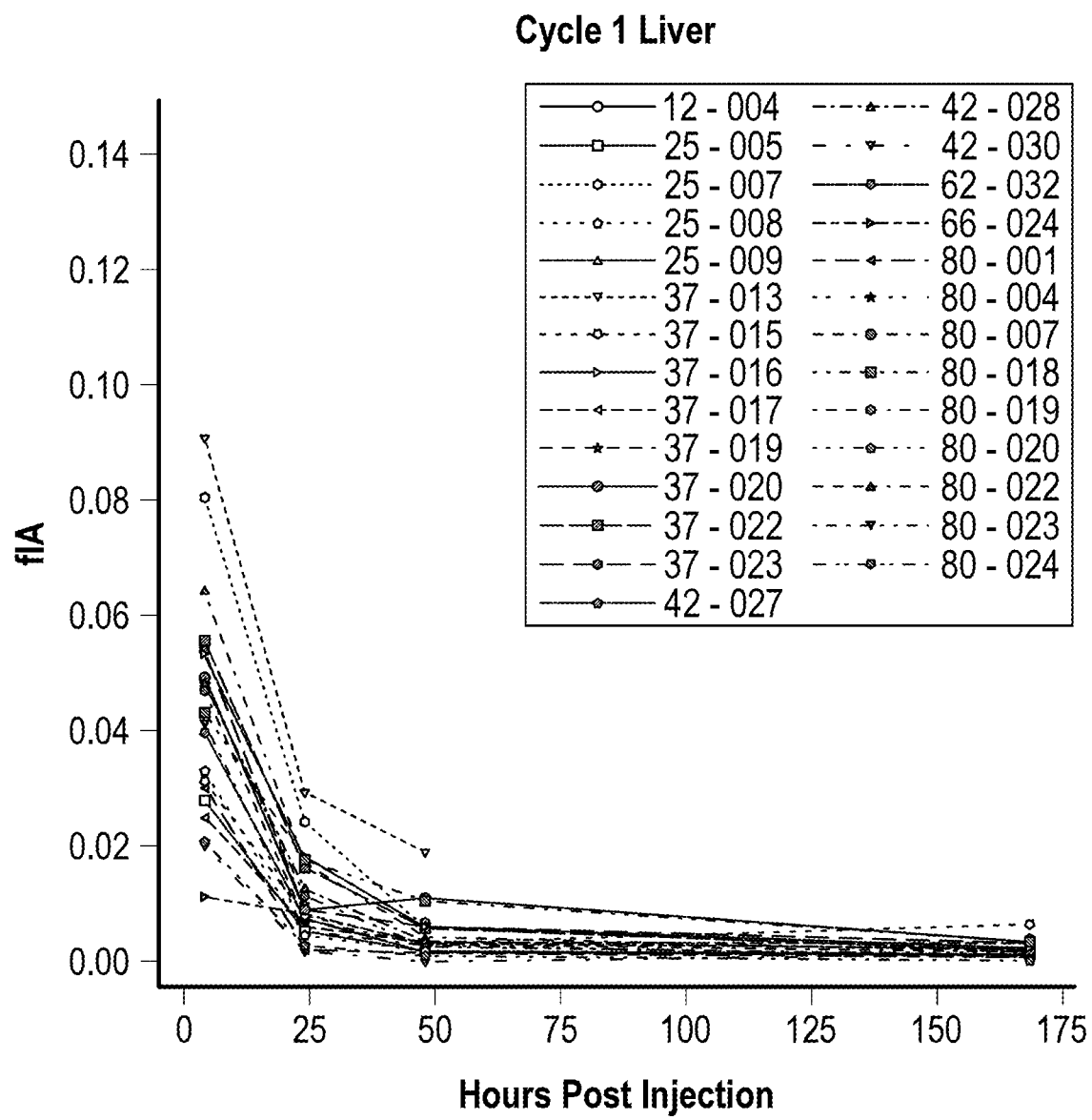
FIG. 21 shows the liver time-activity curve expressed as fraction of injected activity for each patient imaged at cycle 1.
Figure 22:
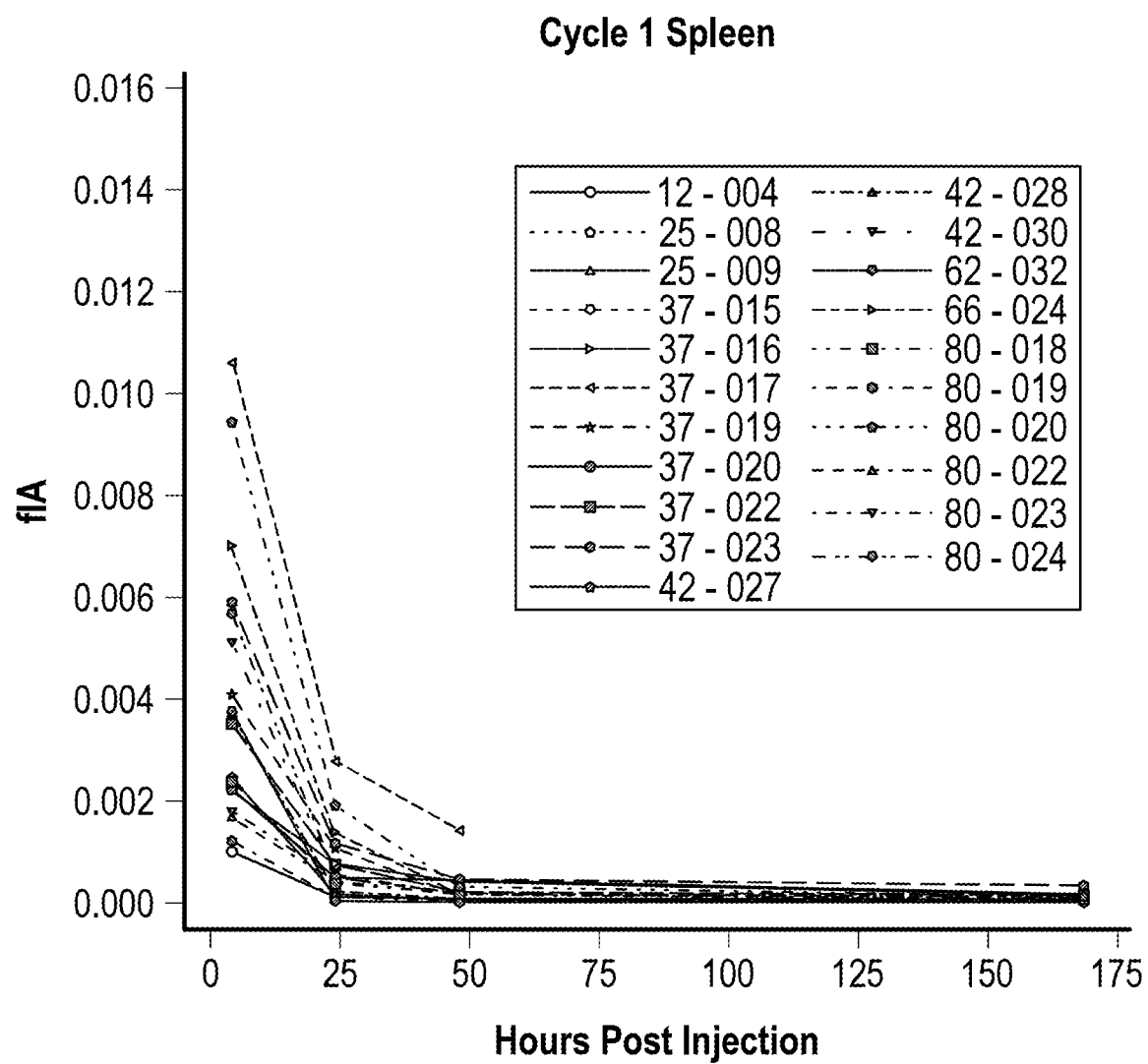
FIG. 22 shows the spleen time-activity curve expressed as fraction of injected activity for each patient imaged at cycle 1.
Figure 23:
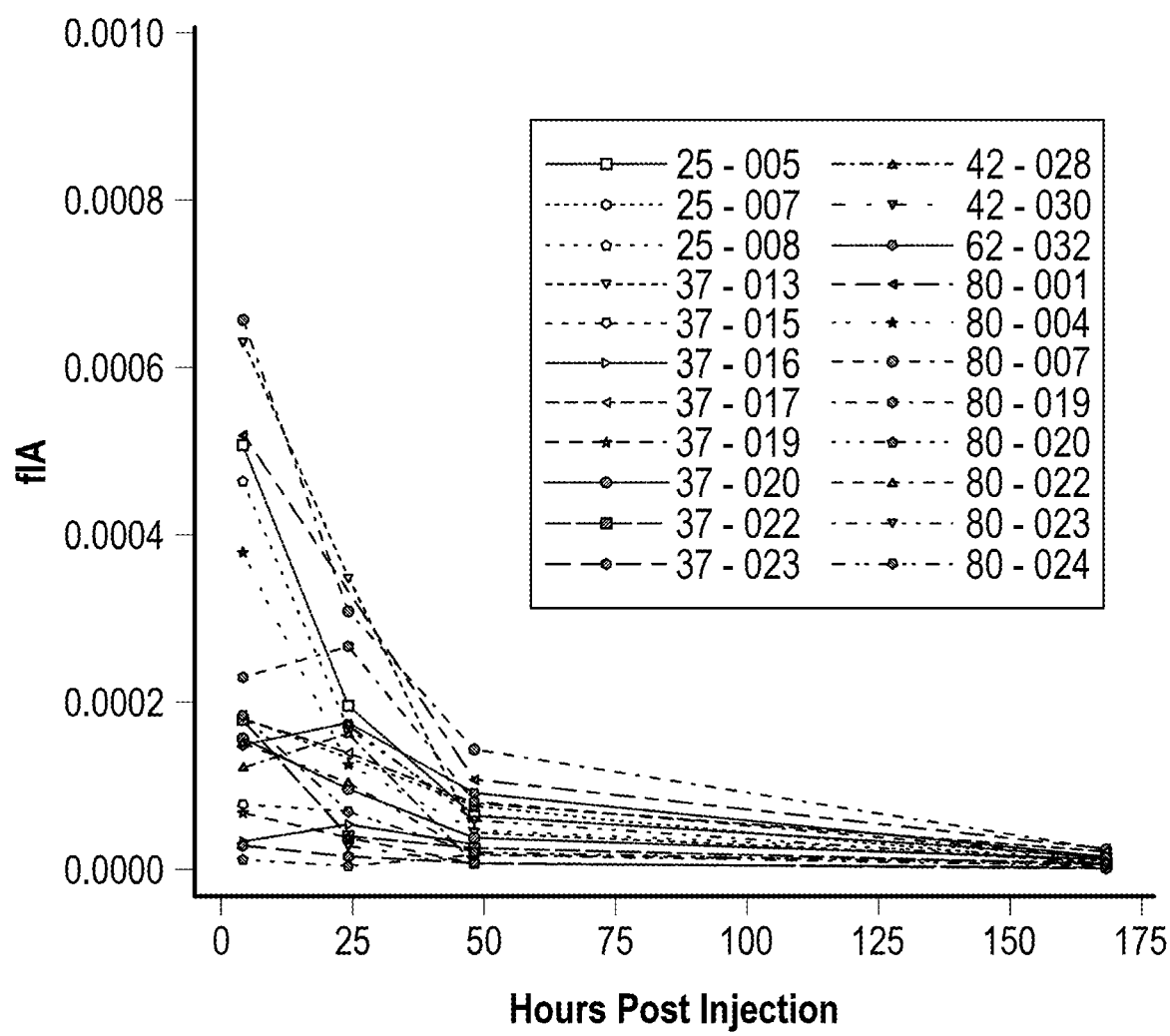
FIG. 23 shows the lacrimal glands time-activity curve expressed as fraction of injected activity for each patient imaged at cycle 1. Lacrimal glands were not in the SPECT field of view for 5 patients (42-027; 80-018; 66-024; 25-009 and 12-004).
Figure 24:
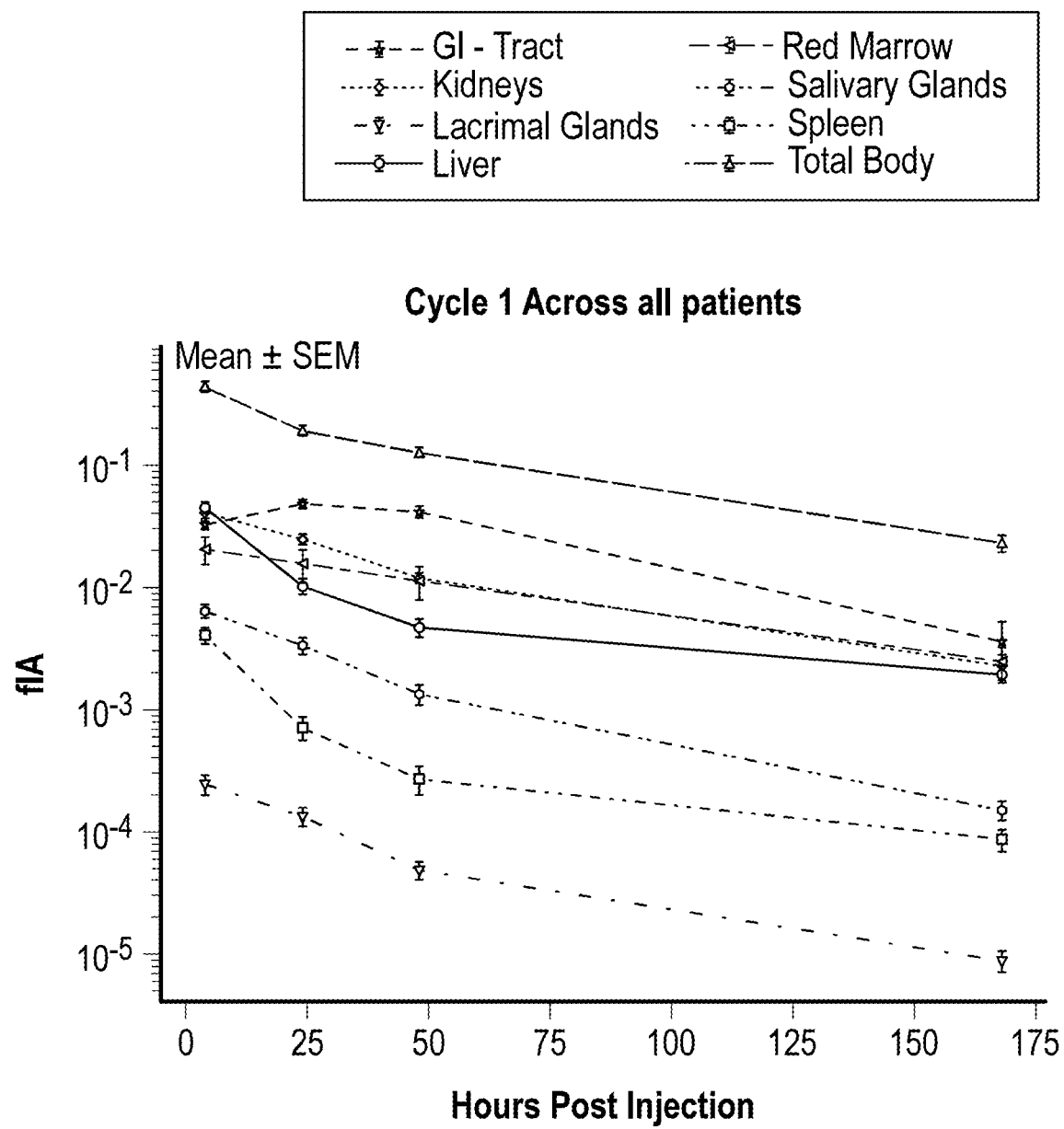
FIG. 24 shows the cycle 1 averaged time-activity curves for all source organs, in semi-logarithmic scale.
Figure 25:
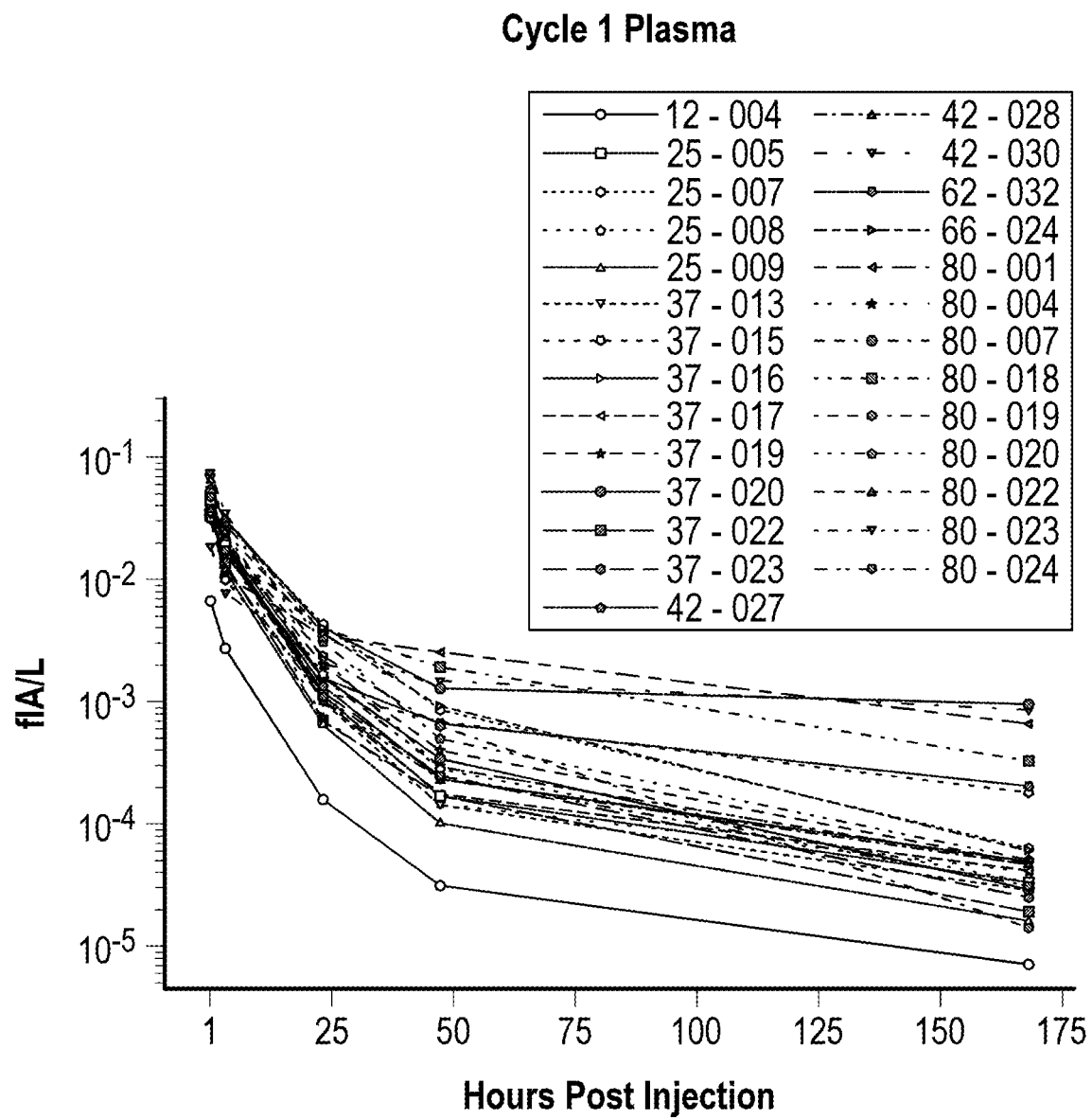
FIG. 25 shows the plasma time-activity curve in fraction of injected activity per Liter for patients at cycle 1 (n=27) in semi-logarithmic scale.

Given the significant bone involvement, this patient was determined to have superscan by the site Principal Investigator (PI), which is an exclusion criterion. In line with the high bone involvement in this patient, the estimated bone marrow uptake was also high, as shown in FIG. 18. Consequently, even if the dosimetry and PK analysis were performed, the biodistribution and dose values of this patient were removed from all aggregated data in this report (mean, standard deviation, and average curves).

The whole-body time-activity curves were fitted with bi-exponential equation and the two components were used for the distribution and elimination half-life. The mean half-lives (excluding patient 42-030) were distribution half-life of 2.16±1.30 hours and the elimination half-life of 46.29±23.83 hours.

Regarding the TACs in the various organs (kidney, liver, spleen, salivary glands, lacrimal glands, GI tract), the profiles were rather similar among the different patients, with some expected variability. Unsurprisingly, the variability is more pronounced in the GI tract.

Figure 15:
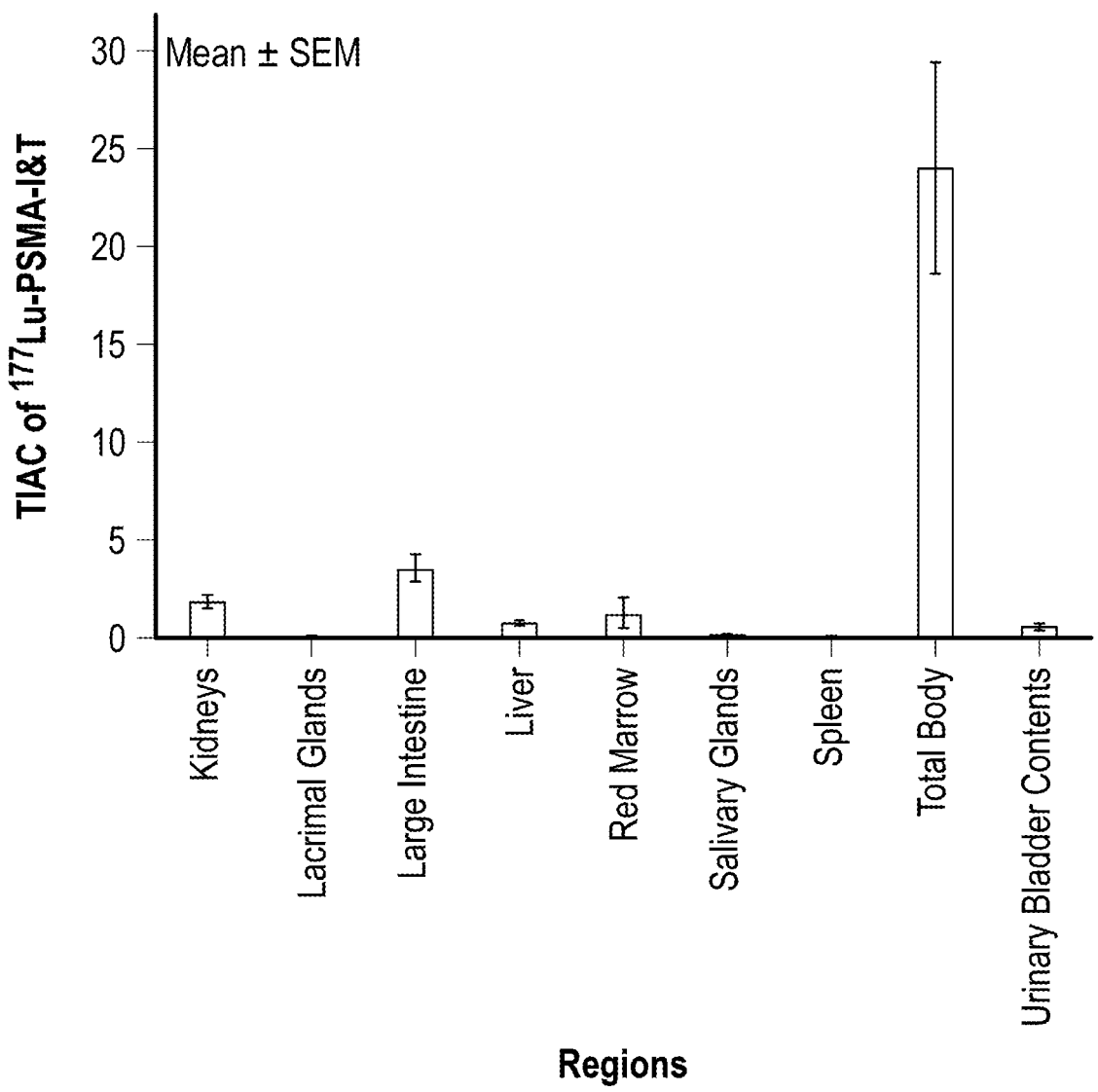
FIG. 15 presents a chart of the TIAC of 177Lu-PSMA-I&T (hours) against regions of the body.

FIG. 15 reports the TACs for all source organs averaged across the patients analysed (excluding patient 42-030 who had a superscan). As already observed from the individual profiles, whole body TACs showed an initial rapid clearance with a mean activity retention at 4 h of 44%±13% (min=24%; max=78%), followed by a second phase characterized by a slower clearance.

The mean TACs in other organs exhibit similar behavior, particularly during the elimination phase.

Cycle 1 Dosimetry

Mirroring the biodistribution data, the absorbed radiation dose per gram of tissue was higher in the organs responsible for the elimination of the tracer, i.e. kidneys (0.41±0.15 Gy/GBq), urinary bladder (0.41±0.05 Gy/GBq) and some parts of the GI tract, i.e. left colon (0.47±0.31 Gy/GBq) and rectum (0.44±0.30 Gy/GBq). Salivary and lacrimal glands also showed moderate absorbed radiation dose (0.19±0.16 and 0.40±0.36 Gy/GBq, respectively). To note for patient 12-004 the Salivary Glands were not in the field of view of the scans so no Salivary glands TIAC could be computed, this patient is excluded from the Salivary glands absorbed dose aggregate metrics.

The mean absorbed dose for bone marrow was 0.08±0.12 Gy/GBq). The high variability of the marrow dose is due to some patients having unusually high doses to the bone marrow (42-027, 62-032, 80-018, 80-024, 37-013, 37-016). In two out of these six patients (42-027 and 62-032), the high marrow dose estimation was likely due to the presence of an isolated metastasis in the vertebrae that were segmented to obtain the image-based marrow dosimetry (L2-L4). Because of the methodology of bone marrow dose estimation, the presence of a metastatic lesion within the VOI, leads to an overestimation of the bone marrow absorbed radiation dose. In the other four patients, the images showed a diffuse bone metastatic disease, resulting in a higher and more diffused radioactivity distribution in the bone tissue, with consequently higher marrow dose estimation. Excluding these six specific cases and the patient with a superscan, the remaining 20 patients would have had a mean red marrow absorbed dose of 0.02±0.02 Gy/GBq.

Average doses to all target organs are reported in Table 16.

TABLE 16

Average Cycle 1 Absorbed Dose Estimates (n = 26)

| Target Organ | Absorbed Dose (Gy/GBq) | | | | | |
| --- | --- | --- | --- | --- | --- | --- |
| | Mean | SD | min | max | median | COV |
| Adrenals | 0.02 | 0.02 | 0.01 | 0.08 | 0.02 | 0.71 |
| Brain | 0.01 | 0.02 | 0.00 | 0.07 | 0.01 | 1.06 |
| Esophagus | 0.02 | 0.02 | 0.00 | 0.07 | 0.01 | 1.02 |
| Eyes | 0.01 | 0.02 | 0.00 | 0.07 | 0.01 | 1.06 |
| Gallbladder wall | 0.02 | 0.02 | 0.00 | 0.07 | 0.01 | 0.89 |
| Heart wall | 0.02 | 0.02 | 0.00 | 0.07 | 0.01 | 1.02 |
| Kidneys | 0.41 | 0.15 | 0.17 | 0.81 | 0.37 | 0.36 |

TABLE 16-continued

Average Cycle 1 Absorbed Dose Estimates (n = 26)

| Target Organ | Absorbed Dose (Gy/GBq) | | | | | |
| --- | --- | --- | --- | --- | --- | --- |
| | Mean | SD | min | max | median | COV |
| Left colon | 0.47 | 0.31 | 0.01 | 1.53 | 0.41 | 0.67 |
| Liver | 0.04 | 0.02 | 0.01 | 0.10 | 0.03 | 0.56 |
| Lungs | 0.01 | 0.02 | 0.00 | 0.07 | 0.01 | 1.03 |
| Osteogenic cells | 0.05 | 0.07 | 0.00 | 0.29 | 0.02 | 1.40 |
| Pancreas | 0.02 | 0.02 | 0.00 | 0.07 | 0.01 | 0.92 |
| Prostate | 0.02 | 0.02 | 0.01 | 0.07 | 0.01 | 0.84 |
| Rectum | 0.44 | 0.30 | 0.01 | 1.46 | 0.39 | 0.67 |
| Red Marrow | 0.08 | 0.12 | 0.00 | 0.49 | 0.03 | 1.56 |
| Right Colon | 0.25 | 0.17 | 0.01 | 0.82 | 0.22 | 0.66 |
| Salivary Glands | 0.19 | 0.16 | 0.03 | 0.80 | 0.15 | 0.82 |
| Small intestine | 0.05 | 0.03 | 0.01 | 0.15 | 0.04 | 0.59 |
| Spleen | 0.03 | 0.02 | 0.01 | 0.11 | 0.02 | 0.76 |
| Stomach Wall | 0.02 | 0.02 | 0.00 | 0.07 | 0.01 | 0.99 |
| Testes | 0.01 | 0.02 | 0.00 | 0.07 | 0.01 | 1.02 |
| Thymus | 0.01 | 0.02 | 0.00 | 0.07 | 0.01 | 1.05 |
| Thyroid | 0.01 | 0.02 | 0.00 | 0.07 | 0.01 | 1.06 |
| Urinary Bladder wall | 0.41 | 0.05 | 0.33 | 0.50 | 0.41 | 0.12 |
| Lacrimal Glands | 0.40 | 0.36 | 0.04 | 1.19 | 0.26 | 0.90 |
| Total Body | 0.02 | 0.02 | 0.01 | 0.09 | 0.02 | 0.74 |

The calibration factors of the individual patients were similar (<10% difference) to those determined at site setup, with the exception of two patients at cycle 1 from one site.

These two patients (80-018 and 80-023) showed discrepancies in both calibration and efficiency factors, with differences of approximately +135% and −45%, respectively, from the reference values determined at site setup (Table 6). Since the same discrepancy was found in the calibration factor for the SPECT and the efficiency factor for the gamma counter, we concluded that these discrepancies may have been due to errors in the measurement of the standard reference value. After quality control of the acquisition and reconstruction parameters, we concluded that the whole-body images of these two patients were acquired correctly, and the issue appeared limited to the measurement of the calibration factors. This conclusion was corroborated by the dosimetry results of these two patients, which were well within the range of the other patients.

TABLE 17

SPECT calibration factors and Gamma counter efficiency factors from site 80

| Patient | SPECT calibration factor Cycle 1 value (Bq/counts) | % diff C1 vs site set up | Gamma counter efficiency factor | % diff C1 vs site set up (Bq/cps) |
| --- | --- | --- | --- | --- |
| 80-001 | 23.84 | 17% | 21.79 | 4% |
| 80-004 | 19.22 | 4% | 15.42 | 30% |
| 80-007 | 18.77 | 6% | 19.07 | 9% |
| 80-018 | 95.81 | 131% | 110.29 | 136% |
| 80-019 | 18.29 | 9% | 19.28 | 8% |
| 80-020 | 18.72 | 7% | 19.64 | 6% |
| 80-022 | 20.33 | 2% | 21.80 | 4% |

TABLE 17-continued

SPECT calibration factors and Gamma counter efficiency factors from site 80

| Patient | SPECT calibration factor Cycle 1 value (Bq/counts) | % diff C1 vs site set up | Gamma counter efficiency factor | % diff C1 vs site set up (Bq/cps) |
|---|---|---|---|---|
| 80-023 | 12.66 | 45% | 13.12 | 46% |
| 80-024 | 22.05 | 10% | 23.02 | 10% |
| Mean | 20.18 | 8 ± 0.05 | 20.00 | |
| Site set up | 20.03 | | 20.89 | |

Cycle 1 PK Monitoring

Figure 16:
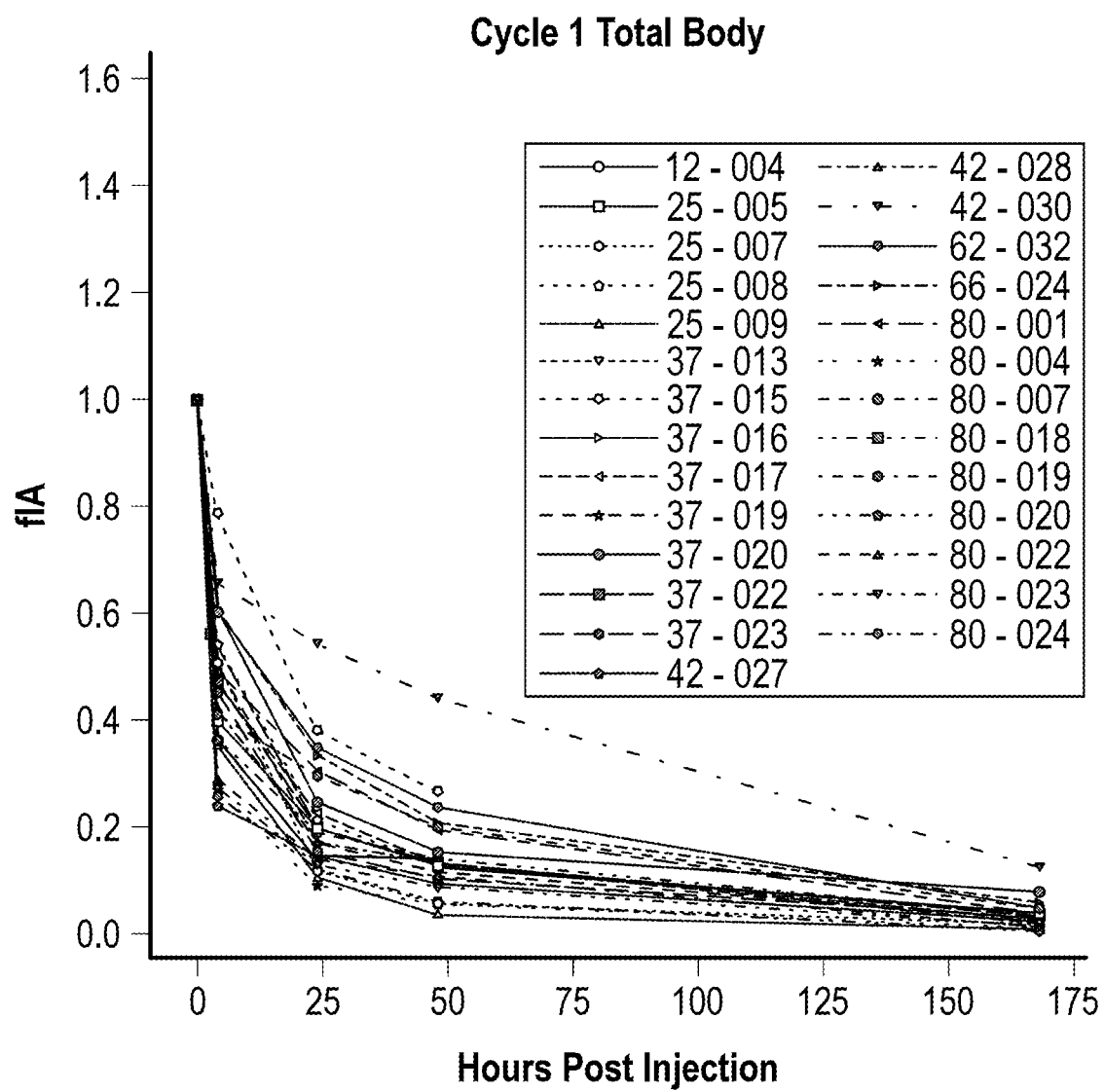
FIG. 16 shows the whole-body time-activity curve expressed as fraction of injected activity for each patient imaged at cycle 1. The curve with the slowest washout belongs to the patient with a superscan.
Figure 17:
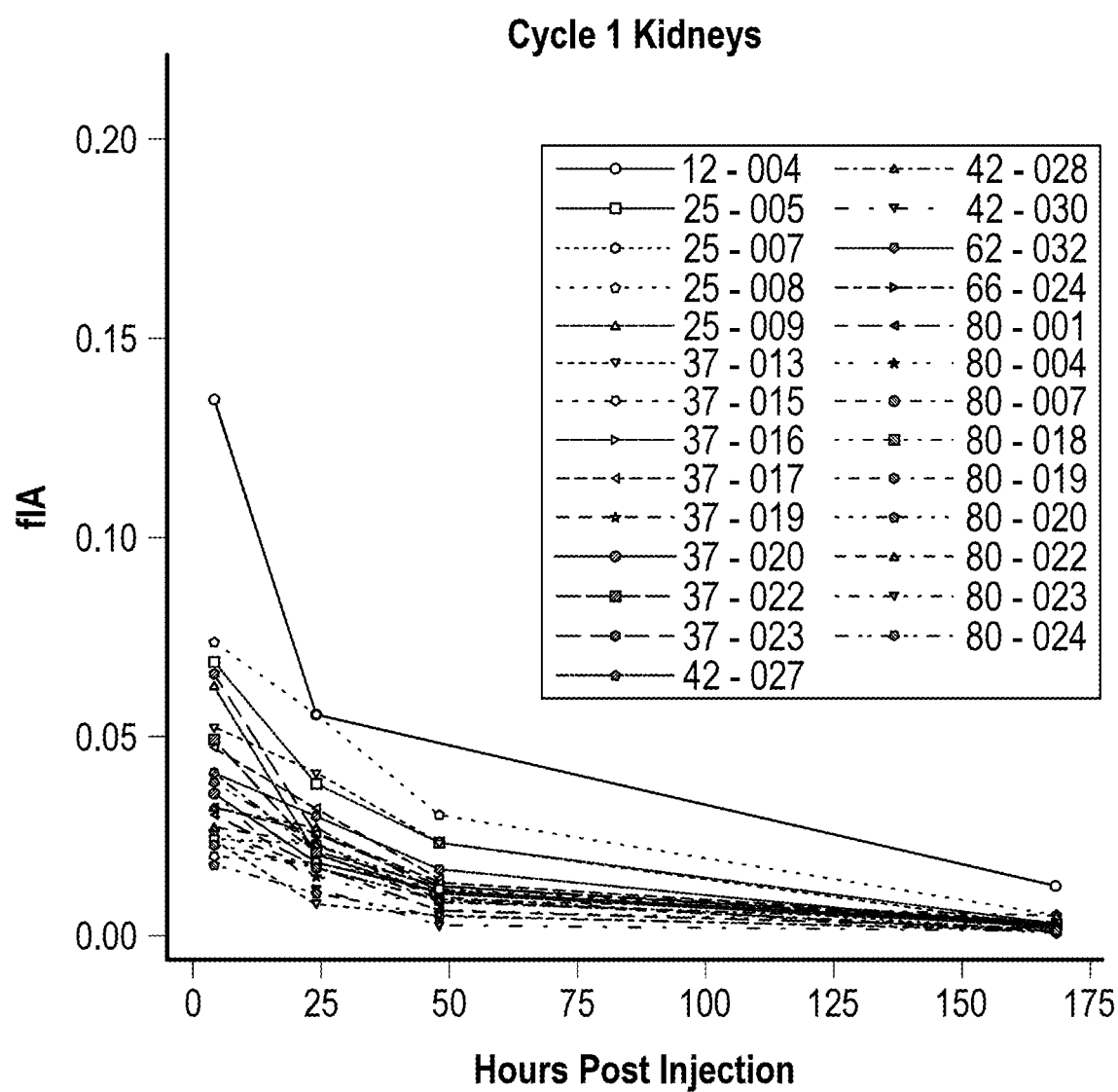
FIG. 17 shows the kidney time-activity curve expressed as fraction of injected activity for each patient imaged at cycle 1.

Plasma PK modelling results are reported in Tables 7A and 7B. Plasma data was fitted with a bi-exponential curve. As shown in FIG. 16 the plasma concentration decreased over time with a similar profile in all patients, initially with a faster decline (mean distribution half-life was 1.89±0.34 h) followed by a slower, prolonged decrease. The mean elimination half-life was 14.70±10.10 hours. Patient 42-030 demonstrated an outlier half-life value of 113.96 h. which aligns with the patient's whole body and bone marrow TACs, in which the radioactivity was taken up by the numerous bone metastases.

The time of peak concentration always corresponds to the time of the first post-administration blood sample taken one hour after injection. Likely, the peak value occurred shortly after injection, but was not captured by the sampling schedule applied in this study. Therefore, the peak concentration value reflects the value measured at the time of the first sample, and not the true peak value in the plasma. Notably, the time to peak for patient 80-007 is at 127 minutes, rather than one hour after injection, due to the first post-administration sample in that patient being acquired with a delay.

While the elimination phase of the plasma profile appears to be prolonged in most patients, it should be noted that the concentration levels at later timepoints are very low. Indeed, the clearance values (13.06±16.50 L/h) indicate a rather rapid clearance of most of the injected dose from the body. Part of the injected activity is captured in the target-expressing tissues and tumors, as indicated by the moderate-to-high distribution volume.

TABLE 18

Cycle 1 PK plasma modelling results

| Patient | Distribution Half-Life (h) | Elimination Half-Life (h) | Peak Concentration Value (fIA/L) | Time of Peak Concentration (min) |
|---|---|---|---|---|
| 25-007 | 2.22 | 10.35 | 0.05 | 56.00 |
| 80-007 | 2.21 | 23.96 | 0.05 | 127.00 |
| 80-024 | 1.67 | 16.65 | 0.05 | 47.00 |
| 42-028 | 1.14 | 9.61 | 0.04 | 53.00 |
| 80-018 | 2.14 | 24.34 | 0.03 | 60.00 |
| 37-016 | 1.88 | 15.32 | 0.05 | 51.00 |
| 37-023 | 1.93 | 9.32 | 0.04 | 60.00 |
| 37-022 | 1.69 | 10.58 | 0.05 | 58.00 |
| 12-004 | 2.13 | 10.59 | 0.01 | 61.00 |
| 80-019 | 2.19 | 12.43 | 0.04 | 60.00 |
| 80-020 | 1.69 | 10.02 | 0.06 | 50.00 |
| 37-017 | 2.31 | 10.46 | 0.04 | 63.00 |
| 42-030 | 1.81 | 113.96 | 0.02 | 61.00 |
| 80-022 | 1.66 | 9.19 | 0.07 | 57.00 |
| 37-019 | 1.78 | 12.50 | 0.04 | 55.00 |
| 80-001 | 1.35 | 53.30 | 0.03 | 52.00 |
| 80-004 | 1.77 | 10.35 | 0.04 | 68.00 |

TABLE 18-continued

Cycle 1 PK plasma modelling results

| Patient | Distribution Half-Life (h) | Elimination Half-Life (h) | Peak Concentration Value (fIA/L) | Time of Peak Concentration (min) |
|---|---|---|---|---|
| 25-008 | 2.12 | 9.28 | 0.04 | 60.00 |
| 80-023 | 1.92 | 8.16 | 0.07 | 60.00 |
| 37-020 | 2.39 | 10.35 | 0.04 | 71.00 |
| 25-009 | 1.66 | 8.92 | 0.03 | 60.00 |
| 37-013 | 1.30 | 35.48 | 0.04 | 51.00 |
| 37-015 | 2.03 | 8.68 | 0.05 | 52.00 |
| 42-027 | 2.42 | 11.79 | 0.03 | 65.00 |
| 62-032 | 1.46 | 19.98 | 0.04 | 33.00 |
| 66-024 | 2.05 | 11.28 | 0.06 | 40.00 |
| 25-005 | 2.04 | 9.41 | 0.05 | 69.00 |
| Mean | 1.89 | 14.70 | 0.04 | 59.19 |
| stdev | 0.34 | 10.10 | 0.01 | 16.20 |
| min | 1.14 | 8.16 | 0.01 | 33.00 |
| max | 2.42 | 53.30 | 0.07 | 127.00 |
| median | 1.93 | 10.52 | 0.04 | 59.00 |
| COV | 0.18 | 0.69 | 0.31 | 0.27 |

TABLE 19

Cycle 1 PK plasma modelling results

| Patient | Vd (L) | Vc (L) | AUC Total (fIA/L × min) | Clearance Rate (L/h) |
|---|---|---|---|---|
| 25-007 | 54.60 | 14.74 | 34.60 | 3.66 |
| 80-007 | 165.33 | 11.55 | 33.81 | 4.78 |
| 80-024 | 296.49 | 15.53 | 19.09 | 12.34 |
| 42-028 | 148.91 | 14.35 | 15.16 | 10.74 |
| 80-018 | 136.62 | 21.87 | 30.05 | 3.89 |
| 37-016 | 93.01 | 15.83 | 27.64 | 4.21 |
| 37-023 | 134.00 | 16.82 | 20.58 | 9.97 |
| 37-022 | 273.75 | 13.76 | 19.49 | 17.94 |
| 12-004 | 1365.03 | 111.78 | 3.07 | 89.38 |
| 80-019 | 112.27 | 17.80 | 25.59 | 6.26 |
| 80-020 | 139.07 | 11.45 | 25.58 | 9.62 |
| 37-017 | 115.14 | 20.41 | 21.49 | 7.63 |
| 42-030 | 463.99 | 38.22 | 26.70 | 2.82 |
| 80-022 | 62.71 | 10.76 | 31.83 | 4.73 |
| 37-019 | 383.51 | 18.90 | 15.14 | 21.26 |
| 80-001 | 222.08 | 22.65 | 28.67 | 2.89 |
| 80-004 | 308.54 | 15.26 | 17.09 | 20.65 |
| 25-008 | 108.16 | 21.10 | 19.85 | 8.08 |
| 80-023 | 67.50 | 9.92 | 34.96 | 5.73 |
| 37-020 | 118.24 | 17.87 | 24.13 | 7.92 |
| 25-009 | 227.51 | 22.51 | 13.46 | 17.68 |
| 37-013 | 540.13 | 14.72 | 17.93 | 10.55 |
| 37-015 | 177.78 | 16.91 | 18.79 | 14.19 |
| 42-027 | 291.02 | 25.15 | 15.54 | 17.10 |
| 62-032 | 307.91 | 17.72 | 19.50 | 10.68 |
| 66-024 | 64.25 | 12.87 | 37.86 | 3.95 |
| 25-005 | 187.12 | 15.24 | 21.09 | 13.78 |
| Mean | 234.64 | 20.29 | 22.77 | 13.06 |
| stdev | 257.46 | 19.07 | 8.04 | 16.50 |
| min | 54.60 | 9.92 | 3.07 | 2.89 |
| max | 1365.03 | 111.78 | 37.86 | 89.38 |
| median | 157.12 | 16.33 | 20.84 | 9.79 |
| COV | 1.10 | 0.94 | 0.35 | 1.26 |

Cycle 3 Biodistribution and Dosimetry Results

A subgroup of 16 out of the 27 patients underwent and additional dosimetry assessment at Cycle 3. Among these, three patients had dosimetry performed based on images taken at 4 timepoints, while the remaining patients had dosimetry performed at 1 or 2 imaging timepoints only.

Similarly to Cycle 1, the highest uptake and organ absorbed radiation dose in Cycle 3 was predominantly seen in the kidneys, urinary bladder, lacrimal glands, GI tract, and salivary glands.

The organ absorbed radiation doses were compared to the mean organ absorbed radiation doses from Cycle 1 for the same subset of patients, as shown in Tables 8A and 8B. The dosimetry estimations obtained at cycle 3 align closely with those from cycle 1. At this timepoint, the kidneys had the highest dose (0.49±0.19 Gy/GBq) but, for most organs, the estimated absorbed dose values were similar to or lower compared to cycle 1. The average absorbed dose for the kidneys and urinary bladder wall was slightly higher at cycle 3 compared to cycle 1, but this difference remains within the expected variability range.

For the three patients whose dosimetry at cycle 3 was calculated using 4 image timepoints, the organ absorbed radiation dose values are also within the variability ranges observed at Cycle 1.

In conclusion, the dosimetry estimation performed at cycle 3 supports the approach of predicting cumulative absorbed dose based on extrapolation from cycle 1 data in this patient population.

TABLE 20

Mean, SD, Min and Max Organ Absorbed Radiation Dose estimates for the 16 patients imaged at cycle 1 and 3

| Target Organ | Absorbed Dose in Cycle 1 (Gy/GBq) (N = 16) | | | |
|---|---|---|---|---|
| | Mean | SD | min | max |
| Adrenals | 0.02 | 0.02 | 0.01 | 0.08 |
| Brain | 0.01 | 0.02 | 0.00 | 0.07 |
| Esophagus | 0.01 | 0.02 | 0.00 | 0.07 |
| Eyes | 0.01 | 0.02 | 0.00 | 0.07 |
| Gallbladder wall | 0.02 | 0.02 | 0.00 | 0.07 |
| Heart wall | 0.01 | 0.02 | 0.00 | 0.07 |
| Kidneys | 0.41 | 0.17 | 0.17 | 0.81 |
| Left colon | 0.52 | 0.37 | 0.01 | 1.53 |
| Liver | 0.04 | 0.03 | 0.01 | 0.10 |
| Lungs | 0.01 | 0.02 | 0.00 | 0.07 |
| Osteogenic cells | 0.04 | 0.05 | 0.00 | 0.19 |
| Pancreas | 0.02 | 0.02 | 0.00 | 0.07 |
| Prostate | 0.02 | 0.02 | 0.01 | 0.07 |
| Rectum | 0.50 | 0.35 | 0.01 | 1.46 |
| Red Marrow | 0.05 | 0.08 | 0.00 | 0.28 |
| Right Colon | 0.28 | 0.20 | 0.01 | 0.82 |
| Salivary Glands | 0.17 | 0.18 | 0.03 | 0.80 |
| Small intestine | 0.06 | 0.04 | 0.01 | 0.15 |
| Spleen | 0.03 | 0.03 | 0.01 | 0.11 |
| Stomach Wall | 0.02 | 0.02 | 0.00 | 0.07 |
| Testes | 0.01 | 0.02 | 0.00 | 0.07 |
| Thymus | 0.01 | 0.02 | 0.00 | 0.07 |
| Thyroid | 0.01 | 0.02 | 0.00 | 0.07 |
| Urinary Bladder wall | 0.40 | 0.04 | 0.33 | 0.47 |
| Lacrimal Glands[a] | 0.39 | 0.36 | 0.04 | 1.19 |
| Total Body | 0.02 | 0.02 | 0.01 | 0.09 |

[a]Lacrimal glands absorbed dose was calculated using OLINDA sphere model that assume local deposition of the dose.

TABLE 21

Mean, SD, Min and Max Organ Absorbed Radiation Dose estimates for the 16 patients imaged at cycle 1 and 3

| Target Organ | Absorbed Dose in Cycle 3 (Gy/GBq) (N = 16) | | | |
|---|---|---|---|---|
| | Mean | SD | min | max |
| Adrenals | 0.02 | 0.01 | 0.01 | 0.03 |
| Brain | 0.01 | 0.00 | 0.00 | 0.02 |
| Esophagus | 0.01 | 0.01 | 0.00 | 0.02 |
| Eyes | 0.01 | 0.00 | 0.00 | 0.02 |
| Gallbladder wall | 0.01 | 0.01 | 0.00 | 0.02 |
| Heart wall | 0.01 | 0.01 | 0.00 | 0.02 |
| Kidneys | 0.49 | 0.19 | 0.19 | 0.85 |
| Left colon | 0.41 | 0.21 | 0.07 | 0.94 |
| Liver | 0.06 | 0.04 | 0.00 | 0.15 |
| Lungs | 0.01 | 0.00 | 0.00 | 0.02 |
| Osteogenic cells | 0.02 | 0.02 | 0.00 | 0.09 |
| Pancreas | 0.01 | 0.01 | 0.00 | 0.02 |
| Prostate | 0.01 | 0.01 | 0.01 | 0.02 |
| Rectum | 0.39 | 0.20 | 0.06 | 0.90 |
| Red Marrow | 0.03 | 0.04 | 0.00 | 0.17 |
| Right Colon | 0.22 | 0.12 | 0.04 | 0.51 |
| Salivary Glands | 0.20 | 0.16 | 0.04 | 0.69 |
| Small intestine | 0.04 | 0.02 | 0.01 | 0.10 |
| Spleen | 0.03 | 0.03 | 0.01 | 0.12 |
| Stomach Wall | 0.01 | 0.01 | 0.00 | 0.02 |
| Testes | 0.01 | 0.00 | 0.00 | 0.02 |
| Thymus | 0.01 | 0.00 | 0.00 | 0.02 |
| Thyroid | 0.01 | 0.00 | 0.00 | 0.02 |
| Urinary Bladder wall | 0.45 | 0.08 | 0.36 | 0.70 |
| Lacrimal Glands[a] | 0.29 | 0.20 | 0.10 | 0.73 |
| Total Body | 0.02 | 0.01 | 0.01 | 0.03 |

[a]Lacrimal glands absorbed dose was calculated using OLINDA sphere model that assume local deposition of the dose.

Cycle 3 PK Modelling

Blood samples were obtained for 15 out of 16 patients at cycle 3. Patients 12-004 had blood taken only at the 24 h timepoint and, therefore, was not included in the plasma PK analysis. Consistent with Cycle 1, the time-course of plasma concentrations was similar among the patients. The ranges of PK parameters obtained at cycle 3 were similar to those from Cycle 1 data (Tables 9A and 9B).

TABLE 22

Cycle 3 PK plasma modelling results (n = 15)

| Patient | Distribution Half-Life (h) | Elimination Half-Life (h) | Peak Concentration Value (fIA/L) | Time of Peak Concentration (min) |
|---|---|---|---|---|
| 25-007 | 3.17 | 10.67 | 0.06 | 60.00 |
| 80-007 | 2.61 | 18.37 | 0.04 | 60.00 |
| 80-018 | 2.22 | 14.16 | 0.05 | 61.00 |
| 37-016 | 2.07 | 12.51 | 0.04 | 60.00 |
| 80-019 | 1.69 | 11.70 | 0.05 | 68.00 |
| 80-020 | 1.88 | 10.92 | 0.06 | 61.00 |
| 37-017 | 2.30 | 9.33 | 0.04 | 66.00 |
| 80-022 | 2.06 | 9.92 | 0.07 | 61.00 |
| 37-019 | 1.64 | 8.16 | 0.04 | 55.00 |
| 80-004 | 2.07 | 9.10 | 0.04 | 60.00 |
| 25-008 | 2.55 | 9.11 | 0.03 | 65.00 |
| 37-020 | 2.28 | 10.32 | 0.04 | 59.00 |
| 25-009 | 1.85 | 9.75 | 0.03 | 60.00 |
| 37-015 | 2.11 | 9.63 | 0.05 | 59.00 |
| 25-005 | 2.07 | 9.75 | 0.05 | 55.00 |
| 37-017 | 2.30 | 9.33 | 0.04 | 66.00 |

TABLE 22-continued

Cycle 3 PK plasma modelling results (n = 15)

| Patient | Distribution Half-Life (h) | Elimination Half-Life (h) | Peak Concentration Value (fIA/L) | Time of Peak Concentration (min) |
|---|---|---|---|---|
| Mean | 2.17 | 10.89 | 0.05 | 60.67 |
| stdev | 0.39 | 2.56 | 0.01 | 3.52 |
| min | 1.64 | 8.16 | 0.03 | 55.00 |
| max | 3.17 | 18.37 | 0.07 | 68.00 |
| median | 2.07 | 9.92 | 0.04 | 60.00 |
| COV | 0.18 | 0.23 | 0.22 | 0.06 |

TABLE 23

Cycle 3 PK plasma modelling results (n = 15)

| Patient | Vd (L) | Vc (L) | AUC Total (fIA/L × min) | Clearance Rate (L/h) |
|---|---|---|---|---|
| 25-007 | 51.46 | 15.13 | 39.62 | 3.34 |
| 80-007 | 152.16 | 18.12 | 28.52 | 5.74 |
| 80-018 | 61.59 | 16.40 | 36.09 | 3.01 |
| 37-016 | 73.36 | 17.66 | 29.33 | 4.07 |
| 80-019 | 129.70 | 11.98 | 26.16 | 7.68 |
| 80-020 | 106.80 | 11.38 | 29.32 | 6.78 |
| 37-017 | 105.05 | 21.49 | 20.20 | 7.81 |
| 80-022 | 70.92 | 10.66 | 36.74 | 4.95 |
| 37-019 | 171.89 | 16.42 | 16.57 | 14.60 |
| 80-004 | 239.78 | 16.53 | 19.01 | 18.27 |
| 25-008 | 121.21 | 24.53 | 17.88 | 9.22 |
| 37-020 | 126.73 | 17.80 | 23.21 | 8.52 |
| 25-009 | 361.81 | 20.07 | 13.86 | 25.73 |
| 37-015 | 158.71 | 13.50 | 24.55 | 11.43 |
| 25-005 | 191.15 | 14.30 | 22.70 | 13.59 |
| 37-017 | 105.05 | 21.49 | 20.20 | 7.81 |
| Mean | 141.49 | 16.40 | 25.58 | 9.65 |
| stdev | 79.92 | 3.82 | 7.72 | 6.24 |
| min | 51.46 | 10.66 | 13.86 | 3.01 |
| max | 361.81 | 24.53 | 39.62 | 25.73 |
| median | 126.73 | 16.42 | 24.55 | 7.81 |
| COV | 0.56 | 0.23 | 0.30 | 0.65 |

Conclusions

The biodistribution, PK, and dosimetry analysis of a population of patients injected with $^{177}$Lu-PSMA-I&T shows that the organs with moderate to high physiological uptake and absorbed dose are primarily those involved in the elimination of the radiopharmaceutical and/or those expressing PSMA. These include kidneys (0.41±0.15 Gy/GBq), urinary bladder (0.41±0.05 Gy/GBq), salivary and lacrimal glands (0.19±0.16 and 0.40±0.36 Gy/GBq, respectively) and some parts of the GI tract (left colon, 0.47±0.31 Gy/GBq, and rectum, 0.44±0.30 Gy/GBq).

The mean red marrow absorbed radiation dose was 0.08±0.12 Gy/GBq. The high variability observed for this parameter, calculated using the image-based method, is attributed to the presence of diffuse bone metastatic disease in some patients, leading to an increased bone uptake of $^{177}$Lu-PSMA-I&T, and consequently higher absorbed radiation dose in the marrow. Additionally, few patients had metastases in the lumbar region (L2-L4), where the image for bone marrow dosimetry is obtained, potentially leading to overestimation of the marrow absorbed dose in these cases.

PK results demonstrated consistent elimination profile of the radiopharmaceutical from plasma across patients. In particular, the plasma kinetic showed a monotonically decreasing trend across all patients, fitting well with a bi-exponential model.

Overall, the dosimetry data for the main organs of interest were within the expected ranges, as compared to values published in the literature for $^{177}$Lu-PSMA-I&T, derived from various studies, employing different dosimetry methodologies.

Notably, cycle 3 data showed dosimetry and PK values similar to those from cycle 1. This consistency suggests that the values obtained at cycle 1 can be reliably used to extrapolate the cumulative absorbed dose of subsequent cycles.

All references cited herein are hereby incorporated by reference. The foregoing is offered primarily for purposes of illustration. It will be readily apparent to those skilled in the art that further drugs can be included, and that the components, additives, proportions, methods of formulation, methods of use, and other parameters described herein can be modified further or substituted in various ways without departing from the spirit and scope of the invention.

Example 5: Evaluate the Safety and Efficacy of $^{177}$Lu-PSMA-I&T Radioligand Therapy Compared to Hormone Therapy in Men with Metastatic Castration-Resistant Prostate Cancer (mCRPC)

Eclipse is a Phase 3, open-label, multicenter, randomized trial evaluating the safety and efficacy of $^{177}$Lu-PSMA-I&T radioligand therapy compared to hormone therapy in men with metastatic castration-resistant prostate cancer (mCRPC). $^{177}$Lu-PSMA-I&T is a radioactive therapeutic agent that specifically targets the prostate specific membrane antigen (PSMA) that is expressed on both primary and metastatic prostate cancer cells.

A sub-study was conducted to evaluate the PK and radiation dosimetry of $^{177}$Lu-PSMA-I&T, in which patients underwent PK sampling and SPECT/CT imaging after the first and third $^{177}$Lu-PSMA I&T infusion.

Methods

Data Acquisition: All participating sites underwent a rigorous site setup process during which all dose calibrators, scanners, and gamma counters used in the sub-study were calibrated. Sites were allowed to enroll patients in the sub-study only after the completion and approval of all site setup processes by Invicro.

Patients underwent SPECT/CT imaging, with anatomical coverage typically extending from the salivary glands to the pelvis, following the administration of a targeted 7.4±10% GBq of $^{177}$Lu-PSMA-I&T at cycle 1. SPECT/CT imaging was performed at four timepoints: 4 h, 24 h, 48 h, and 168 h post-injection. Additionally, a subset of patients imaged at Cycle 1 (16 out of 27), were also imaged at Cycle 3 (Table 7 in Appendix 1).

Image acquisition and reconstruction protocols were standardized across all imaging timepoints and patients at each site. Furthermore, each site consistently utilized the same SPECT/CT scanner throughout the duration of the study to ensure uniformity.

In general, raw projection data was acquired into a 128×128 matrix with medium energy general purpose (MEGP) collimation using a step and shoot acquisition mode, acquiring 60 projections per detector (180 degrees rotation per detector), 20 seconds per projection, with an acquisition zoom of 1.0, and a 20% (±10%) energy window centered over 208 keV.

A low-dose CT scan was performed prior to beginning the SPECT scan for attenuation correction. Sites were instructed to use the Institutional standard parameters for acquisition of the low-dose CT. Institutional standard reconstruction parameters were used. Scatter correction was required to be applied using a 20% (±10%) scatter window centered over 170 keV.

PK plasma samples were collected at pre-Infusion, 1 h, 4 h, 24 h, 48 h, and 168 h, and counted for radioactivity. Blood samples were first centrifuged to extract plasma, and then the radioactivity in plasma was counted in a gamma counter.

For a detailed summary of site qualification and set up and data acquisition procedures, refer to the Technical Operations Manual (TOM) (Appendix 2).

Image Analysis Methods
Image Pre-processing and Segmentation

The imaging data was analysed using Invicro's VivoQuant software, a validated software used in a 21 CFR § 11-compliant workflow. The general quantification approach was based on the principles detailed in the Medical Internal Radiation Dose (MIRD) Pamphlet No. 16,[1] No 23,[2] and No 26,[3] as appropriate.

SPECT images were calibrated in units of Becquerel (Bq) using a calibration factor derived from a source of known activity, measured during site set up with the same acquisition and reconstruction parameters employed for patient imaging. A patient-specific calibration factor was also derived at each clinical time point after acquisition of the patient SPECT/CT. As a quality control measure, if the patient-specific calibration factor differed by more than 10% from the site set up calibration factor, an investigation was conducted.

Volume of interest (VOI) (kidneys, bladder, liver, lumbar vertebrae L2-L4, lacrimal glands, salivary glands [parotid and submandibular glands], and whole body) were delineated on each dataset by a trained image analyst. The GI tract and spleen were delineated only in a subset of patients where these organs displayed visible uptake. Organs were segmented either by drawing the entire contour of the organ, or by placing a sphere in a representative region of the organ and then multiplying by the organ's effective mass (based on patient's height and weight).[4] Segmentation methods for each organ are specified in Table 1 and were consistently applied to each patient.

Figure 27:
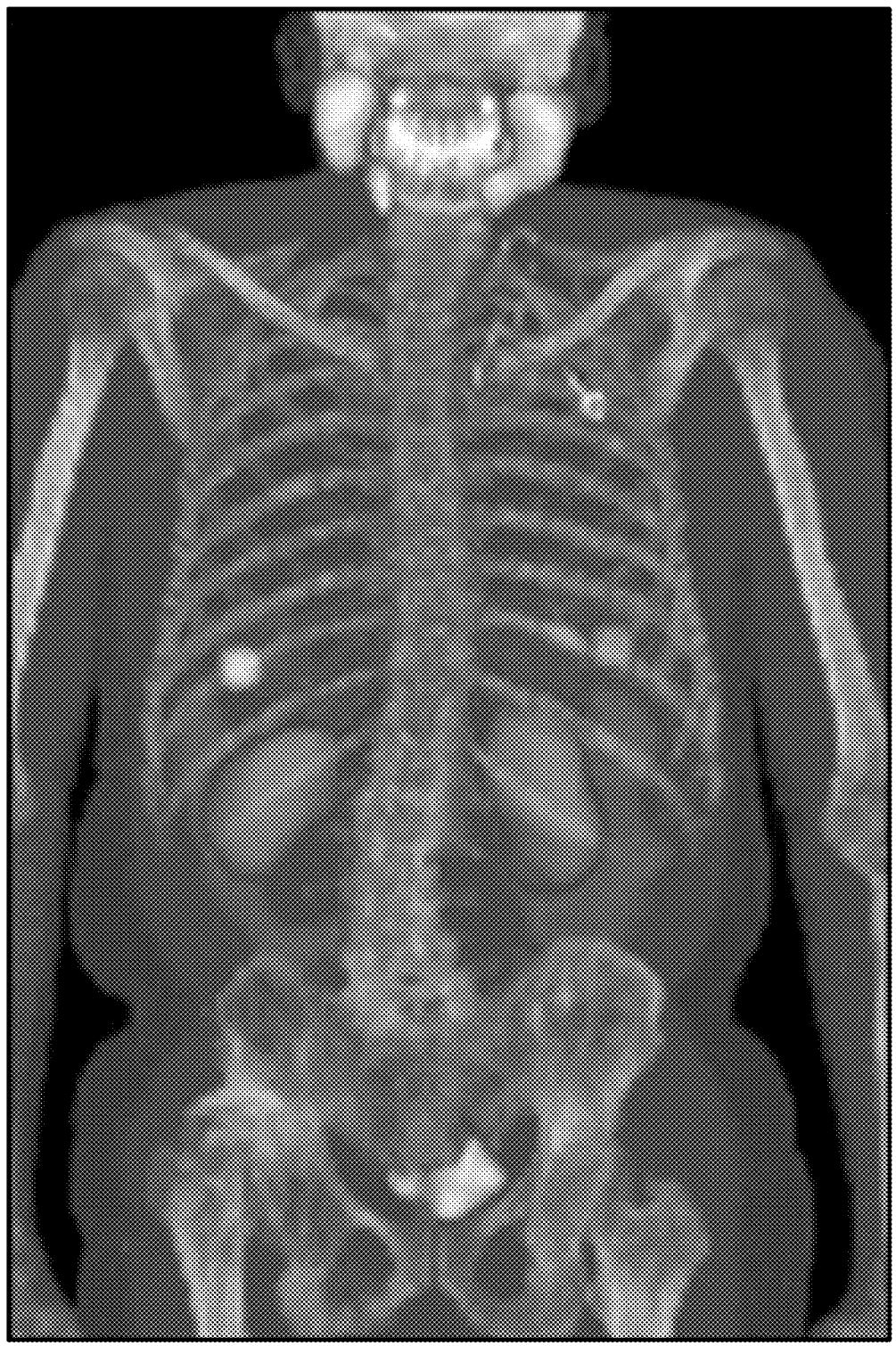
FIG. 27 presents organ delineation on a representative patient.
Figure 28:
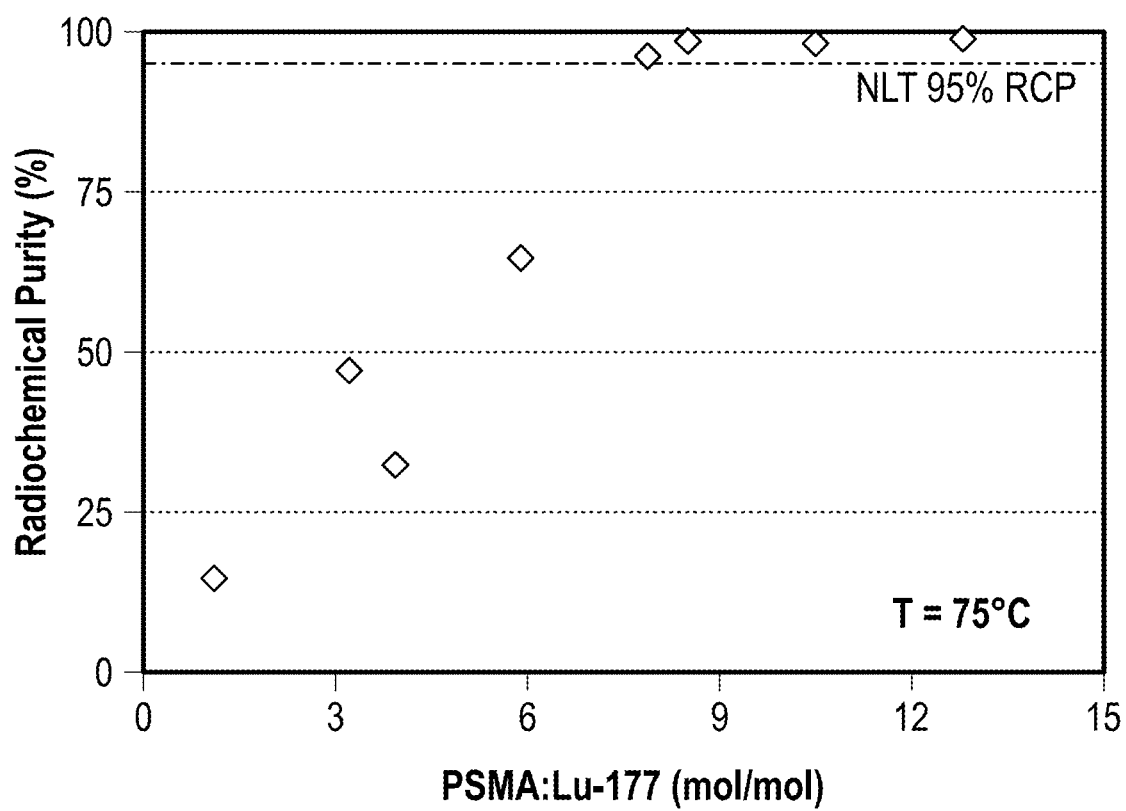
FIG. 28 presents PSMA: Lu-177 (mol/mol) graph showing unsuitable projected radiochemical formation at formulation below 11.0:1.0.

A maximum intensity projection (MIPs) CT image with segmented regions is shown for a representative patient in FIG. 27.

TABLE 24

Organ VOIs and delineation method

| Organ | Method |
|---|---|
| Bladder | CT and SPECT Uptake |
| Liver | Sphere based off CT |
| Spleen | Sphere based off CT |
| Kidney | SPECT Uptake |
| L2-L4 | CT |
| Salivary Glands | SPECT Uptake |
| GI Tract | SPECT Uptake |
| Lacrimal Glands | SPECT Uptake |

Plasma Quantitative Analysis

Whole blood samples were collected as detailed in the protocol Schedule of Events i.e. pre-injection, and then at 1 h, 4 h, 24 h, 48 h, and 168 h post-injection. The samples were first centrifuged to separate plasma, and the radioactivity in the plasma was then measured using a gamma counter. Plasma concentrations were subsequently fitted with a bi-exponential function to derive outcome parameters such as the half-life and clearance rate of the radiopharmaceutical in the plasma.

Normal Organ Dosimetry Analysis

Clearance of the radiopharmaceutical was derived from a data-appropriate fit of each organ's TAC. Depending on the TAC's shape, the data was fitted with the sum of one, two, or three exponentials, or using a rise and fall model. Fitting was performed with in-house Python software. TIACs were calculated through analytical integration of the curve fit extrapolated to infinity. If no appropriate fit was found, the area under the curve (AUC) was estimated using the sum of the trapezoidal integration of imaging measurements and physical decay from the last timepoint onward (the fraction of injected activity at t=0 was set to zero for organs and to 1 for the whole body). A whole-body TAC was derived from delineating the imaged body. The remainder activity was determined by subtracting the cumulative organ TIACs from the whole body TIAC.

Organ TIACs were input into OLINDA 2.2.3 for the computation of organ and whole-body absorbed doses, using International Commission on Radiological Protection (ICRP)-103 weighing factors. The ICRP-89 derived male phantom was used for dose estimation. Organs and body mass as defined by ICRP-89 were scaled based on height and mass using patient effective mass.[4] The voiding bladder model as implemented in OLINDA was used to determine bladder TIAC, assuming a voiding interval of 4 hours. The human alimentary tract model (HAT model) described in ICRP 100 and implemented in OLINDA was used to compute doses to the small intestine, right colon, left colon and rectum for patients showing clearance through the GI tract. The fraction of injected activity (fIA) cleared via the GI tract was determined by taking the peak fIA in the GI tract over all the imaging timepoints. Red marrow dose estimation was derived from segmenting the Lumbar Vertebrae L2-L4 as seen on CT. The Red Marrow mass in L2-L4 was assumed to be 6.7% of the total red marrow mass.5

Single Time Point Dosimetry Analysis Cycle 3

To evaluate potential changes in the tracer's kinetics and uptake after multiple treatment cycles, 16 of the 27 patients included in the dosimetry sub study, were imaged at both cycle 1 and cycle 3. Among these, at cycle 3, three patients were imaged at all 4 timepoints and the other 13 were imaged at one or two timepoints only (24 h, 48 h or both 24 h and 48 h) (Table 7 in Appendix 1). For these 13 patients, the TACs obtained at cycle 1 were used for each source organ and scaled to the normalized activity value(s) measured at Cycle 3. For patients imaged at two timepoints, the TACs were preferably scaled using the average scaling factor between the two timepoints. If the two timepoints yielded significantly different scaling factors, the more conservative timepoint was preferred, provided the dose estimation derived was reasonable.

Data Acquisition Quality Control

Quantitative accuracy of each SPECT image was controlled using a $^{177}$Lu reference standard of known activity. Before a patient was scanned, a reference standard was prepared by injecting 100 µCi (taken from the patient dose vial) into a 100 mL saline bag. The saline bag's radioactivity was subsequently imaged immediately after each imaging timepoint using the same acquisition and reconstruction parameters. The number of counts in the images attributed to the reference standard activity was measured, and the calibration factor was obtained by dividing the number of counts by the known activity in the reference standard at the time of imaging. This calibration factor is expected to be the same (<10% difference compared to the value determined at site setup) for all images acquired with the same SPECT/CT system. For patients where the calibration factor differed by more than 10% compared to the site set-up, an investigation was launched to determine the cause of this variation, and if it reflected a difference in patient data acquisition and/or reconstruction.

Gamma-counted plasma samples were quality controlled using the same $^{177}$Lu reference standard by measuring 0.5 ml of the 100 mL in the saline bag. For each patient, triplicates were made and measured right before all plasma samples were counted. A long-lived isotope was also counted to ensure that the protocol was properly followed by each site. Similarly to the imaging standard, when the gamma counter efficiency factor differed by more than 10% compared to that at site set-up, an investigation was launched to determine the cause of this variation, and if it reflected a difference in data acquisition.

Results

All twenty-seven (27) patients enrolled in the sub-study had SPECT/CT images acquired for dosimetry purposes at the first cycle. Sixteen out of the 27 patients were additionally imaged at cycle 3 as described in Section 4.4.1. The activity injected into each patient at cycles 1 and 3 is shown in Table 25.

TABLE 25

177Lu-PSMA-I&T Injected Activity at cycle 1 and 3

| Patient ID | Cycle 1 (GBq) | Cycle 3 (GBq) |
|---|---|---|
| 12-004 | 7.93 | 7.97 |
| 25-005 | 7.58 | 7.51 |
| 25-007 | 7.56 | 7.44 |
| 25-008 | 7.21 | 7.35 |
| 25-009 | 7.71 | 7.72 |
| 37-013 | 7.42 | NA |
| 37-015 | 7.49 | 7.53 |
| 37-016 | 7.46 | 7.50 |
| 37-017 | 7.59 | 7.53 |
| 37-019 | 7.35 | 7.40 |
| 37-020 | 7.19 | 7.37 |
| 37-022 | 7.48 | NA |
| 37-023 | 7.53 | NA |
| 42-027 | 7.56 | NA |
| 42-028 | 7.62 | NA |
| 42-030 | 7.56 | NA |
| 62-032 | 7.48 | NA |
| 66-024 | 7.26 | NA |
| 80-001 | 7.67 | NA |
| 80-004 | 7.52 | 7.22 |
| 80-007 | 7.54 | 7.14 |
| 80-018 | 7.31 | 7.16 |
| 80-019 | 7.43 | 7.58 |
| 80-020 | 7.39 | 7.42 |
| 80-022 | 7.32 | 7.48 |
| 80-023 | 7.44 | NA |
| 80-024 | 7.49 | NA |
| Mean | 7.48 | 7.46 |
| SD | 0.16 | 0.20 |

Dosimetry analysis included all acquired and/or evaluable imaging. Patient 37-016 did not have SPECT/CT imaging conducted at the 168 h timepoint, and thus the results were based on only 3 timepoints for this patient. For patient 12-004, the 48 h scan presented unrealistically high values (the whole-body fraction of injected activity at 48 h was above that at 4 h and 24 h, despite no additional activity was administered to the patient after the initial $^{177}$Lu-PSMA-I&T injection). In addition, the image quality at 48 h was unusually poor for unknown reasons. Therefore, this timepoint was excluded from further analysis, and dosimetry was performed using the 4 h, 24 h and 168 h SPECT images.

Cycle 1 Biodistribution

Based on the images and dosimetry data, physiologic uptake of $^{177}$Lu-PSMA-I&T was predominantly observed in the kidneys, urinary bladder, lacrimal glands, GI tract, and salivary glands. $^{177}$Lu-PSMA-I&T was primarily excreted through the urine, as indicated by visible accumulation in the urinary bladder. In 25 patients, uptake in the intestines was observed, while no appreciable uptake was found in 2 of the patients analysed (80-004 and 25-005). Salivary glands were not in the SPECT/CT field of view for 1 patient (12-004), and lacrimal glands were outside the field of view for 5 patients (12-004, 25-009, 42-027, 80-018, 66-024). $^{177}$Lu-PSMA-I&T distribution in a patient imaged over time is represented in FIG. 27.

The individual time-activity curves for each source organ, expressed as fIA at the different timepoints are shown in FIGS. 17-25. Note: the time-activity curves in these figures are not decay corrected to time of injection.

All patients showed similar whole-body clearance except for patient 42-030 who had a visibly slower clearance. This slower clearance was likely due to the patient's diffuse bone metastatic disease, confirmed by exposure measurements performed by the site 24 hours after investigational product (IP) injection. An ionization chamber (Ludlum 9DP*) was used for the measurement, performed 1 meter from the patient. After each cycle, this patient had dose rates approximately three times higher than those of the other two patients from the same site:

patient 42-027:7 uSv/h; 6 uSv/h; 5 uSv/h.
patient 42-028:6 uSv/h; 8 uSv/h; 5 uSv/h.
patient 42-030:16 uSv/h; 18 uSv/h; 17 uSv/h.

Given the significant bone involvement, this patient was determined to have superscan by the site Principal Investigator (PI), which is an exclusion criterion. In line with the high bone involvement in this patient, the estimated bone marrow uptake was also high, as shown in FIG. 18. Consequently, even if the dosimetry and PK analysis were performed, the biodistribution and dose values of this patient were removed from all aggregated data in this report (mean, standard deviation, and average curves).

The whole-body time-activity curves were fitted with bi-exponential equation and the two components were used for the distribution and elimination half-life. The mean half-lives (excluding patient 42-030) were distribution half-life of 2.16±1.30 hours and the elimination half-life of 46.29±23.83 hours.

Regarding the TACs in the various organs (kidney, liver, spleen, salivary glands, lacrimal glands, GI tract), the profiles were rather similar among the different patients, with some expected variability. Unsurprisingly, the variability is more pronounced in the GI tract.

Cycle 1 Dosimetry

Mirroring the biodistribution data, the absorbed radiation dose per gram of tissue was higher in the organs responsible for the elimination of the tracer, i.e. kidneys (0.41±0.15 Gy/GBq), urinary bladder (0.41±0.05 Gy/GBq) and some parts of the GI tract, i.e. left colon (0.47±0.31 Gy/GBq) and rectum (0.44±0.30 Gy/GBq). Salivary and lacrimal glands also showed moderate absorbed radiation dose (0.19±0.16 and 0.40±0.36 Gy/GBq, respectively). To note for patient 12-004 the Salivary Glands were not in the field of view of the scans so no Salivary glands TIAC could be computed, this patient is excluded from the Salivary glands absorbed dose aggregate metrics.

The mean absorbed dose for bone marrow was 0.08±0.12 Gy/GBq). The high variability of the marrow dose is due to some patients having unusually high doses to the bone marrow (42-027, 62-032, 80-018, 80-024, 37-013, 37-016).

In two out of these six patients (42-027 and 62-032), the high marrow dose estimation was likely due to the presence of an isolated metastasis in the vertebrae that were segmented to obtain the image-based marrow dosimetry (L2-L4). Because of the methodology of bone marrow dose estimation, the presence of a metastatic lesion within the VOI, leads to an overestimation of the bone marrow absorbed radiation dose. In the other four patients, the images showed a diffuse bone metastatic disease, resulting in a higher and more diffused radioactivity distribution in the bone tissue, with consequently higher marrow dose estimation. Excluding these six specific cases and the patient with a superscan, the remaining 20 patients would have had a mean red marrow absorbed dose of 0.02±0.02 Gy/GBq.

Average doses to all target organs are reported in Table 26 and individual doses are reported in Appendix 1.

TABLE 26

Average Cycle 1 Absorbed Dose Estimates (n = 26)

| Target Organ | Absorbed Dose (Gy/GBq) | | | | | |
|---|---|---|---|---|---|---|
| | Mean | SD | min | max | median | COV |
| Adrenals | 0.02 | 0.02 | 0.01 | 0.08 | 0.02 | 0.71 |
| Brain | 0.01 | 0.02 | 0.00 | 0.07 | 0.01 | 1.06 |
| Esophagus | 0.02 | 0.02 | 0.00 | 0.07 | 0.01 | 1.02 |
| Eyes | 0.01 | 0.02 | 0.00 | 0.07 | 0.01 | 1.06 |
| Gallbladder wall | 0.02 | 0.02 | 0.00 | 0.07 | 0.01 | 0.89 |
| Heart wall | 0.02 | 0.02 | 0.00 | 0.07 | 0.01 | 1.02 |
| Kidneys | 0.41 | 0.15 | 0.17 | 0.81 | 0.37 | 0.36 |
| Left colon | 0.47 | 0.31 | 0.01 | 1.53 | 0.41 | 0.67 |
| Liver | 0.04 | 0.02 | 0.01 | 0.10 | 0.03 | 0.56 |
| Lungs | 0.01 | 0.02 | 0.00 | 0.07 | 0.01 | 1.03 |
| Osteogenic cells | 0.05 | 0.07 | 0.00 | 0.29 | 0.02 | 1.40 |
| Pancreas | 0.02 | 0.02 | 0.00 | 0.07 | 0.01 | 0.92 |
| Prostate | 0.02 | 0.02 | 0.01 | 0.07 | 0.01 | 0.84 |
| Rectum | 0.44 | 0.30 | 0.01 | 1.46 | 0.39 | 0.67 |
| Red Marrow | 0.08 | 0.12 | 0.00 | 0.49 | 0.03 | 1.56 |
| Right Colon | 0.25 | 0.17 | 0.01 | 0.82 | 0.22 | 0.66 |
| Salivary Glands | 0.19 | 0.16 | 0.03 | 0.80 | 0.15 | 0.82 |
| Small intestine | 0.05 | 0.03 | 0.01 | 0.15 | 0.04 | 0.59 |
| Spleen | 0.03 | 0.02 | 0.01 | 0.11 | 0.02 | 0.76 |
| Stomach Wall | 0.02 | 0.02 | 0.00 | 0.07 | 0.01 | 0.99 |
| Testes | 0.01 | 0.02 | 0.00 | 0.07 | 0.01 | 1.02 |
| Thymus | 0.01 | 0.02 | 0.00 | 0.07 | 0.01 | 1.05 |
| Thyroid | 0.01 | 0.02 | 0.00 | 0.07 | 0.01 | 1.06 |
| Urinary Bladder wall | 0.41 | 0.05 | 0.33 | 0.50 | 0.41 | 0.12 |
| Lacrimal Glands | 0.40 | 0.36 | 0.04 | 1.19 | 0.26 | 0.90 |
| Total Body | 0.02 | 0.02 | 0.01 | 0.09 | 0.02 | 0.74 |

Data Quality Control Results

The calibration factors of the individual patients were similar (<10% difference) to those determined at site setup, with the exception of two patients at cycle 1 from one site.

These two patients (80-018 and 80-023) showed discrepancies in both calibration and efficiency factors, with differences of approximately +135% and −45%, respectively, from the reference values determined at site setup (Table 8 in Appendix 1). Since the same discrepancy was found in the calibration factor for the SPECT and the efficiency factor for the gamma counter, we concluded that these discrepancies may have been due to errors in the measurement of the standard reference value. After quality control of the acquisition and reconstruction parameters, we concluded that the whole-body images of these two patients were acquired correctly, and the issue appeared limited to the measurement of the calibration factors. This conclusion was corroborated by the dosimetry results of these two patients, which were well within the range of the other patients.

Cycle 1 PK Modelling

Plasma PK modelling results are reported in Table 4, also see FIGS. 12-13 and 14-25. Plasma data was fitted with a bi-exponential curve. The plasma concentration decreased over time with a similar profile in all patients, initially with a faster decline (mean distribution half-life was 1.89±0.34 h) followed by a slower, prolonged decrease. The mean elimination half-life was 14.70±10.10 hours. Patient 42-030 demonstrated an outlier half-life value of 113.96 h. which aligns with the patient's whole body and bone marrow TACs, in which the radioactivity was taken up by the numerous bone metastases.

The time of peak concentration always corresponds to the time of the first post-administration blood sample taken one hour after injection. Likely, the peak value occurred shortly after injection, but was not captured by the sampling schedule applied in this study. Therefore, the peak concentration value reflects the value measured at the time of the first sample, and not the true peak value in the plasma. Notably, the time to peak for patient 80-007 is at 127 minutes, rather than one hour after injection, due to the first post-administration sample in that patient being acquired with a delay.

While the elimination phase of the plasma profile appears to be prolonged in most patients, it should be noted that the concentration levels at later timepoints are very low. Indeed, the clearance values (13.06±16.50 L/h) indicate a rather rapid clearance of most of the injected dose from the body. Part of the injected activity is captured in the target-expressing tissues and tumors, as indicated by the moderate-to-high distribution volume.

TABLE 27

Cycle 1 PK plasma modelling results

| Patient | Distribution Half-Life (h) | Elimination Half-Life (h) | Peak Concentration Value (fIA/L) | Time of Peak Concentration (min) | Vd (L) | Vc (L) | AUC Total (fIA/L × min) | Clearance Rate (L/h) |
|---|---|---|---|---|---|---|---|---|
| 25-007 | 2.22 | 10.35 | 0.05 | 56.00 | 54.60 | 14.74 | 34.60 | 3.66 |
| 80-007 | 2.21 | 23.96 | 0.05 | 127.00 | 165.33 | 11.55 | 33.81 | 4.78 |
| 80-024 | 1.67 | 16.65 | 0.05 | 47.00 | 296.49 | 15.53 | 19.09 | 12.34 |
| 42-028 | 1.14 | 9.61 | 0.04 | 53.00 | 148.91 | 14.35 | 15.16 | 10.74 |
| 80-018 | 2.14 | 24.34 | 0.03 | 60.00 | 136.62 | 21.87 | 30.05 | 3.89 |
| 37-016 | 1.88 | 15.32 | 0.05 | 51.00 | 93.01 | 15.83 | 27.64 | 4.21 |
| 37-023 | 1.93 | 9.32 | 0.04 | 60.00 | 134.00 | 16.82 | 20.58 | 9.97 |
| 37-022 | 1.69 | 10.58 | 0.05 | 58.00 | 273.75 | 13.76 | 19.49 | 17.94 |
| 12-004 | 2.13 | 10.59 | 0.01 | 61.00 | 1365.03 | 111.78 | 3.07 | 89.38 |

TABLE 27-continued

Cycle 1 PK plasma modelling results

| Patient | Distribution Half-Life (h) | Elimination Half-Life (h) | Peak Concentration Value (fIA/L) | Time of Peak Concentration (min) | Vd (L) | Vc (L) | AUC Total (fIA/L × min) | Clearance Rate (L/h) |
|---|---|---|---|---|---|---|---|---|
| 80-019 | 2.19 | 12.43 | 0.04 | 60.00 | 112.27 | 17.80 | 25.59 | 6.26 |
| 80-020 | 1.69 | 10.02 | 0.06 | 50.00 | 139.07 | 11.45 | 25.58 | 9.62 |
| 37-017 | 2.31 | 10.46 | 0.04 | 63.00 | 115.14 | 20.41 | 21.49 | 7.63 |
| 42-030 | 1.81 | 113.96 | 0.02 | 61.00 | 463.99 | 38.22 | 26.70 | 2.82 |
| 80-022 | 1.66 | 9.19 | 0.07 | 57.00 | 62.71 | 10.76 | 31.83 | 4.73 |
| 37-019 | 1.78 | 12.50 | 0.04 | 55.00 | 383.51 | 18.90 | 15.14 | 21.26 |
| 80-001 | 1.35 | 53.30 | 0.03 | 52.00 | 222.08 | 22.65 | 28.67 | 2.89 |
| 80-004 | 1.77 | 10.35 | 0.04 | 68.00 | 308.54 | 15.26 | 17.09 | 20.65 |
| 25-008 | 2.12 | 19.28 | 0.04 | 60.00 | 108.16 | 21.10 | 19.85 | 8.08 |
| 80-023 | 1.92 | 8.16 | 0.07 | 60.00 | 67.50 | 9.92 | 34.96 | 5.73 |
| 37-020 | 2.39 | 10.35 | 0.04 | 71.00 | 118.24 | 17.87 | 24.13 | 7.92 |
| 25-009 | 1.66 | 8.92 | 0.03 | 60.00 | 227.51 | 22.51 | 13.46 | 17.68 |
| 37-013 | 1.30 | 35.48 | 0.04 | 51.00 | 540.13 | 14.72 | 17.93 | 10.55 |
| 37-015 | 2.03 | 8.68 | 0.05 | 52.00 | 177.78 | 16.91 | 18.79 | 14.19 |
| 42-027 | 2.42 | 11.79 | 0.03 | 65.00 | 291.02 | 25.15 | 15.54 | 17.10 |
| 62-032 | 1.46 | 19.98 | 0.04 | 33.00 | 307.91 | 17.72 | 19.50 | 10.68 |
| 66-024 | 2.05 | 11.28 | 0.06 | 40.00 | 64.25 | 12.87 | 37.86 | 3.95 |
| 25-005 | 2.04 | 9.41 | 0.05 | 69.00 | 187.12 | 15.24 | 21.09 | 13.78 |
| Mean | 1.89 | 14.70 | 0.04 | 59.19 | 234.64 | 20.29 | 22.77 | 13.06 |
| stdev | 0.34 | 10.10 | 0.01 | 16.20 | 257.46 | 19.07 | 8.04 | 16.50 |
| min | 1.14 | 8.16 | 10.01 | 33.00 | 54.60 | 9.92 | 3.07 | 2.89 |
| max | 2.42 | 53.30 | 0.07 | 127.00 | 1365.03 | 111.78 | 37.86 | 89.38 |
| median | 1.93 | 10.52 | 0.04 | 59.00 | 157.12 | 16.33 | 20.84 | 9.79 |
| COV | 0.18 | 0.69 | 0.31 | 0.27 | 1.10 | 0.94 | 0.35 | 1.26 |

Cycle 3 Biodistribution and Dosimetry Results

A subgroup of 16 out of the 27 patients underwent and additional dosimetry assessment at Cycle 3. Among these, three patients had dosimetry performed based on images taken at 4 timepoints, while the remaining patients had dosimetry performed at 1 or 2 imaging timepoints only, as described in Section 4.4.1.

Similarly to Cycle 1, the highest uptake and organ absorbed radiation dose in Cycle 3 was predominantly seen in the kidneys, urinary bladder, lacrimal glands, GI tract, and salivary glands (individual and aggregate values for the TIACs of the target organs are in Appendix 1).

Figure 26:
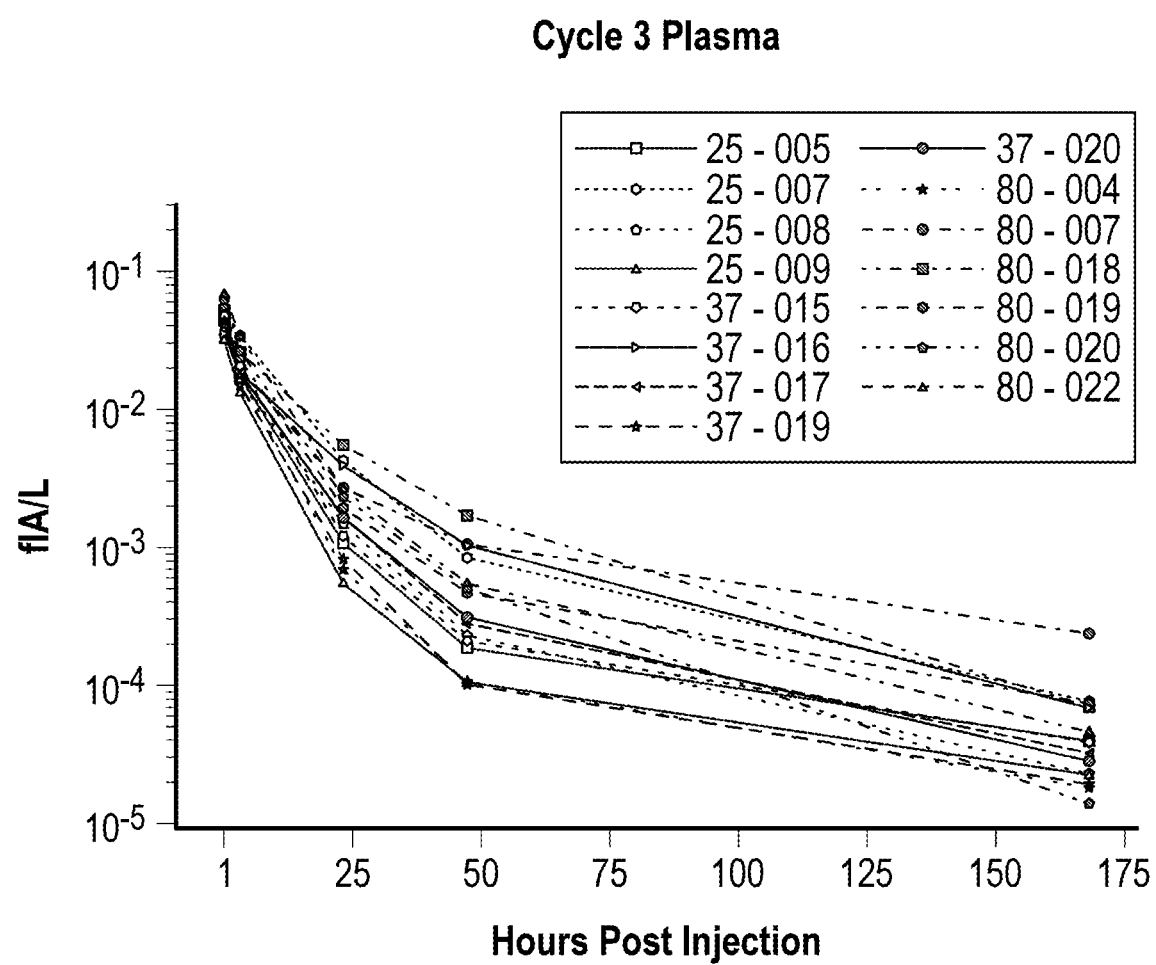
FIG. 26 presents plasma time-activity curve in fraction of injected activity per Liter for patients at cycle 3 (n=15).

The organ absorbed radiation doses were compared to the mean organ absorbed radiation doses from Cycle 1 for the same subset of patients, as shown in Table 5. The dosimetry estimations obtained at cycle 3 align closely with those from cycle 1. See FIG. 26. At this timepoint, the kidneys had the highest dose (0.49±0.19 Gy/GBq) but, for most organs, the estimated absorbed dose values were similar to or lower compared to cycle 1. The average absorbed dose for the kidneys and urinary bladder wall was slightly higher at cycle 3 compared to cycle 1, but this difference remains within the expected variability range.

For the three patients whose dosimetry at cycle 3 was calculated using 4 image timepoints, the organ absorbed radiation dose values are also within the variability ranges observed at Cycle 1.

In conclusion, the dosimetry estimation performed at cycle 3 supports the approach of predicting cumulative absorbed dose based on extrapolation from cycle 1 data in this patient population

TABLE 28

Mean, SD, Min and Max Organ Absorbed Radiation Dose estimates for the 16 patients imaged at cycle 1 and 3

| Target Organ | Absorbed Dose in Cycle 1 (Gy/GBq) (N = 16) | | | | Absorbed Dose in Cycle 3 (Gy/GBq) (N = 16) | | | |
|---|---|---|---|---|---|---|---|---|
| | Mean | SD | min | max | Mean | SD | min | max |
| Adrenals | 0.02 | 0.02 | 0.01 | 0.08 | 0.02 | 0.01 | 0.01 | 0.03 |
| Brain | 0.01 | 0.02 | 0.00 | 0.07 | 0.01 | 0.00 | 0.00 | 0.02 |
| Esophagus | 0.01 | 0.02 | 0.00 | 0.07 | 0.01 | 0.01 | 0.00 | 0.02 |
| Eyes | 0.01 | 0.02 | 0.00 | 0.07 | 0.01 | 0.00 | 0.00 | 0.02 |
| Gallbladder wall | 0.02 | 0.02 | 0.00 | 0.07 | 0.01 | 0.01 | 0.00 | 0.02 |
| Heart wall | 0.01 | 0.02 | 0.00 | 0.07 | 0.01 | 0.01 | 0.00 | 0.02 |
| Kidneys | 0.41 | 0.17 | 0.17 | 0.81 | 0.49 | 0.19 | 0.19 | 0.85 |
| Left colon | 0.52 | 0.37 | 0.01 | 1.53 | 0.41 | 0.21 | 0.07 | 0.94 |
| Liver | 0.04 | 0.03 | 0.01 | 0.10 | 0.06 | 0.04 | 0.00 | 0.15 |
| Lungs | 0.01 | 0.02 | 0.00 | 0.07 | 0.01 | 0.00 | 0.00 | 0.02 |
| Osteogenic cells | 0.04 | 0.05 | 0.00 | 0.19 | 0.02 | 0.02 | 0.00 | 0.09 |
| Pancreas | 0.02 | 0.02 | 0.00 | 0.07 | 0.01 | 0.01 | 0.00 | 0.02 |
| Prostate | 0.02 | 0.02 | 0.01 | 0.07 | 0.01 | 0.01 | 0.01 | 0.02 |
| Rectum | 0.50 | 0.35 | 0.01 | 1.46 | 0.39 | 0.20 | 0.06 | 0.90 |

TABLE 28-continued

Mean, SD, Min and Max Organ Absorbed Radiation Dose estimates for the 16 patients imaged at cycle 1 and 3

| Target Organ | Absorbed Dose in Cycle 1 (Gy/GBq) (N = 16) | | | | Absorbed Dose in Cycle 3 (Gy/GBq) (N = 16) | | | |
|---|---|---|---|---|---|---|---|---|
| | Mean | SD | min | max | Mean | SD | min | max |
| Red Marrow | 0.05 | 0.08 | 0.00 | 0.28 | 0.03 | 0.04 | 0.00 | 0.17 |
| Right Colon | 0.28 | 0.20 | 0.01 | 0.82 | 0.22 | 0.12 | 0.04 | 0.51 |
| Salivary Glands | 0.17 | 0.18 | 0.03 | 0.80 | 0.20 | 0.16 | 0.04 | 0.69 |
| Small intestine | 0.06 | 0.04 | 0.01 | 0.15 | 0.04 | 0.02 | 0.01 | 0.10 |
| Spleen | 0.03 | 0.03 | 0.01 | 0.11 | 0.03 | 0.03 | 0.01 | 0.12 |
| Stomach Wall | 0.02 | 0.02 | 0.00 | 0.07 | 0.01 | 0.01 | 0.00 | 0.02 |
| Testes | 0.01 | 0.02 | 0.00 | 0.07 | 0.01 | 0.00 | 0.00 | 0.02 |
| Thymus | 0.01 | 0.02 | 0.00 | 0.07 | 0.01 | 0.00 | 0.00 | 0.02 |
| Thyroid | 0.01 | 0.02 | 0.00 | 0.07 | 0.01 | 0.00 | 0.00 | 0.02 |
| Urinary Bladder wall | 0.40 | 0.04 | 0.33 | 0.47 | 0.45 | 0.08 | 0.36 | 0.70 |
| Lacrimal Glands[a] | 0.39 | 0.36 | 0.04 | 1.19 | 0.29 | 0.20 | 0.10 | 0.73 |
| Total Body | 0.02 | 0.02 | 0.01 | 0.09 | 0.02 | 0.01 | 0.01 | 0.03 |

[a]Lacrimal glands absorbed dose was calculated using OLINDA sphere model that assume local deposition of the dose.

Cycle 3 PK Modelling

Blood samples were obtained for 15 out of 16 patients at cycle 3. Patients 12-004 had blood taken only at the 24 h timepoint and, therefore, was not included in the plasma PK analysis. Consistent with Cycle 1, the time-course of plasma concentrations was similar among the patients. The ranges of PK parameters obtained at cycle 3 were similar to those from Cycle 1 data (Table 29). See Table 29: Cycle 3 PK plasma modelling results (n=15)

| Patient | Distribution Half-Life (h) | Elimination Half-Life (h) | Peak Concentration Value (fIA/L) | Time of Peak Concentration (min) | Vd (L) | Vc (L) | AUC Total (fIA/L × min) | Rate Clearance (L/h) |
|---|---|---|---|---|---|---|---|---|
| 25-007 | 3.17 | 10.67 | 0.06 | 60.00 | 51.46 | 15.13 | 39.62 | 3.34 |
| 80-007 | 2.61 | 18.37 | 0.04 | 60.00 | 152.16 | 18.12 | 28.52 | 5.74 |
| 80-018 | 2.22 | 14.16 | 0.05 | 61.00 | 61.59 | 16.40 | 36.09 | 3.01 |
| 37-016 | 2.07 | 12.51 | 0.04 | 60.00 | 73.36 | 17.66 | 29.33 | 4.07 |
| 80-019 | 1.69 | 11.70 | 0.05 | 68.00 | 129.70 | 11.98 | 26.16 | 7.68 |
| 80-020 | 1.88 | 10.92 | 0.06 | 61.00 | 106.80 | 11.38 | 29.32 | 6.78 |
| 37-017 | 2.30 | 9.33 | 0.04 | 66.00 | 105.05 | 21.49 | 20.20 | 17.81 |
| 80-022 | 2.06 | 9.92 | 0.07 | 61.00 | 70.92 | 10.66 | 36.74 | 4.95 |
| 37-019 | 1.64 | 8.16 | 0.04 | 55.00 | 171.89 | 16.42 | 16.57 | 14.60 |
| 80-004 | 2.07 | 9.10 | 0.04 | 60.00 | 239.78 | 16.53 | 19.01 | 18.27 |
| 25-008 | 2.55 | 9.11 | 0.03 | 65.00 | 121.21 | 24.53 | 17.88 | 9.22 |
| 37-020 | 2.28 | 10.32 | 0.04 | 59.00 | 126.73 | 17.80 | 23.21 | 8.52 |
| 25-009 | 1.85 | 9.75 | 0.03 | 60.00 | 361.81 | 20.07 | 13.86 | 25.73 |
| 37-015 | 2.11 | 9.63 | 0.05 | 59.00 | 158.71 | 13.50 | 24.55 | 11.43 |
| 25-005 | 2.07 | 9.75 | 0.05 | 55.00 | 191.15 | 14.30 | 22.70 | 13.59 |
| 37-017 | 2.30 | 9.33 | 0.04 | 66.00 | 105.05 | 21.49 | 20.20 | 7.81 |
| Mean | 2.17 | 10.89 | 0.05 | 60.67 | 141.49 | 16.40 | 25.58 | 9.65 |
| stdev | 0.39 | 2.56 | 0.01 | 3.52 | 79.92 | 3.82 | 7.72 | 6.24 |
| min | 1.64 | 8.16 | 0.03 | 55.00 | 51.46 | 10.66 | 13.86 | 3.01 |
| max | 3.17 | 18.37 | 0.07 | 68.00 | 361.81 | 24.53 | 39.62 | 25.73 |
| median | 2.07 | 9.92 | 0.04 | 60.00 | 126.73 | 16.42 | 24.55 | 7.81 |
| COV | 0.18 | 0.23 | 0.22 | 0.06 | 0.56 | 0.23 | 0.30 | 0.65 |

Conclusions

The biodistribution, PK, and dosimetry analysis of a population of patients injected with $^{177}$Lu-PSMA-I&T shows that the organs with moderate to high physiological uptake and absorbed dose are primarily those involved in the elimination of the radiopharmaceutical and/or those expressing PSMA. These include kidneys (0.41±0.15 Gy/GBq), urinary bladder (0.41±0.05 Gy/GBq), salivary and lacrimal glands (0.19±0.16 and 0.40±0.36 Gy/GBq, respectively) and some parts of the GI tract (left colon, 0.47±0.31 Gy/GBq, and rectum, 0.44±0.30 Gy/GBq).

The mean red marrow absorbed radiation dose was 0.08±0.12 Gy/GBq. The high variability observed for this parameter, calculated using the image-based method, is attributed to the presence of diffuse bone metastatic disease in some patients, leading to an increased bone uptake of $^{177}$Lu-PSMA-I&T, and consequently higher absorbed radiation dose in the marrow. Additionally, few patients had metastases in the lumbar region (L2-L4), where the image for bone marrow dosimetry is obtained, potentially leading to overestimation of the marrow absorbed dose in these cases.

PK results demonstrated consistent elimination profile of the radiopharmaceutical from plasma across patients. In particular, the plasma kinetic showed a monotonically decreasing trend across all patients, fitting well with a bi-exponential model.

Overall, the dosimetry data for the main organs of interest were within the expected ranges, as compared to values published in the literature for $^{177}$Lu-PSMA-I&T, derived from various studies, employing different dosimetry methodologies.

Notably, cycle 3 data showed dosimetry and PK values similar to those from cycle 1. This consistency suggests that the values obtained at cycle 1 can be reliably used to extrapolate the cumulative absorbed dose of subsequent cycles.

Example 6: Imaging Center Training and Set Up

Technical Operations Manual SPECT/CT & Gamma Counter Data

Always ensure consistent scan parameters are used across time points. The same scanner must be used for all assessments within and across all patients, unless otherwise approved by Invicro or the study sponsor.

Acquire images according to the trial-specific process standards within and according to the protocol's Schedule of Activities. Image acquisition and documentation should not deviate from the clinical trial protocol; however, the TOM may provide expanded information and processes All SPECT/CT scans and gamma counter data, and corresponding documents must be submitted to Invicro preferably within 24 hours, but no more than 3 business days following the final imaging and blood collection time point for each patient per cycle. All gamma counter data must be submitted to Invicro within 24 hours of the final blood collection timepoint for the cycle per patient.

Respond promptly to queries generated by Invicro (preferably within 24 hours but no more than 5 days).

Confirm that all technologists or other personnel who will be performing scans for this protocol are property trained on the study-specific acquisition and reconstruction parameters, as well as data submission and query handling procedures.

Regulatory compliance: All site personnel must comply with the International Council for Harmonization E6 (R2) guidelines on Good Clinical Practice (GCP) when documenting acquisition, archiving images, and submitting image data to Invicro.

Confidentiality: Follow regional privacy practices to de-identify (ie, redact) all patient information (name, medical record number, etc) before submitting image data to Invicro. Submitters should pay particular attention to data that are likely to include protected health information such as DICOM headers, CT dose reports, image overlays, and screenshots.

Schedule of Activities

Your imaging center may scan and collect samples from the first patient following completion of all training and approval requirements. After the scans from the first patient are approved, scanning and sample collection for the remainder of the patients may begin, according to the protocol Schedule of Activities, as summarized in Table 60.

TABLE 30

PK Sub-study Schedule of Activities

| Time Post-Injection[a] | Study Drug Administration [b] | Blood Sampling for PK | SPECT/CT Imaging |
|---|---|---|---|
| Pre-injection Time = 0 | X | X | |
| 1 hour (±15 min) | | X | |
| 4 hours (±30 min) | — | X | X |

| Tam Post-Injection[a] | Study Drug Administration[b] | Blood Sampling for PK | SPECT/CT Imaging |
|---|---|---|---|
| 24 hours (±2 hours) | | X | X |
| 43 hours (±2 hours) | | X | X |
| 7 ± 1 days | | X | X | a Times shown are relative to in $^{177}$Lu-PSMA-I&T infusion. When assessments occur in the same window, the order of the assessments is Blood Sampling then SPECT/CT Imaging. The actual time and date of each assessment will be recorded.
b During Treatment Cycles 1-4, patients will receive a single infusion of $^{177}$Lu-PSMA-I&T. Twenty percent of patents (first 6 patients) to be enrolled in the sub-study, will undergo PK sampling and SPECTICT imaging after ther first and third $^{177}$Lu-PSMA I&T infusion (Week 0 and Week 12). Data generated from those 6 patents at 4 selected time points at cycle 1 (4 hours, 1, 2, 7 +1 −1 days). and at cycle 3 (24 and/or 48 hours per investigator's choice), will be analyzed to determine if differences in drug kinetics or uptake are observed between week 0 and Week 12. If only one SPECT/CT timepoint is chosen by the investigator for cycle 3, the 24 hour time point is preferred. If no significant differences are observed between cycle 1 and cycle 3 for the set of the 6 patents, PK sampling and SPECT/CT triaging will be pertained after the first cycle only (Week 0) for the remaining 24 patients.

Image Data Submission Timelines

All SPECT/CT scans and gamma counter data, and corresponding documents must be submitted to Invicro preferably within 24 hours, but no more than 3 business days following the final imaging and blood collection time point for each patient per cycle.

Imaging center setup: Participating imaging centers will be required to complete Invicro's setup procedures prior to conducting study patient imaging. The purpose of these procedures is to ensure each imaging center participating in the study meets the high level of standard required by Invicro and the study sponsor, provide technologists and supporting staff with training on study imaging requirements, assess the performance of the imaging equipment to be used for the study, and ensure the protocols to be followed for patient imaging are property established.

The following procedures are included as part of setup.

Site Imaging Center Questionnaire
↓
Technical Site Training
↓
SPECT Phantom Acquisition and/or Protocol Screenshot Submission and Approval (per scanner)

↓
Approval to Scan First Subject
↓
Approval to Scan All Subsequent Subjects

Technical Assessment Questionnaire

The initial step in the setup process is the centers completion of a technical assessment questionnaire. This form provides Invicro with contact information for key individuals, address information, specific scanner and computer system capabilities, and other specifications necessary for satisfactory completion of the study. Invicro will provide a brief overview of the setup process to the site and imaging center at the time of sending the questionnaire.

The completed questionnaire is reviewed by Invicro for initial assessment of the imaging centers technical capabilities. If the center meets the technical standards required to perform as a participating center, Invicro will contact the center informing them of the next steps necessary for completion of the qualification process for the study described in the following paragraphs.

In certain cases where Invicro has recently worked with, or is currently working with, an imaging center on another study and has already collected a questionnaire, the requirement for the center to complete a new questionnaire may be waived.

Technical Site Training

The imaging center training for this trial will be conducted via teleconference.

The teleconference training will be among the imaging center staff, the clinical site personnel, and an Invicro setup specialist. During this meeting the overall objectives and rationale for the imaging component of the clinical trial are reviewed. Individual responsibilities for obtaining the imaging measures and a walk-through of the communication flow, logistics, and potential problems (eg, scanner availability, etc,) at the site are discussed and questions addressed Imaging centers may be required to acquire and transfer phantom data to Invicro. The phantom data will be analyzed and used to assess scanner performance. Details regarding phantom preparation, acquisition, and reconstruction, will be provided in a separate document. Please note, the acquisition and transfer of phantom data may be waived if Invicro has recent phantom data on record from the participating imaging center.

In addition, imaging centers will be required to build the study-specific protocol in their scanner and may be asked to submit screenshots of the relevant parameters to Invicro for review and approval.

Please note, at least one primary staff member (technologist, physicist, or physician) responsible for the conduct of study imaging must be Trained by Invicro. It is the responsibility of the imaging center to ensure all additional personnel are trained peer-to-peer by the primary staff member initially trained by Invicro and are supplied with a copy of this TOM, as well as all other study materials. All additional training activities must be documented, with a copy of this training documentation provided to the referring clinical sites. Please contact Invicro for assistance with additional training or questions.

Approval to scan First Patient: Following completion of the technical setup procedures, an 'Approval to Scan' notification and a detailed technical site setup report summarizing the dose, acquisition and reconstruction parameters, image archival, and the approved method of image transfer will be sent to the imaging center, with a copy to the clinical site and sponsor designees. The approval notification and technical report should be archived.

Please Note: This 'Approval to Scan' notification indicates that the imaging center is now ready to scan their first study patient only.

Approval to scan all subsequent patients: After the first study patient has been imaged, the imaging center will be instructed to transfer the images to Invicro within 24 hours of acquisition for QC review. Once the patient images have passed QC, the imaging center and clinical coordinator will be notified via email that they have been approved to continue imaging additional patients. Sites will be notified within approximately 5 business days of receipt of the first patient data (barring no queries). Should the first patient scan not pass QC review, Invicro will communicate with the imaging and clinical personnel regarding how to resolve the issue prior to moving forward with additional patient imaging Please Note: The imaging center MUST wait for the 'Approval to Scan Subsequent Patient' notification in the study.

Please Note: The clinical coordinator should NOT schedule a second patient for imaging until Invicro has reviewed the first patient and it has passed QC.

Technical Binder: The imaging center will receive a link to an electronic technical binder containing all essential imaging study documents including, but not limited to, a copy of this TOM, the training presentation, radiopharmaceutical information, and key Invicro contact information. These documents are to be printed and made available to any staff which will need access to this information. Additionally, Invicro recommends each imaging center file all study related communications (e.g., emails or faxes).

Please Note: Study related documents may be updated throughout the Trial and will be distributed to your imaging center.

Scan identification: It is very important that the imaging center uses a standard file naming convention so that all scans can be easily identified by Invicro. The patient naming convention will be provided by the clinical site personnel in accordance with the study specific requirements.

The site number is assigned to the clinical sites in the trial, not the imaging centers. Therefore, imaging centers that are receiving referrals from several clinical sites will need to use the clinical site number associated with the site the patient is being referred from, on the data submission form and in the naming of the scans when data is transmitted to Invicro. The clinical study site numbers in this trial are comprised of 2 digits.

In this study, patients will be assigned a 5-digit Patient ID. This Patient ID is composed of the 2-digit site number (represented as XX), and 3 digits unique to the patient (represented by YYY). The naming conventions are summarized in Table 31.

| Visit | Scan File | Numbers for |
|---|---|---|
| All Visits | 5-digit. | 5-digit screening ID |

Please note: the 5-digit Patient ID number should be populated in both the Patient Name and ID fields with the Date of Birth arbitrarily populated with January 1970 when setting up an acquisition on the scanner or during the de-identification of the scan file $^{177}$Lu-PSMA-I&T Administration The study drug, $^{177}$Lu-PSMA-I&T, is a novel radiotherapeutic that will be characterized for efficacy, and dosimetry for the treatment of mCRPC. Patients participating in the PK and Radiation Dosimetry Sub-study will have 4 injections of $^{177}$Lu-PSMA-I&T, followed by SPECT/CT and blood collection at certain timepoints depending on the cycle as detailed in Table 30.

Important Reminders for all Sites:

$^{177}$Lu-PSMA-I&T is a radioactive drug and should be handled with appropriate safety measures to minimize radiation exposure. Radiopharmaceuticals should be received, used, and administered only by authorized persons in designated clinical settings, and handled with strict adherence to local regulation.

The responsible clinical physician for the study should confirm the patients suitability for undergoing the imaging study in accord with the inclusion/exclusion criteria in clinical protocol.

Refer to Study Procedure Manual and the Investigators Brochure for $^{177}$Lu-PSMA-I&T for full details on dose ordering, receipt, handling, administration, and destruction/decay.

$^{177}$Lu-PSMA-I&T Dose Ordering $^{177}$Lu-PSMA-I&T doses will be produced and supplied from a central manufacturing site.

The order for $^{177}$Lu-PSMA-I&T will be placed by the imaging center at least 2 weeks prior to the week of planned dosing. Imaging center staff must be aware of production schedules, approximate time of dose delivery and product expiration time to facilitate scheduling with the clinical staff.

$^{177}$Lu-PSMA-I&T Dosing Information

Dose Calibrator Calibration

Before scheduling patients to be injected with $^{177}$Lu-PSMA-I&T, your imaging center must confirm that the dose calibrator to be used has been accurately calibrated to measure Lu-177. The close calibrator dial setting established for this isotope as part of site setup must be used for all patient injections. Invicro will work with imaging center personnel to review the calibration procedure.

$^{177}$Lu-PSMA-I&T Dose Preparation $^{177}$Lu-PSMA-I&T is a ready-to-use, sterile formulation in a single-dose vial. The glass vial containing the radiopharmaceutical is kept in a lead shielded container until use, and the shield label will state the expiration date and time for each vial shipped. $^{177}$Lu-PSMA-I&T injection solution is administered as supplied. The radioactivity in the vial should be measured in a calibrated radiation dose calibrator prior to, and after administration to the patient. The administered dose will be automatically calculated.

Patient Preparation

Prior to $^{177}$Lu-PSMA-I&T administration, the following will be performed: Cooling of the patients' salivary glands may be performed by placing ice packs over the parotid and submandibular glands for 30 minutes prior to and up to 4 hours after the injection of $^{177}$Lu-PSMA-I&T to reduce the risk of salivary gland radiation injuries. The patient should be encouraged to void frequently. The patient should be encouraged to drink 2 liters of liquid daily for 2 days following $^{177}$Lu-PSMA-I&T administration. An intravenous (IV) line will be inserted for administration of $^{177}$Lu-PSMA-I&T, according to site standard procedures.

$^{177}$Lu-PSMA-I&T Dose Administration

Patients will receive a single IV dose of 200 mCi (7.4 GBq)±10% of $^{177}$Lu-PSMA-I&T as an infusion over a minimum of 10 minutes, using the sites standard radioligand therapy administration procedures.

$^{177}$Lu-PSMA-I&T will be administered every 6 weeks for 4 cycles or until radiographic progression of disease. Based on evaluation of dose-limiting toxicities for the patient, the dosing cycle for $^{177}$Lu-PSMA-I&T may be extended. Additionally, the $^{177}$Lu-PSMA-I&T dose should be held and/or reduced to 160 mCi (5.9 GBq)±10% if dose-limiting toxicity if noted.

See the study protocol for full details on the evaluation of dose-limiting toxicities and the impact on $^{177}$Lu-PSMA-I&T dose.

Imaging Protocol

Reference Standard

Prepare a reference standard by injecting approximately 100 μCi of $^{177}$Lu-PSMA-I&T from the residual dose into a 100 mL saline bag. The reference standard will be acquired immediately following each patient SPECT/CT scan as a separate scan using the same acquisition and reconstruction parameters as are used for the patient scan.

Please note: The same reference standard must be used for elf SPECT/CT scans acquired for a given patient Cycle. The reference standard must therefore be appropriately labeled with the Patient ID prior to storage. The reference standard should be held for decay as per local regulations.

SPECT/CT Imaging

The patient should be informed about the total acquisition time and positioned for maximum comfort, lying supine on the scanner table with their head in a head holder. SPECT/CT anatomical coverage should start with the salivary glands fully in the field of view (FOV) and extend through the pelvis. Coverage of the kidneys must be prioritized in situations where two or three FOVs are unable to be obtained due to patient comfort.

In general, raw projection data will be acquired into a 128×128 matrix with MEGP collimation using a step and shoot acquisition mode, acquiring 60 projections per detector (180 degrees rotation per detector), 20 seconds per projection, with an acquisition zoom of 1.0, and a 20% (±10%) energy window centered over 208 kev.

To optimize image quality, detector heads should be as close as possible, and remain consistent for each time point of a given patient. A low-dose CT scan will be performed priorto beginning the SPECT scan for attenuation correction. Institutional standard parameters may be used for the low-dose CT. Institutional standard reconstruction parameters may be used if approved for use by Invicro. Scatter correction is required to be applied using a 20% (±10%) scatter window centered over 170 kev.

The start time of each SPECT/CT scan must be recorded for later entry into the iPACS submission form when submitting to Invicro.

Please note: A reference standard of known activity of Lu-177 must be acquired immediately following each patient SPECT/CT scan as a separate scan using the same acquisition (only FOV required) and reconstruction parameters as are used for the patient scan.

Please note: Invicro will determine and approve the exact parameters to be used for this study as part of the setup procedures prior to patient imaging.

Please note: Invicro will collect both the raw projection and corrected reconstructions for each time point.

Pharmacokinetic (PK) Sample for Radioactivity Measurement

PK plasma samples will be collected according to the schedule displayed in Table 60 and counted for radioactivity. For each sample, collect sufficient sample volume for triplicate aliquots to meet the measurement requirements of your institution's gamma counter and perform measurements according to standard procedure. Blood will be processed and plasma will be measured on the gamma counter, as described in the following subsections.

Blood Sample Preparation

All blood samples drawn must be aliquoted 3 times, labeled appropriately, and stored per standard procedure for later measurement of plasma in the qualified gamma counter. All samples will be counted as a group for each patient for each Cycle, no later than 24 hours following the final sample collection.

Each aliquot of plasma must be 0.5 mL in volume for gamma counting. Sufficient volume at each time point must be collected to achieve 0.5 mL for each of the 3 required aliquots per sample type in addition to other required PK analyses.

For each blood sample time point, label the tubes to be used for gamma counter measurements with the appropriate subject ID, sample time point, sample type, and aliquot number.

For each aliquoted sample, measure and record the weight of the labeled empty tube and again measure and record the weight of the tube plus the aliquoted sample. Tube weights should be recorded in grams up to 3 decimal places, if possible, in the Gamma Counter Workbook. Weight measurements must be performed using a laboratory grade scale approved for the weight ranges expected for this study.

Plasma Preparation for Gamma Counting

The following procedure is intended for plasma gamma counting. Please note, Invicro does not guarantee that plasma obtained with this procedure will be suitable for any other assay. Please refer to the instructions provided within the Technical eBinder from the manufacturer for blood draw and Removal of BD Hemogard™.

Collect 5 ml of blood in a BD PPT system (Plasma Protein Preservation Tube-draw volume of 5 mL).

After collection of whole blood in the BD PPT™ Tube, immediately and gently invert the BD PPT™ Tube 8-10 times. After mixing, the whole blood specimen may be stored up to six (6) hours at room temperature until centrifugation.

Centrifuge at 18-25° C. at 1100 g for 10 min. The resulting supernatant is designated plasma.

Following centrifugation, immediately aliquot the liquid component (plasma):

To obtain an undiluted plasma sample, remove the BD Hemogard™ Closure (See Instructions for Removal of BD Hemogard™ Closure Section) and aliquot 0.5 ml of plasma into the tubes used for gamma counting using a transfer pipette. NOTE: When using a transfer pipette be sure NOT to disturb the gel barrier with the tip of the pipette.

Repeat 2 times to get 3 tubes containing 0.5 ml of plasma.

Note, for each aliquoted sample, measure and record the weight of the labeled empty tube and again measure and record the weight of the tube plus the aliquoted sample. Tube weights should be recorded in grams up to 3 decimal places, if possible, in the Gamma Counter Workbook (see Section 73). Weight measurements must be performed using a laboratory grade scale approved for the weight ranges expected for this study.

The aliquots can be stored at room temperature until gamma counted. All samples will be counted as a group for each patient for each Cycle, no later Than 24 tours following the final sample collection.

Gamma Counter Measurements: All patient samples must be counted for 60 seconds, with a counting energy window of 102-229 keV. Decay Correction and Background Subtraction functions should be turned Off.

As noted above, the 3, 0.5 mL aliquots drawn from the reference standard during initial preparation must also be counted with the samples. In addition, 3 empty (blank) tubes must be placed in the gamma counter when the samples are measured to account for background. Lastly, a long-lived gamma counter reference source (i.e., Cs-137) must also be included.

The completed Gamma Counter Workbook, and all gamma counter output files (PDFs, .txts, etc.) must be submitted to Invicro at the time of each data transfer by selecting the Gamma Counter Submission Form (see Appendix 2). The Workbook must be completed electronically and checked for accuracy prior to transferring to Invicro.

Please note: When measuring multiple samples in one single run, to avoid cross talk between sample types, please place and count the above-mentioned samples (blanks, reference standard samples, and long-lived reference source) in separate racks, it is imperative that all samples be properly positioned as recorded in the Gamma Counter Workbook provided and counted as a group for each patient for each Cycle, no later than 24 hours following the final sample collection.

Please note: Variations from the above procedures will be discussed and documented as part of Invicro's imaging center setup.

Gamma Counter Data Documentation: The following file types will be required to be transferred to Invicro with each data submission: gamma counter output file(s) (if available) and the Gamma Counter Workbook.

Gamma counter output file(s)—The output file is the direct raw output from the gamma counter containing the counts-per-minute (CPM) values for each sample and can be submitted in the site's standard format (e.g., .PDF, .txt, etc.).

Please notify Invicro if your gamma counter does not provide an output file.

Gamma Counter Workbook—The Gamma Counter Workbook is an electronic tabular format file provided to each site by Invicro for standardized data submission. Template Workbooks to be completed for each patient are located within the Technical Binder provided by Invicro with your Approval notification. The Gamma Counter Workbook must be completed electronically by each site and allows for interpretation of the output file(s) and captures the sample counting results.

The Gamma Counter Workbook records the sample type (blood, blank, long-lived reference source, etc.), the sample aliquot number (1, 2, or 3), the weight (in grams) of each empty tube and the weight of the tube plus the sample, the time each sample was collected (24 hr clock), the time each sample was counted (24 hr clock), the total counts and the CPM result.

Following data entry into the Workbook, review the Verify inputs tab. The Verify Inputs tab is meant to identify any data entry discrepancies or sample outliers. The tube weight measurements and CPM values will automatically populate on the Verify Inputs tab with the values recorded on the Key File Tab.

Please note: Values higher than 10 (% in the Coefficient of Variation column of the Verify Inputs Tab should be double-checked to ensure the data entry was performed correctly. Outlier samples should be recounted to verify the accuracy of the measurement. To avoid queries, please document the reason for any identified outliers and/or confirm the data has been verified as accurate.

All gamma counter output files and Gamma Counter Workbooks MUST be archived following submission to Invicro.

Patient Safety and Adverse Events: Each patient needs to be monitored for adverse events (AEs) while they are at the imaging center. An AE is defined as any unfavorable and unintended sign including an abnormal laboratory finding, symptom or disease associated with the use of a medical treatment or procedure, regardless of whether it is considered related to the medical treatment or procedure, that occurs during the course of the study.

The clinical site Principal Investigator (PI) is responsible for reporting AEs to the study sponsor and should follow AE reporting procedures described in the study protocol. Although not anticipated to happen frequently, AEs may occur during the patient's visit to the imaging center, and therefore, it is very important for the imaging centers to contact their respective clinical study site personnel immediately (i.e., PI or study coordinator) if they become aware of any AEs during the imaging procedures. The clinical study coordinator should be contacted by phone and the time of that call documented along with specific information related to the adverse event.

Please note: Archive the original document completed for the adverse event in the Technical Binder and send a copy to the clinical coordinator.

Image Data Archiving and Submission:

Data Submission Checklist: All imaging metadata and data files should be sent through iPACS. Modality specific electronic submission forms are required to be completed within iPACS for each data submission.

Projection and Reconstructed SPECT image data

Gamma Counter Workbook and all associated gamma counter outputs

Completed information contained in the iPACS submission form

Prior to submission, scans should be assessed for completeness, artifact and/or patient motion and any relevant information documented accordingly in the iPACS submission form.

Quality control and calibrations: QC measures are to be performed according to the center and the camera manufacturers standard procedures as implemented in the center's QC program for the SPECT/CT camera and close calibrator.

Scanner Quarry Assurance: The SPECT camera should have and maintain up-to-date flood uniformity corrections (intrinsic and extrinsic) and center of rotation (COR) corrections. Invicro recommends that calibrations are to be completed on a schedule based on manufacturer recommendations and requirements. In addition, a daily $^{57}$Co flood scan should be done at the beginning of the day the scanning is to be completed. The $^{57}$Co flood scan should be visually inspected for abnormalities. If there is a possibility that the abnormality could impact the quality of the SPECT scan the study patients visit should be rescheduled. Verification that the daily QC scan has been performed should be documented on the iPACS submission form.

Software upgrades, changes in hardware and any other manipulations or changes to the imaging camera should be recorded on the iPACS submission form.

Dose Calibrator: The dose calibrator and gamma counter approved for study use must be calibrated in accordance with nationally recognized standards and/or manufacturers recommendation, at the time of install, after any maintenance/repair procedure that could affect performance and routinely throughout the course of the study. QC checks must be performed in accordance with nationally recognized standards and for manufacturers recommendation. A record of your QC schedule should be retained. All routine QC measures performed are to be documented on Invicro's technical assessment questionnaire as part of setup.

Phantom Data: Invicro may request a phantom scan to be acquired on the SPECT/CT scanner intended for use in the study as part of the initial setup and qualification procedures or at any time throughout the course of a study. Phantoms may be requested if imaging centers are new to Invicro, an imaging center prefers to use a scanner which Invicro has not previously qualified, or the phantom data previously collected by Invicro does not meet the requirements of the study. A phantom acquisition may also be requested should a qualified SPECT/CT scanner undergo significant maintenance during the study, or if scanner performance issues are noticed during QC review of study patient data.

In addition, as calibration factors will be derived from the phantom performed as part of setup, periodic phantoms may be requested to assess the stability of the SPECT/CT scanners performance.

Scanner replacements and upgrades: If your center will be replacing or upgrading your SPECT scanner or acquisition software, it is critical that you inform Invicro prior to the replacement or upgrade occurring, so that Invicro can take the necessary steps to ensure the continuity of the imaging outcome measures in this longitudinal research study. Invicro may need to revisit the imaging center to acquire another phantom.

Numerous examples are provided herein to enhance the understanding of the present disclosure. A specific set of statements are provided as follows.

Statement 1: A method comprising administering to a human patient in need thereof a radiopharmaceutical composition comprising 177Lu-PSMA I&T, wherein the absorbed radiation dose per gram of tissue in the human patient's kidneys is from about 0.2 Gy/GBq to about 0.6 Gy/GBq, from about 0.25 Gy/GBq to about 0.55 Gy/GBq, from about 0.3 Gy/GBq to about 0.5 Gy/GBq, or from about 0.35 Gy/GBq to about 0.45 Gy/GBq.

Statement 2: A method comprising administering to a human patient in need thereof a radiopharmaceutical composition comprising $^{177}$Lu-PSMA I&T, wherein the absorbed radiation dose per gram of tissue in the human patient's kidneys is ≤0.60 Gy/GBq, ≤0.55 Gy/GBq, ≤0.50 Gy/GBq, ≤0.45 Gy/GBq, ≤0.40 Gy/GBq, ≤0.35 Gy/GBq, ≤0.30 Gy/GBq, ≤0.25 Gy/GBq, ≤0.20 Gy/GBq, or ≤0.15 Gy/GBq.

Statement 3: The method of statement 1, wherein the absorbed radiation dose per gram of tissue in the human patient's kidneys is from about 0.25 Gy/GBq to about 0.55 Gy/GBq.

Statement 4: The method of statement 1, wherein the absorbed radiation dose per gram of tissue in the human patient's kidneys is from about 0.3 Gy/GBq to about 0.5 Gy/GBq.

Statement 5: The method of statement 1, wherein the mean absorbed radiation dose per gram of tissue in the human patient's kidneys is about 0.39±0.15 Gy/GBq.

Statement 6: The method of statement 1, wherein the mean absorbed radiation dose per gram of tissue in the human patient's kidneys is about 0.40±0.15 Gy/GBq.

Statement 7: The method of statement 1, wherein the mean absorbed radiation dose per gram of tissue in the human patient's kidneys is about 0.41±0.15 Gy/GBq.

Statement 8: The method of statement 1, wherein the mean absorbed radiation dose per gram of tissue in the human patient's kidneys is about 0.42±0.15 Gy/GBq.

Statement 9: The method of statement 1, wherein the mean absorbed radiation dose per gram of tissue in the human patient's kidneys is about 0.43±0.15 Gy/GBq.

Statement 10: The method of statement 1, wherein the mean absorbed radiation dose per gram of tissue in the human patient's kidneys is about 0.45±0.15 Gy/GBq.

Statement 11: The method of statement 1, wherein the mean absorbed radiation dose per gram of tissue in the human patient's kidneys is ≤0.39 Gy/GBq.

Statement 12: The method of statement 1, wherein the mean absorbed radiation dose per gram of tissue in the human patient's kidneys is ≤0.40 Gy/GBq.

Statement 13: The method of statement 1, wherein the mean absorbed radiation dose per gram of tissue in the human patient's kidneys is ≤0.41 Gy/GBq.

Statement 14: The method of statement 1, wherein the mean absorbed radiation dose per gram of tissue in the human patient's kidneys is ≤0.42 Gy/GBq.

Statement 15: The method of statement 25, wherein the standard deviation of the mean absorbed radiation dose per gram of tissue in the human patient's kidneys is ≤0.19 Gy/GBq, ≤0.18 Gy/GBq, ≤0.17 Gy/GBq, ≤0.16 Gy/GBq, or ≤0.15 Gy/GBq.

Statement 16: The method of statement 1, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 17: The method of statement 1, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 18: The method of statement 1, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 19: The method of statement 1, wherein the composition comprises about 7.1 GBq to about 7.6 GBq of 177Lu-PSMA I&T.

Statement 20: The method of statement 1, wherein the composition comprises 7.4±15% GBq of 177Lu-PSMA I&T.

Statement 21: The method of statement 1, wherein the composition comprises 7.4±10% GBq of 177Lu-PSMA I&T.

Statement 22: The method of statement 1, wherein the composition comprises 7.4±5% GBq of 177Lu-PSMA I&T.

Statement 23: The method of statement 1, wherein the composition comprises about 7.4 GBq of 177Lu-PSMA I&T.

Statement 24: The method of statement 1, wherein the absorbed radiation dose is determined via SPECT imaging, planar imaging, or a combination thereof.

Statement 25: A method comprising administering to a human patient in need thereof a radiopharmaceutical composition comprising 177Lu-PSMA I&T, wherein the absorbed radiation dose per gram of tissue in the human patient's lacrimal glands is from about 0.01 Gy/GBq to about 1.5 Gy/GBq.

Statement 26: A method comprising administering to a human patient in need thereof a radiopharmaceutical composition comprising 177Lu-PSMA I&T, wherein the absorbed radiation dose per gram of tissue in the human patient's lacrimal glands is ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq.

Statement 27: The method of statement 25, wherein the absorbed radiation dose per gram of tissue in the human patient's lacrimal glands is from about 0.1 Gy/GBq to about 0.8 Gy/GBq.

Statement 28: The method of statement 25, wherein the absorbed radiation dose per gram of tissue in the human patient's lacrimal glands is about 0.01, 0.05, 0.1, 0.2, 0.3, 0.4, 0.5, 0.6, 0.7, 0.8, 0.9, 1.0, 1.1, 1.2, 1.3, 1.4, or 1.5 Gy/GBq.

Statement 29: The method of statement 25, wherein the mean absorbed radiation dose per gram of tissue in the human patient's lacrimal glands is 0.37±0.36 Gy/GBq.

Statement 30: The method of statement 25, wherein the mean absorbed radiation dose per gram of tissue in the human patient's lacrimal glands is 0.38±0.36 Gy/GBq.

Statement 31: The method of statement 25, wherein the mean absorbed radiation dose per gram of tissue in the human patient's lacrimal glands is 0.39±0.36 Gy/GBq.

Statement 32: The method of statement 25, wherein the mean absorbed radiation dose per gram of tissue in the human patient's lacrimal glands is 0.40±0.36 Gy/GBq.

Statement 33: The method of statement 25, wherein the mean absorbed radiation dose per gram of tissue in the human patient's lacrimal glands is ≤0.40 Gy/GBq.

Statement 34: The method of statement 25, wherein the mean absorbed radiation dose per gram of tissue in the human patient's lacrimal glands is ≤0.50 Gy/GBq.

Statement 35: The method of statement 25, wherein the mean absorbed radiation dose per gram of tissue in the human patient's lacrimal glands is ≤0.60 Gy/GBq.

Statement 36: The method of statement 25, wherein the mean absorbed radiation dose per gram of tissue in the human patient's lacrimal glands is ≤0.70 Gy/GBq.

Statement 37: The method of statement 25, wherein the mean absorbed radiation dose per gram of tissue in the human patient's lacrimal glands is ≤0.80 Gy/GBq.

Statement 38: The method of statement 25, wherein the mean absorbed radiation dose per gram of tissue in the human patient's lacrimal glands is ≤0.90 Gy/GBq.

Statement 39: The method of statement 25, wherein the mean absorbed radiation dose per gram of tissue in the human patient's lacrimal glands is ≤1.0 Gy/GBq.

Statement 40: The method of statement 25, wherein the standard deviation of the mean absorbed radiation dose per gram of tissue in the human patient's lacrimal glands is ≤0.37 Gy/GBq.

Statement 41: The method of statement 25, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0

Statement 42: The method of statement 25, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 43: The method of statement 25, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 44: The method of statement 25, wherein the composition comprises about 7.1 GBq to about 7.6 GBq of 177Lu-PSMA I&T.

Statement 45: The method of statement 25, wherein the composition comprises 7.4±15% GBq of 177Lu-PSMA I&T.

Statement 46: The method of statement 25, wherein the composition comprises 7.4±10% GBq of 177Lu-PSMA I&T.

Statement 47: The method of statement 25, wherein the composition comprises 7.4±5% GBq of 177Lu-PSMA I&T.

Statement 48: The method of statement 25, wherein the composition comprises about 7.4 GBq of 177Lu-PSMA I&T.

Statement 49: The method of statement 2525, wherein the absorbed radiation dose is determined via SPECT imaging, planar imaging, or a combination thereof.

Statement 50: A method comprising administering to a human patient in need thereof a radiopharmaceutical composition comprising 177Lu-PSMA I&T, wherein the absorbed radiation dose per gram of tissue in the human patient's salivary glands is from about 0.01 Gy/GBq to about 1.0 Gy/GBq.

Statement 51: A method comprising administering to a human patient in need thereof a radiopharmaceutical composition comprising 177Lu-PSMA I&T, wherein the absorbed radiation dose per gram of tissue in the human patient's salivary glands is ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq.

Statement 52: The method of statement 50, wherein the absorbed radiation dose per gram of tissue in the human patient's salivary glands is from about 0.1 Gy/GBq to about 0.5 Gy/GBq.

Statement 53: The method of statement 50, wherein the absorbed radiation dose per gram of tissue in the human patient's salivary glands is from about 0.01, 0.05, 0.1, 0.2, 0.3, 0.4, 0.5, 0.6, 0.7, 0.8, 0.9, or about 1.0 Gy/GBq.

Statement 54: The method of statement 50, wherein the mean absorbed radiation dose per gram of tissue in the human patient's salivary glands is about 0.17±0.16 Gy/GBq.

Statement 55: The method of statement 50, wherein the mean absorbed radiation dose per gram of tissue in the human patient's salivary glands is about 0.18±0.16 Gy/GBq.

Statement 56: The method of statement 50, wherein the mean absorbed radiation dose per gram of tissue in the human patient's salivary glands is about 0.19±0.16 Gy/GBq.

Statement 57: The method of statement 50, wherein the mean absorbed radiation dose per gram of tissue in the human patient's salivary glands is about 0.20±0.16 Gy/GBq.

Statement 58: The method of statement 50, wherein the mean absorbed radiation dose per gram of tissue in the human patient's salivary glands is ≤0.18 Gy/GBq.

Statement 59: The method of statement 50, wherein the mean absorbed radiation dose per gram of tissue in the human patient's salivary glands is ≤0.19 Gy/GBq.

Statement 60: The method of statement 50, wherein the mean absorbed radiation dose per gram of tissue in the human patient's salivary glands is ≤0.20 Gy/GBq.

Statement 61: The method of statement 50, wherein the mean absorbed radiation dose per gram of tissue in the human patient's salivary glands is ≤0.21 Gy/GBq.

Statement 62: The method of statement 50, wherein the mean absorbed radiation dose per gram of tissue in the human patient's salivary glands is ≤0.22 Gy/GBq.

Statement 63: The method of statement 50, wherein the mean absorbed radiation dose per gram of tissue in the human patient's salivary glands is ≤0.23 Gy/GBq.

Statement 64: The method of statement 50, wherein the mean absorbed radiation dose per gram of tissue in the human patient's salivary glands is ≤0.24 Gy/GBq.

Statement 65: The method of statement 50, wherein the mean absorbed radiation dose per gram of tissue in the human patient's salivary glands is ≤0.25 Gy/GBq.

Statement 66: The method of statement 50, wherein the mean absorbed radiation dose per gram of tissue in the human patient's salivary glands is ≤0.26 Gy/GBq.

Statement 67: The method of statement 50, wherein the mean absorbed radiation dose per gram of tissue in the human patient's salivary glands is ≤0.27 Gy/GBq.

Statement 68: The method of statement 50, wherein the mean absorbed radiation dose per gram of tissue in the human patient's salivary glands is ≤0.28 Gy/GBq.

Statement 69: The method of statement 50, wherein the mean absorbed radiation dose per gram of tissue in the human patient's salivary glands is ≤0.29 Gy/GBq.

Statement 70: The method of statement 50, wherein the mean absorbed radiation dose per gram of tissue in the human patient's salivary glands is ≤0.30 Gy/GBq.

Statement 71: The method of statement 50, wherein the standard deviation of the mean absorbed radiation dose per gram of tissue in the human patient's salivary glands is ≤0.25 Gy/GBq, ≤0.24 Gy/GBq, ≤0.23 Gy/GBq, ≤0.22 Gy/GBq, ≤0.21 Gy/GBq, ≤0.20 Gy/GBq, ≤0.19 Gy/GBq, ≤0.18 Gy/GBq, ≤0.17 Gy/GBq, or ≤0.16 Gy/GBq.

Statement 72: The method of statement 50, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 73: The method of statement 50, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 74: The method of statement 50, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 75: The method of statement 50, wherein the composition comprises about 7.1 GBq to about 7.6 GBq of 177Lu-PSMA I&T.

Statement 76: The method of statement 50, wherein the composition comprises 7.4±15% GBq of 177Lu-PSMA I&T.

Statement 77: The method of statement 50, wherein the composition comprises 7.4±10% GBq of 177Lu-PSMA I&T.

Statement 78: The method of statement 50, wherein the composition comprises 7.4±5% GBq of 177Lu-PSMA I&T.

Statement 79: The method of statement 50, wherein the composition comprises about 7.4 GBq of 177Lu-PSMA I&T.

Statement 80: The method of statement 50, wherein the absorbed radiation dose is determined via SPECT imaging, planar imaging, or a combination thereof.

Statement 81: A method comprising administering to a human patient in need thereof a radiopharmaceutical composition comprising 177Lu-PSMA I&T, wherein the absorbed radiation dose per gram of tissue in the human patient's left colon is from about 0.01 Gy/GBq to about 1.6 Gy/GBq.

Statement 82: A method comprising administering to a human patient in need thereof a radiopharmaceutical composition comprising 177Lu-PSMA I&T, wherein the absorbed radiation dose per gram of tissue in the human patient's left colon is ≤1.6 Gy/GBq, ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq.

Statement 83: The method of statement 81, wherein the absorbed radiation dose per gram of tissue in the human patient's left colon is from about 0.1 Gy/GBq to about 0.8 Gy/GBq.

Statement 84: The method of statement 81, wherein the absorbed radiation dose per gram of tissue in the human patient's left colon is about 0.01, 0.05, 0.1, 0.2, 0.3, 0.4, 0.5, 0.6, 0.7, 0.8, 0.9, 1.0, 1.1, 1.2, 1.3, 1.4, 1.5, or about 1.6 Gy/GBq.

Statement 85: The method of statement 81, wherein the mean absorbed radiation dose per gram of tissue in the human patient's left colon is 0.45±0.31 Gy/GBq.

Statement 86: The method of statement 81, wherein the mean absorbed radiation dose per gram of tissue in the human patient's left colon is 0.46±0.31 Gy/GBq.

Statement 87: The method of statement 81, wherein the mean absorbed radiation dose per gram of tissue in the human patient's left colon is 0.47±0.31 Gy/GBq.

Statement 88: The method of statement 81, wherein the mean absorbed radiation dose per gram of tissue in the human patient's left colon is ≤0.47 Gy/GBq.

Statement 89: The method of statement 81, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0

Statement 90: The method of statement 81, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 91: The method of statement 81, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 92: The method of statement 81, wherein the composition comprises about 7.1 GBq to about 7.6 GBq of 177Lu-PSMA I&T.

Statement 93: The method of statement 81, wherein the composition comprises 7.4±15% GBq of 177Lu-PSMA I&T.

Statement 94: The method of statement 81, wherein the composition comprises 7.4±10% GBq of 177Lu-PSMA I&T.

Statement 95: The method of statement 81, wherein the composition comprises 7.4±5% GBq of 177Lu-PSMA I&T.

Statement 96: The method of statement 81 wherein the composition comprises about 7.4 GBq of 177Lu-PSMA I&T.

Statement 97: The method of statement 81, wherein the absorbed radiation dose is determined via SPECT imaging, planar imaging, or a combination thereof.

Statement 98: A method comprising administering to a human patient in need thereof a radiopharmaceutical composition comprising 177Lu-PSMA I&T, wherein the absorbed radiation dose per gram of tissue in the human patient's rectum is from about 0.01 Gy/GBq to about 1.5 Gy/GBq.

Statement 99: A method comprising administering to a human patient in need thereof a radiopharmaceutical composition comprising 177Lu-PSMA I&T, wherein the absorbed radiation dose per gram of tissue in the human patient's rectum is ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq.

Statement 100: The method of statement 98, wherein the absorbed radiation dose per gram of tissue in the human patient's rectum is from about 0.1 Gy/GBq to about 0.8 Gy/GBq.

Statement 101: The method of statement 98, wherein the absorbed radiation dose per gram of tissue in the human patient's rectum is about 0.01, 0.05, 0.1, 0.2, 0.3, 0.4, 0.5, 0.6, 0.7, 0.8, 0.9, 1.0, 1.1, 1.2, 1.3, 1.4, or about 1.5 Gy/GBq.

Statement 102: The method of statement 98, wherein the mean absorbed radiation dose per gram of tissue in the human patient's rectum is 0.44±0.30 Gy/GBq.

Statement 103: The method of statement 98, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0

Statement 104: The method of statement 98, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 105: The method of statement 98, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 106: The method of statement 98, wherein the composition comprises about 7.1 GBq to about 7.6 GBq of 177Lu-PSMA I&T.

Statement 107: The method of statement 98, wherein the composition comprises 7.4±15% GBq of 177Lu-PSMA I&T.

Statement 108: The method of statement 98, wherein the composition comprises 7.4±10% GBq of 177Lu-PSMA I&T.

Statement 109: The method of statement 98, wherein the composition comprises 7.4±5% GBq of 177Lu-PSMA I&T.

Statement 110: The method of statement 98, wherein the composition comprises about 7.4 GBq of 177Lu-PSMA I&T.

Statement 111: The method of statement 98, wherein the absorbed radiation dose is determined via SPECT imaging, planar imaging, or a combination thereof.

Statement 112: The method according to any of the previous statements, wherein anatomical coverage of the imaging extends from the salivary glands to the pelvis.

Statement 113: A method comprising administering to a human patient in need thereof a radiopharmaceutical composition comprising 177Lu-PSMA I&T, wherein the fraction of activity of the 177Lu-PSMA I&T in the whole body of the human patient is about 0.5 or less within 24 hours, 48 hours, or 168 hours after administration of the composition.

Statement 114: A method comprising administering to a human patient in need thereof a radiopharmaceutical composition comprising 177Lu-PSMA I&T, wherein the fraction of activity of the 177Lu-PSMA I&T in the whole body of the human patient is ≤0.5, ≤0.4, ≤0.3, ≤0.2, or ≤0.1 within 24 hours, 48 hours, or 168 hours after administration of the composition.

Statement 115: The method of statement 98, wherein the fraction of activity of the the 177Lu-PSMA I&T in the whole body of the human patient is about 0.5, 0.4, 0.3, 0.2, 0.1, or less than 0.1 within 24 hours, 48 hours, or 168 hours after administration of the composition.

Statement 115: The method of statement 98, wherein the fraction of activity of the 177Lu-PSMA I&T in the whole body of the human patient is about 0.4 or less within 48 hours or 168 hours after administration of the composition.

Statement 116: The method of statement 98, wherein the fraction of activity of the 177Lu-PSMA I&T in the whole body of the human patient is about 0.4, about 0.3, about 0.2, about 0.1, or less than 0.1 within 48 hours or 168 hours after administration of the composition.

Statement 117: The method of statement 98, wherein the fraction of activity of the 177Lu-PSMA I&T in the whole body of the human patient is about 0.2 or less within 168 hours after administration of the composition.

Statement 118: The method of statement 98, wherein the administration is via injection.

Statement 119: The method of statement 98, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 120: The method of statement 98, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 121: The method of statement 98, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 122: The method of statement 98, wherein the composition comprises about 7.1 GBq to about 7.6 GBq of 177Lu-PSMA I&T.

Statement 123: The method of statement 98, wherein the composition comprises 7.4±15% GBq of 177Lu-PSMA I&T.

Statement 124: The method of statement 98, wherein the composition comprises 7.4±10% GBq of 177Lu-PSMA I&T.

Statement 125: The method of statement 98, wherein the composition comprises 7.4±5% GBq of 177Lu-PSMA I&T.

Statement 126: The method of statement 98, wherein the composition comprises about 7.4 GBq of 177Lu-PSMA I&T.

Statement 127: The method of statement 98, wherein the fraction of activity is determined via SPECT imaging, planar image-based dosimetry, or a combination thereof.

Statement 128: A method comprising administering to a human patient in need thereof a radiopharmaceutical composition comprising 177Lu-PSMA I&T, wherein the fraction of activity of the 177Lu-PSMA I&T in the kidneys of the human patient is about 0.05 or less within 24 hours, 48 hours, or 168 hours after administration of the composition.

Statement 129: A method comprising administering to a human patient in need thereof a radiopharmaceutical composition comprising 177Lu-PSMA I&T, wherein the fraction of activity of the 177Lu-PSMA I&T in the kidneys of the human patient is ≤0.05, ≤0.04, ≤0.03, ≤0.02, or ≤0.01 within 24 hours, 48 hours, or 168 hours after administration of the composition.

Statement 130: The method of statement 129, wherein the fraction of activity of the 177Lu-PSMA I&T in the kidneys of the human patient is about 0.05, about 0.04, about 0.03, about 0.02, about 0.01, or less than 0.01 within 24 hours, 48 hours, or 168 hours after administration of the composition.

Statement 131: The method of statement 129, wherein the fraction of activity of the 177Lu-PSMA I&T in the kidneys of the human patient is ≤0.040 within 48 hours or 168 hours after administration of the composition.

Statement 132: The method of statement 129, wherein the fraction of activity of the 177Lu-PSMA I&T in the kidneys of the human patient is about 0.040 or less, about 0.035 or less, or about 0.030 or less within 48 hours or 168 hours after administration of the composition.

Statement 133: The method of statement 129, wherein the fraction of activity of the 177Lu-PSMA I&T in the kidneys of the human patient is about 0.04, 0.03, 0.02, 0.01, or less than 0.01 within 48 hours or 168 hours after administration of the composition.

Statement 134: The method of statement 129, wherein the fraction of activity of the 177Lu-PSMA I&T in the kidneys of the human patient is about 0.03 or less within 168 hours after administration of the composition.

Statement 135: The method of statement 129, wherein the fraction of activity of the 177Lu-PSMA I&T in the kidneys of the human patient is about 0.03, 0.02, 0.01, or less than 0.01 within 168 hours after administration of the composition.

Statement 136: The method of statement 129, wherein the administration is via injection.

Statement 137: The method of statement 129, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 138: The method of statement 129, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 139: The method of statement 129, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 140: The method of statement 129, wherein the composition comprises about 7.1 GBq to about 7.6 GBq of 177Lu-PSMA I&T.

Statement 141: The method of statement 129, wherein the composition comprises 7.4±15% GBq of 177Lu-PSMA I&T.

Statement 142: The method of statement 129, wherein the composition comprises 7.4±10% GBq of 177Lu-PSMA I&T.

Statement 143: The method of statement 129, wherein the composition comprises 7.4±5% GBq of 177Lu-PSMA I&T.

Statement 144: The method of statement 129, wherein the composition comprises about 7.4 GBq of 177Lu-PSMA I&T.

Statement 145: The method of statement 129, wherein the fraction of activity is determined via SPECT imaging, planar imaging, or a combination thereof.

Statement 146: A method comprising administering to a human patient in need thereof a radiopharmaceutical composition comprising 177Lu-PSMA I&T, wherein the fraction of activity of the 177Lu-PSMA I&T in the red marrow of the human patient is about 0.08 or less within 24 hours, 48 hours, or 168 hours after administration of the composition.

Statement 147: A method comprising administering to a human patient in need thereof a radiopharmaceutical composition comprising 177Lu-PSMA I&T, wherein the fraction of activity of the 177Lu-PSMA I&T in the red marrow of the human patient is ≤0.08, ≤0.07, ≤0.06, ≤0.05, ≤0.04, ≤0.03, ≤0.02, ≤0.01, or less within 24 hours, 48 hours, or 168 hours after administration of the composition.

Statement 148: The method of statement 147, wherein the fraction of activity of the 177Lu-PSMA I&T in the red marrow of the human patient is about 0.08, 0.07, 0.06, 0.05, 0.04, 0.03, 0.02, 0.01, or less than 0.01 within 24 hours, 48 hours, or 168 hours after administration of the composition.

Statement 149: The method of statement 147, wherein the fraction of activity of the 177Lu-PSMA I&T in the red marrow of the human patient is about 0.06 or less within 48 hours or 168 hours after administration of the composition.

Statement 150: The method of statement 147, wherein the fraction of activity of the 177Lu-PSMA I&T in the red marrow of the human patient is about 0.06, 0.05, 0.04, 0.03, 0.02, 0.01, or less than 0.01 within 48 hours or 168 hours after administration of the composition.

Statement 151: The method of statement 147, wherein the fraction of activity of the 177Lu-PSMA I&T in the red marrow of the human patient is about 0.04 or less within 168 hours after administration of the composition.

Statement 152: The method of statement 147, wherein the fraction of activity of the 177Lu-PSMA I&T in the red marrow of the human patient is about 0.04, 0.03, 0.02, 0.01, or less than 0.01 within 168 hours after administration of the composition.

Statement 153: The method of statement 147, wherein the administration is via injection.

Statement 154: The method of statement 147, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 155: The method of statement 147, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 156: The method of statement 147, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 157: The method of statement 147, wherein the composition comprises about 7.1 GBq to about 7.6 GBq of 177Lu-PSMA I&T.

Statement 158: The method of statement 147, wherein the composition comprises 7.4±15% GBq of 177Lu-PSMA I&T.

Statement 159: The method of statement 147, wherein the composition comprises 7.4±10% GBq of 177Lu-PSMA I&T.

Statement 160: The method of statement 147, wherein the composition comprises 7.4±5% GBq of 177Lu-PSMA I&T.

Statement 161: The method of statement 147, wherein the composition comprises about 7.4 GBq of 177Lu-PSMA I&T.

Statement 162: The method of statement 147, wherein the fraction of activity is determined via SPECT imaging, planar imaging, or a combination thereof.

Statement 163: A method comprising administering to a human patient in need thereof a radiopharmaceutical composition comprising 177Lu-PSMA I&T, wherein the fraction of activity of the 177Lu-PSMA I&T in the salivary glands of the human patient is about 0.015 or less within 24 hours, 48 hours, or 168 hours after administration of the composition.

Statement 164: A method comprising administering to a human patient in need thereof a radiopharmaceutical composition comprising 177Lu-PSMA I&T, wherein the fraction of activity of the 177Lu-PSMA I&T in the salivary glands of the human patient is ≤0.015, ≤0.014, ≤0.013, ≤0.012, ≤0.011, ≤0.010, ≤0.009, ≤0.008, ≤0.007, ≤0.006, ≤0.005, ≤0.004, ≤0.003, ≤0.002, ≤0.001, or less within 24 hours, 48 hours, or 168 hours after administration of the composition.

Statement 165: The method of statement 164, wherein the fraction of activity of the 177Lu-PSMA I&T in the salivary glands of the human patient is about 0.015, 0.014, 0.013, 0.012, 0.011, 0.010, 0.009, 0.008, 0.007, 0.006, 0.005, 0.004, 0.003, 0.002, 0.001 or less than 0.001 within 24 hours, 48 hours, or 168 hours after administration of the composition.

Statement 166: The method of statement 164, wherein the fraction of activity of the 177Lu-PSMA I&T in the salivary glands of the human patient is about 0.007 or less within 48 hours or 168 hours after administration of the composition.

Statement 167: The method of statement 164, wherein the fraction of activity of the 177Lu-PSMA I&T in the salivary glands of the human patient is about 0.007, 0.006, 0.005, 0.004, 0.003, 0.002, 0.001 or less than 0.001 within 48 hours or 168 hours after administration of the composition.

Statement 168: The method of statement 164, wherein the fraction of activity of the 177Lu-PSMA I&T in the salivary glands of the human patient is about 0.004 or less within 168 hours after administration of the composition.

Statement 169: The method of statement 164, wherein the fraction of activity of the 177Lu-PSMA I&T in the salivary glands of the human patient is about 0.004, 0.003, 0.002, 0.001 or less than 0.001 within 168 hours after administration of the composition.

Statement 170: The method of statement 164, wherein the administration is via injection.

Statement 171: The method of statement 164, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 172: The method of statement 164, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 173: The method of statement 164, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 174: The method of statement 164, wherein the composition comprises about 7.1 GBq to about 7.6 GBq of 177Lu-PSMA I&T.

Statement 175: The method of statement 164, wherein the composition comprises 7.4±15% GBq of 177Lu-PSMA I&T.

Statement 176: The method of statement 164, wherein the composition comprises 7.4±10% GBq of 177Lu-PSMA I&T.

Statement 177: The method of statement 164, wherein the composition comprises 7.4±5% GBq of 177Lu-PSMA I&T.

Statement 178: The method of statement 164, wherein the composition comprises about 7.4 GBq of 177Lu-PSMA I&T.

Statement 179: The method of statement 164, wherein the fraction of activity is determined via SPECT imaging, planar imaging, or a combination thereof.

Statement 180: A method comprising administering to a human patient in need thereof a radiopharmaceutical composition comprising 177Lu-PSMA I&T, wherein the fraction of activity of the 177Lu-PSMA I&T in the gastrointestinal tract of the human patient is about 0.10 or less within 24 hours, 48 hours, or 168 hours after administration of the composition.

Statement 181: A method comprising administering to a human patient in need thereof a radiopharmaceutical composition comprising 177Lu-PSMA I&T, wherein the fraction of activity of the 177Lu-PSMA I&T in the gastrointestinal tract of the human patient is ≤0.10, ≤0.09, ≤0.08, ≤0.07, ≤0.06, ≤0.05, ≤0.04, ≤0.03, ≤0.02, ≤0.01, or less within 24 hours, 48 hours, or 168 hours after administration of the composition.

Statement 182: The method of statement 181, wherein the fraction of activity of the 177Lu-PSMA I&T in the gastrointestinal tract of the human patient is about 0.10, 0.09, 0.08, 0.07, 0.06, 0.05, 0.04, 0.03, 0.02, 0.01 or less than 0.01 within 24 hours, 48 hours, or 168 hours after administration of the composition.

Statement 183: The method of statement 181, wherein the fraction of activity of the 177Lu-PSMA I&T in the gastrointestinal tract of the human patient is about 0.10 or less within 48 hours or 168 hours after administration of the composition.

Statement 184: The method of statement 181, wherein the fraction of activity of the 177Lu-PSMA I&T in the gastrointestinal tract of the human patient is about 0.10, 0.09, 0.08, 0.07, 0.06, 0.05, 0.04, 0.03, 0.02, 0.01 or less than 0.01 within 48 hours or 168 hours after administration of the composition.

Statement 185: The method of statement 181, wherein the fraction of activity of the 177Lu-PSMA I&T in the gastrointestinal tract of the human patient is about 0.05 or less within 168 hours after administration of the composition.

Statement 186: The method of statement 181, wherein the fraction of activity of the 177Lu-PSMA I&T in the gastrointestinal tract of the human patient is about 0.05, 0.04, 0.03, 0.02, 0.01, or less than 0.01 within 168 hours after administration of the composition.

Statement 187: The method of statement 181, wherein the administration is via injection.

Statement 188: The method of statement 181, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 189: The method of statement 181, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 190: The method of statement 181, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 191: The method of statement 181, wherein the composition comprises about 7.1 GBq to about 7.6 GBq of 177Lu-PSMA I&T.

Statement 192: The method of statement 181, wherein the composition comprises 7.4±15% GBq of 177Lu-PSMA I&T.

Statement 193: The method of statement 181, wherein the composition comprises 7.4±10% GBq of 177Lu-PSMA I&T.

Statement 194: The method of statement 181, wherein the composition comprises 7.4±5% GBq of 177Lu-PSMA I&T.

Statement 195: The method of statement 181, wherein the composition comprises about 7.4 GBq of 177Lu-PSMA I&T.

Statement 196: The method of statement 181, wherein the fraction of activity is determined via SPECT imaging, planar imaging, or a combination thereof.

Statement 197: A method comprising administering to a human patient in need thereof a radiopharmaceutical composition comprising 177Lu-PSMA I&T, wherein the fraction of activity of the 177Lu-PSMA I&T in the liver of the human patient is about 0.04 or less within 24 hours, 48 hours, or 168 hours after administration of the composition.

Statement 198: A method comprising administering to a human patient in need thereof a radiopharmaceutical composition comprising 177Lu-PSMA I&T, wherein the fraction of activity of the 177Lu-PSMA I&T in the liver of the human patient is ≤0.04, ≤0.03, ≤0.02, ≤0.01, or less within 24 hours, 48 hours, or 168 hours after administration of the composition.

Statement 199: The method of statement 198, wherein the fraction of activity of the 177Lu-PSMA I&T in the liver of the human patient is about 0.04, 0.03, 0.02, 0.01 or less than 0.01 within 24 hours, 48 hours, or 168 hours after administration of the composition.

Statement 200: The method of statement 198, wherein the fraction of activity of the 177Lu-PSMA I&T in the liver of the human patient is about 0.02 or less within 48 hours or 168 hours after administration of the composition.

Statement 201: The method of statement 198, wherein the fraction of activity of the 177Lu-PSMA I&T in the liver of the human patient is about 0.02, 0.01, or less than 0.01 within 48 hours or 168 hours after administration of the composition.

Statement 202: The method of statement 198, wherein the fraction of activity of the 177Lu-PSMA I&T in the liver of the human patient is about 0.01 or less within 168 hours after administration of the composition.

Statement 203: The method of statement 198, wherein the administration is via injection.

Statement 204: The method of statement 198, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 205: The method of statement 198, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 206: The method of statement 198, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 207: The method of statement 198, wherein the composition comprises about 7.1 GBq to about 7.6 GBq of 177Lu-PSMA I&T.

Statement 208: The method of statement 198, wherein the composition comprises 7.4±15% GBq of 177Lu-PSMA I&T.

Statement 209: The method of statement 198, wherein the composition comprises 7.4±10% GBq of 177Lu-PSMA I&T.

Statement 210: The method of statement 198, wherein the composition comprises 7.4±5% GBq of 177Lu-PSMA I&T.

Statement 211: The method of statement 198, wherein the composition comprises about 7.4 GBq of 177Lu-PSMA I&T.

Statement 212: The method of statement 198, wherein the fraction of activity is determined via SPECT imaging, planar imaging, or a combination thereof.

Statement 213: A method comprising administering to a human patient in need thereof a radiopharmaceutical composition comprising 177Lu-PSMA I&T, wherein the fraction of activity of the 177Lu-PSMA I&T in the spleen of the human patient is about 0.004 or less within 24 hours, 48 hours, or 168 hours after administration of the composition.

Statement 214: A method comprising administering to a human patient in need thereof a radiopharmaceutical composition comprising 177Lu-PSMA I&T, wherein the fraction of activity of the 177Lu-PSMA I&T in the spleen of the human patient is ≤0.004, ≤0.003, ≤0.002, ≤0.001 or less within 24 hours, 48 hours, or 168 hours after administration of the composition.

Statement 215: The method of statement 214, wherein the fraction of activity of the 177Lu-PSMA I&T in the spleen of the human patient is about 0.004, 0.003, 0.002, 0.001 or less than 0.001 within 24 hours, 48 hours, or 168 hours after administration of the composition.

Statement 216: The method of statement 214, wherein the fraction of activity of the 177Lu-PSMA I&T in the spleen of the human patient is about 0.002 or less within 48 hours or 168 hours after administration of the composition.

Statement 217: The method of statement 214, wherein the fraction of activity of the 177Lu-PSMA I&T in the spleen of the human patient is about 0.002, 0.001, or less than 0.001 within 48 hours or 168 hours after administration of the composition.

Statement 218: The method of statement 214, wherein the fraction of activity of the 177Lu-PSMA I&T in the spleen of the human patient is about 0.001 or less within 168 hours after administration of the composition.

Statement 219: The method of statement 214, wherein the administration is via injection.

Statement 220: The method of statement 214, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 221: The method of statement 214, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 222: The method of statement 214, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 223: The method of statement 214, wherein the composition comprises about 7.1 GBq to about 7.6 GBq of 177Lu-PSMA I&T.

Statement 224: The method of statement 214, wherein the composition comprises 7.4±15% GBq of 177Lu-PSMA I&T.

Statement 225: The method of statement 214, wherein the composition comprises 7.4±10% GBq of 177Lu-PSMA I&T.

Statement 226: The method of statement 214, wherein the composition comprises 7.4±5% GBq of 177Lu-PSMA I&T.

Statement 227: The method of statement 214, wherein the composition comprises about 7.4 GBq of 177Lu-PSMA I&T.

Statement 228: The method of statement 214, wherein the fraction of activity is determined via SPECT imaging, planar imaging, or a combination thereof.

Statement 229: A method comprising administering to a human patient in need thereof a radiopharmaceutical composition comprising 177Lu-PSMA I&T, wherein the fraction of activity of the 177Lu-PSMA I&T in the lacrimal glands of the human patient is about 0.0004 or less within 24 hours, 48 hours, or 168 hours after injection of the composition.

Statement 230: A method comprising administering to a human patient in need thereof a radiopharmaceutical composition comprising 177Lu-PSMA I&T, wherein the fraction of activity of the 177Lu-PSMA I&T in the lacrimal glands of the human patient is ≤0.0004, ≤0.0003, ≤0.0002, ≤0.0001, or less within 24 hours, 48 hours, or 168 hours after injection of the composition.

Statement 231: The method of statement 230, wherein the fraction of activity of the 177Lu-PSMA I&T in the spleen of the human patient is about 0.0004, 0.0003, 0.0002, 0.0001 or less than 0.0001 within 24 hours, 48 hours, or 168 hours after administration of the composition.

Statement 232: The method of statement 230, wherein the fraction of activity of the 177Lu-PSMA I&T in the spleen of the human patient is about 0.0002 or less within 48 hours or 168 hours after administration of the composition.

Statement 233: The method of statement 230, wherein the fraction of activity of the 177Lu-PSMA I&T in the spleen of the human patient is about 0.0002, 0.0001, or less than 0.0001 within 48 hours or 168 hours after administration of the composition.

Statement 234: The method of statement 230, wherein the fraction of activity of the 177Lu-PSMA I&T in the spleen of the human patient is less than 0.0001 within 168 hours after administration of the composition.

Statement 235: The method of statement 230, wherein the administration is via injection.

Statement 236: The method of statement 230, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 237: The method of statement 230, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 238: The method of statement 230, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 239: The method of statement 230, wherein the composition comprises about 7.1 GBq to about 7.6 GBq of 177Lu-PSMA I&T.

Statement 240: The method of statement 230, wherein the composition comprises 7.4±15% GBq of 177Lu-PSMA I&T.

Statement 241: The method of statement 230, wherein the composition comprises 7.4±10% GBq of 177Lu-PSMA I&T.

Statement 242: The method of statement 230, wherein the composition comprises 7.4±5% GBq of 177Lu-PSMA I&T.

Statement 243: The method of statement 230, wherein the composition comprises about 7.4 GBq of 177Lu-PSMA I&T.

Statement 244: The method of statement 230, wherein the fraction of activity is determined via SPECT imaging, planar imaging, or a combination thereof.

Statement 245: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the absorbed radiation dose per gram of tissue in the human patient's kidneys is from about 0.2 Gy/GBq to about 0.6 Gy/GBq, from about 0.25 Gy/GBq to about 0.55 Gy/GBq, from about 0.3 Gy/GBq to about 0.5 Gy/GBq, or from about 0.35 Gy/GBq to about 0.45 Gy/GBq.

Statement 246: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the absorbed radiation dose per gram of tissue in the human patient's kidneys is ≤0.60 Gy/GBq, ≤0.55 Gy/GBq, ≤0.50 Gy/GBq, ≤0.45 Gy/GBq, ≤0.40 Gy/GBq, ≤0.35 Gy/GBq, ≤0.30 Gy/GBq, ≤0.25 Gy/GBq, ≤0.20 Gy/GBq, or ≤0.15 Gy/GBq.

Statement 247: The method of statement 246, wherein the absorbed radiation dose per gram of tissue in the human patient's kidneys is from about 0.25 Gy/GBq to about 0.55 Gy/GBq.

Statement 248: The method of statement 246, wherein the absorbed radiation dose per gram of tissue in the human patient's kidneys is from about 0.3 Gy/GBq to about 0.5 Gy/GBq.

Statement 249: The method of statement 246, wherein the mean absorbed radiation dose per gram of tissue in the human patient's kidneys is about 0.39±0.15 Gy/GBq.

Statement 250: The method of statement 246, wherein the mean absorbed radiation dose per gram of tissue in the human patient's kidneys is about 0.40±0.15 Gy/GBq.

Statement 251: The method of statement 246, wherein the mean absorbed radiation dose per gram of tissue in the human patient's kidneys is about 0.41±0.15 Gy/GBq.

Statement 252: The method of statement 246, wherein the mean absorbed radiation dose per gram of tissue in the human patient's kidneys is about 0.42±0.15 Gy/GBq.

Statement 253: The method of statement 246, wherein the mean absorbed radiation dose per gram of tissue in the human patient's kidneys is about 0.43±0.15 Gy/GBq.

Statement 254: The method of statement 246, wherein the mean absorbed radiation dose per gram of tissue in the human patient's kidneys is about 0.45±0.15 Gy/GBq.

Statement 255: The method of statement 246, wherein the mean absorbed radiation dose per gram of tissue in the human patient's kidneys is ≤0.39 Gy/GBq.

Statement 256: The method of statement 246, wherein the mean absorbed radiation dose per gram of tissue in the human patient's kidneys is ≤0.40 Gy/GBq.

Statement 257: The method of statement 246, wherein the mean absorbed radiation dose per gram of tissue in the human patient's kidneys is ≤0.41 Gy/GBq.

Statement 258: The method of statement 246, wherein the mean absorbed radiation dose per gram of tissue in the human patient's kidneys is ≤0.42 Gy/GBq.

Statement 259: The method of statement 246, wherein the standard deviation of the mean absorbed radiation dose per gram of tissue in the human patient's kidneys is ≤0.19 Gy/GBq, ≤0.18 Gy/GBq, ≤0.17 Gy/GBq, ≤0.16 Gy/GBq, or ≤0.15 Gy/GBq.

Statement 260: The method of statement 246, wherein the composition has a molar ratio of PSMA I&T to 177Lu from about 4.0:1.0 to about 8.0:1.0, from about 4.4:1.0 to about 7.6:1.0, from about 4.5:1.0 to about 5.5:1.0, or from about 5.0:1.0 to about 6.0:1.0.

Statement 261: The method of statement 246, wherein the composition has a molar ratio of PSMA I&T to 177Lu of about 3.0:1, about 3.5:1, about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 262: The method of statement 246, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 263: The method of statement 246, wherein the composition comprises about 7.1 GBq to about 7.6 GBq of 177Lu-PSMA I&T.

Statement 264: The method of statement 246, wherein the composition comprises 7.4±15% GBq of 177Lu-PSMA I&T.

Statement 265: The method of statement 246, wherein the composition comprises 7.4±10% GBq of 177Lu-PSMA I&T.

Statement 266: The method of statement 246, wherein the composition comprises 7.4±5% GBq of 177Lu-PSMA I&T.

Statement 267: The method of statement 246, wherein the composition comprises about 7.4 GBq of 177Lu-PSMA I&T.

Statement 268: The method of statement 246, wherein the absorbed radiation dose is determined via SPECT imaging, planar imaging, or a combination thereof.

Statement 269: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the absorbed radiation dose per gram of tissue in the human patient's lacrimal glands is from about 0.01 Gy/GBq to about 1.5 Gy/GBq.

Statement 270: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the absorbed radiation dose per gram of tissue in the human patient's lacrimal glands is ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq.

Statement 271: The method of statement 270, wherein the absorbed radiation dose per gram of tissue in the human patient's lacrimal glands is from about 0.1 Gy/GBq to about 0.8 Gy/GBq.

Statement 272: The method of statement 270, wherein the absorbed radiation dose per gram of tissue in the human patient's lacrimal glands is about 0.01, 0.05, 0.1, 0.2, 0.3, 0.4, 0.5, 0.6, 0.7, 0.8, 0.9, 1.0, 1.1, 1.2, 1.3, 1.4, or 1.5 Gy/GBq.

Statement 273: The method of statement 270, wherein the mean absorbed radiation dose per gram of tissue in the human patient's lacrimal glands is 0.37±0.36 Gy/GBq.

Statement 274: The method of statement 270, wherein the mean absorbed radiation dose per gram of tissue in the human patient's lacrimal glands is 0.38±0.36 Gy/GBq.

Statement 275: The method of statement 270, wherein the mean absorbed radiation dose per gram of tissue in the human patient's lacrimal glands is 0.39±0.36 Gy/GBq.

Statement 276: The method of statement 270, wherein the mean absorbed radiation dose per gram of tissue in the human patient's lacrimal glands is 0.40±0.36 Gy/GBq.

Statement 277: The method of statement 270, wherein the mean absorbed radiation dose per gram of tissue in the human patient's lacrimal glands is ≤0.40 Gy/GBq.

Statement 278: The method of statement 270, wherein the mean absorbed radiation dose per gram of tissue in the human patient's lacrimal glands is ≤0.50 Gy/GBq.

Statement 279: The method of statement 270, wherein the mean absorbed radiation dose per gram of tissue in the human patient's lacrimal glands is ≤0.60 Gy/GBq.

Statement 280: The method of statement 270, wherein the mean absorbed radiation dose per gram of tissue in the human patient's lacrimal glands is ≤0.70 Gy/GBq.

Statement 281: The method of statement 270, wherein the mean absorbed radiation dose per gram of tissue in the human patient's lacrimal glands is ≤0.80 Gy/GBq.

Statement 282: The method of statement 270, wherein the mean absorbed radiation dose per gram of tissue in the human patient's lacrimal glands is ≤0.90 Gy/GBq.

Statement 283: The method of statement 270, wherein the mean absorbed radiation dose per gram of tissue in the human patient's lacrimal glands is ≤1.0 Gy/GBq.

Statement 284: The method of statement 270, wherein the standard deviation of the mean absorbed radiation dose per gram of tissue in the human patient's lacrimal glands is ≤0.37 Gy/GBq.

Statement 285: The method of statement 270, wherein the composition has a molar ratio of PSMA I&T to 177Lu from about 4.0:1.0 to about 8.0:1.0, from about 4.4:1.0 to about 7.6:1.0, from about 4.5:1.0 to about 5.5:1.0, or from about 5.0:1.0 to about 6.0:1.0

Statement 286: The method of statement 270, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 287: The method of statement 270, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 288: The method of statement 270, wherein the composition comprises about 7.1 GBq to about 7.6 GBq of 177Lu-PSMA I&T.

Statement 289: The method of statement 270, wherein the composition comprises 7.4±15% GBq of 177Lu-PSMA I&T.

Statement 290: The method of statement 270, wherein the composition comprises 7.4±10% GBq of 177Lu-PSMA I&T.

Statement 291: The method of statement 270, wherein the composition comprises 7.4±5% GBq of 177Lu-PSMA I&T.

Statement 292: The method of statement 270, wherein the composition comprises about 7.4 GBq of 177Lu-PSMA I&T.

Statement 293: The method of statement 27025, wherein the absorbed radiation dose is determined via SPECT imaging, planar imaging, or a combination thereof.

Statement 294: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the absorbed radiation dose per gram of tissue in the human patient's salivary glands is from about 0.01 Gy/GBq to about 1.0 Gy/GBq.

Statement 295: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the absorbed radiation dose per gram of tissue in the human patient's salivary glands is ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq.

Statement 296: The method of statement 295, wherein the absorbed radiation dose per gram of tissue in the human patient's salivary glands is from about 0.1 Gy/GBq to about 0.5 Gy/GBq.

Statement 297: The method of statement 295, wherein the absorbed radiation dose per gram of tissue in the human patient's salivary glands is from about 0.01, 0.05, 0.1, 0.2, 0.3, 0.4, 0.5, 0.6, 0.7, 0.8, 0.9, or about 1.0 Gy/GBq.

Statement 298: The method of statement 295, wherein the mean absorbed radiation dose per gram of tissue in the human patient's salivary glands is about 0.17±0.16 Gy/GBq.

Statement 299: The method of statement 295, wherein the mean absorbed radiation dose per gram of tissue in the human patient's salivary glands is about 0.18±0.16 Gy/GBq.

Statement 300: The method of statement 295, wherein the mean absorbed radiation dose per gram of tissue in the human patient's salivary glands is about 0.19±0.16 Gy/GBq.

Statement 301: The method of statement 295, wherein the mean absorbed radiation dose per gram of tissue in the human patient's salivary glands is about 0.20±0.16 Gy/GBq.

Statement 302: The method of statement 295, wherein the mean absorbed radiation dose per gram of tissue in the human patient's salivary glands is ≤0.18 Gy/GBq.

Statement 303: The method of statement 295, wherein the mean absorbed radiation dose per gram of tissue in the human patient's salivary glands is ≤0.19 Gy/GBq.

Statement 304: The method of statement 295, wherein the mean absorbed radiation dose per gram of tissue in the human patient's salivary glands is ≤0.20 Gy/GBq.

Statement 305: The method of statement 295, wherein the mean absorbed radiation dose per gram of tissue in the human patient's salivary glands is ≤0.21 Gy/GBq.

Statement 306: The method of statement 295, wherein the mean absorbed radiation dose per gram of tissue in the human patient's salivary glands is ≤0.22 Gy/GBq.

Statement 307: The method of statement 295, wherein the mean absorbed radiation dose per gram of tissue in the human patient's salivary glands is ≤0.23 Gy/GBq.

Statement 308: The method of statement 295, wherein the mean absorbed radiation dose per gram of tissue in the human patient's salivary glands is ≤0.24 Gy/GBq.

Statement 309: The method of statement 295, wherein the mean absorbed radiation dose per gram of tissue in the human patient's salivary glands is ≤0.25 Gy/GBq.

Statement 310: The method of statement 295, wherein the mean absorbed radiation dose per gram of tissue in the human patient's salivary glands is ≤0.26 Gy/GBq.

Statement 311: The method of statement 295, wherein the mean absorbed radiation dose per gram of tissue in the human patient's salivary glands is ≤0.27 Gy/GBq.

Statement 312: The method of statement 295, wherein the mean absorbed radiation dose per gram of tissue in the human patient's salivary glands is ≤0.28 Gy/GBq.

Statement 313: The method of statement 295, wherein the mean absorbed radiation dose per gram of tissue in the human patient's salivary glands is ≤0.29 Gy/GBq.

Statement 314: The method of statement 295, wherein the mean absorbed radiation dose per gram of tissue in the human patient's salivary glands is ≤0.30 Gy/GBq.

Statement 315: The method of statement 295, wherein the standard deviation of the mean absorbed radiation dose per gram of tissue in the human patient's salivary glands is ≤0.25 Gy/GBq, ≤0.24 Gy/GBq, ≤0.23 Gy/GBq, ≤0.22 Gy/GBq, ≤0.21 Gy/GBq, ≤0.20 Gy/GBq, ≤0.19 Gy/GBq, ≤0.18 Gy/GBq, ≤0.17 Gy/GBq, or ≤0.16 Gy/GBq.

Statement 316: The method of statement 295, wherein the composition has a molar ratio of PSMA I&T to 177Lu from about 4.0:1.0 to about 8.0:1.0, from about 4.4:1.0 to about 7.6:1.0, from about 4.5:1.0 to about 5.5:1.0, or from about 5.0:1.0 to about 6.0:1.0.

Statement 317: The method of statement 295, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 318: The method of statement 295, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 319: The method of statement 295, wherein the composition comprises about 7.1 GBq to about 7.6 GBq of 177Lu-PSMA I&T.

Statement 320: The method of statement 295, wherein the composition comprises 7.4±15% GBq of 177Lu-PSMA I&T.

Statement 321: The method of statement 295, wherein the composition comprises 7.4±10% GBq of 177Lu-PSMA I&T.

Statement 322: The method of statement 295, wherein the composition comprises 7.4±5% GBq of 177Lu-PSMA I&T.

Statement 323: The method of statement 295, wherein the composition comprises about 7.4 GBq of 177Lu-PSMA I&T.

Statement 324: The method of statement 295, wherein the absorbed radiation dose is determined via SPECT imaging, planar imaging, or a combination thereof.

Statement 325: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the absorbed radiation dose per gram of tissue in the human patient's left colon is from about 0.01 Gy/GBq to about 1.6 Gy/GBq.

Statement 326: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the absorbed radiation dose per gram of tissue in the human patient's left colon is ≤1.6 Gy/GBq, ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq.

Statement 327: The method of statement 326, wherein the absorbed radiation dose per gram of tissue in the human patient's left colon is from about 0.1 Gy/GBq to about 0.8 Gy/GBq.

Statement 328: The method of statement 326, wherein the absorbed radiation dose per gram of tissue in the human patient's left colon is about 0.01, about 0.05, about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, or about 1.6 Gy/GBq.

Statement 329: The method of statement 326, wherein the mean absorbed radiation dose per gram of tissue in the human patient's left colon is 0.45±0.31 Gy/GBq.

Statement 330: The method of statement 326, wherein the mean absorbed radiation dose per gram of tissue in the human patient's left colon is 0.46±0.31 Gy/GBq.

Statement 331: The method of statement 326, wherein the mean absorbed radiation dose per gram of tissue in the human patient's left colon is 0.47±0.31 Gy/GBq.

Statement 332: The method of statement 326, wherein the mean absorbed radiation dose per gram of tissue in the human patient's left colon is ≤0.47 Gy/GBq.

Statement 333: The method of statement 326, wherein the composition has a molar ratio of PSMA I&T to 177Lu from about 4.0:1.0 to about 8.0:1.0, from about 4.4:1.0 to about 7.6:1.0, from about 4.5:1.0 to about 5.5:1.0, or from about 5.0:1.0 to about 6.0:1.0.

Statement 334: The method of statement 326, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 335: The method of statement 326, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 336: The method of statement 326, wherein the composition comprises about 7.1 GBq to about 7.6 GBq of 177Lu-PSMA I&T.

Statement 337: The method of statement 326, wherein the composition comprises 7.4±15% GBq of 177Lu-PSMA I&T.

Statement 338: The method of statement 326, wherein the composition comprises 7.4±10% GBq of 177Lu-PSMA I&T.

Statement 339: The method of statement 326, wherein the composition comprises 7.4±5% GBq of 177Lu-PSMA I&T.

Statement 340: The method of statement 326 wherein the composition comprises about 7.4 GBq of 177Lu-PSMA I&T.

Statement 341: The method of statement 326, wherein the absorbed radiation dose is determined via SPECT imaging, planar imaging, or a combination thereof.

Statement 342: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the absorbed radiation dose per gram of tissue in the human patient's rectum is from about 0.01 Gy/GBq to about 1.5 Gy/GBq.

Statement 343: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the absorbed radiation dose per gram of tissue in the human patient's rectum is ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq.

Statement 344: The method of statement 343, wherein the absorbed radiation dose per gram of tissue in the human patient's rectum is from about 0.1 Gy/GBq to about 0.8 Gy/GBq.

Statement 345: The method of statement 343, wherein the absorbed radiation dose per gram of tissue in the human patient's rectum is about 0.01, about 0.05, about 0.1, about 0.2, about 0.3, about 0.4, about 0.5, about 0.6, about 0.7, about 0.8, about 0.9, about 1.0, about 1.1, about 1.2, about 1.3, about 1.4, or about 1.5 Gy/GBq.

Statement 346: The method of statement 343, wherein the mean absorbed radiation dose per gram of tissue in the human patient's rectum is 0.44±0.30 Gy/GBq.

Statement 347: The method of statement 343, wherein the composition has a molar ratio of PSMA I&T to 177Lu from about 4.0:1.0 to about 8.0:1.0, from about 4.4:1.0 to about 7.6:1.0, from about 4.5:1.0 to about 5.5:1.0, or from about 5.0:1.0 to about 6.0:1.0.

Statement 348: The method of statement 343, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 349: The method of statement 343, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 350: The method of statement 343, wherein the composition comprises about 7.1 GBq to about 7.6 GBq of 177Lu-PSMA I&T.

Statement 351: The method of statement 343, wherein the composition comprises 7.4±15% GBq of 177Lu-PSMA I&T.

Statement 352: The method of statement 343, wherein the composition comprises 7.4±10% GBq of 177Lu-PSMA I&T.

Statement 353: The method of statement 343, wherein the composition comprises 7.4±5% GBq of 177Lu-PSMA I&T.

Statement 354: The method of statement 343, wherein the composition comprises about 7.4 GBq of 177Lu-PSMA I&T.

Statement 355: The method of statement 343, wherein the absorbed radiation dose is determined via SPECT imaging, planar imaging, or a combination thereof.

Statement 356: The method of statement 269, wherein anatomical coverage of the imaging extends from the salivary glands to the pelvis.

Statement 357: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the whole body of the human patient is about 0.5 or less within 24 hours, 48 hours, or 168 hours after administration of the composition.

Statement 358: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the whole body of the human patient is ≤0.5, ≤0.4, ≤0.3, ≤0.2, or ≤0.1 within 24 hours, 48 hours, or 168 hours after administration of the composition.

Statement 359: The method of statement 358, wherein the fraction of activity of the 177Lu-PSMA I&T in the whole body of the human patient is about 0.5, about 0.4, about 0.3, about 0.2, about 0.1, or less than 0.1 within 24 hours, 48 hours, or 168 hours after administration of the composition.

Statement 360: The method of statement 358, wherein the fraction of activity of the 177Lu-PSMA I&T in the whole body of the human patient is about 0.4 or less within 48 hours or 168 hours after administration of the composition.

Statement 361: The method of statement 358, wherein the fraction of activity of the 177Lu-PSMA I&T in the whole body of the human patient is about 0.4, about 0.3, about 0.2, about 0.1, or less than 0.1 within 48 hours or 168 hours after administration of the composition.

Statement 362: The method of statement 358, wherein the fraction of activity of the 177Lu-PSMA I&T in the whole body of the human patient is about 0.2 or less within 168 hours after administration of the composition.

Statement 363: The method of statement 358, wherein the administration is via injection.

Statement 364: The method of statement 358, wherein the composition has a molar ratio of PSMA I&T to 177Lu from about 4.0:1.0 to about 8.0:1.0, from about 4.4:1.0 to about 7.6:1.0, from about 4.5:1.0 to about 5.5:1.0, or from about 5.0:1.0 to about 6.0:1.0.

Statement 365: The method of statement 358, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 366: The method of statement 358, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 367: The method of statement 358, wherein the composition comprises about 7.1 GBq to about 7.6 GBq of 177Lu-PSMA I&T.

Statement 368: The method of statement 358, wherein the composition comprises 7.4±15% GBq of 177Lu-PSMA I&T.

Statement 369: The method of statement 358, wherein the composition comprises 7.4±10% GBq of 177Lu-PSMA I&T.

Statement 370: The method of statement 358, wherein the composition comprises 7.4±5% GBq of 177Lu-PSMA I&T.

Statement 371: The method of statement 358, wherein the composition comprises about 7.4 GBq of 177Lu-PSMA I&T.

Statement 372: The method of statement 358, wherein the fraction of activity is determined via SPECT imaging, planar image-based dosimetry, or a combination thereof.

Statement 373: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the kidneys of the human patient is about 0.05 or less within 24 hours, 48 hours, or 168 hours after administration of the composition.

Statement 374: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the kidneys of the human patient is ≤0.05, ≤0.04, ≤0.03, ≤0.02, or ≤0.01 within 24 hours, 48 hours, or 168 hours after administration of the composition.

Statement 375: The method of statement 374, wherein the fraction of activity of the 177Lu-PSMA I&T in the kidneys of the human patient is about 0.05, about 0.04, about 0.03, about 0.02, about 0.01, or less than 0.01 within 24 hours, 48 hours, or 168 hours after administration of the composition.

Statement 376: The method of statement 374, wherein the fraction of activity of the 177Lu-PSMA I&T in the kidneys of the human patient is ≤0.040 within 48 hours or 168 hours after administration of the composition.

Statement 377: The method of statement 374, wherein the fraction of activity of the 177Lu-PSMA I&T in the kidneys of the human patient is about 0.040 or less, about 0.035 or less, or about 0.030 or less within 48 hours or 168 hours after administration of the composition.

Statement 378: The method of statement 374, wherein the fraction of activity of the 177Lu-PSMA I&T in the kidneys of the human patient is about 0.04, about 0.03, about 0.02, about 0.01, or less than 0.01 within 48 hours or 168 hours after administration of the composition.

Statement 379: The method of statement 374, wherein the fraction of activity of the 177Lu-PSMA I&T in the kidneys of the human patient is about 0.03 or less within 168 hours after administration of the composition.

Statement 380: The method of statement 374, wherein the fraction of activity of the 177Lu-PSMA I&T in the kidneys of the human patient is about 0.03, about 0.02, about 0.01, or less than 0.01 within 168 hours after administration of the composition.

Statement 381: The method of statement 374, wherein the administration is via injection.

Statement 382: The method of statement 374, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 383: The method of statement 374, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 384: The method of statement 374, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 385: The method of statement 374, wherein the composition comprises about 7.1 GBq to about 7.6 GBq of 177Lu-PSMA I&T.

Statement 386: The method of statement 374, wherein the composition comprises 7.4±15% GBq of 177Lu-PSMA I&T.

Statement 387: The method of statement 374, wherein the composition comprises 7.4±10% GBq of 177Lu-PSMA I&T.

Statement 388: The method of statement 374, wherein the composition comprises 7.4±5% GBq of 177Lu-PSMA I&T.

Statement 389: The method of statement 374, wherein the composition comprises about 7.4 GBq of 177Lu-PSMA I&T.

Statement 390: The method of statement 374, wherein the fraction of activity is determined via SPECT imaging, planar imaging, or a combination thereof.

Statement 391: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the red marrow of the human patient is about 0.08 or less within 24 hours, 48 hours, or 168 hours after administration of the composition.

Statement 392: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the red marrow of the human patient is ≤0.08, ≤0.07, ≤0.06, ≤0.05, ≤0.04, ≤0.03, ≤0.02, ≤0.01, or less within 24 hours, 48 hours, or 168 hours after administration of the composition.

Statement 393: The method of statement 392, wherein the fraction of activity of the 177Lu-PSMA I&T in the red marrow of the human patient is about 0.08, about 0.07, about 0.06, about 0.05, about 0.04, about 0.03, about 0.02, about 0.01, or less than 0.01 within 24 hours, 48 hours, or 168 hours after administration of the composition.

Statement 394: The method of statement 392, wherein the fraction of activity of the 177Lu-PSMA I&T in the red marrow of the human patient is about 0.06 or less within 48 hours or 168 hours after administration of the composition.

Statement 395: The method of statement 392, wherein the fraction of activity of the 177Lu-PSMA I&T in the red marrow of the human patient is about 0.06, about 0.05, about 0.04, about 0.03, about 0.02, about 0.01, or less than 0.01 within 48 hours or 168 hours after administration of the composition.

Statement 396: The method of statement 392, wherein the fraction of activity of the 177Lu-PSMA I&T in the red marrow of the human patient is about 0.04 or less within 168 hours after administration of the composition.

Statement 397: The method of statement 392, wherein the fraction of activity of the 177Lu-PSMA I&T in the red marrow of the human patient is about 0.04, about 0.03, about 0.02, about 0.01, or less than 0.01 within 168 hours after administration of the composition.

Statement 398: The method of statement 392, wherein the administration is via injection.

Statement 399: The method of statement 392, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 400: The method of statement 392, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 401: The method of statement 392, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 402: The method of statement 392, wherein the composition comprises about 7.1 GBq to about 7.6 GBq of 177Lu-PSMA I&T.

Statement 403: The method of statement 392, wherein the composition comprises 7.4±15% GBq of 177Lu-PSMA I&T.

Statement 404: The method of statement 392, wherein the composition comprises 7.4±10% GBq of 177Lu-PSMA I&T.

Statement 405: The method of statement 392, wherein the composition comprises 7.4±5% GBq of 177Lu-PSMA I&T.

Statement 406: The method of statement 392, wherein the composition comprises about 7.4 GBq of 177Lu-PSMA I&T.

Statement 407: The method of statement 392, wherein the fraction of activity is determined via SPECT imaging, planar imaging, or a combination thereof.

Statement 408: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the salivary glands of the human patient is about 0.015 or less within 24 hours, 48 hours, or 168 hours after administration of the composition.

Statement 409: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the salivary glands of the human patient is ≤0.015, ≤0.014, ≤0.013, ≤0.012, ≤0.011, ≤0.010, ≤0.009, ≤0.008, ≤0.007, ≤0.006, ≤0.005, ≤0.004, ≤0.003, ≤0.002, ≤0.001, or less within 24 hours, 48 hours, or 168 hours after administration of the composition.

Statement 410: The method of statement 409, wherein the fraction of activity of the 177Lu-PSMA I&T in the salivary glands of the human patient is about 0.015, about 0.014, about 0.013, about 0.012, about 0.011, about 0.010, about 0.009, about 0.008, about 0.007, about 0.006, about 0.005, about 0.004, about 0.003, about 0.002, about 0.001, or less than 0.001 within 24 hours, 48 hours, or 168 hours after administration of the composition.

Statement 411: The method of statement 409, wherein the fraction of activity of the 177Lu-PSMA I&T in the salivary glands of the human patient is about 0.007 or less within 48 hours or 168 hours after administration of the composition.

Statement 412: The method of statement 409, wherein the fraction of activity of the 177Lu-PSMA I&T in the salivary glands of the human patient is about 0.007, about 0.006, about 0.005, about 0.004, about 0.003, about 0.002, about 0.001 or less than 0.001 within 48 hours or 168 hours after administration of the composition.

Statement 413: The method of statement 409, wherein the fraction of activity of the 177Lu-PSMA I&T in the salivary glands of the human patient is about 0.004 or less within 168 hours after administration of the composition.

Statement 414: The method of statement 409, wherein the fraction of activity of the 177Lu-PSMA I&T in the salivary glands of the human patient is about 0.004, about 0.003, about 0.002, ≤0.001, about 0.001, or less than 0.001 within 168 hours after administration of the composition.

Statement 415: The method of statement 409, wherein the administration is via injection.

Statement 416: The method of statement 409, wherein the composition has a molar ratio of PSMA I&T to 177Lu from about 4.0:1.0 to about 8.0:1.0, from about 4.5:1.0 to about 5.5:1.0, or from about 5.0:1.0 to about 6.0:1.0.

Statement 417: The method of statement 409, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 418: The method of statement 409, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 419: The method of statement 409, wherein the composition comprises about 7.1 GBq to about 7.6 GBq of 177Lu-PSMA I&T.

Statement 420: The method of statement 409, wherein the composition comprises 7.4±15% GBq of 177Lu-PSMA I&T.

Statement 421: The method of statement 409, wherein the composition comprises 7.4±10% GBq of 177Lu-PSMA I&T.

Statement 422: The method of statement 409, wherein the composition comprises 7.4±5% GBq of 177Lu-PSMA I&T.

Statement 423: The method of statement 409, wherein the composition comprises about 7.4 GBq of 177Lu-PSMA I&T.

Statement 424: The method of statement 409, wherein the fraction of activity is determined via SPECT imaging, planar imaging, or a combination thereof.

Statement 425: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the gastrointestinal tract of the human patient is about 0.10 or less within 24 hours, 48 hours, or 168 hours after administration of the composition.

Statement 426: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the gastrointestinal tract of the human patient is ≤0.10, ≤0.09, ≤0.08, ≤0.07, ≤0.06, ≤0.05, ≤0.04, ≤0.03, ≤0.02, ≤0.01, or less within 24 hours, 48 hours, or 168 hours after administration of the composition.

Statement 427: The method of statement 426, wherein the fraction of activity of the 177Lu-PSMA I&T in the gastrointestinal tract of the human patient is about 0.10, about 0.09, about 0.08, about 0.07, about 0.06, about 0.05, about 0.04, about 0.03, about 0.02, about 0.01, or less than 0.01 within 24 hours, 48 hours, or 168 hours after administration of the composition.

Statement 428: The method of statement 426, wherein the fraction of activity of the 177Lu-PSMA I&T in the gastrointestinal tract of the human patient is ≤0.10 or about 0.10 or less within 48 hours or 168 hours after administration of the composition.

Statement 429: The method of statement 426, wherein the fraction of activity of the 177Lu-PSMA I&T in the gastrointestinal tract of the human patient is about 0.10, about 0.09, about 0.08, about 0.07, about 0.06, about 0.05, about 0.04, about 0.03, about 0.02, about 0.01, or less than 0.01 within 48 hours or 168 hours after administration of the composition.

Statement 430: The method of statement 426, wherein the fraction of activity of the 177Lu-PSMA I&T in the gastrointestinal tract of the human patient is about 0.05 or less within 168 hours after administration of the composition.

Statement 431: The method of statement 426, wherein the fraction of activity of the 177Lu-PSMA I&T in the gastrointestinal tract of the human patient is about 0.05, about 0.04, about 0.03, about 0.02, about 0.01, or less than 0.01 within 168 hours after administration of the composition.

Statement 432: The method of statement 426, wherein the administration is via injection.

Statement 433: The method of statement 426, wherein the composition has a molar ratio of PSMA I&T to 177Lu from about 4.0:1.0 to about 8.0:1.0, from about 4.4:1.0 to about 7.6:1.0, from about 4.5:1.0 to about 5.5:1.0, or from about 5.0:1.0 to about 6.0:1.0.

Statement 434: The method of statement 426, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 435: The method of statement 426, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 436: The method of statement 426, wherein the composition comprises about 7.1 GBq to about 7.6 GBq of 177Lu-PSMA I&T.

Statement 437: The method of statement 426, wherein the composition comprises 7.4±15% GBq of 177Lu-PSMA I&T.

Statement 438: The method of statement 426, wherein the composition comprises 7.4±10% GBq of 177Lu-PSMA I&T.

Statement 439: The method of statement 426, wherein the composition comprises 7.4±5% GBq of 177Lu-PSMA I&T.

Statement 440: The method of statement 426, wherein the composition comprises about 7.4 GBq of 177Lu-PSMA I&T.

Statement 441: The method of statement 426, wherein the fraction of activity is determined via SPECT imaging, planar imaging, or a combination thereof.

Statement 442: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the liver of the human patient is about 0.04 or less within 24 hours, 48 hours, or 168 hours after administration of the composition.

Statement 443: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the liver of the human patient is ≤0.04, ≤0.03, ≤0.02, ≤0.01, or less within 24 hours, 48 hours, or 168 hours after administration of the composition.

Statement 444: The method of statement 443, wherein the fraction of activity of the 177Lu-PSMA I&T in the liver of the human patient is about 0.04, about 0.03, about 0.02, about 0.01, or less than 0.01 within 24 hours, 48 hours, or 168 hours after administration of the composition.

Statement 445: The method of statement 442, wherein the fraction of activity of the 177Lu-PSMA I&T in the liver of the human patient is about 0.02 or less within 48 hours or 168 hours after administration of the composition.

Statement 446: The method of statement 442, wherein the fraction of activity of the 177Lu-PSMA I&T in the liver of the human patient is about 0.02, about 0.01, or less than 0.01 within 48 hours or 168 hours after administration of the composition.

Statement 447: The method of statement 442, wherein the fraction of activity of the 177Lu-PSMA I&T in the liver of the human patient is about 0.01 or less within 168 hours after administration of the composition.

Statement 448: The method of statement 442, wherein the administration is via injection.

Statement 449: The method of statement 442, wherein the composition has a molar ratio of PSMA I&T to 177Lu from about 4.0:1.0 to about 8.0:1.0, from about 4.4:1.0 to about 7.6:1.0, from about 4.5:1.0 to about 5.5:1.0, or from about 5.0:1.0 to about 6.0:1.0.

Statement 450: The method of statement 442, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 451: The method of statement 442, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 452: The method of statement 442, wherein the composition comprises about 7.1 GBq to about 7.6 GBq of 177Lu-PSMA I&T.

Statement 453: The method of statement 442, wherein the composition comprises 7.4±15% GBq of 177Lu-PSMA I&T.

Statement 454: The method of statement 442, wherein the composition comprises 7.4±10% GBq of 177Lu-PSMA I&T.

Statement 455: The method of statement 442, wherein the composition comprises 7.4±5% GBq of 177Lu-PSMA I&T.

Statement 456: The method of statement 442, wherein the composition comprises about 7.4 GBq of 177Lu-PSMA I&T.

Statement 457: The method of statement 442, wherein the fraction of activity is determined via SPECT imaging, planar imaging, or a combination thereof.

Statement 458: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the spleen of the human patient is about 0.004 or less within 24 hours, 48 hours, or 168 hours after administration of the composition.

Statement 459: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the spleen of the human patient is ≤0.004, ≤0.003, ≤0.002, ≤0.001 or less within 24 hours, 48 hours, or 168 hours after administration of the composition.

Statement 460: The method of statement 459, wherein the fraction of activity of the 177Lu-PSMA I&T in the spleen of the human patient is ≤0.004, about 0.04, ≤0.003, about 0.003, ≤0.002, about 0.002, ≤0.001, about 0.001, or less than 0.001 within 24 hours, 48 hours, or 168 hours after administration of the composition.

Statement 461: The method of statement 459, wherein the fraction of activity of the 177Lu-PSMA I&T in the spleen of the human patient is about 0.002 or less within 48 hours or 168 hours after administration of the composition.

Statement 462: The method of statement 459, wherein the fraction of activity of the 177Lu-PSMA I&T in the spleen of the human patient is about 0.002, about 0.001, or less than 0.001 within 48 hours or 168 hours after administration of the composition.

Statement 463: The method of statement 459, wherein the fraction of activity of the 177Lu-PSMA I&T in the spleen of the human patient is about 0.001 or less within 168 hours after administration of the composition.

Statement 464: The method of statement 459, wherein the administration is via injection.

Statement 465: The method of statement 459, wherein the composition has a molar ratio of PSMA I&T to 177Lu from about 4.0:1.0 to about 8.0:1.0, from about 4.4:1.0 to about 7.6:1.0, from about 4.5:1.0 to about 5.5:1.0, or from about 5.0:1.0 to about 6.0:1.0.

Statement 466: The method of statement 459, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 467: The method of statement 459, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 468: The method of statement 459, wherein the composition comprises about 7.1 GBq to about 7.6 GBq of 177Lu-PSMA I&T.

Statement 469: The method of statement 459, wherein the composition comprises 7.4±15% GBq of 177Lu-PSMA I&T.

Statement 470: The method of statement 459, wherein the composition comprises 7.4±10% GBq of 177Lu-PSMA I&T.

Statement 471: The method of statement 459, wherein the composition comprises 7.4±5% GBq of 177Lu-PSMA I&T.

Statement 472: The method of statement 459, wherein the composition comprises about 7.4 GBq of 177Lu-PSMA I&T.

Statement 473: The method of statement 459, wherein the fraction of activity is determined via SPECT imaging, planar imaging, or a combination thereof.

Statement 474: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the lacrimal glands of the human patient is about 0.0004 or less within 24 hours, 48 hours, or 168 hours after injection of the composition.

Statement 475: A method comprising administering to a human patient in need thereof a radiopharmaceutical composition comprising 177Lu-PSMA I&T, wherein the molar ratio of the PSMA I&T to 177Lu is from 3.0:1.0 to 8.0:1.0, the composition comprises a radiochemical purity of ≥95% for at least 72 hours after manufacture, and wherein the fraction of activity of the 177Lu-PSMA I&T in the lacrimal glands of the human patient is ≤0.0004, ≤0.0003, ≤0.0002, ≤0.0001, or less within 24 hours, 48 hours, or 168 hours after injection of the composition.

Statement 476: The method of statement 475, wherein the fraction of activity of the 177Lu-PSMA I&T in the spleen of the human patient is about 0.0004, about 0.0003, about 0.0002, about 0.0001, or less than 0.0001 within 24 hours, 48 hours, or 168 hours after administration of the composition.

Statement 477: The method of statement 475, wherein the fraction of activity of the 177Lu-PSMA I&T in the spleen of the human patient is about 0.0002 or less within 48 hours or 168 hours after administration of the composition.

Statement 478: The method of statement 475, wherein the fraction of activity of the 177Lu-PSMA I&T in the spleen of the human patient is about 0.0002, about 0.0001, or less than 0.0001 within 48 hours or 168 hours after administration of the composition.

Statement 479: The method of statement 475, wherein the fraction of activity of the 177Lu-PSMA I&T in the spleen of the human patient is less than 0.0001 within 168 hours after administration of the composition.

Statement 480: The method of statement 475, wherein the administration is via injection.

Statement 481: The method of statement 475, wherein the composition has a molar ratio of PSMA I&T to 177Lu from about 4.0:1.0 to about 8.0:1.0, from about 4.4:1.0 to about 7.6:1.0, from about 4.5:1.0 to about 5.5:1.0, or from about 5.0:1.0 to about 6.0:1.0.

Statement 482: The method of statement 475, wherein the composition has a molar ratio of PSMA I&T to 177Lu of about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

Statement 483: The method of statement 475, wherein the composition has a molar ratio of PSMA I&T to 177Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

Statement 484: The method of statement 475, wherein the composition comprises about 7.1 GBq to about 7.6 GBq of 177Lu-PSMA I&T.

Statement 485: The method of statement 475, wherein the composition comprises 7.4±15% GBq of 177Lu-PSMA I&T.

Statement 486: The method of statement 475, wherein the composition comprises 7.4±10% GBq of 177Lu-PSMA I&T.

Statement 487: The method of statement 475, wherein the composition comprises 7.4±5% GBq of 177Lu-PSMA I&T.

Statement 488: The method of statement 475, wherein the composition comprises about 7.4 GBq of 177Lu-PSMA I&T.

Statement 489: The method of statement 475, wherein the fraction of activity is determined via SPECT imaging, planar imaging, or a combination thereof.

| | | | Batch specific | | | | | Dose specific | | | | | | |
|---|---|---|---|---|---|---|---|---|---|---|---|---|---|---|
| Subject ID | DOSE ID | BATCH NO. | RCP*, % | RAC*, MBq/mL | MA*, GBq/μmol | Lu-PSMA, μg/mL | PSMA, μg/mL | Other PSMA, μg/ml | Measured PSMA Sum, μg/mL | Theoretical PSMA Sum, μg/ml | Lu-PSMA μg/dose | Measured PSMA Sum μg/dose | Theoretical PSMA Sum μg/dose | Dose Vol, mL | Dose Act**, MBq |
| 80-018 | 80-018 | LKMI2348A-1 | 99.2 | 559 | 212 | 1.4 | 2.0 | 0.7 | 4.1 | 5.9 | 23.5 | 68.9 | 99.8 | 16.80 | 7276 |
| 42-027 | 42-027 | LKMI2405A-1 | 98.1 | 608 | 184 | 1.5 | 2.8 | 0.8 | 5.1 | 5.9 | 21.1 | 71.6 | 83.4 | 14.04 | 7380 |
| 37-015 | 37-015 | LKMI2327A-1 | 98.9 | 596 | 209 | 1.3 | 2.3 | 0.8 | 4.4 | 5.9 | 21.3 | 72.1 | 97.3 | 16.39 | 7396 |
| 37-016 | 37-016 | LKMI2327A-1 | 98.9 | 596 | 209 | 1.3 | 2.3 | 0.8 | 4.4 | 5.9 | 21.3 | 72.1 | 97.3 | 16.39 | 7396 |
| 37-023 | 37-023 | LKMI2402A-1 | 99.0 | 592 | 196 | 1.7 | 2.4 | 0.6 | 4.7 | 5.9 | 27.9 | 77.0 | 97.3 | 16.39 | 7469 |
| 37-022 | 37-022 | LKMI2402A-1 | 99.0 | 592 | 196 | 1.7 | 2.4 | 0.6 | 4.7 | 5.9 | 27.9 | 77.0 | 97.3 | 16.39 | 7469 |
| 37-017 | 37-017 | LKMI2329G-1 | 99.1 | 565 | 195 | 1.5 | 2.5 | 0.5 | 4.5 | 6.4 | 25.9 | 77.7 | 109.7 | 17.26 | 7485 |
| 42-030 | 42-030 | LKMI2411A-1 | 98.5 | 586 | 189 | 1.4 | 2.9 | 0.5 | 4.8 | 5.9 | 22.4 | 76.8 | 95.1 | 16.01 | 7401 |
| 62-032 | 62-032 | LKMI2402A-2 | 98.9 | 570 | 185 | 1.7 | 2.4 | 0.7 | 4.8 | 5.9 | 28.0 | 79.0 | 97.8 | 16.46 | 7400 |
| 80-024 | 80-024 | LKMI2407A-1 | 98.8 | 604 | 191 | 1.5 | 2.6 | 0.8 | 4.9 | 5.9 | 24.3 | 79.5 | 96.3 | 16.22 | 7475 |
| 80-023 | 80-023 | LKMI2407A-1 | 98.8 | 604 | 191 | 1.5 | 2.6 | 0.8 | 4.9 | 5.9 | 24.3 | 79.5 | 96.3 | 16.22 | 7475 |
| 25-008 | 25-008 | LKMI2322A-1 | 98.5 | 616 | 191 | 1.6 | 2.5 | 0.9 | 5.0 | 5.9 | 25.4 | 79.4 | 94.3 | 15.88 | 7450 |
| 37-019 | 37-019 | LKMI2348G-1 | 99.2 | 590 | 190 | 1.4 | 2.5 | 0.9 | 4.8 | 6.4 | 23.5 | 80.4 | 106.5 | 16.75 | 7416 |
| 80-019 | 80-019 | LKMI2402A-2 | 98.9 | 570 | 185 | 1.7 | 2.4 | 0.7 | 4.8 | 5.9 | 29.0 | 82.0 | 101.5 | 17.08 | 7462 |
| 25-009 | 25-009 | LKMI2327G-1 | 98.8 | 580 | 183 | 1.4 | 2.5 | 1.0 | 4.9 | 6.4 | 23.6 | 82.6 | 107.1 | 16.85 | 7533 |
| 25-007 | 25-007 | LKMI2320G-2 | 99.1 | 604 | 182 | 1.3 | 2.3 | 1.5 | 5.1 | 6.4 | 21.0 | 82.2 | 102.5 | 16.12 | 7428 |
| 66-024 | 66-024 | LKMI2409G-1 | 98.8 | 556 | 172 | 1.5 | 2.9 | 0.6 | 5.0 | 6.4 | 25.6 | 85.3 | 108.4 | 17.05 | 7445 |
| 42-028 | 42-028 | LKMI2405G-1 | 98.5 | 572 | 163 | 1.5 | 3.1 | 0.8 | 5.4 | 6.4 | 24.8 | 89.2 | 104.9 | 16.51 | 7482 |
| 80-022 | 80-022 | LKMI2406G-1 | 98.7 | 548 | 163 | 1.5 | 3.1 | 0.6 | 5.2 | 6.4 | 26.7 | 92.6 | 113.2 | 17.81 | 7488 |
| 80-020 | 80-020 | LKMI2406G-1 | 98.7 | 548 | 163 | 1.5 | 3.1 | 0.6 | 5.2 | 6.4 | 26.7 | 92.6 | 113.2 | 17.81 | 7488 |
| 37-020 | 37-020 | LKMI2352A-1 | 99.1 | 594 | 169 | 2.1 | 2.3 | 1.1 | 5.5 | 5.9 | 34.4 | 90.0 | 97.2 | 16.37 | 7186 |
| 12-004 | 12-004 | LKMI2315G-1 | 99.1 | 563 | 152 | 1.3 | 3.5 | 0.9 | 5.7 | 6.4 | 22.6 | 99.2 | 110.6 | 17.40 | 7497 |
| 80-007 | 80-007 | LKMI2318B-1 | 98.4 | 586 | 143 | 1.4 | 3.7 | 1.2 | 6.3 | 5.9 | 23.4 | 105.1 | 99.1 | 16.68 | 7549 |
| 80-001 | 80-001 | LKMI2316G-1 | 98.6 | 588 | 139 | 1.4 | 3.9 | 1.2 | 6.5 | 6.4 | 23.4 | 108.5 | 106.1 | 16.69 | 7410 |
| 37-013 | 37-013 | LKMI2319A-1 | 98.9 | 576 | 138 | 1.4 | 3.2 | 1.8 | 6.4 | 5.9 | 23.7 | 108.5 | 100.7 | 16.95 | 7390 |
| 25-005 | 25-005 | LKMI2316A-1 | 98.9 | 585 | 136 | 1.4 | 3.7 | 1.5 | 6.6 | 6.4 | 23.5 | 110.6 | 106.5 | 16.75 | 7458 |
| 80-004 | 80-004 | LKMI2317G-1 | 98.5 | 585 | 126 | 1.4 | 3.8 | 1.9 | 7.1 | 6.4 | 23.5 | 119.1 | 106.6 | 16.77 | 7455 |

RCP = Radiochemical Purity
RAC = Radioactivity Concentration
MA = Molar Activity
*at the time of release
**at the calibration time
Other PSMA means PSMA I&T chelated with non-active metal impurities (mainly Zn, Fe and Cu)

| PSMA Content, μg | PSMA Content, nmol | Ratio** (PSMA: Lu-177) | Kidneys (Gy/GBq) | Lacrimal Glands (Gy/GBq) | Salivary Glands (Gy/GBq) | Liver (Gy/GBq) |
|---|---|---|---|---|---|---|
| 68.9 | 44.3 | 4.4 | 0.31 | N/A | 0.11 | 0.04 |
| 71.6 | 46.3 | 4.6 | 0.36 | N/A | 0.16 | 0.02 |
| 72.1 | 46.6 | 4.6 | 0.32 | 0.19 | 0.06 | 0.02 |
| 72.1 | 46.6 | 4.6 | 0.54 | 0.20 | 0.00 | 0.02 |
| 77.0 | 49.4 | 4.8 | 0.28 | 0.07 | 0.19 | 0.06 |
| 77.0 | 49.4 | 4.8 | 0.56 | 0.06 | 0.10 | 0.02 |
| 77.7 | 50.0 | 4.9 | 0.41 | 0.66 | 0.04 | 0.04 |
| 76.8 | 49.7 | 4.9 | 0.23 | 0.08 | 0.11 | 0.03 |
| 79.0 | 50.8 | 5.0 | 0.53 | 0.16 | 0.15 | 0.03 |
| 79.5 | 51.3 | 5.0 | 0.30 | 0.26 | 0.26 | 0.03 |
| 79.5 | 51.3 | 5.0 | 0.38 | 0.47 | 0.19 | 0.07 |
| 79.4 | 51.2 | 5.0 | 0.81 | 0.63 | 0.12 | 0.03 |
| 80.4 | 52.0 | 5.1 | 0.24 | 0.08 | 0.20 | 0.10 |
| 82.0 | 52.7 | 5.1 | 0.17 | 0.07 | 0.32 | 0.05 |
| 82.6 | 53.5 | 5.2 | 0.29 | N/A | 0.16 | 0.02 |
| 82.2 | 53.4 | 5.2 | 0.34 | 0.54 | 0.03 | 0.02 |
| 85.3 | 55.1 | 5.4 | 0.55 | N/A | 0.09 | 0.02 |
| 89.2 | 57.8 | 5.6 | 0.43 | 0.38 | 0.39 | 0.08 |
| 92.6 | 59.9 | 5.8 | 0.05 | 0.05 | 0.13 | 0.09 |
| 92.6 | 59.9 | 5.8 | 0.45 | 0.04 | 0.14 | 0.01 |
| 90.0 | 57.7 | 5.8 | 0.35 | 0.09 | 0.80 | 0.04 |
| 99.2 | 64.6 | 6.3 | 0.57 | N/A | 0.27 | 0.04 |
| 105.1 | 68.5 | 6.6 | 0.48 | 1.19 | 0.18 | 0.06 |
| 108.5 | 70.8 | 6.9 | 0.27 | 0.94 | 0.29 | 0.07 |
| 108.5 | 70.7 | 7.0 | 0.27 | 1.09 | 0.10 | 0.05 |
| 110.6 | 72.1 | 7.0 | 0.64 | 0.68 | 0.03 | 0.03 |
| 119.1 | 77.8 | 7.6 | 0.28 | 0.62 | 0.28 | 0.02 |

What is claimed is:

1. A method comprising administering to a human patient in need thereof a radiopharmaceutical composition comprising $^{177}$Lu-PSMA I&T, wherein the molar ratio of the PSMA I&T to $^{177}$Lu is from 3.0:1.0 to 8.0:1.0, the composition comprises a radiochemical purity of ≥95% for at least 72 hours after manufacture, and wherein the absorbed radiation dose per gram of tissue in the human patient's kidneys is from about 0.2 Gy/GBq to about 0.6 Gy/GBq, from about 0.25 Gy/GBq to about 0.55 Gy/GBq, from about 0.3 Gy/GBq to about 0.5 Gy/GBq, or from about 0.35 Gy/GBq to about 0.45 Gy/GBq.

2. The method of claim 1, wherein the absorbed radiation dose per gram of tissue in the human patient's kidneys is from about 0.25 Gy/GBq to about 0.55 Gy/GBq.

3. The method of claim 1, wherein the absorbed radiation dose per gram of tissue in the human patient's kidneys is from about 0.3 Gy/GBq to about 0.5 Gy/GBq.

4. The method of claim 1, wherein the mean absorbed radiation dose per gram of tissue in the human patient's kidneys is about 0.39±0.15 Gy/GBq.

5. The method of claim 1, wherein the mean absorbed radiation dose per gram of tissue in the human patient's kidneys is about 0.40±0.15 Gy/GBq.

6. The method of claim 1, wherein the mean absorbed radiation dose per gram of tissue in the human patient's kidneys is about 0.41±0.15 Gy/GBq.

7. The method of claim 1, wherein the mean absorbed radiation dose per gram of tissue in the human patient's kidneys is about 0.42±0.15 Gy/GBq.

8. The method of claim 1, wherein the mean absorbed radiation dose per gram of tissue in the human patient's kidneys is about 0.43±0.15 Gy/GBq.

9. The method of claim 1, wherein the mean absorbed radiation dose per gram of tissue in the human patient's kidneys is about 0.45±0.15 Gy/GBq.

10. The method of claim 1, wherein the mean absorbed radiation dose per gram of tissue in the human patient's kidneys is ≤0.39 Gy/GBq.

11. The method of claim 1, wherein the mean absorbed radiation dose per gram of tissue in the human patient's kidneys is ≤0.40 Gy/GBq.

12. The method of claim 1, wherein the mean absorbed radiation dose per gram of tissue in the human patient's kidneys is ≤0.41 Gy/GBq.

13. The method of claim 1, wherein the mean absorbed radiation dose per gram of tissue in the human patient's kidneys is ≤0.42 Gy/GBq.

14. The method of claim 1, wherein the standard deviation of the mean absorbed radiation dose per gram of tissue in the human patient's kidneys is ≤0.19 Gy/GBq, ≤0.18 Gy/GBq, ≤0.17 Gy/GBq, ≤0.16 Gy/GBq, or ≤0.15 Gy/GBq.

15. The method of claim 1, wherein the composition has a molar ratio of PSMA I&T to $^{177}$Lu from about 4.0:1.0 to about 8.0:1.0, from about 4.4:1.0 to about 7.6:1.0, from about 4.5:1.0 to about 5.5:1.0, or from about 5.0:1.0 to about 6.0:1.0.

16. The method of claim 1, wherein the composition has a molar ratio of PSMA I&T to $^{177}$Lu of about 3.0:1, about 3.5:1, about 4.0:1.0, about 4.5:1.0, about 5.0:1.0, about 5.5:1.0, about 6.0:1.0, about 6.5:1.0, about 7.0:1.0, about 7.5:1.0, or about 8.0:1.0.

17. The method of claim 1, wherein the composition has a molar ratio of PSMA I&T to $^{177}$Lu from about 5.1:1.0 to about 5.9:1.0, from about 5.2:1.0 to about 5.8:1.0, from about 5.3:1.0 to about 5.7:1.0, or from about 5.4:1.0 to about 5.6:1.0.

18. The method of claim 1, wherein the composition has a molar ratio of PSMA I&T to $^{177}$Lu from 4.4:1.0 to 7.6:1.0.

19. The method of claim 1, wherein the composition comprises about 7.1 GBq to about 7.6 GBq of $^{177}$Lu-PSMA I&T.

20. The method of claim 1, wherein the composition comprises 7.4±15% GBq of $^{177}$Lu-PSMA I&T.

21. The method of claim 1, wherein the composition comprises 7.4±10% GBq of $^{177}$Lu-PSMA I&T.

22. The method of claim 1, wherein the composition comprises 7.4±5% GBq of $^{177}$Lu-PSMA I&T.

23. The method of claim 1, wherein the composition comprises about 7.4 GBq of $^{177}$Lu-PSMA I&T.

24. The method of claim 1, wherein the absorbed radiation dose is determined via SPECT imaging, planar imaging, or a combination thereof.

25. A method comprising administering to a human patient in need thereof a radiopharmaceutical composition comprising $^{177}$Lu-PSMA I&T, wherein the molar ratio of the PSMA I&T to $^{177}$Lu is from 3.0:1.0 to 8.0:1.0, the composition comprises a radiochemical purity of ≥95% for at least 72 hours after manufacture, and wherein the absorbed radiation dose per gram of tissue in the human patient's kidneys is ≤0.60 Gy/GBq, ≤0.55 Gy/GBq, ≤0.50 Gy/GBq, ≤0.45 Gy/GBq, ≤0.40 Gy/GBq, ≤0.35 Gy/GBq, ≤0.30 Gy/GBq, ≤0.25 Gy/GBq, ≤0.20 Gy/GBq, or ≤0.15 Gy/GBq.

26. A method comprising administering to a human patient in need thereof a radiopharmaceutical composition comprising $^{177}$Lu-PSMA I&T, wherein the molar ratio of the PSMA I&T to $^{177}$Lu is from 3.0:1.0 to 8.0:1.0, the composition comprises a radiochemical purity of ≥95% for at least 72 hours after manufacture, and wherein the absorbed radiation dose per gram of tissue in the human patient's lacrimal glands is from about 0.01 Gy/GBq to about 1.5 Gy/GBq.

27. A method comprising administering to a human patient in need thereof a radiopharmaceutical composition comprising $^{177}$Lu-PSMA I&T, wherein the molar ratio of the PSMA I&T to $^{177}$Lu is from 3.0:1.0 to 8.0:1.0, the composition comprises a radiochemical purity of ≥95% for at least 72 hours after manufacture, and wherein the absorbed radiation dose per gram of tissue in the human patient's lacrimal glands is ≤1.5 Gy/GBq, ≤1.4 Gy/GBq, ≤1.3 Gy/GBq, ≤1.2 Gy/GBq, ≤1.1 Gy/GBq, ≤1.0 Gy/GBq, ≤0.9 Gy/GBq, ≤0.8 Gy/GBq, ≤0.7 Gy/GBq, ≤0.6 Gy/GBq, ≤0.5 Gy/GBq, ≤0.4 Gy/GBq, ≤0.3 Gy/GBq, ≤0.2 Gy/GBq, or ≤0.1 Gy/GBq.

28. The method of claim 27, wherein the composition has a molar ratio of PSMA I&T to $^{177}$Lu from about 4.0:1.0 to about 8.0:1.0, from about 4.4:1.0 to about 7.6:1.0, from about 4.5:1.0 to about 5.5:1.0, or from about 5.0:1.0 to about 6.0:1.0.

29. The method of claim 27, wherein the composition has a molar ratio of PSMA I&T to $^{177}$Lu from 4.4:1.0 to 7.6:1.0.

30. The method of claim 27, wherein the absorbed radiation dose is determined via SPECT imaging, planar imaging, or a combination thereof.

* * * * *